United States Patent
Bitenc et al.

(10) Patent No.: US 11,898,199 B2
(45) Date of Patent: Feb. 13, 2024

(54) DETECTION OF COLORECTAL CANCER AND/OR ADVANCED ADENOMAS

(71) Applicant: Universal Diagnostics, S.A., Seville (ES)

(72) Inventors: Marko Bitenc, Ljubljana (SI); Kristi Kruusmaa, Ljubljana (SI); Juan Martinez-Barea, Seville (ES); Christian Hense, Seville (ES); Marko Chersicola, Ljubljana (SI); Primož Knap, Ljubljana (SI)

(73) Assignee: Universal Diagnostics, S.A., Seville (ES)

( * ) Notice: Subject to any disclaimer, the term of this patent is extended or adjusted under 35 U.S.C. 154(b) by 615 days.

(21) Appl. No.: 16/680,427

(22) Filed: Nov. 11, 2019

(65) Prior Publication Data
US 2021/0139948 A1    May 13, 2021

(51) Int. Cl.
*C12Q 1/686* (2018.01)

(52) U.S. Cl.
CPC ....... *C12Q 1/686* (2013.01); *C12Q 2600/154* (2013.01); *G01N 2800/52* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | |
|---|---|---|
| 6,265,171 B1 | 7/2001 | Herman et al. |
| 6,605,432 B1 | 8/2003 | Huang |
| 6,812,339 B1 | 11/2004 | Venter et al. |
| 7,144,701 B2 | 12/2006 | Huang |
| 7,745,391 B2 | 6/2010 | Mintz et al. |
| 7,807,358 B1 | 10/2010 | Huang |
| 8,048,634 B2 | 11/2011 | Lai |
| 9,745,622 B2 | 8/2017 | An et al. |
| 9,850,523 B1 | 12/2017 | Chudova et al. |
| 10,006,925 B2 | 6/2018 | Bitenc et al. |
| 10,301,680 B2 | 5/2019 | Ahlquist et al. |
| 10,392,666 B2 | 8/2019 | Lo et al. |
| 10,428,388 B2 | 10/2019 | An et al. |
| 11,001,898 B2 | 5/2021 | Bitenc et al. |
| 11,118,228 B2 | 9/2021 | Allawi et al. |
| 11,345,967 B2 | 5/2022 | Morris |
| 11,396,679 B2 | 7/2022 | Bitenc et al. |
| 11,530,453 B2 | 12/2022 | Bitenc et al. |
| 2007/0237813 A1 | 10/2007 | Misawa et al. |
| 2007/0298506 A1* | 12/2007 | Ordway ............... C12Q 1/6886 536/23.1 |
| 2010/0167940 A1 | 7/2010 | Feinberg |
| 2010/0240549 A1 | 9/2010 | Brown |
| 2010/0298158 A1 | 11/2010 | DePinho et al. |
| 2011/0318738 A1 | 12/2011 | Jones et al. |
| 2012/0289581 A1* | 11/2012 | Chang ............... A61P 35/00 435/6.12 |
| 2013/0012410 A1 | 1/2013 | Zou et al. |
| 2013/0085681 A1 | 4/2013 | Deciu et al. |
| 2013/0189684 A1 | 7/2013 | Ehrich et al. |
| 2013/0288247 A1 | 10/2013 | Mori et al. |
| 2014/0128283 A1 | 5/2014 | Feinberg et al. |
| 2015/0011403 A1 | 1/2015 | Lo et al. |
| 2015/0072866 A1 | 3/2015 | Weisburg et al. |
| 2015/0152505 A1 | 6/2015 | Lapointe et al. |
| 2016/0333416 A1 | 11/2016 | Babiarz et al. |
| 2016/0355885 A1 | 12/2016 | Weinhausel et al. |
| 2017/0016048 A1 | 1/2017 | Blauwkamp et al. |
| 2017/0101674 A1 | 4/2017 | So et al. |
| 2017/0298439 A1* | 10/2017 | Ahlquist ............ G16H 50/20 |
| 2017/0335401 A1 | 11/2017 | Allawi et al. |

(Continued)

FOREIGN PATENT DOCUMENTS

| | | |
|---|---|---|
| EP | 2481813 A1 | 8/2012 |
| EP | 2497834 A2 | 9/2012 |

(Continued)

OTHER PUBLICATIONS

Genecards, ALKAL1 Gene—ALK and LTK Ligand 1, 2022. (Year: 2022).*
Petko, Aberrantly Methylated CDKN2A, MGMT and MLH1 in Colon Polyps and in Fecal DNA from Patients with Colorectal Polyps, Clinical Cancer Research, 11: 1203-1209, 2005. (Year: 2005).*
UCSC Genome Browser 1, CpG Island Info, Band 9p21.3, 2020. (Year: 2020).*
UCSC Genome Browser 2, CpG Island Info, Band 8q11.23, 2020. (Year: 2020).*

(Continued)

*Primary Examiner* — Angela M. Bertagna
*Assistant Examiner* — Carolyn L Greene
(74) *Attorney, Agent, or Firm* — Choate, Hall & Stewart LLP; William R. Haulbrook; Samuel R. Polio

(57) ABSTRACT

The present disclosure provides, among other things, methods of screening for colorectal cancer, methods of screening for advanced adenoma, methods of screening for the presence of either colorectal cancer or advanced adenoma (or both), and compositions related thereto. In various embodiments, the present disclosure provides methods for colorectal cancer and/or advanced adenoma screening that includes analysis of methylation status of one or more methylation biomarkers, and compositions related thereto. In various embodiments, the present disclosure provides methods for colorectal cancer and/or advanced adenoma screening that include screening methylation status of one or more methylation biomarkers in cfDNA, e.g., in ctDNA. In various embodiments, the present disclosure provides methods for colorectal cancer and/or advanced adenoma screening that include screening methylation status of one or more methylation biomarkers in cfDNA, e.g., in ctDNA, using MSRE-qPCR.

11 Claims, 18 Drawing Sheets

Specification includes a Sequence Listing.

(56) References Cited

U.S. PATENT DOCUMENTS

| | | |
|---|---|---|
| 2017/0356051 A1 | 12/2017 | Ishioka et al. |
| 2017/0369948 A1 | 12/2017 | Markowitz et al. |
| 2018/0051338 A1 | 2/2018 | West et al. |
| 2018/0119137 A1 | 5/2018 | Matsuguchi et al. |
| 2018/0148777 A1 | 5/2018 | Kirkizlar et al. |
| 2018/0245157 A1 | 8/2018 | Allawi et al. |
| 2018/0251859 A1 | 9/2018 | Ahlquist et al. |
| 2018/0258498 A1 | 9/2018 | Ahlquist et al. |
| 2018/0305765 A1 | 10/2018 | Feber et al. |
| 2018/0363063 A1 | 12/2018 | Guerrero-Preston et al. |
| 2019/0025308 A1 | 1/2019 | Cummings et al. |
| 2019/0032149 A1 | 1/2019 | Van Engeland et al. |
| 2019/0085406 A1 | 3/2019 | Mortimer et al. |
| 2019/0112645 A1 | 4/2019 | Woodhouse et al. |
| 2019/0161805 A1 | 5/2019 | Ahlquist et al. |
| 2019/0161806 A1 * | 5/2019 | Ahlquist ............... C12Q 1/682 |
| 2019/0256921 A1 | 8/2019 | Mueller et al. |
| 2019/0256924 A1 | 8/2019 | Vogelstein et al. |
| 2019/0352721 A1 | 11/2019 | Kusunoki et al. |
| 2020/0017916 A1 | 1/2020 | Ren |
| 2020/0157640 A1 | 5/2020 | Letourneur et al. |
| 2020/0340062 A1 | 10/2020 | Salhia |
| 2020/0377954 A1 | 12/2020 | Bitenc et al. |
| 2020/0377959 A1 | 12/2020 | Bitenc et al. |
| 2021/0230707 A1 | 7/2021 | Bitenc et al. |
| 2021/0277487 A1 | 9/2021 | Bitenc et al. |
| 2021/0324477 A1 | 10/2021 | Xiang et al. |
| 2021/0332440 A1 | 10/2021 | Kruusmaa et al. |
| 2021/0355542 A1 | 11/2021 | Bitenc et al. |
| 2021/0404010 A1 | 12/2021 | Bitenc et al. |
| 2021/0404011 A1 | 12/2021 | Bitenc et al. |
| 2022/0106644 A1 | 4/2022 | Taylor et al. |
| 2022/0136058 A1 | 5/2022 | Allawi et al. |
| 2022/0186323 A1 | 6/2022 | Mortimer et al. |
| 2022/0228221 A1 | 7/2022 | Curtis |
| 2022/0389521 A1 | 12/2022 | Bitenc et al. |
| 2022/0411878 A1 | 12/2022 | Kruusmaa |
| 2023/0183815 A1 | 6/2023 | Bitenc et al. |

FOREIGN PATENT DOCUMENTS

| | | | |
|---|---|---|---|
| EP | 2886659 A1 | 6/2015 | |
| EP | 2899275 A1 | 7/2015 | |
| EP | 2977467 A2 | 1/2016 | |
| WO | WO-02/081749 A2 | 10/2002 | |
| WO | WO-2005/001142 A2 | 1/2005 | |
| WO | WO-2007/149269 A2 | 12/2007 | |
| WO | WO-2010/118559 A1 | 10/2010 | |
| WO | WO-2012/034170 A1 | 3/2012 | |
| WO | WO-2012/047899 A2 | 4/2012 | |
| WO | WO-2012/104642 A1 | 8/2012 | |
| WO | WO-2012/154979 A2 | 11/2012 | |
| WO | WO-2012/167145 A2 | 12/2012 | |
| WO | WO-2012/170715 A1 | 12/2012 | |
| WO | WO-2013/057581 A2 | 4/2013 | |
| WO | WO-2013/097868 A1 | 7/2013 | |
| WO | WO-2014/032227 A1 | 3/2014 | |
| WO | WO-2014/062218 A1 | 4/2014 | |
| WO | WO-2015/116837 A1 | 8/2015 | |
| WO | WO-2015/153283 A1 | 10/2015 | |
| WO | WO-2015/153284 A1 | 10/2015 | |
| WO | WO-2015/159292 A2 | 10/2015 | |
| WO | WO-2016/060278 A1 | 4/2016 | |
| WO | WO-2016/109782 A2 | 7/2016 | |
| WO | WO-2017/012592 A1 | 1/2017 | |
| WO | WO-2017/043497 A1 | 3/2017 | |
| WO | WO-2017/048932 A1 | 3/2017 | |
| WO | WO-2017/192221 A1 | 11/2017 | |
| WO | WO-2017/201606 A1 | 11/2017 | |
| WO | WO-2017/212428 A1 | 12/2017 | |
| WO | WO-2018/087129 A1 | 5/2018 | |
| WO | WO-2018/119452 A2 | 6/2018 | |
| WO | WO-2018119452 A2 * | 6/2018 | ......... C12N 15/1065 |
| WO | WO-2018/140781 A1 | 8/2018 | |
| WO | WO-2018/195211 A1 | 10/2018 | |
| WO | WO-2018/209361 A2 | 11/2018 | |
| WO | WO-2019/068082 A1 | 4/2019 | |
| WO | WO-2019/175876 A2 | 9/2019 | |
| WO | WO-2019175876 A2 * | 9/2019 | ......... C12N 15/1006 |
| WO | WO-2020/069350 A1 | 4/2020 | |
| WO | WO-2020/232109 A1 | 11/2020 | |
| WO | WO-2020/239895 A2 | 12/2020 | |
| WO | WO-2020/239896 A1 | 12/2020 | |
| WO | WO-2021/016441 A1 | 1/2021 | |
| WO | WO-2021/041726 A1 | 3/2021 | |
| WO | WO-2021/094017 A1 | 5/2021 | |
| WO | WO-2021/216477 A1 | 10/2021 | |
| WO | WO-2022/003572 A1 | 1/2022 | |

OTHER PUBLICATIONS

Gibson, Pathology of premalignant colorectal neoplasia, Digestive Endoscopy, 38: 312-323, 2016. (Year: 2016).*
Genecards, GAD2 Gene—Glutamate Decarboxylase 2, 2023. (Year: 2023).*
Genecards, MYO3A Gene—Myosin IIIA, 2023. (Year: 2023).*
UCSC Genome Browser 3, CpG Island Info, Band 10p12.1, 2022. (Year: 2022).*
UCSC Genome Browser 4, CpG Island Info, Band 20q13.31, 2022. (Year: 2022).*
Chen, J. et. al., DNA methylation biomarkers in stool for early screening of colorectal cancer, Journal of Cancer, 10(21):5264-5271, (2019).
Chen, J.J., et. al., DNA methylation assay for colorectal carcinoma, Cancer Biology & Medicine, 14(1):42-49, (2017).
DOE Joint Genome Institute, AC012313, (2003).
DOE Joint Genome Institute, AC024563, (2002).
International Search Report for PCT/EP2020/064813 filed May 28, 2020, 8 pages, dated Dec. 22, 2020.
Kok-Sin, T., et. al., Identification of diagnostic markers in colorectal cancer via integrative epigenomics and genomics data, Oncology Reports, 34:22-32, (2015).
Kutsenko, A., et. al., NotI flanking sequences: a tool for gene discovery and verification of the human genome, Nucleic Acids Research, 30(14):3163-3170, (2002).
Lowe, T., et. al., A Computer program for selection of oligonucleotide primers for polymerase chain reactions, Nucleic Acids Research. 18(7):1757-1761, (1990).
Mitchell, S.M. et. al., A panel of genes methylated with high frequency in colorectal cancer, BMC cancer biomed central, 14(1): 54, (2014).
Written Opinion for PCT/EP2020/064813 filed May 28, 2020, 13 pages, dated Dec. 22, 2020.
Yang, Y., et. al., Identification of regulatory role of DNA methylation in colon cancer gene expression via systematic bioinformatics analysis, Medicine, 96(47):1-7, (2017).
Adusumalli, S. et al., Methodological aspects of whole-genome bisulfite sequencing analysis, Briefings in Bioinformatics, 16(3):369-379, (2014).
Bacolod, M. D. et al., Application of Multiplex Bisulfite PCR-Ligase Detection Reaction-Real-Time Quantitative PCR Assay in Interrogating Bioinformatically Identified, Blood-Based Methylation Markers for Colorectal Cancer, The Journal of Molecular Diagnostics, 22(7):886-900, (2020).
Zhang, S. et al., CRISPR/Cas9-mediated knockout of NSD1 suppresses the hepatocellular carcinoma development via the NSD1/H3/Wnt10b signaling pathway, Journal of Experimental and Clinical Cancer Research, 38(1):467, (2019).
Aberle, D.R., et al., Reduced lung-cancer mortality with low-dose computed tomographic screening, National Lung Screening Trial Research Team, 365(5):395-409, (2011).
Andersson, I., et al., Mammographic screening and mortality from breast cancer: the Malmö mammographic screening trial, 297(6654): 943-8, (1988).
Breast Cancer Screening (PDQ®)-Health Professional Version, <https://www.cancer.gov/types/breast/hp/breast-screening-pdq#section/all>. Retrieved on Jul. 17, 2020.

(56) References Cited

OTHER PUBLICATIONS

Demissie, K., et al., Empirical comparison of the results of randomized controlled trials and case-control studies in evaluating the effectiveness of screening mammography, 51(2):81-91, (1998).
Krueger, F. and Andrews, S.R., Bismark: a flexible aligner and methylation caller for Bisulfite-Seq applications, Bioinformatics, 27(11):1571-2, (2011).
QIAamp® Circulating Nucleic Acid Handbook, For concentration and purification of free-circulating DNA, RNA, miRNA, and viral nucleic acids from human plasma, serum, urine, or other cell-free body fluids, Oct. 2019.
QIAamp@ MinElute® ccfDNA Handbook, For concentration and purification of circulation cell-free DNA from plasma or serum, Jan. 2020.
Rahib, L., et. al., Projecting cancer incidence and deaths to 2030: the unexpected burden of thyroid, liver, and pancreas cancers in the United States, 74(11):2913-21, (2014).
The Cancer Genome Atlas Program, <https://www.cancer.gov/about-nci/organization/ccg/research/structural-genomics/tcga>.
Vainio, H., et al., IARC Handbooks of Cancer Prevention Programme Head: Harri Vainio. vol. 7: Breast Cancer Screening, pp. 1-236, (2002).
International Search Report for PCT/EP2020/076220 filed Sep. 21, 2020, 5 pages, dated Nov. 23, 2020.
Lam, K. et al., DNA methylation based biomakers in colorectal cancer: A systematic review, Elsevier Science BV, Biochimica et Biophysica Acta 1866:106-1202 (2016).
Li, H. et. al., Identification of novel DNA methylation markers in colorectal cancer using MIRA-based microarrays, Oncology Reports, National Hellenic Research Foundation, 28(1):99-104, (2012).
Written Opinion for PCT/EP2020/076220 filed Sep. 21, 2020, 6 pages, dated Nov. 23, 2020.
Galanopoulos, M., et. al., Abnormal DNA methylation as a cell-free circulating DNA biomarker for colorectal cancer detection: A review of literature, World Journal of Gastrointestinal Oncology, 9(4):142-152, (2017).
International Search Report for PCT/EP2020/064815 filed May 28, 2020, 6 pages, dated Apr. 9, 2020.
Kordowski., F., et al., Aberrant DNA methylation of ADAMTS16 in colorectal and other epithlial cancers, BMC Cancer, 18(1):4, (2018).
Kruusmaa, K. et. al., MSRE-qPCR for analysis of gene specific methylation can be accurately used for detection and validation of colorectal cancer-specific patterns, 4Bio Summit (Jan. 1, 2018). <www.universaldx.com/wp-content/uploads/2017/05/4Bio-poster-November-2018.pdf>. Retrieved on Aug. 19, 2020.
Melnikov, A. A., et. al., MSRE-PCR for analysis of gene-specific DNA methylation, Nucleic Acids Research, 33(10): e93-e93, (2015).
Written Opinion for PCT/EP2020/064815 filed May 28, 2020, 6 pages, dated Apr. 9, 2020.
Yan, H., et. al., Identifying CpG sites with different differential methylation frequencies in colorectal cancer tissues based on individualized differential methylation analysis, Open Access Impact Journal, 29(8): 47356-47364, (2017).
Blesa, J. R. et al., NRF-1 is the major transcription factor regulating the expression of the human TOMM34 gene, Biochemistry and Cell Biology, Biochem Cell Biol., 86(1):46-56, (2008).
Liu, W-B et al., TMEM196 acts as a novel functional tumour suppressor inactivated by DNA methylation and is a potential prognostic biomarker in lung cancer, Oncotarget, 6(25):21225-21239, (2015).
Margolin, G. et al., Robust Detection of DNA Hypermethylation of ZNF154 as a Pan-Cancer Locus with in Silico Modeling for Blood-Based Diagnostic Development, The Journal of Molecular Diagnostics, 18(2):283-298, (2016).
Mitchell, S. M. et al., A panel of genes methylated with high frequency in colorectal cancer, BMC Cancer, Biomed Central, London, GB, 14(1):54, 15 pages, (2014).
Zhou, X. et al., Identification of epigenetic modulators in human breast cancer by integrated analysis of DNA methylation and RNA-Seq data, Epigenetics, 13(5):473-489, (2018).

Adler, A. et al., Improving compliance to colorectal cancer screening using blood and stool based tests in patients refusing screening colonoscopy in Germany, BMC Gastroenterology, 14:183, (2014).
Beikircher, G. et al., Multiplexed and Sensitive DNA Methylation Testing Using Methylation-Sensitive Restriction Enzymes "MSRE-qPCR", DNA Methylation Protocols, Methods in Molecular Biology 1708:Ch21:407-424, (2018).
Bray, F. et al., Global Cancer Statistics 2018: GLOBOCAN Estimates of Incidence and Mortality Worldwide for 36 Cancers in 185 Countries, CA Cancer J Clin., 68:394-424, (2018).
Calderwood, A. H. et al., Colon adenoma features and their impact on risk of future advanced adenomas and colorectal cancer, World Journal of Gastrointestinal Oncology, 8(12):826-834, (2016).
Capman, M. et al., MethyLight and Digital MethyLight, DNA Methylation Protocols, Methods in Molecular Biology, 1708:CH25:497-513, (2018).
Chang, C. P.-Y. et al., Elevated cell-free serum DNA detected in patients with myocardial infarction, Clinica Chimica Acta 327:95-101, (2003).
Chen, Y. et al., Tissue-independent and tissue-specific patterns of DNA methylation alteration in cancer, Epigenetics & Chromatin, 9:10, (2016).
Chiu, R. W. K. et al., Noninvasive prenatal diagnosis of fetal chromosomal aneuploidy by massively parallel genomic sequencing of DNA in maternal plasma, PNAS, 105(51):20458-20463, (2008).
Esteller, M., CpG island hypermethylation and tumor suppressor genes: a booming present, a brighter future, Oncogene, 21:5427-5440, (2002).
Fackler, M. J. and Sukumar, S., Quantitation of DNA Methylation by Quantitative Multiplex Methylation-Specific PCR (QM-MSP) Assay, DNA Methylation Protocols, Methods in Molecular Biology, 1708:CH24:473-496, (2018).
Fan, C.H. et al., Noninvasive diagnosis of fetal aneuploidy by shotgun sequencing DNA from maternal blood, Proceedings of The National Academy of Sciences, 105(42):16266-16271 (2008).
Frommer, M. et al., A genomic sequencing protocol that yields a positive display of 5-methylcytosine residues in individual DNA strands, Proc. Natl. Acad. Sci. USA, 89:1827-1831, (1992).
Galeazzi, M. et al., Dosage and characterization of circulating DNA: present usage and possible applications in systemic autoimmune disorders, Autoimmunity Reviews, 2:50-55, (2003).
Gasc, C. et al., Survey and Summary: Sequence capture by hybridization to explore modern and ancient genomic diversity in model and nonmodel organisms, Nucleic Acids Research, 44(10):4504-4518, (2016).
Gonzalgo, M. L. and Liang, G., Methylation-sensitive single-nucleotide primer extension (Ms-SNuPE) for quantitative measurement of DNA methylation, Nature Protocols, 2(8):1931-1936, (2007).
Hemmasi, G., et al., Prevalence of colorectal adenoma in an average-risk population aged 40-50 versus 50-60 years, European Journal of Cancer Prevention (ECP), pp. 1-5, (2014).
Herman, J. G. et al., Methylation-specific PCR: A novel PCR assay for methylation status of CpG islands, Proc. Natl. Acad. Sci. USA, 93:9821-9826, (1996).
Hussmann, D. and Hansen, L. L., Methylation-Sensitive High Resolution Melting (MS-HRM), DNA Methylation Protocols, Methods in Molecular Biology, 1708:CH28:551-571, (2018).
Imperiale, T. F. et al., Multitarget Stool DNA Testing for Colorectal-Cancer Screening, Correspondence to the Editor, The New England Journal of Medicine, doi:10.1056/NEJMc1405215, 371(2):184-188, (2014).
Imperiale, T. F. et al., Multitarget Stool DNA Testing for Colorectal-Cancer Screening, The New England Journal of Medicine, 370(14):1287-1297, (2014).
Ivanov, M. et al., In-solution hybrid capture of bisulfite-converted DNA for targeted bisulfite sequencing of 174 ADME genes, Nucleic Acids Research, 46(6):e72, 9 pages, (2013).
Karsenti, D. et al., Adenoma and advanced neoplasia detection rates increase from 45 years of age, World Journal of Gastroenterology, 25(4): 447-456 (2019).

(56) References Cited

OTHER PUBLICATIONS

Laird, P. W., Applications of Next-Generation Sequencing: Principles and challenges of genomewide DNA methylation analysis, Nature Review, Genetics, 11:191-203, (2010).

Leon, S. A. et al., Free DNA in the Serum of Cancer Patients and the Effect of Therapy, Cancer Research, 37:646-650, (1977).

Liles, E. G. et al., Uptake of a colorectal cancer screening blood test is higher than of a fecal test offered in clinic: A randomized trial, Cancer Treatment and Research Communications, 10:27-31, (2017).

Liu, Y. et al., Methylation-sensitive enrichment of minor DNA alleles using a double-strand DNA-specific nuclease, Nucleic Acids Research, 45(6):e39, 11 pages, (2017).

Masser, D. R. et al., Targeted DNA Methylation Analysis by Next-generation Sequencing, Jounarl of Visualized Experiments, www.jove.com, @Creative Commons Attribution-NonCommercial License, 96:e52488, 11 pages, (2015).

Meyer, D. et al., Package 'e1071', Misc Functions of the Department of Statistics, Probability Theory Group (Formerly: E1071), Tu Wien, HTTPS://cran.r-project.org/web/packages/e1071/index.html, 63 pages, (2019).

Nakamura, A. et al., Relationship between sodium excretion and pioglitazone-induced edema, Journal of Diabetes Investigation, 1(5):208-211, (2010).

Navarro, M. et al., Colorectal cancer population screening programs worldwide in 2016: An Update, World J Gastroenterol, 23(20):3632-3642, (2017).

O'Connell B., and Crockett S., The clinical impact of serrated colorectal polyps, Dove Press Journal, Clinical Epidemiology, 9: 113-125 (2017).

Oh, T. et al., Genome-Wide Identification and Validation of a Novel Methylation Biomarker, SDC2, for Blood-Based Detection of Colorectal Cancer, The Journal of Molecular Diagnostics, 15(4):498-507, (2013).

Potter, N. T. et al., Validation of a Real-Time PCR-Based Qualitative Assay for the Detection of Methylated SEPT9 DNA in Human Plasma, Clinical Chemistry, 60(9):1183-1191, (2014).

Schwarzenbach, H. et al., Cell-free nucleic acids as biomarkers in cancer patients, Nature Reviews / Cancer, 11:426-437, (2011).

Shaukat, A. et al., Long-Term Mortality after Screening for Colorectal Cancer, The New England Journal of Medicine, 369(12):1106-1114, (2013).

Singh, K. E. et al., Colorectal Cancer Incidence Among Young Adults in California, Journal of Adolescent and Young Adult Oncology, 3(4):176-184, (2014).

Snyder, M.W. et al., Cell-free DNA Comprises an In vivo Nucleosome footprint that informs its Tissues-Of-Origin, Cell, 164: pp. 57-68, (2016).

Swarup, V. and Rajeswari, M.R., Circulating (cell-free) nucleic acids—A promising, non-invasive tool for early detection of several human diseases, FEBS Letters 581:795-799, (2007).

Van der Vlugt, M. et al., Adherence to colorectal cancer screening: four rounds of faecal immunochemical test-based screening, British Journal of Cancer, 116(1):44-49, (2017).

Wittenberger, T. et al., DNA methylation markers for early detection of women's cancer: promise and challenges, Epigenomics, 6(3):311-327, (2014).

Adalsteinsson, V.A. et al., Scalable whole-exome sequencing of cell-free DNA reveals high concordance with metastatic tumors, Nat. Commun., 8(1):1324, (2017).

Exner, R. et al., Potential of DNA methylation in rectal cancer as diagnostic and prognostic biomarkers, Br. J. Cancer, 113(7):1035-1045 (2015).

Heidary, M. et al., The dynamic range of circulating tumor DNA in metastatic breast cancer, Breast Cancer Res., 16(4):421, (2014).

Kirkizlar, E. et al., Detection of Clonal and Subclonal Number Variants in Cell-Free DNA from Patients with Breast Cancer Using a Massively Multiplexed PCR Methodology, Transl. Oncol., 8(5):407-416, (2015).

Kukita, Y. et al., High-fidelity target sequencing of individual molecules identified using barcode sequences: de novo detection and absolute quantitation of mutations in plasma cell-free DNA from cancer patients, DNA Res., 22(4):269-277, (2015).

Leary, R.J. et al., Detection of chromosomal alterations in the circulation of cancer patients with whole-genome sequencing, Sci. Transl. Med., 4(162):162ra154, (2012).

Lianidou, E., Detection and relevance of epigenetic markers on ctDNA: recent advances and future outlook, Mol. Oncol., 15(6):1683-1700, (2021).

Michels, K.B., The promises and challenges of epigenetic epidemiology, Exp. Gerontol., 45(4):297-301, (2010).

Perakis, S. et al., Advances in Circulating Tumor DNA Analysis, Adv. Clin. Chem., 80:73-153, (2017).

Pulverer, W. et al., The stem cell signature of CHH/CHG methylation is not present in 271 cancer associated 5'UTR gene regions, Biochimie, 94(11):2345-2352 (2012).

Wan, M. et al., Identification of Smoking-Associated Differentially Methylated Regions Using Reduced Representation Bisulfite Sequencing and Cell type-Specific Enhancer Activation and Gene Expression, Environ. Health Perspect. 126(4):047015 (2018).

* cited by examiner

| | | Colorectal Cancer | Control | Non Advanced Adenoma |
|---|---|---|---|---|
| Training Set | Female | 25 | 50 | 6 |
| | Male | 29 | 50 | 6 |
| | Age (range) | 67(43-82) | 63(34-82) | 61(54-66) |
| | | Proximal | Distal | |
| | Localized | 8 | 22 | |
| | Advanced | 5 | 14 | |
| | Unknown | 1 | 4 | |

FIG. 2

| | | Colorectal Cancer | Advanced Adenoma | Control | Non Advanced Adenoma |
|---|---|---|---|---|---|
| Validation Set | Female | 44 | 17 | 133 | 70 |
| | Male | 49 | 28 | 119 | 70 |
| | Age (range) | 66(47-84) | 61(50-83) | 61(33-83) | 66(50-82) |
| | | Proximal | Distal | | |
| | Localized | 22 | 28 | | |
| | Advanced | 12 | 31 | | |

FIG. 3

SEQUENCE LISTING

<160> NUMBER OF SEQ ID NOS: 317

<210> SEQ ID NO 1
<211> LENGTH: 297
<212> TYPE: DNA
<213> ORGANISM: Homo sapiens

<400> SEQUENCE: 1
tcgctcctct gctccaacaa cttatacttg ctcttttgcc tttgaatttc tgaggtttag    60
tgagttcgat tagccgcgtg ctcagaatca agttcgggaa gaaagaggag gaggatgaag   120
cggacaagaa ggaggacgac ggcgaaaaga aggccaaaca cagcatcgac ggcatcctgg   180
gcgacaaagg tagggaactt ccctgggctg cgaggcccca gcccgggttt tcccacgctc   240
cggtgtgcgg gccagtggtt cgctcccgcc gccggagcag gcgaccagaa ctccagc      297

<210> SEQ ID NO 2
<211> LENGTH: 242
<212> TYPE: DNA
<213> ORGANISM: Homo sapiens

<400> SEQUENCE: 2
cgaggtcgtg gagcggcagc agctgcagcc ggagcagcac cagcaacagc aacagcgagc    60
gggacggagt taggaccgct cggagcgcac aggtctcgag gtagtataag gtttgctatc   120
cttccacttg ctggcagttg cagaagaaga tctgcttttt aagtgaaacg tacatgccac   180
ccctccgagg gctgcggctt ccccgggctt gcttctttgc cgctcctctt tccggctctc   240
gc                                                                   242

<210> SEQ ID NO 3
<211> LENGTH: 257
<212> TYPE: DNA

<213> ORGANISM: Homo sapiens

<400> SEQUENCE: 3

| | | | | | |
|---|---|---|---|---|---|
| cgacgcacgg | acccggggac | ctcgacactc | gctaggaggc | aagccctatt | cctcagccgg | 60 |
| gcgcccctcg | tctcccgctc | tctccatgga | cccctctcct | ggcaaatcgc | ccgcagagcg | 120 |
| agcttggaga | tgcgagggaa | actgaagccc | caagggtgcc | ccgtcctggg | agcctggctg | 180 |
| tctgcgggt | ccccccgcatt | ccgcagtagt | aatacaggag | ggccggggc | ttctacccca | 240 |
| acctccgctc | cccttcg | | | | | 257 |

<210> SEQ ID NO 4
<211> LENGTH: 264
<212> TYPE: DNA
<213> ORGANISM: Homo sapiens

<400> SEQUENCE: 4

| | | | | | |
|---|---|---|---|---|---|
| cgtcctgcgc | aggaccggca | gcccgaggcg | gagacgaagg | gggcccgcag | ggactcctgg | 60 |
| ccttgcgtct | tgggagagcg | cacgctggcc | tgcgctacac | acacacactt | cacagttgcg | 120 |
| ctgaaacaga | gtcgggtttt | ctgtacagga | gataaaatga | cggtagtgtg | tgtgtttttt | 180 |
| gaaagagctg | ttaaaaagct | aagttcttct | catttcagtg | agagttcccc | cttggattgt | 240 |
| ttgtgcgtgt | attcaattca | gccg | | | | 264 |

<210> SEQ ID NO 5
<211> LENGTH: 191
<212> TYPE: DNA
<213> ORGANISM: Homo sapiens

<400> SEQUENCE: 5

| | | | | | |
|---|---|---|---|---|---|
| cgagctgatc | gagcggcagc | ggctggagct | gcggcagcag | gagctgcggg | cgcgctacaa | 60 |
| cctcagccag | ggcggctacg | aggagctgga | gcgcgtcgtg | ctgcgcctca | gccgcacaa | 120 |
| ggccggcgtg | cagtggcgct | tcgccggctc | cttctacttc | gccatcaccg | tcatcaccac | 180 |
| catcggtaac | g | | | | | 191 |

<210> SEQ ID NO 6
<211> LENGTH: 1319
<212> TYPE: DNA
<213> ORGANISM: Homo sapiens

<400> SEQUENCE: 6

| | | | | | |
|---|---|---|---|---|---|
| acgactgttc | tggacccagt | ttataaagac | tgcctggctg | gccaggaaat | ccccagagg | 60 |
| cctccttccg | tgtccccggg | ccaaatctgt | gaagagaaaa | cggaaggcta | ccatgtcacg | 120 |
| aaaaactatg | atcaaataaa | ttattatgcc | ttttctccta | ttgatctgcc | ttttgtcaac | 180 |
| tgattttcag | tgaaccttcg | gagagccatg | gggaagtttt | cccttccc | ctacagggct | 240 |
| ctgaatctga | aggtaagagt | gagcctatag | ggggaacctt | ctggctccct | cacaggaact | 300 |
| gactgagcag | gagttggaaa | agccacttgg | attcccattt | cctcaactcc | ccgccaatac | 360 |
| caaggcgtct | gttttttacag | gctctttcgt | ggtgttctgg | gcacattcaa | cttccaatgc | 420 |
| agctgagagg | gtcgggaaca | gttagagaac | aggggtggca | gccgcccggg | aggctgcaag | 480 |
| gcgctcgccc | gcaacgcaca | ggcgcgcgcg | gcgcacccgg | cctccggcct | ccccaggtcg | 540 |
| ggcctggcag | ctgcgggaag | gaggtcagcg | cagccgccac | acttcgcccg | ggcgctggcc | 600 |
| cgaccccgacc | gccggcgact | ctctggcagc | gcccggagac | cgccagcccc | tgggccgccc | 660 |
| gtccgcagag | cccccctccgc | cccgggaccc | tcgcgcgcag | ctcaagttgg | gagccccgct | 720 |

```
ccgcaggcga gcgcgcgccc accacccaca cccactgcca ctcatgcaca ccgcgggtcc      780
ggagatgccc ccgagcgttt taaaatccag aaacatcaca tggtagccac atccggcggc      840
tgttacctgc tcgcagcacc cagaccctcg ccctggtttc ccgggagccc gcaaacccgg      900
cacgcgggct gcgcgccctc ccgcaagcca ccgctcagcg ccagcgcgcc ggcaagccgc      960
ctaccttagg ggtctgcact tcaggtcccg tcggcacctc caacttcctc ttggttaccc     1020
agaagaacag cagcaccgtg atccagagca ccccgaagac tggcagaacc agccgacgag     1080
tcaggcgccg catggtcccc tttgccgctt cctctccgcg gcgctacgtc ccgggggcac     1140
cccccggcgg tcagggttgg cggggcagga gtcctggcga gcgcctcgct ctggggagct     1200
ctagacccag gatccggttg gaggggcggc aggatcctgc aaggcgccct tcccgcttcg     1260
aagagaagcg agcctgggtg gggggtgcag ggcgacccga aacgtggcag ggaaggacc     1319
```

<210> SEQ ID NO 7
<211> LENGTH: 723
<212> TYPE: DNA
<213> ORGANISM: Homo sapiens

<400> SEQUENCE: 7

```
gcgtctgaga catttctcac tctggcactc taagcaatgc aataacccaa ctcctcatgg       60
cccaaagccc cagactctgg ttttcagaca aacaacaac aacaacaaca acaacaaaaa      120
cccaccgtta tgacagtcct gccgctgagc taaccagaac ctggctgcac tactttccat      180
tcactgccca acccttcct gccttgcaga cttggaaagc aaaaatgaca ttttggaaaa      240
cctggttcac cttcccagcc agaagtgcag aactgcatgc ctcaacctcc aacttcggac      300
aggcctcctg acagcgaaga tcagaggctc agggcacccc ggggcccctc aggcagggaa      360
cgtgcattcc caccccgtac tccctcgca ccgaagctgc acatgctcct tcttccctgc      420
cttcctctgc atgctccttg gacccaagct gaacccttc ttcctctctc catctacaat      480
tacaaacgca aattctcagc caaggatgaa agaagtaaat tgtaggctcg cacaatatca      540
ataattccgc gggtcacagc atcccgcaca aggacgcctt cttattgcat aattaacgcg      600
aggaaggctc ttcccgctac tcccgcgaac tagggaggtc ttcaagtcgc caaaacacac      660
cgggatgtgg ctcgccagga caaaacccgc gggttccccg gttttccgt gcgccccgcg      720 gcg                                                                   723
```

<210> SEQ ID NO 8
<211> LENGTH: 325
<212> TYPE: DNA
<213> ORGANISM: Homo sapiens

<400> SEQUENCE: 8

```
gtttgcttgt tctcactctg cagccgcagc cagtggcgcc gctaccaagg tccccgcctc       60
gccatccggg tcctgcctga gcatccttat tggtgctcag ggctaggcgt gcattgctgc      120 tagggggcgcg gaaaggttta tcgtgggtgg atgctgcccg gggcttgagt ggttttttaga      180 ggtcttgagt ggctcactct ccaatcagcg cttttctagag acagcgtggt cagcgtactt      240
gcttactttc aggattgcga gacgtcttta acccttgctg atcggctgac gctgcagctt      300
cctgtggctt cctgctcatt tcccg                                            325
```

<210> SEQ ID NO 9
<211> LENGTH: 1395
<212> TYPE: DNA

<213> ORGANISM: Homo sapiens

<400> SEQUENCE: 9

| | | |
|---|---|---|
| cggatcttct cggacgcctc tggcttgggg ctgcgggaag cgtgggctgc ccggggcgca | 60 |
| gtgtgcggag accctctagg cgggcgggga cgccccacgc ggcgacctga gcaccgacct | 120 |
| catgcaacgg gaccgaacct tgggacccgg gcagcaggag ctctgttccc ttcacctcca | 180 |
| gcttggtttg agggatactg atgaaggaaa ccggggtttt cccgtcctgc gcggagagcc | 240 |
| tcggcgccca aaatcgaaag gccgggagtt gttctgcagg cttttgcaaac aggttgactg | 300 |
| agggtttcct ttcccgtagc gctgactgcg aaatctgtgc ataggcgttc agtgccagtg | 360 |
| gaggatagct gagcaagcca agaagttttg cagcttcctc tgatttatcg gtggagtgtc | 420 |
| aggaggctgt agcaacagtt tacatttccc ctgtccctgc gagtggctag ggcaagctg | 480 |
| ggctcggacg tgatatcctg ctgtttgtgg agaggaaact gggaacgggg cttgagagtg | 540 |
| aggggcaggg aggggggggac aggcatattt tctactgcat cgcccatctg cacctgtccc | 600 |
| ctttgctgtc ttacatgtcc catagtatta aagttatttg aataagcaaa tgaacccgc | 660 |
| tctttggtga ccgcgtattt tgaagttgga aactttgca ggggacgagg gaatgttgag | 720 |
| gagggggcgt taagctctct cactctatcc cttttttaaag acaagaaaaa aactttcgtt | 780 |
| ggcgaaggtg gtacttttt cttttggaat gtctgagctc agagcttccc ataagaggta | 840 |
| ttgcgattca atactgtaca gtcaaggtga agttccacta agattatggg accgtggcat | 900 |
| attctacgga agataccagg gttccttggc gctctgttca ttgccagggt ggtctgctga | 960 |
| aagccggcag tttcccaccc tcagactcct tggagctctt taaatgacgg tctgcctggt | 1020 |
| gtttctcagc ggtacacctg tgagtgctct gttatcatgg aaatggtaac ccatgcaggt | 1080 |
| agggctcatg ccaaccagac tgtggtgggg tgtgtgtgtg tttgtgtgtg tgtgtataca | 1140 |
| tgcgcgtgcg tgtgaacgtg tgtgtttgga gtttccttt gacaggtaat ctttggatgt | 1200 |
| caaagggata cagttatttg tctggcagtg tcagggcaat ctgagtttct cgagtaacta | 1260 |
| ggaggaggta atctccaggg aagccttttt gtgctcttga ctgtctactc agcagttggt | 1320 |
| gaaggcttcc tgaaagccac ttagggtgtt actaaccaaa tcaagaagtc ttactcagtg | 1380 |
| gtgagtgaaa gctcg | 1395 |

<210> SEQ ID NO 10
<211> LENGTH: 197
<212> TYPE: DNA
<213> ORGANISM: Homo sapiens

<400> SEQUENCE: 10

| | | |
|---|---|---|
| gcgactgctc tgcggttccc caaagctcct cctacccaga cggcgacagt ttggatgctg | 60 |
| aggttggaaa gcaggacagg ggacactcct gagtgcagct cggagcgggg aaagccgaat | 120 |
| tccgggggct gaagaggccg cgcaggggac gagcgcctgc gatgcggagc gtggacttct | 180 |
| tgggccgtac ccctgcg | 197 |

<210> SEQ ID NO 11
<211> LENGTH: 1848
<212> TYPE: DNA
<213> ORGANISM: Homo sapiens

<400> SEQUENCE: 11

| | | |
|---|---|---|
| ccgatatata aactccacac atggtatctt tttagaaatg atttgcatac atttaagttg | 60 |
| gtgtggacac accttcaaag agaggcagag gtgtatgaat tcctaatgag aatgagagta | 120 |

```
tagtcaccaa tcagaaccct tcctcacatt ctccaaatcg cttgtatttc accatttctc      180
tccacgcagc agaattttg  acatgggaca tttcttgctc tcattctttc tttccttcca      240
atttactgta aggcattaag tgaaacttct tcagctatgg tgtgtggcac aaaaacatcg      300
cagcgcagga atgcatggaa tagaagggtc ctttcccttc cagaactctg taagcgtcaa      360
acgccgaccc ttggctccat ctcccgctcc cctgacctct tgtcactgtg ccatttccct      420
cctgtgcttt ctgccacttg gaaaatatc  gtatatcctt tacaagaccg ctactttctc      480
tcctctgttc acatttctcc attaccatcc acatttctc  aaaacattcc gacgggtttt      540
gaagtggggt tttcaacctc cctcgactgt gatagccgaa gtcccttcaa gaaagaaaaa      600
tgatgttgga aatactagta acaaataaag tatcacggaa atccccaccc aagcgatacg      660
gtttccttga cgcgcccta  accaaggcgt taagtttagc ctgacagcat ccctccctcc      720
tttcggttcc tggcctgatg agccgcctcc acctgcgagc ggtgcaggca ttttgttgt       780 cgactaaccc cctctagcgc cgaactggcg gcatccgagc cgcggctgcc aggccgggag      840
aaggctgggc ttggccgggc tctgcagcgc tccgggctcc gtccctgccc tgggcgcccg      900
cctccgccgc ggggcgaggt ggtggagacc cggacgccg  agggtcctcc cagtcagcac      960
gccgcgttgc cccggccctg gggcggggc  cgcggagtcc caccaagtgg cccgcgcctc     1020
ggcttccggg agacccgagc gcggggaggg agtgggtgcc gcgaggggc  ggctcgcgcg     1080 gggagagccg tcagcccacg gcgcccctgc gctgctgtgg atgtggccac gcgccactcg     1140
gcccttggac tgctaggaga gcgcggcccg acgccaccac gccgtggacg ctcgggggacc    1200 cctgaatccc agcgtcaagg ctgcgacgat gctcgtgacc tccaccgcga agtcacctcc     1260
gcaaggcgac gcaaggacct cggcgatccc gggcgccgta cacccgccac tttccagcct     1320
catgtaaccc cccctctgct gcttcctccc ggcgctttgc ttttctacaa ctggaagccg     1380
cgaaggcggc tactgcgctg agccgctcgc tctgctggtc aagtttgggc gaccccgcgcg    1440 gaggagggtc gggctgactg ccgccgctga gctgtccccg gacgggagcg cctgtccacg     1500
gcactcaccc cctccagcgg tggaaatgtg gagaagtaag tgggaggcgg tgtcgggaac     1560
tgactcctct taaaacggtc ggcgccgctg ctctgaaatg ggcggctaag tgcttgtggg     1620
actaagggcg gcctcagaga tgcccggaaa atcgctgcca cggccagagt gcggcgcaga     1680
cgcggcagag ttggaggtgt ccgcggtgca ggctgctgcc cacgccgctc aggccaggtg     1740
ctgagggctc agcccgcgcc tcggccgaac cactctcagc ccgttgagc  cacctcgtcc     1800 gcccggcttt catcgcaccg gccagaggaa agttcccgcg ccccccac                  1848

<210> SEQ ID NO 12
<211> LENGTH: 680
<212> TYPE: DNA
<213> ORGANISM: Homo sapiens

<400> SEQUENCE: 12
gcgcagccga gtaccgcccg aaggctgtcc ccatcagtgc gtgtctgctg ccgggcagcg       60
gcagcatcca acctgcttta ttcctcctgc ctgcagcgcc acagcgagcg agcgagcgag      120
gagggggaga gagggagtct gtctgcaaag tgctgctccc tggtgctcag aggcggctgc      180
tccagctcca actctcattc atttcgccgg ttaacatgag agatcatggc cgccttcggg      240
cttctcagct atgagcagag accgctgaag cgccccggc  tcgggccgcc cgacgtctac      300
ccacaggacc ccaagcagaa ggaggtaagg gcgccggcgg cctccccggc aaccggggcc      360
```

-continued

```
gcgctctgca gcactgaccc ggggccaagt tggcccagcg ggcatcgccg gcgctgcggt      420
ggaagaggtc ggggaggggg attagaggcg ggggccaggc tggggtgct gggcgacccc       480 ccggcggcgg agaccgagcg gctgtcagtc cccgcgctcc actgggcgc tcgctttcca       540 tgtgccggtc gctttcccgt tgccgggcct tgcacggcgc cgccgggcgc ttctcgggct      600
tcttccctgc cgaaaccttg ctcgctctca cccgtttctg cctgctttat ttttcttctt     660
gccgcttcgg taaatcgtcg                                                  680
```

<210> SEQ ID NO 13
<211> LENGTH: 762
<212> TYPE: DNA
<213> ORGANISM: Homo sapiens

<400> SEQUENCE: 13

```
cggccggtct tttgccccgg gctcaatggc tggattgtgg aaactgcacc cgccttcagg      60
ttgttgagca actgatggga cgatctcagg gaccggcgtt tacgaaaggt aatttattct     120
tcgcactctt cataataggg gtcgcccctgg ccgggcgcag gcggcggcat ccaccgggcg    180
ggcaacaaga gggggtgcgg ggtgcatgca cactcgccct tccactcaca cactcgccct    240
cacacacaca cacactcatc cggtcgtggt gcggggcggg aagggaacct cctggctggt    300
gggcgctcgg gtctggcgcg ggttggagtt ttttccagcc attgggcgat ttgaccggcc    360
gaggggagtg aggggataa gagactgggc gcattcgcag ctgcacacgc tggggaatag     420
gaacagttcc cacccgtta atttttccctc tcctctcacc ccagtggcat ccctggtgg     480 gggcagaaag cggacaggag ggcgactttt ctccgtcagg ctggaactgg tgccgctgga    540
ggcgggagcg ggctggagga cggacagggt ctgggtgaga agctgggctc tgggaagatg    600
gaaaatgcag ggtgccgagc ccggcgcgat tctcccctaa cgcttgcctg gagcatccct    660 ggccccttt gcccaggtcg cgcccctgag tcttggagtc gcgctgcctc cccgcgccct    720
gcctgttgtg tctccttcac ggcagtttgg tttagacctg cg                       762
```

<210> SEQ ID NO 14
<211> LENGTH: 660
<212> TYPE: DNA
<213> ORGANISM: Homo sapiens

<400> SEQUENCE: 14

```
cgagcgtcct gctccttcgc ccggcttcgc cttctctcat aagggtggcc ggggggcccac     60 gaacttgcag ggtggcggcc ctgcgcccctc cagcccggc ggggacgggc acgattgctc    120
gtagtctggg gtgctgcggt gcggggtgct gcccagggtg tccggccgc cgccactgag     180 cgctggggcg cgcgaatcca gctgcagccg ctgctgccct gcgccggttc cctcaggctg    240
cgggcgctgc gctcctgatc tcgccggtgg ctgcgcctgg gcacgcactt gccgcgggcg    300
gggcgggctt gggacagtg ggagcgagca ggcagagcgg agtaagcggt ccgtgtgtgt    360
gtgtctgtat gtttgtgtgt gtgtgtgtgt gtgtgtataa tgtgtgcgtg caaggaggag    420
cttagtgtga tgtcaaagcc cctgggattc tcttgccatg ttcccttggt ctctctttat   480
gggcagcagc gaccctgtc gggtctcaaa ttcaacctca atcggcgact taatctaggt    540
ggaggtaaag aggaagcgac ccctcgacct ttgagtacgg gaataacttc ctgagcgtta   600
catttagcaa atgtatgtgc ctctcgtaaa cgaccctccc gtttgctgga agtactgccg    660
```

<210> SEQ ID NO 15
<211> LENGTH: 1258

```
<212> TYPE: DNA
<213> ORGANISM: Homo sapiens

<400> SEQUENCE: 15
cgccgccgcg tttccctaaa cccctctcct cagaaaacgg agcccactcc ccacccacat    60
ccggcggccg cggcccccgc ctcggagcag cgcgcgcgtg tgcccgggga tgtgggtgcg   120
cggaacttac gtctcggaat ttgttccact gtccgacttc cttgtcatac tgagagattg   180
tggtgagcca ttgtttatca tccagaaaat taccgccgtc cgaccgcccc ccggctgcag   240
ccaccgccgc ggcagctgcg agagactgac tgcaccaagc ggctgcacac acacacagta   300
cggctgacac cttgagcatc tgggagagga cacaacgg ggggtgggggg ggcatgtcag    360
tgtcaaataa ggggtacgaa gccaggagcg accctggaaa acatgcatta gcaacgacga   420
gggtagaggg aggaggagac aagcagaggc aagcgtgtcc cctccccgca ggctttaccc   480
ccaaaagccg ggcactcaca cacacgcaga cccagaggag gagaggtggg tataaggaag   540
caagccccag ccgcagcagc ccgagcgggc acaaaaccgc ttcctggcac atcaccttgt   600
tgtgagccag cactgtgctc gcagctcctg ctggaaatgc agccctgctc tgccaactcg   660
ctgctttctg gagctgctgc acgcgccgcc gtctcgagcc gtccactcag ctccctgcgc   720
ccggcgcgct ccccccatct ccaccctccc ttcgcgcgcg gatctccagc ttactcccct   780
ccgttccccc tccctcccccg acctccgtttt ttttcctctt ccacctcctc ctatcccacc   840
ttcctctcgc tggatcccag ctacagttgg ctccggatag gacgcttggc tggagccaga   900
ggacgaggta gctcctagcc taggaatcct tatctgcttt gtaacctctc ccctccagaa   960
gaggttctca tgttcgcgag acagcctgct cattctctgc tcctggattt aacacaaagt  1020
gtactatctc tcgcagttgc ctctgctcca caatttccag ggttgtcagg cagacgtgag  1080
aaacaagatc tgaggaaaac tttatgcatt aataaataag aatacctgga cttcctaccc  1140
tgtaaagctc ctgaactcag ctcctcccta agaaaggcc atctatccac aaggtcttgg   1200
gagatctgtt taatttcaga aaatttaaag tttgctgtga gcttctggat tactaccg    1258

<210> SEQ ID NO 16
<211> LENGTH: 640
<212> TYPE: DNA
<213> ORGANISM: Homo sapiens

<400> SEQUENCE: 16
gcgggctggg gttggaagag taactcgggc tgcgggctga acgcagtcgg caaccgcgga    60
agagcagcat ctcccctgcg cctgtggata cgccagtcca gggatggcga gtgctttctc   120
ctccccagct tctccctcgc tcttcgaggt gactcgtggg accctgcgtc ctagtgctgg   180
gtgtgaatcg gctatttcac acccagttct tcctcccctc cgccacacgc agtcacattc   240
ctggagctat tccaagctgc ctccgctaag caccgaataa gcggaccctg cctggaaact   300
tgagcgaagc tgaactgcgc cgaactccac cgtccagtga cccgagccag tgtggacgcc   360
cttttaatca cgctgtttac ccaggtggaa tttaggaaga atcagccttc agcctcaacc   420
tcaaaccttt tgtgcaaatg ggcacttcgt ttggaaaggg actagaaatt gtccccagtc   480
tggccctgca ccagcaccctt cctctgctca aacctgtaca aagtggaagt tttaggaagt   540
ttccatttct cgtgccccgt ttcaacttgc tccccaaaga gaacatgaaa acgtgggaac   600
tcgggaggac agagatctcc ctgtaatcgc ctcgctattc                         640

<210> SEQ ID NO 17
```

```
<211> LENGTH: 572
<212> TYPE: DNA
<213> ORGANISM: Homo sapiens

<400> SEQUENCE: 17
cgggcctcaa atgggaactt tggccagaaa atgtggtggg aggtgccctg cacccgcttt      60
gggctcgcgt ggggaagggg cactcagggt gtgtccgtcc tacgggcttt ctcgttcctc     120
cagcagaact tctagcggag tttgccaact acttccacta tggctaccac gagtgcatga     180
agaacctggt gcattacctc accacggtgg agcggatgga gaccaaggac acgaagtacg     240
cgcgcatcct cgccttcttg cagtccaagg cccgcctggg cgcggagccc gcctttccgc     300
cgctgggttc gctcccggag ccggatttct cctatcagct gcaccctgcg gggcccgaat     360
tcgctggtca cagcccggggc gaggccgctg tgttcccgca gggctctggt gccgggcctt     420 tccctggcc gcctggcgcg gcccgcagcc ccgcgctgcc ctacctgccc agcgcgccag     480
tgccgctcgc tagcccagcg cagcagcaca gccccttcct gacaccggtg cagggcctgg     540
accggcatta cctcaacctg atcggccacg cg                                    572

<210> SEQ ID NO 18
<211> LENGTH: 248
<212> TYPE: DNA
<213> ORGANISM: Homo sapiens

<400> SEQUENCE: 18
gcgaggggtc cggcatcact cgcgcgctcc ggaaacccgc gtgagccgct gttcctgccg      60
cgctcccatc tgagtgacag gcttgtttca gagctccgca gacctctaag cctggccctc     120
accctgcgtg gagagaacgc ccgggcttgg cggagagacg agaaaaccga ggctcccgga     180
ggcagacaag gactctgcca aaaccggacg ccgcggcggt ggcagaattc gaccctggga     240
tttgccgc                                                              248

<210> SEQ ID NO 19
<211> LENGTH: 282
<212> TYPE: DNA
<213> ORGANISM: Homo sapiens

<400> SEQUENCE: 19
ccgtgacgac ttataaaagc ccaggggcaa gcggtccgga taacggctag cctgaggagc      60
tgctgcgaca gtccactacc tttttcgaga gtgactcccg ttgtcccaag gcttcccaga     120
gcgaacctgt gcggctgcag gcaccggcgc gtcgagtttc cggcgtccgg aaggaccgag     180
ctcttctcgc ggatccagtg ttccgtttcc agccccccaat ctcagagcgg agccgacaga    240
gagcagggaa ccggcatggc caaagccgcg gcgatcggca tc                        282

<210> SEQ ID NO 20
<211> LENGTH: 1031
<212> TYPE: DNA
<213> ORGANISM: Homo sapiens

<400> SEQUENCE: 20
gcgccgctgc tgggacgcgg cgcggacccg catcattgcg cgcagcagcc gctgcagcag      60
ccgccgggga ccgcggagcc gggacgcccc cgctcggccc gcgccccgct ccccgcccca     120 ccccgcccg ccgggcccag caacgcaggg tgcctaggag ccgcgggctg cgcagggagg     180
cgggcagcgg ccctcgcgcg cttctgccgc ccccggagcc ggcgcgcggc gagcgcaggg     240
cgagcgcgcg tcgggcggcg gccgcgctgg ggggcgtgag gcgagcggcg cggagagcgg     300
```

```
caggggcgaa acttcgcggg ccagatgccc gagggcgcgg cggcgctgcc aggctgccgc      360
tgctgcccct gcgggccccg agcgcgcctc cgcaggcggc actgcccgcg gcgcggcgtg      420
tgcaccgagc gagtgaaggt atgtgtggcg ggcgcggctg gagctgccgc cgccgccgcc      480
gccgcgccag caggtcctaa tgcctgtcac ttcccaggac gctggcagca gcagcagccc      540
ggagcccccg agccctcggc aggtttgcgt gtccttcccc gcgatctgat tggataaagt      600
gggggctcga cggtggccga cgtgggacag tctggctgtg caggggtct cggaaaccat       660 gggttattgc agtggcaggt gcacgcttat ctttatctgt ggcatgcaac tggtaagtga      720
cacttgggtc cccttattct gtaatgtgtc tttgagatag tgggcagggg agtgcagcaa      780
agggtctgcc attgactaga atggacgaaa aagataaaag agaaggtgac agatatattg      840
cctatattga agatgatttc agggagacgc actctggggt acaggagagg tgagcctttc      900
cgttcccacc tatttctgtc cctttttaaga cagtttggca ggtgcgggtt aaacttgtct     960
ttaatttctt taggaaaagc aagatgtagc tcttgttctt tatgctttgc attcctattc     1020
atgtaacaac g                                                         1031

<210> SEQ ID NO 21
<211> LENGTH: 795
<212> TYPE: DNA
<213> ORGANISM: Homo sapiens

<400> SEQUENCE: 21
gcgacccaaa ccggggatgc agggagctcg cttggcccct ttgaaggccg actccgcaat       60
aagcagtttt tcctttaaat aaccgtagtg gatttgagag aattttccat ggctgaaaag      120
agaaacagga gctgtaggca acatccctaa atttataata atgcatgtaa acatgctaca      180
taccacatat atgtatatgt gcataaatat ggatgtggtt gggcacatac ctatctagac      240
accattgact tgcctggtca agaataaga cttagacatt tcgtgcctgg gaaatggtgc       300
agtttatctt taaggagact agaaaaataa gagatgaggc tcacgttgca cggatgacat      360
cactagcttt tggctgcgcg ctcggtgttc tcgtctgtgg gttttagcca aggctgcagc      420
tacccgcgcc ggacgagaga gcgcggcagc agcttcctcc ggcgcccgca cccgggcaat     480
gcgatttccc cagtcccctg ggcgcagcct gggctctcgc gcctcccggg caccagccga     540
gcctgcgagg cctcggagcc gccgcggcta gaggaggagg cgacgagggg aagccgagtg     600
acccagcctc cctcccccac cctctcccca ttcatctcgg cgaccaccgc gcgccgggag    660
ccggatcgtg ggacgccgag gccaggacgg gattctctgc acgctgtcga gtgagccggc    720
atctcggcgc ccgggtgggc tgcgaagaaa atggtgcaat ctgagagcga ctgagcccag   780
ctgggcagag cagac                                                       795

<210> SEQ ID NO 22
<211> LENGTH: 160
<212> TYPE: DNA
<213> ORGANISM: Homo sapiens

<400> SEQUENCE: 22
ccggtgctcc cagaccccct tccttctcaa acacgcatca gacactttgc accaagaaaa       60
aacaaagggc atccctcctg gggccacctc tgcccctgt ccaggtacgc gctgtctggc      120
gcgccctgcg tgggggccgc aggttcagac acccgggcgc                            160

<210> SEQ ID NO 23
```

```
<211> LENGTH: 554
<212> TYPE: DNA
<213> ORGANISM: Homo sapiens

<400> SEQUENCE: 23
acgcttctca tttattttat atttatacaa acagcgcttc cctgaaaaat cagggtatcg      60
ttcaagattt tatctttatt cacagaagtt ttaaaatttt taacttttat atgcacaaga    120
cagttctgat ttgttgaatt aagtgaccgc gggtgtgcta atgcttctaa aaaacagcat    180
tagccttctc ccatcaaaag tccggaagct gcccttcagt cgtcaaagtg tttgccttaa    240
tttgcaatcg ttatgacttg agccaaatgc ttatacctca tttgtgtcgt atatgtgaag    300
atacaattgc aaatcgttca cgaccttgag tcaagacctt gagtttcctg aggtcaggag    360
accgttaggg aatgtgagtg tcccagacgg gcgctgagcc cagctcggag acccaccccg    420
cccgtagcag cggcgcgggc cccagagagc cccgcactcg gccgcgcctc agttacgctg    480
actcggctgt gcccgcagtg tcgcgctgtc gcgtagccag gtgtcgccgg gctggcgcgg    540
ttatttatga ctgc                                                       554

<210> SEQ ID NO 24
<211> LENGTH: 1732
<212> TYPE: DNA
<213> ORGANISM: Homo sapiens

<400> SEQUENCE: 24
acacgacttc tctgcctgtg gatgtctcat gaccctctag agcagcgact ttttcctccc      60
tcattccttc cactcccctc gggcatctaa gtagcaggaa cctgactgtc caaagttgat    120
ttgggagcag ccggctgccc ttctaaaatg atctaggaaa ggtgccagta acataagccg    180
ccgcctgctg aaactggcgc ttcctcagcc actcgctgcg gccagcgtga aggggaggg     240 gaaaggggca ttcctggcac ggtcaggtgt ctacggacag caatcttagt taattctcaa    300
aaccccggaa gatccagaaa tggggtgctg acagggacct aacctgtcca ccaccccctcg    360 gtcggtggga ctgaaaccca tgtctttgag ctgctttacc agtttatttc caaaaagtcc    420
tcctacacct gggaagggac atagaaagct gatcccattg ccagccggat ttctttactt    480
aactctcaac cgtggtaaat ctaattcgct tacgacctct ttccgagagc tgggaatctg    540
cagagatgct ctgttttctg ctgtactaat ctcaggcttc ccaaagcgag tgcctcgccc    600
agctcctagg ggaatccacg gagccccagg cgcagggcaa aggatggggc gggatgggga    660
catcgtacct gcgctccggg agcgctgggg agtccggccg gccccggccg cggggaggaa    720
aagcaacggc ttgggctcct tatccgtgac gcgcgctccc ctgcgccccc ggggcctccc    780
gtgggctccg tgcggggaca aagccagcgc cagcaggaag agtgcgggca aaggggcgcc    840
gggcttaagg ggccgcatgt tcgcaagccg ggaggagaga gcgggagact ccgggaggat    900
cccgacgcag gtccggaggg tgcgcggccc aagagaaggc cagcgggacc acagcgcggc    960
tacgcggccg gccgcagtct tcaccgcgcg cctgcccttg tctacgtccc ggggtcggc    1020 tggagctgca ctgggactcg gtcctcagtg tgccgaagcc taagcgctgc ggggcgcggg    1080
gcgggaacgg gaggcggtgc ctgggccac ggggtcgtcc cccaggatga gggcgtgtcc    1140
cagcgcgcgg gaccctcgga agtccgcgct gggccgggcg ggcaccagcc tcggactcag    1200
cgggtctcag ggctccctgc gcaacgcctg cctcggatcc ggaccccggg ctcgctctct    1260
ggtcgccgtc cccgggagga cccagtaggg taactgccgc gtcgcccccgg cggttctccc    1320 tgggctctgt ctcccgccgc ctccacccccc cgagcctcgg ggtccgtcac ggcttcccct    1380
```

```
ggctggcggg gtcagtagaa cccgcggcgc ctaggtccgg acggaaaaaa gcagggccgg    1440
ggtgcggcct ggatgagcgg agatctccgc gccttgggct caaaggtgcg gggtgcgctc    1500
tgctgccgag cccctgctcg ctcaggaaca ctggccacgc cgtcacgcca gccgcccctg    1560
ccccaggtct ggaggcccga cctgctctcc taggcgcagc accgcgttct cttccgcgtg    1620
ggggagcggc gggcggaaga ggtctggggc tgggcaccgg ggacacgcgc ccagctcccc    1680
tggcctccct gggggagtg gccggtttca gtgcttcccc aggtgaaatc gc              1732
```

```
<210> SEQ ID NO 25
<211> LENGTH: 527
<212> TYPE: DNA
<213> ORGANISM: Homo sapiens

<400> SEQUENCE: 25
gcggcggcag cagcagcagc agcagcagca gcagcaagaa atccaaagag caaaaggcgc      60
tgcggcttaa catcaatgcc cgagagcgcc ggcggatgca cgacctgaac gacgcgctgg    120
acgagctgcg cgcggtgatc ccctacgcgc acagcccctc ggtgcgaaag ctctccaaga    180
tcgccacgct gctgctcgcc aagaactaca tcctcatgca ggcgcaggcc ctggaggaga    240
tgcggcgcct agtcgcctac ctcaaccagg gccaggccat ctcggctgcc tccctgccca    300
gctcggcggc tgcagcggca gcagctgctg ccctgcaccc ggcgtcggc gcctacgagc    360 aggcagccgg ctaccgcgttc agcgccggac tgccccggc tgcctcctgc ccggagaagt    420
gcgccctgtt taacagcgtc tcctccagcc tctgcaaaca gtgcacggag aagccttaaa    480 cacaccccg aaaacacaa gaccgaccca aaatctagag gaaagcg                    527
```

```
<210> SEQ ID NO 26
<211> LENGTH: 211
<212> TYPE: DNA
<213> ORGANISM: Homo sapiens

<400> SEQUENCE: 26
cgccgctagc ccccgtcata tcttctccgc tttcgcttct ccactctagc cgggggtggg     60
gtgggtgggg ttggggtctc cgcggggtt tccggccccg cggcccgctc ccgggtgtgc    120
ctggaggagt tctcccctctg tggcgcgcgg gagccctgtg atgcgtcagc cggcgggacg    180
gatgagttgc ttctccggga aaccgtcctc g                                   211
```

```
<210> SEQ ID NO 27
<211> LENGTH: 315
<212> TYPE: DNA
<213> ORGANISM: Homo sapiens

<400> SEQUENCE: 27
cggccggctg ctgcttacgc gggtaacctg tcggaaagcc ttgtttgttt ttctggaaaa     60
gtcgctgcaa tggacacagc gttgcgcggt ttccctgcgc gcctgggcg cttttttgtct    120 tcgccctccg tggatggagg ctgagcgcct cagccatttt gagagctctg gaaatttat    180 tagcatttta aaatttgcat tctcgaccga agattaaagt gcaaattact ttgaagatgt    240
tttaaagcac gcttaagaat tttaaagaat atgcgcaggt ggaaaaaagc gcgccagggt    300
ttgagatttg gtccg                                                     315
```

```
<210> SEQ ID NO 28
<211> LENGTH: 142
<212> TYPE: DNA
```

<213> ORGANISM: Homo sapiens

<400> SEQUENCE: 28

| cgatggccca gctcctcagc caggtccacg ggcagacggc cccaggcatc gcgcacgtcc | 60 |
| agccgcgccc cggccggtg cagcaccacc agcgtgtcca ggaagccctc ccgggcagcg | 120 |
| tcgtgcacgg gtcgggtgag ag | 142 |

<210> SEQ ID NO 29
<211> LENGTH: 217
<212> TYPE: DNA
<213> ORGANISM: Homo sapiens

<400> SEQUENCE: 29

| cgcgccggcg ggggcagcgc cggccgccga ttagttttat ctcggaacgt caattgactt | 60 |
| agactgattg gcttcctgcc gccaatgtca attaaattgc aaatgcttgg cggaggccgg | 120 |
| cgcgagcggg cggcctcctt cccggggcg ccgcgctcag ccttctcttt gcgccacgtt | 180 |
| cggccgcagc tgaattcatt tctccttcca cgtcgcg | 217 |

<210> SEQ ID NO 30
<211> LENGTH: 62
<212> TYPE: DNA
<213> ORGANISM: Homo sapiens

<400> SEQUENCE: 30

| ccggtggtgg ggtcgtagtg gtttccgagg ttggtgacca cgtcgtcgaa cttgagcacc | 60 |
| tc | 62 |

<210> SEQ ID NO 31
<211> LENGTH: 306
<212> TYPE: DNA
<213> ORGANISM: Homo sapiens

<400> SEQUENCE: 31

| cgggtccgag accctcgtag tgtggggaat ttcctgggag gaagatacta cgcggggccg | 60 |
| ggagcagaat ttgctccagg cactgggcca gtccatgagg gctccaggat ccaggggccc | 120 |
| cactcccttc tcgccgggct ccgggccaag gaagcgcggc cggagtcccg ggaagcccct | 180 |
| cggcagccag ccaagggccc tgcgaggatg tggatggcgc ggatggcgcg gcctccacct | 240 |
| gcgggcagtg gagagagcgg cgagaggaag aatattcccc gcgagccggg ataaggggcc | 300 |
| ccttcg | 306 |

<210> SEQ ID NO 32
<211> LENGTH: 718
<212> TYPE: DNA
<213> ORGANISM: Homo sapiens

<400> SEQUENCE: 32

| acgtatctaa acaccattac caggctccac cagcccctct gctcctcagc ttagaggagt | 60 |
| tttaaaacc tgttgagaat tatcgcagat acgtttggcc attatccagt cgtttcgatt | 120 |
| gtgcctttcc taaatgtccg cggttggcag aacgtgggag gaagaggacc cgcctaactc | 180 |
| ggggtaggtg gggacgcgct gctcactgtg gtgaggttga cacttgggcc ctgggtttca | 240 |
| cttgcaggtg ctgggcggcg gagagccccg agaaggagga ggagagagag ccagcagcca | 300 |
| accccctacga cttcaggagg ctcctgcgca aaacctccca gcgccggcgc ctcgtccagc | 360 |
| agtcctaacc gttcaacgag gcagtcaccg ccgtcggaag gcgctggagc ctgcggggca | 420 |

| | |
|---|---|
| gcaggggcca agcaggcact ctggggctgg caccagcagg cactgaagct gcggccctga | 480 |
| tctccgcaga ggctgcctgc tgcgctcggc cctcaagtgc ccgggccggc cttcgtgctc | 540 |
| cgaaacaaga gacctgggag ccctcgggaa acctcccccg acgctctctc tcggaactcc | 600 |
| cgcaccctcc tttctcacca gcccgccagt tgtggcaacc ctgtccttgt tcccctaatc | 660 |
| tatcactttg ttcttttttt ttgtgactcc tgtggactcc actgcgcctg ggatctcg | 718 |

<210> SEQ ID NO 33
<211> LENGTH: 314
<212> TYPE: DNA
<213> ORGANISM: Homo sapiens

<400> SEQUENCE: 33

| | |
|---|---|
| cgcggagaaa cctggcgggg ccccggactc cccggcttgg aaaagcgat gactgccctg | 60 |
| aactgctggg gcgttcgaaa tttccagggt cccgaccctc cgtgggtac gcgcgacttc | 120 |
| ggcgcagatg tcagtccgct gccttccggg ttgagggagc gaggactcca gacgacccca | 180 |
| gggccgctgt ccaggcccag cccgcgttc tccacctcgc cacctcgctc tgcggctcca | 240 |
| gcctggagat ctacggactt cattgcgatc tcttgcgcag tgtagtcgcc ctctatccct | 300 |
| agccccgagt cccg | 314 |

<210> SEQ ID NO 34
<211> LENGTH: 1352
<212> TYPE: DNA
<213> ORGANISM: Homo sapiens

<400> SEQUENCE: 34

| | |
|---|---|
| cgcggggaaa gttggcgcgc gcctgaccgc gcctggaagc cgcgcggtgc cagggccgag | 60 |
| ttgtccccca agtttctgcg gcgatttgtc actccctggg gatctggcgg tctgaatccc | 120 |
| gcggggcctc cggctcaggg attctgagcg ctgggagaga gaagcccgcg cttttcccgg | 180 |
| ggacctgcgc ttgagctggt gcttgtgcgg gttcgtcctg aatggtagcg attcgagttg | 240 |
| ttttctgctt ttcttctccc ccagacagtg agtttgtgga agcctcgccc gcatcctaca | 300 |
| gcccagacga gttaggtaag tctgctcatt ttgtctttta tttcttggtc gcaattctgc | 360 |
| ccgagaactg cgagtttggg gggcgtccat aggaactcag ctagggatgg gctggggtt | 420 |
| ggagggcgga gggaaagggt caggggacac ctgctgcctt cgcggccgga accgccttt | 480 |
| cctcggcgct gtgctttcgg gggtggcagg gcaagtgtcc aatgagccgt gcgtgtgtgt | 540 |
| gtgtgtgcgt gcgtgtgcgt gtgtgtgtgt gtgagtgcgt gtgtgtgcgt gttcgtctgg | 600 |
| ggcagtggtg ctgctccgag gagcctggca cagcaaactt ccagagctgg ggcttctgaa | 660 |
| acctgcgctc atcttgccgg gaggacacag cggcgactgg ttctgacttg ccaagtacct | 720 |
| ggcacgagaa ggacgtcgtg tgggtcgtcc ttaccctgaa tttaatgaag tcaggggctg | 780 |
| aaaacggcgc tgtaatcatt aaactgtaag acctaggagc tgcttccctc cctgatttct | 840 |
| attcctcagt tagcctgtag gtgtctcgag ataggacatt ccatcctcat gcctgtcatg | 900 |
| gtaagtggag atttgcgatg ggtgaaccgg acactcttg tcaagagaca ggctgaagag | 960 |
| agagtgaaga gaaggaaatg cgaatgggca ggatctctct aactcttcct gccacccatt | 1020 |
| ctcactcggt ggcttagtgg ctctcttttt tttttcttct gctttcaagg ttagtttagc | 1080 |
| tgctactggt ctgggctatc aagtctctcc ttactgttct ttcatcacta gcctgaatat | 1140 |
| cttgccttcc taagatgaaa tgaaaggatt tattttatga tatatgttga cagtaaagga | 1200 |

```
ggaggggaac tgtccacaaa cagcggttta aatatgttta tcctcagtaa cacactcagc   1260
tgtggcaccc tgtccctggt cagcttcttg tgctgggaag aatgtcctca tcaagtccca   1320
caggacctga agcaaaattc cacctcaaca ac                                 1352

<210> SEQ ID NO 35
<211> LENGTH: 668
<212> TYPE: DNA
<213> ORGANISM: Homo sapiens

<400> SEQUENCE: 35 cgaggggaa gtggcttgtc agccccggct ccgggaagag tgaacaataa ggctagggca    60
gccgccccag atcgttatat tcctgggtct aataaagtca ggatcgctgc tttgcttccc   120
ccgccccaga agaataacgg tttgcaaaat ggggcaaaat gggcagaatc gcacggccgt   180
tgttgttggt gtgaccgttg ttgcaccccca gtcgacatga cgttagtttt tcatttgcca   240
aattgctggt tagttgcaaa gcctaccctc ggccgcgagc actgaaggat gggagggtcg   300
agcgccgcgt tttgacagga ggaagtgcgg aggggcggag ggcgaggagg gcgtgattgg   360
ggctgcctgg tgtgtgcgcg cgcgtgtgcg cgcgtgtgtc tttacacgcg ccgcgtgccc   420
agtgttgcac ggggcgggag aagaatggca ggtagccgcc cgaaacacct cgccctgtct   480
cctttctttg ggcgaggttc ccgatcctgg caaagtgtga acaataggga gctgggagga   540
agacagtagt gatgctgccg cgggtggcgg gggttgcgcc gccgcccaga gaacctcggc   600
agtgtgcagg gaggtgcatt tcattttggc tatttccatc ccggcctccc tggaaaattc   660
ttctgtgc                                                            668

<210> SEQ ID NO 36
<211> LENGTH: 497
<212> TYPE: DNA
<213> ORGANISM: Homo sapiens

<400> SEQUENCE: 36
cgacgatttt tgaggccacc cttccttgtc ccgcaatccg atcgctagt aaatgccagc    60 agtatctggg ccttgagtct ggcttttgacc cggcagtatc tacaaataag ggttatcctc   120
tttcccccaa cccacgatgt atcgcagtgg gctccggcag gctgcagact ccagacccct   180
ggagcaccgg cagggcaggg ttggacccct cccggggtgg caaccctcca ctggagtgcc   240
cttcctcatc gtcttgggt taagagttgc cgcccggcca gggcaacagc cagggcaaag   300
ggagagagaa gccgcccgg ggcgagaagg agaaaagtta gagggctgaa caggtgacgc   360
tgagcttgtt ggagcgtgtg tgctccacca cgcaagggcg cggagttcgg ccgcctcatc   420
tcccgccatc tgcgcgcccg ggggcacgtc ctctgcgata gcctggaacc cagactacct   480
gcgcctgcct ggtcccg                                                  497

<210> SEQ ID NO 37
<211> LENGTH: 998
<212> TYPE: DNA
<213> ORGANISM: Homo sapiens

<400> SEQUENCE: 37
gcgcctggat tgctcaagag aggtcaggga aacccctcag aactcctgag acccagagat    60
tgagggaggg gttgaggcgg agtctgcaat gggggctgtc cagcagtagc aagcagcggg   120
ccgatcctgg tggaggggttg ggaggctgct gtcatttat gggtcggcag ccagagtgag    180
agtgtccctg ctgccagagg actacggcgg gctgggcgcg gggtccccgc ctctcgctca   240
```

```
ccacacagac cccgcgcctc ctctggcagc cgcggtggtg gcggcggcag agcctcgccc    300
actccaatcc ccaccctctc catccttagt cattaaagaa cagcagcgcc tggcacgttc    360
ttggaggacc ccgggcgcag aggaggaaag ggagcaggcg cagggggact ggaaaggcag    420
catgcgctcg ccaggagcaa cctcggcgcc cagggtctga ggctgcagcc ccagttcgcc    480
attgtgagcc gccgccgggg gagtccgcta gcgcagccgt gccccgagt ccccgtccgc     540 gcagcgatgg ggcacctgcc cacggggata cacggcgccc gcgcctcct gcctctgctc     600 tggctctttg tgctgttcaa ggtaggggag ctcctccacc ccttttccc agcggtccgg     660 gcggcagccg cgctccggcg ccctcgctct gccgttggga gcggcgcgcc cagggcacg    720 atggcccagc cgcgggaagc gcctgccgtg cagcctgggc gcacgctttg ttgtcctcgc    780
gtgtgcgtgt tcctggtggt cttgagaggt aggggcggg gggaagaata agggaagttt     840
gctccctccg gctttcgccc tttgtgctct tttatcgctg ctgaaatcca catcaaaggt    900
gggcttgttg gatcgtgctt tctcaggcaa aatgaggtca ctttcttttc tggtttccac    960
tgcaccccaa cgctgcttaa cctttccgcc ctccctcg                            998
```

<210> SEQ ID NO 38
<211> LENGTH: 735
<212> TYPE: DNA
<213> ORGANISM: Homo sapiens

<400> SEQUENCE: 38

```
cgatctgaca gcccttcaaa ccaatatact ccctatctct ctctctcccc tggttcaatg     60
acaagatctt tggccaactt cttttctactc ggaccttgct attatttcct actaggcacc    120
cacaaaccct tgcttgttaa actgatctcc ttcaagactc aagaaaagcg ccatgcggct    180
ccctcctagg gctctcctgc cctctcctca ccgatgccga gagtggttct gctggagaac    240
cgccgcgcct gcagttcctg caccttttcc cggagctgcg ccagggaatt acggacgaac    300 tggaagggc cgagaagaaa ggtcttggcc accacctcta gctccaagcc ttttcgctct    360
ttcagacttt ggatcctccc cggggaggac ctccaggagc cccttggcag tttcccgccg    420
cctagggccg actttccat ctcctcctct acctccggct cccggggcgag ggaggccccg     480 cgccgcccct tagactggct gcggccggaa gattgcagcc gctttgagct tactccttgt    540
tttctcataa tcaaggagta tggtggagct gggtcaattt caggcacagc ccagccgagt    600
caggcgaggt ccagagagac ctgactcgcc tggcagcctc aacggacttg tccccgcagc    660
cgttgcggac ctcccggtcg tcatggcgac tgtgaaatgt ggggtggggc gcatgcgttg    720
gaagccattc gcgcg                                                     735
```

<210> SEQ ID NO 39
<211> LENGTH: 359
<212> TYPE: DNA
<213> ORGANISM: Homo sapiens

<400> SEQUENCE: 39

```
ccgtaaagaa ccctgagcta ctactcagac gaagcccccc tccccgccaa taataataat     60
ataatggcgc ggaaactgtg ggcggtggtg gtgacatttc ccacgactca gtggcgcccc    120
cgggcggctc ccaccctccc tccggccggc gcgtctacgc agccccaagt gctggctgcg    180
accctcggat cccaagcata tctggcgatg gagcggcggc agcccgaggc acgtgttgtg    240
tgtgctccga ttgcaaaaga aaaaaaaatg catttcaaac tattaacttt tttttaagcg    300
```

| | |
|---|---|
| tgcaatgccg ggagctgggg gtagacaggt gcaagcgggg gtaggcgccc cgcgcgccc | 359 |

<210> SEQ ID NO 40
<211> LENGTH: 2027
<212> TYPE: DNA
<213> ORGANISM: Homo sapiens

<400> SEQUENCE: 40

| | |
|---|---|
| ccgcgattag ttccggcaga gtgatgcagg tagggatgca gatacagccg agtaggtgag | 60 |
| ctctgcccca accgtctacc caattacaag catctttcgc ctacactgag gacacatcta | 120 |
| aacacagaat ttacaattgt gcatgcgaaa ctttacactt acgttagttg cctcaacctt | 180 |
| tccccttttcc cagtatgctg cagttaggaa tgatttgttc caacacatag aaagccatgc | 240 |
| atctggtagc accagtttgg ggagaaatca gaagcagcaa aatgtttcct ccttgtaaaa | 300 |
| tgtgttgctt cgggctggca aattagcaac tccagagaac aaattcacgg atttgtcgtt | 360 |
| agtcattctc tccacatttc gtctctctta cccactgggt ctgggttctt ctgggcattt | 420 |
| agcacacaca acacatagtt gcacttcttc agctcaggga tattttccac agcagcatgc | 480 |
| ataccatttc catccgatgc caatactgct taagtctcta acttcttgta ggaaacgtca | 540 |
| gagttgcggt gatgatgatt ctctgacagc tatccgggtg acagttgccc gaaaaattcc | 600 |
| taatcggtta tctcttgcgt gcttcagaga ctctgaggcg ctcctttccg tctcgcgtgc | 660 |
| tctccctctc tcccttcccc tctgcccctc tctccttctc cctctcctct ctctgaactg | 720 |
| aatttcttga tataactctc aataagccca gagggagggc gtgactgccc aggccccgcc | 780 |
| cccgggctct gattggcctg catcttgcgg cgcgggcggc cgcagcccgg cgcgagggag | 840 |
| ggagcgcgga acaaggcgct gactgtctcc cagcctcccc tcctccgcgc cccctcggca | 900 |
| gcagcgaaaa cccggaaatc tgatcctggc cccaggagag ccgggttcca tgaggtgcac | 960 |
| tgagcatgct ctgcagggtc cggcgtggga gggacgcgct ggcgctcccc aggcccgggc | 1020 |
| ggaagcggcg ctcgcaggcg ctgaaagcga gcgaccctct gagcccgggt ggtccggcgg | 1080 |
| gcaagggcgg cgcgggagac ccgcagggcg cgggcgcgga tccggggaac cagggccacc | 1140 |
| gctgcgggcg gatgggggtc accgaggcgg ctcgtctcca ggcgcacact tcgcacatct | 1200 |
| ctttgctaag tgaaggggcc aaaatgcaca gatgggggag tctacccagg aacagaggcg | 1260 |
| cgagacgtat agccaccccct gggttgggag cacgagccag cagatccccg gagcgcgtta | 1320 |
| aacggacaac atgcccggtg ctgcaaatag aggcttttgc tggcagggac attggaaaga | 1380 |
| agggcggaga gggagtacag cgaaaggtgg ggaccgcaga atttggaatc tctgcggaga | 1440 |
| ccggaaagaa aattaatcgg agcacttcct acatgcagag ccacggaaac tgccttggaa | 1500 |
| agagaaagtg gcagcgtctg ggtccccctcg gtcagcccgg gccagtcggc tgcgcgtgcg | 1560 |
| aagtctcctc tagcggagcg ggaccggccg cggcggtgga tcgtggcggt ccctgcactt | 1620 |
| ctgctccagc cgcgcctgga aacctgagcc cggactcgcg gctgctgcaa aacccgcttc | 1680 |
| cagcccacct cactgcgaac tttgcttccg aggggctgga aggagtccca ggcagctgtt | 1740 |
| tcccaagctg tggaacactt cctttcccct aggcactttc tgctgattcc aactttcttt | 1800 |
| cctgtgattt tcgtcttttc ccgtgcattt catttctccg actccagctc tgtactaaat | 1860 |
| cctcacaagt ttctcgtttt catacgggaa ctggatggaa tgactcccca aaaaatacag | 1920 |
| ctttatttct caaatactga cccccaaagc actatctagt aatatatttg attgatcttt | 1980 |
| caaagtcagt aaaccacaaa ggtttgtgta atggcttgta cttaacg | 2027 |

```
<210> SEQ ID NO 41
<211> LENGTH: 144
<212> TYPE: DNA
<213> ORGANISM: Homo sapiens

<400> SEQUENCE: 41
acgtacaggg cggtgatcca gtatctaaat tctttgggag aaaatgaata gttccccgc      60 ccccgccctc caggaaaaaa aaaaatctga gaatctgaga atgttcagcg cacccgcgaa    120
tttgcatcgg aggtgcgttt cccc                                          144

<210> SEQ ID NO 42
<211> LENGTH: 604
<212> TYPE: DNA
<213> ORGANISM: Homo sapiens

<400> SEQUENCE: 42
gcgcgccctg gcggctccga gggacctggg ctcgggcttg cggtcgcgtc gcctgggctt     60
tccctgggct gggagcgcgc cgggtctccg ccttgcacgc tgtcaccgcg ggagacgtct    120
cggcctcgcc gcgcgcagag gggacgcgcg gagaggctgg tttctgggcg agcggagagc    180
tttgcccatt aagctgccgg aagaagccaa atcaaaaagc caatctccaa gcctccaaac    240
ggaacgtcac cctatcagct gggagacagc gccgcactga ctgacaagcc gcgcatattt    300
atcctcgcgc gcggagggga gactctcaga acgctcctcg accagcagcg aggaagtcga    360
gcccgcatcc cgcatcccgc atcccgcatc cagagccccc gagggacgaa ttcagatcca    420 accccctgccc cgcggccacc caccctagtc gttggagcct ggcgcccgcg cctcccggcc    480
ggcagcacgt caaaacggcg gcgcgtcctg acctggattc cgccgagttg ggagctccag    540
gcagcaggcg ggcgcgcggc accggctttc cccttgtcct caggagacgc tgcctgcaat    600
tccg                                                                604

<210> SEQ ID NO 43
<211> LENGTH: 233
<212> TYPE: DNA
<213> ORGANISM: Homo sapiens

<400> SEQUENCE: 43
cgcgagcggc tgggtgtcgg tgccctgctc tcctctgggc gccaggatgt tcctgcccag     60
tgcgtgtcca gaatagccgc tcagacaccg gctccaggtt cagccaggcg gggcgcgtcc    120
ctgcctccct ccccctttgcc tgccactgcc ctccttctaa cgagggctca gctccgacta    180
ccccaggcct ccggggaccc tctccggatg cgctccccgc tttgcgcttt gcg           233

<210> SEQ ID NO 44
<211> LENGTH: 261
<212> TYPE: DNA
<213> ORGANISM: Homo sapiens

<400> SEQUENCE: 44
acgcaagttc ccctgactg ggggacgccg cccagctcct ggagcctgcg aaggctcttg      60
aagctgagct tcccagggat accagaaggg acactctcgt gcaattccgg ctagggaaag    120
cgagggaagg tggcggctcc gggcaggag cgagcgagtg ctccacgccg cccgcaggat    180
cgagtgagtc acgcggccgc cagacgaggc cggtggcgca cgcacccgag atccgatgta    240
gtgcaccgcc tcggcgccgc g                                             261

<210> SEQ ID NO 45
```

```
<211> LENGTH: 47
<212> TYPE: DNA
<213> ORGANISM: Homo sapiens

<400> SEQUENCE: 45
cgctcgttgc gacccaggct cagctccgcg gtgcgcaggg cctggcg          47

<210> SEQ ID NO 46
<211> LENGTH: 335
<212> TYPE: DNA
<213> ORGANISM: Homo sapiens

<400> SEQUENCE: 46
ggcggccgcc agctgggagc ccaccaccgc tcgatggtac cgaaccgacc cgtgtagccc     60
cataacccca gcccaactcc gaggagctag cgcagaccgc tctccgccct cagctgcggc    120
gaggcaaggg ctggcagcgc tcggacgcct ccgtcttgcc cttcccatgc ctaagcgcgg    180
ggaattacac gttcccggtg tagaacagac gatcggggct attagggctg ggcggtggga    240 gtggggttg ggagcaccat ttttggctgg acgtgtgtcc agactcatcg tctctggtcc     300
ttaggacccc atcttcctct gcatctccag gtgtc                              335

<210> SEQ ID NO 47
<211> LENGTH: 317
<212> TYPE: DNA
<213> ORGANISM: Homo sapiens

<400> SEQUENCE: 47
cggcggctgg ccaggggcac agagacgcac tccacacaga aacccaggct ggcggggtgg     60
gcggccgggg agccagccct gcagatgtta ctaagtgaaa cctgatgtgg tgacatgaga    120
atccacagaa cgtctcacaa acaacctgcc ccgggatgtt ttggattgag ttttgtggtt    180
atgacgtgaa gaaacctcac atgtcaggat aaaaataacc ctggcttcag tacataacgc    240
gagttacagt tcaacagaac cagatgtgaa aacgtcagcc acccagttca ggcccagcag    300
ggtccctgct ccactcc                                                  317

<210> SEQ ID NO 48
<211> LENGTH: 235
<212> TYPE: DNA
<213> ORGANISM: Homo sapiens

<400> SEQUENCE: 48
cgggtctgga agattgcgct acgggagttc tccgtctgag aggacaactc agctttcgca     60
cgggagggtt gatgcttaac agaattaaaa atatatgtat taagaaccgc aagcccactg    120
tgtgccagcc gccgttggta gttttacacg tgcgatctta tttaatactt cctgggacct    180
aatgagtcag gtgccatcat gatccgttta caggtaagaa agccgccgct cagcg         235

<210> SEQ ID NO 49
<211> LENGTH: 81
<212> TYPE: DNA
<213> ORGANISM: Homo sapiens

<400> SEQUENCE: 49
cgaatcgcac ctcttctcct gtcctaatct caggctccag gcctggcttg cagtttctgg     60
ctcaccgcgc tgcggtcacc g                                              81

<210> SEQ ID NO 50
<211> LENGTH: 24
```

<212> TYPE: DNA
<213> ORGANISM: Homo sapiens

<400> SEQUENCE: 50

```
cgcccccgcg gaaaccgctg ctcg                                             24
```

<210> SEQ ID NO 51
<211> LENGTH: 236
<212> TYPE: DNA
<213> ORGANISM: Homo sapiens

<400> SEQUENCE: 51

```
gcgaggccag actgccccca cacctcctgt agccactgag cgcgaagtgc gttggttccg      60
agcgcgctgg tgggatccac aaagctcgca ttctctcagg aatcccctga gaaattaact    120
gtcccttgcc caacatgtct tctccaggct gtctgctaga gcctcaggcg cctccgccct    180
ccctcccgcg gcaccgtcac cagtgggtag tcacagcctc ccggagccca tagccg        236
```

<210> SEQ ID NO 52
<211> LENGTH: 533
<212> TYPE: DNA
<213> ORGANISM: Homo sapiens

<400> SEQUENCE: 52

```
cgcctccgcg ccgcgcgccg ccgccgcctg gtaccgcccg gccgggagaa ggtgagattc      60
gcgcggcctc gcgcacaccc gcggctggga gctcgggact gcggtgacgg gaggggcagt    120
gtggtgaccc acccaggatt ttttttttt tcccgtgaaa gtcctcaagc ctgtcctctc    180
cctggcccga tcctattgca gcgacagaaa atcagcagcg ggcgggtctg tgtggacctg    240
agggccgcgt ggggaccgag gggggctgtg gcccaaagag tggcagtgag tggcgtcaag    300
gaacccacac tccgcatctg ccactcctag agccgggact agctcccgat cctagcagtt    360
gctctcgaga tcatcccggg agttattggc gagttctggg cctctggagg tttccctgtc    420
agcctccccg gccgccgagg gggcgcgcgc ccaacaaggg ggtctctagc ggccacctgg    480
ggacagaaac agtgaccctg ggcgcgcact ttgcctcccc gttagagatg tcg           533
```

<210> SEQ ID NO 53
<211> LENGTH: 280
<212> TYPE: DNA
<213> ORGANISM: Homo sapiens

<400> SEQUENCE: 53

```
gcggaagccg cgagggatgc agcggcgggg accttggccg gtggaggatg tggaggtgga      60
agtggagcgg atggcgctcc ccaagagctc cgccacgcga ggtttcgggc tcgtggtttt    120
gcttcctccg ggtccccgct ccagggccgc tcggcgcgac gaagacgccg gggacagcgc    180
cgcggggagg gcgctccggg tcgtgcgtgc tgcacccaca aagagcagca gtcccgccac    240
tccgcgcctc cgctgcgtgg gggccgaggg gcgcttctcg                          280
```

<210> SEQ ID NO 54
<211> LENGTH: 535
<212> TYPE: DNA
<213> ORGANISM: Homo sapiens

<400> SEQUENCE: 54

```
cgacatagtc aagcagggct acgtgaaaat ccgcagcagg aagcttgggg tgagtggctc      60
gctcggcttg ctccttcccc ggcgctcgtt cggcccggct ggctgcctgg ggggggggca    120
```

```
gggagaggtg acccgtgcgg gtacagggca gagagggacc cggcccttag gcggatggcc    180
cgcttgttgc ttggccaggt gggggcccac acctgccggg gggctccgca gacggacctg    240
gggactccag gagcgcctga gtccccatcc tcgagtgcac cgggctgtct tcgaccgtgc    300
ggggaagtca gtagacgaaa ggggttgtca gttccaacga ggaacgtgcc ttggaggagg    360
tttctttgcg gtgctatcca cgatggtctg ttctcaaaag tgtgcgcctt tcgggtggaa    420
ctgctgtgtg tggcgacgct cgcgtgtgtt tagaatcacc attttctggt ctccgcttcc    480
caagctcaat tcgaaattcc cgtctgatgc cctcccagcg ccgcgcgtcc ctgcc         535

<210> SEQ ID NO 55
<211> LENGTH: 69
<212> TYPE: DNA
<213> ORGANISM: Homo sapiens

<400> SEQUENCE: 55
gcggtgggcg cggcctgcgg ggatgccggg ctctacggag cagcgcgggg tcccgaagcc     60
ccctaccgc                                                            69

<210> SEQ ID NO 56
<211> LENGTH: 1211
<212> TYPE: DNA
<213> ORGANISM: Homo sapiens

<400> SEQUENCE: 56
cgtaaataaa tgagatttac acaaatagcc attcacaatc atggtcacag tcacctacaa     60
accccattta cacaaatgat caggcacaca atcacactgt cactaaagca cacccacgca    120
ccaggtcgct gtcccaacag taacacacag cccaaagaga aaccctactt cctcacgcat    180
tcaaaacaca cccacctaag ggctgatccc gcactcagag gcctaaaact atagacattc    240
ccttccgcgg cactggtgag ccaggatttc ttaccttcag cattctcagg gaaggctctg    300
gtccaagctc tgattcggat tccaagcgaa gccacgcc cagctcttcc ttctccaccg      360
gcccgggaca tccttacctg cctctacccg gagaccattc ctgcgaggct cctaccggaa    420
gtagctgtgg acagcagtgt cctctgggaa atgcagtccg aggggagagc gcctggggtg    480
gagcgggtgt gttccgccgg gctccgggat gcacttgcgc agtttcaccc gaggctggag    540
tgacgccaac ctgttaatgt tcgttttcgg attctggact tcgggttccg ctgaggacgg    600
atttcggaat aggcacagtg gctgccccga acccctcaag gcggcctccg cgggctgtgg    660
ctgaagataa ttttcggcgg gcgcggacta acccggcttc cctttgtgga gttgtggtga    720
gaaaggtgtt ttgttgtgcg cgtgtccgaa ggtgactccg gaggagaagg tggatatgaa    780
ctgacggtga gggtgtagcg cgtgagattt gtatgtgaaa cgatttaaaa aaaaattttt    840 ttttttggccg ggcgcggtgg ctcacgccaa ggcgggcgga tcaccgagac cagcctgacc    900
aacatggaga aacccgtctc tactaaaaa tacaaaatta gccgggcgtg atggcgcatg     960
cctgtaatcc cagctactcg ggaggctgag gcaggagaat cgcttgaacc cgggaggcag   1020
aggttgcggt gagccgaggt cgcgccattg cactccagcc tgggcgacag agcaactcct   1080
tctcaaacaa acaaacaaaa ctgtatgtca tatatttgac tccatttatt tatttattta   1140
gagacagagt cttcttgccc tgttgcccgg gcaagaaaaa acaaacaaca acaacaacaa   1200
aaaactgtac g                                                       1211

<210> SEQ ID NO 57
<211> LENGTH: 317
```

<212> TYPE: DNA
<213> ORGANISM: Homo sapiens

<400> SEQUENCE: 57

```
gctgccgagt cccccgcagca gggggcgagc aagggactcg cggttgacgg gacacggatc    60
ctctaaggcc cagagtgtcc cgagtagcgg cagtggggag tgctcagggt acgctaatgg   120
tgagtggttg cagttgatgg gacaaaaaac tgtgatggga gttagtgtgg gtgtgtggtt   180
gtgtgtgtga gtgtgacggc acgaataatc tgatggggtg attgtgatat ttggttgcgc   240
gggattatga tgaaatgtgt gatatgtgtg tgattatgat taaggctgta gcgagtgtga   300
acgtggcgaa gtgtgcg                                                  317
```

<210> SEQ ID NO 58
<211> LENGTH: 328
<212> TYPE: DNA
<213> ORGANISM: Homo sapiens

<400> SEQUENCE: 58

```
tcggagatgt gcgggctgca tgcccacgct tcaccgctag gggaggtcag ggctgtgcga    60
tggggaagga agagagtgtc ggggcggtgc agtcggatg ggagaagggt gtcagggcca   120
ctggccccca gctcggcaga gggcagtgtc gggccgcgcg caggcaggga gtgggtgtgg   180
tgtgaggctg gcgctggagc ggtctgggaa tgttaggagg tctagggtat cgcggccctg   240
cgtcctcttg tctggactaa aagtccgggc agttctcccc ggacctggat tgtgggccca   300
gcgacaggtg cttggcgatc tgtgcccg                                      328
```

<210> SEQ ID NO 59
<211> LENGTH: 303
<212> TYPE: DNA
<213> ORGANISM: Homo sapiens

<400> SEQUENCE: 59

```
cgcctgggat tgcgaggtag gtaccgcctg cctgtgtgta ccggggctgc tgtctccggg    60
gaggggcttc tggcggacag gagaaccaag cagcctcagg agctgcctgg gtgtgtgtgt   120
ttctgtgcga gtgttgcata tctctgtgtg tgtttctgtg caagtgttgc atgtctgtgt   180
gtgtgggggg ggtggtgtct ggtgaaaaga atgtgtctcg tgcggtggag cgccgtttct   240
ctgtagtccg cgggctctct tatgcgccct cttgtggtcc caagtgtgct tttcttgttt   300
ttc                                                                 303
```

<210> SEQ ID NO 60
<211> LENGTH: 248
<212> TYPE: DNA
<213> ORGANISM: Homo sapiens

<400> SEQUENCE: 60

```
gtgtgcgtgc ttctgtgcgt gtgtgtgtgt ttgtgcgcgt gcgtgtgctc atgcacggcc    60
ccgtggcagt gctgggtatg agctcttgcc ccagacatgc ccctgcctgc tccctgccag   120
gatctgggga gatggctgta cctggcagcc ctagggtgca gagcagagtg ggcagccgtc   180
cctcgggact ctcagctgcc cacttcttcc cacagtgcct ggccatgcca ggctgcccag   240
aggggcag                                                            248
```

<210> SEQ ID NO 61
<211> LENGTH: 221
<212> TYPE: DNA

<213> ORGANISM: Homo sapiens

<400> SEQUENCE: 61

| | |
|---|---|
| gtgtgttcga gtccctgggt tgcttcctgg ggtctgtggt gctgggtgtg ctatctgcgt | 60 |
| gtgattctct agcgagagat tgtgggcgag tgaccgagtg ggcaaggggc cgtcactgtg | 120 |
| tgtgcgtgat tttgacagtg tgtggtggta gcttctgact ccgcgtgggt cgttgaatgt | 180 |
| atgactggga ccgtttagcg gtggatacac aactgtgtgc g | 221 |

<210> SEQ ID NO 62
<211> LENGTH: 150
<212> TYPE: DNA
<213> ORGANISM: Homo sapiens

<400> SEQUENCE: 62

| | |
|---|---|
| gcgtaatcac gcactgcgca ggcaccgccc gctctgctct aaggtccctc tcactccttc | 60 |
| agcagcccga ggacaatccc ctcaacacta ggccacgcct tgtctccgcc cctctcgtcc | 120 |
| gacccctgga gagaggctgg cgcctgcgcg | 150 |

<210> SEQ ID NO 63
<211> LENGTH: 237
<212> TYPE: DNA
<213> ORGANISM: Homo sapiens

<400> SEQUENCE: 63

| | |
|---|---|
| ccgcccgggg ctcctctgtc ccagctctgc ggcccagggg gtgacgtgat ggcggcagcg | 60 |
| gtgctgacgg accgggccca ggtgagtgga cggtggcttc gcggttgccg cttccttgcc | 120 |
| agcgctgagg cggtttccga agtgggtggg agcccaggta tcccctggat ttgtcttcgc | 180 |
| agtcgtcgtt cgctttggtg tgtggagctg gtttgccact taatttatac ctggccg | 237 |

<210> SEQ ID NO 64
<211> LENGTH: 129
<212> TYPE: DNA
<213> ORGANISM: Homo sapiens

<400> SEQUENCE: 64

| | |
|---|---|
| cggtctcctc gtatccatcc tcgcagtccc caccccaaac taatgttctc ccctgagcaa | 60 |
| atttcgagac acttaaaatc ccagctaaga tcacgtcctt ctattcaaaa ccctcagtta | 120 |
| atctcaacg | 129 |

<210> SEQ ID NO 65
<211> LENGTH: 848
<212> TYPE: DNA
<213> ORGANISM: Homo sapiens

<400> SEQUENCE: 65

| | |
|---|---|
| gcgagttcaa tgtcctccgt tccgtcaagt ttgggtttga gctttgggct cagctgccgt | 60 |
| ggtctggaga cctcgtaggc actctgcaag atgcctcgtt ctgctgcatg cttggggagg | 120 |
| aagttgagct gggtgctgga agttctgaac ccagcatgcc ccgggccgga ggagatttgc | 180 |
| ttggtgtctc cttagcgtcc cgaacaccgc gcgcccctgc tggggtaacc tgaacagctg | 240 |
| gaccccctcaa ctcgatcttt attatcagca ttggggctcc agattccgta cacatctcta | 300 |
| gctctattca ttcttcctag gttgagaacg gacgcattgg gagtcctacg cccgggggaa | 360 |
| aggcaggaga ggggaggaag agaacctgtg ccccctggaag ctagaggaga gcctcgctct | 420 |
| ctctgctgct ctgggttccg caacgaattg agttcgggtt caggcggctg gagcgggcgc | 480 |

```
gggggaggctg aacaatcgcc ggaggcccag gaggggaggc gaatgtacac aggctaagtg    540
gccccactcc aggacaagtg gccctctaag tcggctcagt gtttacctgt ttactttccc    600
aggtagctca aacacgagcg ccttttctgc gctccagggc acgggggccg cccagaggca    660
ccctgctttc ccggcttctg ccctcccacg cctcagcttt acgcccctg ttgtgggggt     720 gcgctctaaa caacagcaaa ccaggcaaga aggaagata caggagagca ggcgaggcct     780
cggcacaccc tacggagggg agcctttctt gtgcctgtgg aagaagtggg ctccgtggac    840
ggcatccg                                                              848
```

<210> SEQ ID NO 66
<211> LENGTH: 79
<212> TYPE: DNA
<213> ORGANISM: Homo sapiens

<400> SEQUENCE: 66

```
gcgcctggag gctgcattga ggccgggctg tgtaaactgt agggtgcctc gccgactcgg     60
agccgcagag actggcggc                                                   79
```

<210> SEQ ID NO 67
<211> LENGTH: 2225
<212> TYPE: DNA
<213> ORGANISM: Homo sapiens

<400> SEQUENCE: 67

```
cgggccttaa ggaatctcag actgcacagc tctgctgtct cattccaggg gtccctgggg     60
tgctccgctc ttgccaattc cgggcacaag gaccacccac tctgcccagc agcctctggc    120
cccactccca ctgccccagc gaaataagtt ccagcttcca ggcatgattg attatttgga    180
acagagcctt ccactccgga ctgagaccca acccctgcag aaagtcctaa actgggctgc    240
gaccactttg ctcccaggag cagaggagca ggggaaaagg ggagaattct ttaaaaaatg    300
acacgcgaga gagttaaaga aggaaaaagg caccaaagtg atgaaacaaa agaactgga    360 gaataagcac tgcacagaga gaaggccgta gcaggaagga ccggcagtga ctttcaacag    420
tgcttgagag cagaattatg gccgcgagag ggagtgcaaa ctgggaggcg gggcaaaccc    480
gggaaagacc tcccaagcag gttctgcgaa ggggccccac cgccttcagc ccgcctgggt    540 cagcctata aggggaaag gggacagaag tctgcagaac agagatccta gcgtagccgc     600
tcagggtacc ttcccaggtc accattgctc ctctgccctc tccacatccg ccctcccgtg    660
agcgcaggat gcacgcacag gcagcggtta caaaactcag cgcaacgttg caacccgcac    720
aaaaggcgca cacaaaatca ttaaaaagaa atacacagag tggaaagaac tcgcacaagc    780
tccaactcgc taaaggtgga aggagtcagg ttacaaactc tccctccccg gcctaaatgc    840
tttgctttag tttgcagaaa atcgtttgtc agtttttttc ttggttattc attattcggg    900
caaatgcaag tatgttttct agctgagttc accaatccaa acctcaaacc acattcctcc    960
actccaggcc tccgttctgt ccgcggactt atgatcctgc ctgccagcag gagtctaccc   1020
tgaagtcgcg tgggatagat aaagtgagga gaggaggatg aatggacaga caaacgagag   1080
caattcttct acctgtgggc tgtcctacgc cttgcagtgc cggtcctgc ggcgaccact    1140 gagcccttc gtcctcgccc tcagtccctt cgtcctcgtc ttcggtctcc gctttcccag   1200
tcggccgggg ctcgtcgtcc acgacccgc acgtgccgcc gacgtcgccc tgccgattcc   1260
gccgcaggag gtggaactgt agtggtgccg gcggcttctc ccctggggcg gcggtggcga   1320
```

```
ggcgctcgct ggcggcgggc agcggctgga tgaaatacgc ctcccccagc aggtagaagg    1380
cgccgcgcac gccctcgcag aggctgaggg cggcagccga gctgggatcg ccattcacgg    1440
tgccggagta gaagcagtgc gccaggtcgg tttccggaag cggcgtctcg acccggatt    1500 tgcgccccac gttctggagc gtgaagccgg gcgccaaaaa gctgctgtcg ggccgcagct    1560
ccagatccag ctgctggtca aaggcgtgca ggcggaggcg cgtggtcccg tgtcccgggg    1620
cgcgctccag ctccggcacc actagctcct cgtcctcctc ggaggggcgc ccgagtgcgt    1680
ccgacacggc cagtagcgcc gcggcgagca gcagcagcgt gggtactggc ccaaagctcc    1740 gagacccgg agcccgctcc gcgttcccca tgtcgctgcc cagcttgcgc cttccgaacc     1800
cctcgggcac agctcgctgc attggagccc caggagacac cgctcgtagc agcgcacgga    1860
gcgagggacc tttagttcgg gtcgggagag caaagcctcg ttggcctgct ctggattgtt    1920
aaaattaaca atttctatta ttcgttggaa gggcgcgcag agccggctac agccgaagct    1980
cccggagtca ctaaaaggag gcgctgcagt tctgccggcg cgcgggaagt ttttcttcca    2040
gcgcaaagtt ggagacactg agaggcaggc gcaggcagag tggctctgct gggacaagaa    2100
gcgctctggg gcgcctccgg ggctgaggca acgcggagat tggtgcctgg cgcccctctt    2160
cggcctccgc cttggctgcg atgttgctca ctctgctcag ggctctcccc tctccgtccg    2220
gtagc                                                                2225

<210> SEQ ID NO 68
<211> LENGTH: 997
<212> TYPE: DNA
<213> ORGANISM: Homo sapiens

<400> SEQUENCE: 68
tcgaactaat ttaatcagat gtaaaattaa tgagaacccc gagacttccg acgtcccact      60
ccagaactcc catccaggtg cggtcgggag ccacagcttc tgaatattcc ttcggaactt     120
ttttctcact tgattcccaa gcctgtcatg gggttctttt tcaatggcac tgacctgcaa     180
ttacccaacg agcagcggga cagccccggg caggacgcat cctgggtggg tgacgtgatc     240
ccgcagtctc ctccccgacc ccatatccca tacaatgatc ctcgcttaca gaagtcaagg     300
gggaaagatg acgcttttcaa agcccgaatc tctttaccct ggagccagaa ccagcgtcgc    360
cgccgtcccc tgcagctcag ccggcaacgc gcgccgagcc tcggggcgca gcttggagac    420
gcgcttgctc gttctgggaa ggggcacggg acgcacggtt ccccggcccc agctgcacag    480
ctcagctcgg ggctctcacc tatcctcgtt cagagccaca ttcggctgcc tccctgacc     540 acccgacaca aagagattcg ccggtggaaa gaatcgattt caaaattcaa gctcaccgct    600
gctcaacaag gcgcgcacgt ttctccccgt ctggcttcac atgtcccaaa cttccagtaa    660
cagaaatgag gaagcagcag ccttccccgg ctgctggcgg aggcagtggg tgtaacttgt    720
gaagtttcgt gctatgatga atctggtcac ttgggtgtgt tggagagggt tggtcgctcc    780
tcccttcctc ctcccaccat cacctccctc ctctccgcct ccctctccaa tttaattctt    840
ccctctggca ttcgccggct gtcactcaga atcccagcac cctcccccacc acatccttgg   900 gggcaatgta tttcgaaaag gtcttaacca ttttacggat gaacctggtc accctgcaca    960
aagcgtgagt gcttgtcaaa taattttcta cagcacg                              997

<210> SEQ ID NO 69
<211> LENGTH: 284
<212> TYPE: DNA
<213> ORGANISM: Homo sapiens
```

-continued

<400> SEQUENCE: 69

```
gcggcgcaag atcaacagcc gcgagcggaa gcgcatgcag gacctgaacc tggccatgga      60
cgccctgcgc gaggtcatcc tgccctactc agcggcgcac tgccagggcg cgcccggccg     120
caagctctcc aagatagcca cgctgctgct cgcccgcaac tacatcctac tgctgggcag     180
ctcgctgcag gagctgcgcc gcgcgctggg cgagggcgcc gggcccgccg cgccgcgcct     240
gctgctggcc gggctgcccc tgctcgccgc cgcgcccggc tccg                     284
```

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
gcaccactag ctcctcgtcc tcct                                              24
```

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
ccggcgcgat tctccctcaa cg                                                22
```

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
gtgcgcggcc caagagaagg                                                   20
```

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
tggggtcgta gtggtttccg aggt                                              24
```

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
gtggaggatg tggaggtgga agtg                                              24
```

-continued

```
<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcatctatgc gggcatggtt actg                                              24

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
acctctgccc cctgtccagg ta                                                22

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ctagggccga cttttccatc tcctc                                             25

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cggcgctttg cttttctaca actg                                              24

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tggagaagta agtgggaggc ggtgt                                             25

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaaaagcgat gactgccctg aactg                                             25

<210> SEQ ID NO 81
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccagcagcca acccctacga cttc                                          24

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
actgaagctg cggccctgat ct                                            22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cgcccgcagg atcgagtgag tc                                            22

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgagaagtca gacgggccgc gtaa                                          24

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgggctgggg ttggaagagt aac                                           23

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggctccgaat cgcacctctt ctcc                                          24

<210> SEQ ID NO 87
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
agggactcct ggccttgcgt ctt                                          23

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctcagttacg ctgactcggc tgtg                                         24

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgaggatgtg gatggcgcgg atg                                          23

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ctgcattgag gccgggctgt gt                                           22

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gcgacgcgtt tccctggtta cct                                          23

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tctaacgagg gctcagctcc gacta                                        25

<210> SEQ ID NO 93
<211> LENGTH: 23
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 93
gggatgggga gtagagggag ggg                                            23

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gcgaggtcat cctgccctac tcag                                           24

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gccttctctt tgcgccacgt tcg                                            23

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
agagtgagag tgtccctgct gcca                                           24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cccactccaa tccccaccct ctcc                                           24

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aactccgagg agctagcgca gac                                            23

<210> SEQ ID NO 99
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 99
gcctaagcgc ggggaattac acgt                                          24

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
aaaagccaat ctccaagcct ccaaacgg                                      28

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcggccaccc accctagtcg ttg                                           23

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gctctgcctg tttgttccgc cc                                            22

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gagcttggag atgcgaggga aact                                          24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcctcggcgc ccaaaatcga aagg                                          24

<210> SEQ ID NO 105
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 105
ggagcgtgga cttcttgggc cg                                            22

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ttcggattct ggacttcggg ttcc                                          24

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggtaggtacc gcctgcctgt gtgta                                         25

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggagtgggtg tggtgtgagg ctgg                                          24

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ctcgcgatgt ttcagggtga gcc                                           23

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gtctcggagc tttgggccag tacc                                          24

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 111
gaggcagcgc gactccaaga ctcag                                         25

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gggacgtaga caagggcagg cg                                            22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tcagcgccgc cacctacagc ac                                            22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gacccggagg aagcaaaacc ac                                            22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cgtggacctg gctgaggagc tg                                            22

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acagcctcgg tcaccgcatc                                               20

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
-continued

<400> SEQUENCE: 117
gagtaagctc aaagcggctg caatc                                            25

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gcagtcagcc cgaccctcct                                                  20

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acttagccgc ccatttcaga gcagc                                            25

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ggaaggcagc ggactgacat ctg                                              23

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ttaggactgc tggacgaggc gccg                                             24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gagggctccc aggtctcttg tttc                                             24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 123
aggcggtgca ctacatcgga tctc                                          24

<210> SEQ ID NO 124
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ctcagatggg agcgcggcag gaacag                                        26

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
atccctggac tggcgtatcc acag                                          24

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tcctgggagt gtgggccggt ga                                            22

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tctgtttcag cgcaactgtg aagtg                                         25

<210> SEQ ID NO 128
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
cccaaccacg cagtcataaa taacc                                         25

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129

-continued ttcctctcgc cgctctctcc actg 24

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
agttgacccg ccgccagtct ct 22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
accccgcgct gctccgtaga 20

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gaccccaggg aacaggcaaa aag 23

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cctaactccg tcccgctcgc tgtt 24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cagcagcgtg gctatcttgg agag 24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgcgcgacgt ggaaggagaa atga                                          24

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gcggggtctg tgtggtgagc gag                                           23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtcctccaag aacgtgccag gcg                                           23

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gcttaggcat gggaagggca agac                                          24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cactcccacc gcccagccct aata                                          24

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
aggataaata tgcgcggctt gtcagtca                                      28

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cgccgttttg acgtgctgcc g                                             21

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gcggcttggc gggctatctg tg                                              22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
cccccggccc tcctgtatta ct                                              22

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
agtcagcgct acgggaaagg aaacc                                           25

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctgcacggcc ggagaagcga at                                              22

<210> SEQ ID NO 146
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcccgccgaa aattatcttc agcca                                           25

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ctgaggctgc ttggttctcc tgtc                                            24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggccgcgata ccctagacct ccta                                          24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
aacacacgaa cagcactcct ccgc                                          24

<210> SEQ ID NO 150
<211> LENGTH: 158
<212> TYPE: DNA
<213> ORGANISM: Homo sapiens

<400> SEQUENCE: 150
gcaccactag ctcctcgtcc tcctgtctcg gagctttggg ccagtaccgc accactagct   60
cctcgtcctc ctcggagggg cgcccgagtg cgtccgacac ggccagtagc gccgcggcga  120
gcagcagcag cgtgggtact ggcccaaagc tccgagac                          158

<210> SEQ ID NO 151
<211> LENGTH: 137
<212> TYPE: DNA
<213> ORGANISM: Homo sapiens

<400> SEQUENCE: 151
ccggcgcgat tctccctcaa cggaggcagc gcgactccaa gactcagccg gcgcgattct   60
ccctcaacgc ttgcctggag catccctggc ccctttgcc caggtcgcgc ccctgagtct   120
tggagtcgcg ctgcctc                                                 137

<210> SEQ ID NO 152
<211> LENGTH: 133
<212> TYPE: DNA
<213> ORGANISM: Homo sapiens

<400> SEQUENCE: 152
gtgcgcggcc caagagaagg gggacgtaga caagggcagg cggtgcgcgg cccaagagaa   60
ggccagcggg accacagcgc ggctacgcgg ccggccgcag tcttcaccgc gcgcctgccc  120
ttgtctacgt ccc                                                     133

<210> SEQ ID NO 153
<211> LENGTH: 174
<212> TYPE: DNA
<213> ORGANISM: Homo sapiens

<400> SEQUENCE: 153
ggggtcgtag tggtttccga ggttcagcgc cgccacctac agcactgggg tcgtagtggt   60
ttccgaggtt ggtgaccacg tcgtcgaact tgagcacctc gtagccttca tgctgccgct  120
tgaggccggc gtagaaggcg atcttgggca ccgtgctgta ggtggcggcg ctga        174

<210> SEQ ID NO 154
<211> LENGTH: 140
<212> TYPE: DNA
<213> ORGANISM: Homo sapiens

<400> SEQUENCE: 154
gtggaggatg tggaggtgga agtggacccg gaggaagcaa aaccacgtgg aggatgtgga    60
ggtggaagtg gagcggatgg cgctccccaa gagctccgcc acgcgaggtt tcgggctcgt   120
ggttttgctt cctccgggtc                                              140

<210> SEQ ID NO 155
<211> LENGTH: 145
<212> TYPE: DNA
<213> ORGANISM: Homo sapiens

<400> SEQUENCE: 155
gcatctatgc gggcatggtt actgcgtgga cctggctgag gagctggcat ctatgcgggc    60
atggttactg cctctggtgc cccccgcagc cgcgcgcagg taccgtgcga catcgcgatg   120
gcccagctcc tcagccaggt ccacg                                        145

<210> SEQ ID NO 156
<211> LENGTH: 153
<212> TYPE: DNA
<213> ORGANISM: Homo sapiens

<400> SEQUENCE: 156
cctctgcccc ctgtccaggt aacagcctcg gtcaccgcat cacctctgcc ccctgtccag    60
gtacgcgctg tctggcgcgc cctgcgtggg ggccgcaggt tcagacaccc gggcgcggcg   120
cggggccctg atggatgcgg tgaccgaggc tgt                                153

<210> SEQ ID NO 157
<211> LENGTH: 164
<212> TYPE: DNA
<213> ORGANISM: Homo sapiens

<400> SEQUENCE: 157
ctagggccga cttttccatc tcctcgagta agctcaaagc ggctgcaatc ctagggccga    60
cttttccatc tcctcctcta cctccggctc ccgggcgagg gaggccccgc gccgccctt   120 agactggctg cggccggaag attgcagccg ctttgagctt actc                   164

<210> SEQ ID NO 158
<211> LENGTH: 156
<212> TYPE: DNA
<213> ORGANISM: Homo sapiens

<400> SEQUENCE: 158
cggcgctttg cttttctaca actggcagtc agcccgaccc tcctcggcgc tttgcttttc    60
tacaactgga agccgcgaag gcggctactg cgctgagccg ctcgctctgc tggtcaagtt   120
tgggcgaccc gcgcggagga gggtcgggct gactgc                            156

<210> SEQ ID NO 159
<211> LENGTH: 133
<212> TYPE: DNA
<213> ORGANISM: Homo sapiens

```
<400> SEQUENCE: 159
tggagaagta agtgggaggc ggtgtactta gccgcccatt tcagagcagc tggagaagta    60
agtgggaggc ggtgtcggga actgactcct cttaaaacgg tcggcgccgc tgctctgaaa   120
tgggcggcta agt                                                      133

<210> SEQ ID NO 160
<211> LENGTH: 155
<212> TYPE: DNA
<213> ORGANISM: Homo sapiens

<400> SEQUENCE: 160
gaaaagcgat gactgccctg aactgggaag gcagcggact gacatctgga aaagcgatga    60
ctgccctgaa ctgctggggc gttcgaaatt tccagggtcc cgaccctccg tggggtacgc   120
gcgacttcgg cgcagatgtc agtccgctgc cttcc                              155

<210> SEQ ID NO 161
<211> LENGTH: 126
<212> TYPE: DNA
<213> ORGANISM: Homo sapiens

<400> SEQUENCE: 161
ccagcagcca acccctacga cttcttagga ctgctggacg aggcgccgcc agcagccaac    60
ccctacgact tcaggaggct cctgcgcaaa acctcccagc gccggcgcct cgtccagcag   120
tcctaa                                                              126

<210> SEQ ID NO 162
<211> LENGTH: 150
<212> TYPE: DNA
<213> ORGANISM: Homo sapiens

<400> SEQUENCE: 162
actgaagctg cggccctgat ctgagggctc ccaggtctct tgtttcactg aagctgcggc    60
cctgatctcc gcagaggctg cctgctgcgc tcggccctca agtgcccggg ccggccttcg   120
tgctccgaaa caagagacct gggagccctc                                    150

<210> SEQ ID NO 163
<211> LENGTH: 129
<212> TYPE: DNA
<213> ORGANISM: Homo sapiens

<400> SEQUENCE: 163
cgcccgcagg atcgagtgag tcaggcggtg cactacatcg gatctccgcc cgcaggatcg    60
agtgagtcac gcggccgcca gacgaggccg gtggcgcacg cacccgagat ccgatgtagt   120
gcaccgcct                                                           129

<210> SEQ ID NO 164
<211> LENGTH: 156
<212> TYPE: DNA
<213> ORGANISM: Homo sapiens

<400> SEQUENCE: 164
tgagaagtca gacgggccgc gtaactcaga tgggagcgcg gcaggaacag tgagaagtca    60
gacgggccgc gtaaggggca gagcgagggg tccggcatca ctcgcgcgct ccggaaaccc   120
gcgtgagccg ctgttcctgc cgcgctccca tctgag                             156
```

```
<210> SEQ ID NO 165
<211> LENGTH: 151
<212> TYPE: DNA
<213> ORGANISM: Homo sapiens

<400> SEQUENCE: 165
cgggctgggg ttggaagagt aacatccctg gactggcgta ccacagcgg gctgggttg      60 gaagagtaac tcgggctgcg ggctgaacgc agtcggcaac cgcggaagag cagcatctcc    120
cctgcgcctg tggatacgcc agtccaggga t                                   151

<210> SEQ ID NO 166
<211> LENGTH: 148
<212> TYPE: DNA
<213> ORGANISM: Homo sapiens

<400> SEQUENCE: 166
ggctccgaat cgcacctctt ctcctcctgg gagtgtgggc cggtgaggct ccgaatcgca    60
cctcttctcc tgtcctaatc tcaggctcca ggcctggctt gcagtttctg gctcaccgcg    120
ctgcggtcac cggcccacac tcccagga                                       148

<210> SEQ ID NO 167
<211> LENGTH: 130
<212> TYPE: DNA
<213> ORGANISM: Homo sapiens

<400> SEQUENCE: 167
agggactcct ggccttgcgt ctttctgttt cagcgcaact gtgaagtgag ggactcctgg    60
ccttgcgtct tgggagagcg cacgctggcc tgcgctacac acacacactt cacagttgcg    120
ctgaaacaga                                                           130

<210> SEQ ID NO 168
<211> LENGTH: 145
<212> TYPE: DNA
<213> ORGANISM: Homo sapiens

<400> SEQUENCE: 168
ctcagttacg ctgactcggc tgtgcccaac cacgcagtca taaataaccc tcagttacgc    60
tgactcggct gtgcccgcag tgtcgcgctg tcgcgtagcc aggtgtcgcc gggctggcgc    120
ggttatttat gactgcgtgg ttggg                                          145

<210> SEQ ID NO 169
<211> LENGTH: 114
<212> TYPE: DNA
<213> ORGANISM: Homo sapiens

<400> SEQUENCE: 169
cgaggatgtg gatggcgcgg atgttcctct cgccgctctc tccactgcga ggatgtggat    60
ggcgcggatg gcgcggcctc cacctgcggg cagtggagag agcggcgaga ggaa          114

<210> SEQ ID NO 170
<211> LENGTH: 121
<212> TYPE: DNA
<213> ORGANISM: Homo sapiens

<400> SEQUENCE: 170
ctgcattgag gccgggctgt gtagttgacc cgccgccagt ctctctgcat tgaggccggg    60
ctgtgtaaac tgtagggtgc ctcgccgact cggagccgca gagactggcg gcgggtcaac    120
```

|   |   |
|---|---|
| t | 121 |

<210> SEQ ID NO 171
<211> LENGTH: 163
<212> TYPE: DNA
<213> ORGANISM: Homo sapiens

<400> SEQUENCE: 171

|   |   |
|---|---|
| gcgacgcgtt tccctggtta cctacccgc gctgctccgt agagcgacgc gtttccctgg | 60 |
| ttacctgcgg ggccgcgtcc cggaggagcc tgagggccaa gagggccggc gcgcggtggg | 120 |
| cgcggcctgc ggggatgccg ggctctacgg agcagcgcgg ggt | 163 |

<210> SEQ ID NO 172
<211> LENGTH: 149
<212> TYPE: DNA
<213> ORGANISM: Homo sapiens

<400> SEQUENCE: 172

|   |   |
|---|---|
| tctaacgagg gctcagctcc gactagaccc cagggaacag gcaaaaagtc taacgagggc | 60 |
| tcagctccga ctaccccagg cctccgggga ccctctccgg atgcgctccc cgctttgcgc | 120 |
| tttgcgcttt ttgcctgttc cctggggtc | 149 |

<210> SEQ ID NO 173
<211> LENGTH: 164
<212> TYPE: DNA
<213> ORGANISM: Homo sapiens

<400> SEQUENCE: 173

|   |   |
|---|---|
| gggatgggga gtagagggag gggcctaact ccgtcccgct cgctgttggg atggggagta | 60 |
| gagggagggg gccctgttgc ctcagcgccc cgaggtcgtg gagcggcagc agctgcagcc | 120 |
| ggagcagcac cagcaacagc aacagcgagc gggacggagt tagg | 164 |

<210> SEQ ID NO 174
<211> LENGTH: 128
<212> TYPE: DNA
<213> ORGANISM: Homo sapiens

<400> SEQUENCE: 174

|   |   |
|---|---|
| gcgaggtcat cctgccctac tcagcagcag cgtggctatc ttggagaggc gaggtcatcc | 60 |
| tgccctactc agcggcgcac tgccagggcg cgcccggccg caagctctcc aagatagcca | 120 |
| cgctgctg | 128 |

<210> SEQ ID NO 175
<211> LENGTH: 107
<212> TYPE: DNA
<213> ORGANISM: Homo sapiens

<400> SEQUENCE: 175

|   |   |
|---|---|
| gccttctctt tgcgccacgt tcgtgcgcga cgtggaagga gaaatgagcc ttctctttgc | 60 |
| gccacgttcg gccgcagctg aattcatttc tccttccacg tcgcgca | 107 |

<210> SEQ ID NO 176
<211> LENGTH: 130
<212> TYPE: DNA
<213> ORGANISM: Homo sapiens

<400> SEQUENCE: 176

|   |   |
|---|---|
| agagtgagag tgtccctgct gccagcgggg tctgtgtggt gagcgagaga gtgagagtgt | 60 | ccctgctgcc agaggactac ggcgggctgg gcgcggggtc cccgcctctc gctcaccaca    120 cagaccccgc                                                           130

<210> SEQ ID NO 177
<211> LENGTH: 119
<212> TYPE: DNA
<213> ORGANISM: Homo sapiens

<400> SEQUENCE: 177
cccactccaa tccccaccct ctccgtcctc aagaacgtg ccaggcgccc actccaatcc     60
ccaccctctc catccttagt cattaaagaa cagcagcgcc tggcacgttc ttggaggac    119

<210> SEQ ID NO 178
<211> LENGTH: 149
<212> TYPE: DNA
<213> ORGANISM: Homo sapiens

<400> SEQUENCE: 178
aactccgagg agctagcgca gacgcttagg catgggaagg gcaagacaac tccgaggagc    60
tagcgcagac cgtctccgc cctcagctgc ggcgaggcaa gggctggcag cgctcggacg    120
cctccgtctt gccttccca tgcctaagc                                      149

<210> SEQ ID NO 179
<211> LENGTH: 123
<212> TYPE: DNA
<213> ORGANISM: Homo sapiens

<400> SEQUENCE: 179
gcctaagcgc ggggaattac acgtcactcc caccgcccag ccctaatagc ctaagcgcgg    60
ggaattacac gttcccggtg tagaacagac gatcggggct attagggctg ggcggtggga   120
gtg                                                                 123

<210> SEQ ID NO 180
<211> LENGTH: 147
<212> TYPE: DNA
<213> ORGANISM: Homo sapiens

<400> SEQUENCE: 180
aaaagccaat ctccaagcct ccaaacggag gataaatatg cgcggcttgt cagtcaaaaa    60
gccaatctcc aagcctccaa acggaacgtc accctatcag ctgggagaca gcgccgcact   120
gactgacaag ccgcgcatat ttatcct                                       147

<210> SEQ ID NO 181
<211> LENGTH: 113
<212> TYPE: DNA
<213> ORGANISM: Homo sapiens

<400> SEQUENCE: 181
gcggccaccc accctagtcg ttgcgccgtt ttgacgtgct gccggcggcc acccacccta    60
gtcgttggag cctggcgccc gcgcctcccg gccggcagca cgtcaaaacg gcg          113

<210> SEQ ID NO 182
<211> LENGTH: 145
<212> TYPE: DNA
<213> ORGANISM: Homo sapiens

<400> SEQUENCE: 182

```
gctctgcctg tttgttccgc ccgcggcttg cgggctatc tgtggctctg cctgtttgtt      60
ccgcccccgc ggaaaccgct gctcgctggg caggggcttt ctgttttgca gccggaacag    120
gaacacagat agcccgccaa gccgc                                          145
```

<210> SEQ ID NO 183
<211> LENGTH: 156
<212> TYPE: DNA
<213> ORGANISM: Homo sapiens

<400> SEQUENCE: 183

```
gagcttggag atgcgaggga aactcccccg gccctcctgt attactgagc ttggagatgc     60
gagggaaact gaagccccaa gggtgccccg tcctgggagc ctggctgtct gcggggtccc    120
ccgcattccg cagtagtaat acaggagggc cgggg                               156
```

<210> SEQ ID NO 184
<211> LENGTH: 139
<212> TYPE: DNA
<213> ORGANISM: Homo sapiens

<400> SEQUENCE: 184

```
gcctcggcgc ccaaaatcga aaggagtcag cgctacggga aaggaaaccg cctcggcgcc     60
caaaatcgaa aggccgggag ttgttctgca ggctttgcaa acaggttgac tgagggtttc    120 cttttcccgta gcgctgact                                                139
```

<210> SEQ ID NO 185
<211> LENGTH: 114
<212> TYPE: DNA
<213> ORGANISM: Homo sapiens

<400> SEQUENCE: 185

```
ggagcgtgga cttcttgggc cgctgcacgg ccggagaagc gaatggagcg tggacttctt     60
gggccgtacc cctgcggctc aagctgcccc ggattcgctt ctccggccgt gcag          114
```

<210> SEQ ID NO 186
<211> LENGTH: 166
<212> TYPE: DNA
<213> ORGANISM: Homo sapiens

<400> SEQUENCE: 186

```
ttcggattct ggacttcggg ttccgcccgc cgaaaattat cttcagccat tcggattctg     60
gacttcgggt tccgctgagg acggatttcg gaataggcac agtggctgcc ccgaacccct    120
caaggcggcc tccgcgggct gtggctgaag ataattttcg gcgggc                   166
```

<210> SEQ ID NO 187
<211> LENGTH: 133
<212> TYPE: DNA
<213> ORGANISM: Homo sapiens

<400> SEQUENCE: 187

```
ggtaggtacc gcctgcctgt gtgtactgag gctgcttggt tctcctgtcg gtaggtaccg     60
cctgcctgtg tgtaccgggg ctgctgtctc cggggagggg cttctggcgg acaggagaac    120
caagcagcct cag                                                       133
```

<210> SEQ ID NO 188
<211> LENGTH: 118
<212> TYPE: DNA
<213> ORGANISM: Homo sapiens

```
<400> SEQUENCE: 188
ggagtgggtg tggtgtgagg ctggggccgc gatacccctag acctcctagg agtgggtgtg    60
gtgtgaggct ggcgctggag cggtctggga atgttaggag gtctagggta tcgcggcc     118

<210> SEQ ID NO 189
<211> LENGTH: 119
<212> TYPE: DNA
<213> ORGANISM: Homo sapiens

<400> SEQUENCE: 189
ctcgcgatgt ttcagggtga gccaacacac gaacagcact cctccgcctc gcgatgtttc    60
agggtgagcc ggacgcaggc gtgcctgcgc agtgcgcgga ggagtgctgt tcgtgtgtt   119

<210> SEQ ID NO 190
<211> LENGTH: 111
<212> TYPE: DNA
<213> ORGANISM: Homo sapiens

<400> SEQUENCE: 190
ggcaccacta gctcctcgtc ctcctcggag gggcgcccga gtgcgtccga cacggccagt    60
agcgccgcgg cgagcagcag cagcgtgggt actggcccaa agctccgaga c            111

<210> SEQ ID NO 191
<211> LENGTH: 91
<212> TYPE: DNA
<213> ORGANISM: Homo sapiens

<400> SEQUENCE: 191
cccggcgcga ttctccctca acgcttgcct ggagcatccc tggccccttt tgcccaggtc    60
gcgcccctga gtcttggagt cgcgctgcct c                                   91

<210> SEQ ID NO 192
<211> LENGTH: 92
<212> TYPE: DNA
<213> ORGANISM: Homo sapiens

<400> SEQUENCE: 192
ggtgcgcggc ccaagagaag gccagcggga ccacagcgcg gctacgcggc cggccgcagt    60
cttcaccgcg cgcctgccct tgtctacgtc cc                                  92

<210> SEQ ID NO 193
<211> LENGTH: 130
<212> TYPE: DNA
<213> ORGANISM: Homo sapiens

<400> SEQUENCE: 193
gtggggtcgt agtggtttcc gaggttggtg accacgtcgt cgaacttgag cacctcgtag    60
ccttcatgct gccgcttgag gccggcgtag aaggcgatct tgggcaccgt gctgtaggtg   120
gcggcgctga                                                          130

<210> SEQ ID NO 194
<211> LENGTH: 95
<212> TYPE: DNA
<213> ORGANISM: Homo sapiens

<400> SEQUENCE: 194
ggtggaggat gtggaggtgg aagtggagcg gatggcgctc cccaagagct ccgccacgcg    60
```

```
aggtttcggg ctcgtggttt tgcttcctcc gggtc                               95

<210> SEQ ID NO 195
<211> LENGTH: 100
<212> TYPE: DNA
<213> ORGANISM: Homo sapiens

<400> SEQUENCE: 195
ggcatctatg cgggcatggt tactgcctct ggtgcccccc gcagccgcgc gcaggtaccg    60
tgcgacatcg cgatggccca gctcctcagc caggtccacg                         100

<210> SEQ ID NO 196
<211> LENGTH: 113
<212> TYPE: DNA
<213> ORGANISM: Homo sapiens

<400> SEQUENCE: 196
cacctctgcc ccctgtccag gtacgcgctg tctggcgcgc cctgcgtggg ggccgcaggt    60
tcagacaccc gggcgcggcg cggggccctg atggatgcgg tgaccgaggc tgt          113

<210> SEQ ID NO 197
<211> LENGTH: 115
<212> TYPE: DNA
<213> ORGANISM: Homo sapiens

<400> SEQUENCE: 197
cctagggccg acttttccat ctcctcctct acctccggct cccgggcgag ggaggccccg    60
cgccgcccct tagactggct gcggccggaa gattgcagcc gctttgagct tactc        115

<210> SEQ ID NO 198
<211> LENGTH: 113
<212> TYPE: DNA
<213> ORGANISM: Homo sapiens

<400> SEQUENCE: 198
ccggcgcttt gcttttctac aactggaagc gcgaaggcg gctactgcgc tgagccgctc     60
gctctgctgg tcaagtttgg gcgacccgcg cggaggaggg tcgggctgac tgc          113

<210> SEQ ID NO 199
<211> LENGTH: 84
<212> TYPE: DNA
<213> ORGANISM: Homo sapiens

<400> SEQUENCE: 199
gtggagaagt aagtgggagg cggtgtcggg aactgactcc tcttaaaacg gtcggcgccg    60
ctgctctgaa atgggcggct aagt                                           84

<210> SEQ ID NO 200
<211> LENGTH: 108
<212> TYPE: DNA
<213> ORGANISM: Homo sapiens

<400> SEQUENCE: 200
ggaaaagcga tgactgccct gaactgctgg ggcgttcgaa atttccaggg tcccgaccct    60
ccgtggggta cgcgcgactt cggcgcagat gtcagtccgc tgccttcc               108

<210> SEQ ID NO 201
<211> LENGTH: 79
<212> TYPE: DNA
<213> ORGANISM: Homo sapiens
```

```
<400> SEQUENCE: 201
gccagcagcc aaccccctacg acttcaggag gctcctgcgc aaaacctccc agcgccggcg      60
cctcgtccag cagtcctaa                                                    79

<210> SEQ ID NO 202
<211> LENGTH: 105
<212> TYPE: DNA
<213> ORGANISM: Homo sapiens

<400> SEQUENCE: 202
cactgaagct gcggccctga tctccgcaga ggctgcctgc tgcgctcggc cctcaagtgc      60
ccgggccggc cttcgtgctc cgaaacaaga gacctgggag ccctc                     105

<210> SEQ ID NO 203
<211> LENGTH: 84
<212> TYPE: DNA
<213> ORGANISM: Homo sapiens

<400> SEQUENCE: 203
ccgcccgcag gatcgagtga gtcacgcggc cgccagacga ggccggtggc gcacgcaccc      60
gagatccgat gtagtgcacc gcct                                             84

<210> SEQ ID NO 204
<211> LENGTH: 107
<212> TYPE: DNA
<213> ORGANISM: Homo sapiens

<400> SEQUENCE: 204
ctgagaagtc agacgggccg cgtaaggggc agagcgaggg gtccggcatc actcgcgcgc      60
tccggaaacc cgcgtgagcc gctgttcctg ccgcgctccc atctgag                   107

<210> SEQ ID NO 205
<211> LENGTH: 105
<212> TYPE: DNA
<213> ORGANISM: Homo sapiens

<400> SEQUENCE: 205
gcgggctggg gttggaagag taactcgggc tgcgggctga acgcagtcgg caaccgcgga      60
agagcagcat ctcccctgcg cctgtggata cgccagtcca gggat                     105

<210> SEQ ID NO 206
<211> LENGTH: 103
<212> TYPE: DNA
<213> ORGANISM: Homo sapiens

<400> SEQUENCE: 206
aggctccgaa tcgcacctct tctcctgtcc taatctcagg ctccaggcct ggcttgcagt      60
ttctggctca ccgcgctgcg gtcaccggcc cacactccca gga                       103

<210> SEQ ID NO 207
<211> LENGTH: 83
<212> TYPE: DNA
<213> ORGANISM: Homo sapiens

<400> SEQUENCE: 207
cagggactcc tggccttgcg tcttgggaga gcgcacgctg gcctgcgcta cacacacaca      60
cttcacagtt gcgctgaaac aga                                              83
```

```
<210> SEQ ID NO 208
<211> LENGTH: 97
<212> TYPE: DNA
<213> ORGANISM: Homo sapiens

<400> SEQUENCE: 208
cctcagttac gctgactcgg ctgtgcccgc agtgtcgcgc tgtcgcgtag ccaggtgtcg    60
ccgggctggc gcggttattt atgactgcgt ggttggg                            97

<210> SEQ ID NO 209
<211> LENGTH: 68
<212> TYPE: DNA
<213> ORGANISM: Homo sapiens

<400> SEQUENCE: 209
gcgaggatgt ggatggcgcg gatggcgcgg cctccacctg cgggcagtgg agagagcggc    60
gagaggaa                                                            68

<210> SEQ ID NO 210
<211> LENGTH: 78
<212> TYPE: DNA
<213> ORGANISM: Homo sapiens

<400> SEQUENCE: 210
gctgcattga ggccgggctg tgtaaactgt agggtgcctc gccgactcgg agccgcagag    60
actggcggcg ggtcaact                                                 78

<210> SEQ ID NO 211
<211> LENGTH: 121
<212> TYPE: DNA
<213> ORGANISM: Homo sapiens

<400> SEQUENCE: 211
ggcgacgcgt ttccctggtt acctgcgggg ccgcgtcccg gaggagcctg agggccaaga    60
gggccggcgc gcggtgggcg cggcctgcgg ggatgccggg ctctacggag cagcgcgggg   120
t                                                                  121

<210> SEQ ID NO 212
<211> LENGTH: 102
<212> TYPE: DNA
<213> ORGANISM: Homo sapiens

<400> SEQUENCE: 212
ttctaacgag ggctcagctc cgactacccc aggcctccgg ggaccctctc cggatgcgct    60
ccccgctttg cgctttgcgc tttttgcctg ttccctgggg tc                     102

<210> SEQ ID NO 213
<211> LENGTH: 118
<212> TYPE: DNA
<213> ORGANISM: Homo sapiens

<400> SEQUENCE: 213
ggggatgggg agtagaggga gggggccctg ttgcctcagc gccccgaggt cgtggagcgg    60
cagcagctgc agccggagca gcaccagcaa cagcaacagc gagcgggacg gagttagg    118

<210> SEQ ID NO 214
<211> LENGTH: 81
<212> TYPE: DNA
<213> ORGANISM: Homo sapiens
```

<400> SEQUENCE: 214
cgcgaggtca tcctgccta ctcagcggcg cactgccagg gcgcgcccgg ccgcaagctc    60
tccaagatag ccacgctgct g    81

<210> SEQ ID NO 215
<211> LENGTH: 61
<212> TYPE: DNA
<213> ORGANISM: Homo sapiens

<400> SEQUENCE: 215
agccttctct ttgcgccacg ttcggccgca gctgaattca tttctccttc cacgtcgcgc    60
a    61

<210> SEQ ID NO 216
<211> LENGTH: 84
<212> TYPE: DNA
<213> ORGANISM: Homo sapiens

<400> SEQUENCE: 216
cagagtgaga gtgtccctgc tgccagagga ctacggcggg ctgggcgcgg ggtccccgcc    60
tctcgctcac cacacagacc ccgc    84

<210> SEQ ID NO 217
<211> LENGTH: 73
<212> TYPE: DNA
<213> ORGANISM: Homo sapiens

<400> SEQUENCE: 217
gcccactcca atccccaccc tctccatcct tagtcattaa agaacagcag cgcctggcac    60
gttcttggag gac    73

<210> SEQ ID NO 218
<211> LENGTH: 103
<212> TYPE: DNA
<213> ORGANISM: Homo sapiens

<400> SEQUENCE: 218
caactccgag gagctagcgc agaccgctct ccgccctcag ctgcggcgag gcaagggctg    60
gcagcgctcg gacgcctccg tcttgccctt cccatgccta agc    103

<210> SEQ ID NO 219
<211> LENGTH: 76
<212> TYPE: DNA
<213> ORGANISM: Homo sapiens

<400> SEQUENCE: 219
tgcctaagcg cggggaatta cacgttcccg gtgtagaaca gacgatcggg gctattaggg    60
ctgggcggtg ggagtg    76

<210> SEQ ID NO 220
<211> LENGTH: 92
<212> TYPE: DNA
<213> ORGANISM: Homo sapiens

<400> SEQUENCE: 220
aaaaagccaa tctccaagcc tccaaacgga acgtcaccct atcagctggg agacagcgcc    60
gcactgactg acaagccgcg catatttatc ct    92

<210> SEQ ID NO 221
<211> LENGTH: 70
<212> TYPE: DNA
<213> ORGANISM: Homo sapiens

<400> SEQUENCE: 221
cgcggccacc caccctagtc gttggagcct ggcgcccgcg cctcccggcc ggcagcacgt     60
caaaacggcg                                                           70

<210> SEQ ID NO 222
<211> LENGTH: 102
<212> TYPE: DNA
<213> ORGANISM: Homo sapiens

<400> SEQUENCE: 222
ggctctgcct gtttgttccg cccccgcgga aaccgctgct cgctgggcag gggctttctg     60
ttttgcagcc ggaacaggaa cacagatagc ccgccaagcc gc                       102

<210> SEQ ID NO 223
<211> LENGTH: 111
<212> TYPE: DNA
<213> ORGANISM: Homo sapiens

<400> SEQUENCE: 223
cgagcttgga gatgcgaggg aaactgaagc cccaagggtg ccccgtcctg ggagcctggc     60
tgtctgcggg gtccccgcca ttccgcagta gtaatacagg agggccgggg g             111

<210> SEQ ID NO 224
<211> LENGTH: 91
<212> TYPE: DNA
<213> ORGANISM: Homo sapiens

<400> SEQUENCE: 224
agcctcggcg cccaaaatcg aaaggccggg agttgttctg caggctttgc aaacaggttg     60
actgagggtt ccttttcccg tagcgctgac t                                   91

<210> SEQ ID NO 225
<211> LENGTH: 71
<212> TYPE: DNA
<213> ORGANISM: Homo sapiens

<400> SEQUENCE: 225
cggagcgtgg acttcttggg ccgtaccccct gcggctcaag ctgccccgga ttcgcttctc    60
cggccgtgca g                                                         71

<210> SEQ ID NO 226
<211> LENGTH: 118
<212> TYPE: DNA
<213> ORGANISM: Homo sapiens

<400> SEQUENCE: 226
tttcggattc tggacttcgg gttccgctga ggacggattt cggaataggc acagtggctg     60
ccccgaaccc ctcaaggcgg cctccgcggg ctgtggctga agataatttt cggcgggc      118

<210> SEQ ID NO 227
<211> LENGTH: 85
<212> TYPE: DNA
<213> ORGANISM: Homo sapiens

<400> SEQUENCE: 227

```
aggtaggtac cgcctgcctg tgtgtaccgg ggctgctgtc tccggggagg ggcttctggc    60
ggacaggaga accaagcagc ctcag                                          85

<210> SEQ ID NO 228
<211> LENGTH: 71
<212> TYPE: DNA
<213> ORGANISM: Homo sapiens

<400> SEQUENCE: 228
gggagtgggt gtggtgtgag gctggcgctg gagcggtctg ggaatgttag gaggtctagg    60
gtatcgcggc c                                                         71

<210> SEQ ID NO 229
<211> LENGTH: 73
<212> TYPE: DNA
<213> ORGANISM: Homo sapiens

<400> SEQUENCE: 229
tctcgcgatg tttcagggtg agccggacgc aggcgtgcct gcgcagtgcg cggaggagtg    60
ctgttcgtgt gtt                                                       73

<210> SEQ ID NO 230
<211> LENGTH: 120
<212> TYPE: DNA
<213> ORGANISM: Homo sapiens

<400> SEQUENCE: 230
ggcgaaaaga aggccaaaca cagcatcgac ggcatcctgg gcgacaaagg tagggaactt    60
ccctgggctg cgaggcccca gcccgggttt tcccacgctc cggtgtgcgg gccagtggtt   120

<210> SEQ ID NO 231
<211> LENGTH: 118
<212> TYPE: DNA
<213> ORGANISM: Homo sapiens

<400> SEQUENCE: 231
ggggatgggg agtagaggga gggggccctg ttgcctcagc gccccgaggt cgtggagcgg    60
cagcagctgc agccggagca gcaccagcaa cagcaacagc gagcgggacg gagttagg    118

<210> SEQ ID NO 232
<211> LENGTH: 69
<212> TYPE: DNA
<213> ORGANISM: Homo sapiens

<400> SEQUENCE: 232
gcaccagcaa cagcaacagc gagcgggacg gagttaggac cgctcggagc gcacaggtct    60
cgaggtagt                                                            69

<210> SEQ ID NO 233
<211> LENGTH: 111
<212> TYPE: DNA
<213> ORGANISM: Homo sapiens

<400> SEQUENCE: 233
cgagcttgga gatgcgaggg aaactgaagc cccaagggtg ccccgtcctg ggagcctggc    60
tgtctgcggg gtcccccgca ttccgcagta gtaatacagg agggccgggg g            111

<210> SEQ ID NO 234
```

```
<211> LENGTH: 83
<212> TYPE: DNA
<213> ORGANISM: Homo sapiens

<400> SEQUENCE: 234
cagggactcc tggccttgcg tcttgggaga gcgcacgctg gcctgcgcta cacacacaca    60
cttcacagtt gcgctgaaac aga                                           83

<210> SEQ ID NO 235
<211> LENGTH: 81
<212> TYPE: DNA
<213> ORGANISM: Homo sapiens

<400> SEQUENCE: 235
gcgctcatcg tgtgcacctt cacctacctg ctggtgggcg ccgcggtctt cgacgcgctg    60
gagtcggagc ccgagctgat c                                             81

<210> SEQ ID NO 236
<211> LENGTH: 94
<212> TYPE: DNA
<213> ORGANISM: Homo sapiens

<400> SEQUENCE: 236
aacagcagca ccgtgatcca gagcaccccg aagactggca gaaccagccg acgagtcagg    60
cgccgcatgg tcccctttgc cgcttcctct ccgc                               94

<210> SEQ ID NO 237
<211> LENGTH: 98
<212> TYPE: DNA
<213> ORGANISM: Homo sapiens

<400> SEQUENCE: 237
cgcacaatat caataattcc gcgggtcaca gcatcccgca caaggacgcc ttcttattgc    60
ataattaacg cgaggaaggc tcttcccgct actcccgc                           98

<210> SEQ ID NO 238
<211> LENGTH: 91
<212> TYPE: DNA
<213> ORGANISM: Homo sapiens

<400> SEQUENCE: 238
gtggctcact ctccaatcag cgctttctag agacagcgtg gtcagcgtac ttgcttactt    60
tcaggattgc gagacgtctt taacccttgc t                                  91

<210> SEQ ID NO 239
<211> LENGTH: 97
<212> TYPE: DNA
<213> ORGANISM: Homo sapiens

<400> SEQUENCE: 239
gcagtgtgcg gagaccctct aggcgggcgg ggacgcccca cgcggcgacc tgagcaccga    60
cctcatgcaa cgggaccgaa ccttgggacc cgggcag                            97

<210> SEQ ID NO 240
<211> LENGTH: 91
<212> TYPE: DNA
<213> ORGANISM: Homo sapiens

<400> SEQUENCE: 240
agcctcggcg cccaaaatcg aaaggccggg agttgttctg caggctttgc aaacaggttg    60
```

```
actgagggtt cctttcccg tagcgctgac t                                   91
```

<210> SEQ ID NO 241
<211> LENGTH: 77
<212> TYPE: DNA
<213> ORGANISM: Homo sapiens

<400> SEQUENCE: 241

```
atcgaaaggc cgggagttgt tctgcaggct ttgcaaacag gttgactgag ggtttccttt   60
cccgtagcgc tgactgc                                                  77
```

<210> SEQ ID NO 242
<211> LENGTH: 87
<212> TYPE: DNA
<213> ORGANISM: Homo sapiens

<400> SEQUENCE: 242

```
gcccatctgc acctgtcccc tttgctgtct tacatgtccc atagtattaa agttatttga   60
ataagcaaat gaacccgct ctttggt                                        87
```

<210> SEQ ID NO 243
<211> LENGTH: 71
<212> TYPE: DNA
<213> ORGANISM: Homo sapiens

<400> SEQUENCE: 243

```
cggagcgtgg acttcttggg ccgtacccct gcggctcaag ctgccccgga ttcgcttctc   60
cggccgtgca g                                                        71
```

<210> SEQ ID NO 244
<211> LENGTH: 113
<212> TYPE: DNA
<213> ORGANISM: Homo sapiens

<400> SEQUENCE: 244

```
ccggcgcttt gcttttctac aactggaagc cgcgaaggcg gctactgcgc tgagccgctc   60
gctctgctgg tcaagtttgg gcgacccgcg cggaggaggg tcgggctgac tgc          113
```

<210> SEQ ID NO 245
<211> LENGTH: 84
<212> TYPE: DNA
<213> ORGANISM: Homo sapiens

<400> SEQUENCE: 245

```
gtggagaagt aagtgggagg cggtgtcggg aactgactcc tcttaaaacg gtcggcgccg   60
ctgctctgaa atgggcggct aagt                                          84
```

<210> SEQ ID NO 246
<211> LENGTH: 85
<212> TYPE: DNA
<213> ORGANISM: Homo sapiens

<400> SEQUENCE: 246

```
tcagctatga gcagagaccg ctgaagcgcc cccggctcgg gccgcccgac gtctacccac   60
aggaccccaa gcagaaggag gtaag                                         85
```

<210> SEQ ID NO 247
<211> LENGTH: 91
<212> TYPE: DNA

<213> ORGANISM: Homo sapiens

<400> SEQUENCE: 247

| cccggcgcga ttctccctca acgcttgcct ggagcatccc tggccccttt tgcccaggtc | 60 |
| gcgcccctga gtcttggagt cgcgctgcct c | 91 |

<210> SEQ ID NO 248
<211> LENGTH: 115
<212> TYPE: DNA
<213> ORGANISM: Homo sapiens

<400> SEQUENCE: 248

| gcccggcttc gccttctctc ataagggtgg ccggggcccc acgaacttgc agggtggcgg | 60 |
| ccctgcgccc tccagccccg gcgggacgg gcacgattgc tcgtagtctg gggtg | 115 |

<210> SEQ ID NO 249
<211> LENGTH: 110
<212> TYPE: DNA
<213> ORGANISM: Homo sapiens

<400> SEQUENCE: 249

| gggcactcac acacacgcag acccagagga ggagaggtgg gtataaggaa gcaagcccca | 60 |
| gccgcagcag cccgagcggg cacaaaaccg cttcctggca catcaccttg | 110 |

<210> SEQ ID NO 250
<211> LENGTH: 98
<212> TYPE: DNA
<213> ORGANISM: Homo sapiens

<400> SEQUENCE: 250

| ggcactcaca cacacgcaga cccagaggag gagaggtggg tataaggaag caagccccag | 60 |
| ccgcagcagc ccgagcgggc acaaaaccgc ttcctggc | 98 |

<210> SEQ ID NO 251
<211> LENGTH: 105
<212> TYPE: DNA
<213> ORGANISM: Homo sapiens

<400> SEQUENCE: 251

| gcgggctggg gttggaagag taactcgggc tgcgggctga acgcagtcgg caaccgcgga | 60 |
| agagcagcat ctcccctgcg cctgtggata cgccagtcca gggat | 105 |

<210> SEQ ID NO 252
<211> LENGTH: 107
<212> TYPE: DNA
<213> ORGANISM: Homo sapiens

<400> SEQUENCE: 252

| cgcatcctcg ccttcttgca gtccaaggcc cgcctgggcg cggagcccgc ctttccgccg | 60 |
| ctgggttcgc tcccggagcc ggatttctcc tatcagctgc accctgc | 107 |

<210> SEQ ID NO 253
<211> LENGTH: 107
<212> TYPE: DNA
<213> ORGANISM: Homo sapiens

<400> SEQUENCE: 253

| ctgagaagtc agacgggccg cgtaagggc agagcgaggg gtccggcatc actcgcgcgc | 60 |
| tccggaaacc cgcgtgagcc gctgttcctg ccgcgctccc atctgag | 107 |

<210> SEQ ID NO 254
<211> LENGTH: 88
<212> TYPE: DNA
<213> ORGANISM: Homo sapiens

<400> SEQUENCE: 254
gcgtaagggg cagagcgagg ggtccggcat cactcgcgcg ctccggaaac ccgcgtgagc      60
cgctgttcct gccgcgctcc catctgag                                        88

<210> SEQ ID NO 255
<211> LENGTH: 86
<212> TYPE: DNA
<213> ORGANISM: Homo sapiens

<400> SEQUENCE: 255
caatctcaga gcggagccga cagagagcag ggaaccggca tggccaaagc cgcggcgatc      60
ggcatcgacc tgggcaccac ctactc                                          86

<210> SEQ ID NO 256
<211> LENGTH: 111
<212> TYPE: DNA
<213> ORGANISM: Homo sapiens

<400> SEQUENCE: 256
gtgtgcaccg agcgagtgaa ggtatgtgtg gcgggcgcgg ctggagctgc cgccgccgcc      60
gccgccgcgc cagcaggtcc taatgcctgt cacttcccag gacgctggca g              111

<210> SEQ ID NO 257
<211> LENGTH: 85
<212> TYPE: DNA
<213> ORGANISM: Homo sapiens

<400> SEQUENCE: 257
ctcacgttgc acggatgaca tcactagctt ttggctgcgc gctcggtgtt ctcgtctgtg      60
ggttttagcc aaggctgcag ctacc                                           85

<210> SEQ ID NO 258
<211> LENGTH: 73
<212> TYPE: DNA
<213> ORGANISM: Homo sapiens

<400> SEQUENCE: 258
caggacggga ttctctgcac gctgtcgagt gagccggcat ctcggcgccc gggtgggctg      60
cgaagaaaat ggt                                                        73

<210> SEQ ID NO 259
<211> LENGTH: 97
<212> TYPE: DNA
<213> ORGANISM: Homo sapiens

<400> SEQUENCE: 259
gcagaagacg cgctgggaa gagctgcgtg acgctcgggg gctggcggct gggccggcag       60
cgcgccgtgg cggcgtgacc tgtccatggt gttgaag                              97

<210> SEQ ID NO 260
<211> LENGTH: 113
<212> TYPE: DNA
<213> ORGANISM: Homo sapiens

<400> SEQUENCE: 260
cacctctgcc ccctgtccag gtacgcgctg tctggcgcgc cctgcgtggg ggccgcaggt    60
tcagacaccc gggcgcggcg cggggccctg atggatgcgg tgaccgaggc tgt          113

<210> SEQ ID NO 261
<211> LENGTH: 97
<212> TYPE: DNA
<213> ORGANISM: Homo sapiens

<400> SEQUENCE: 261
cctcagttac gctgactcgg ctgtgcccgc agtgtcgcgc tgtcgcgtag ccaggtgtcg    60
ccgggctggc gcggttattt atgactgcgt ggttggg                            97

<210> SEQ ID NO 262
<211> LENGTH: 92
<212> TYPE: DNA
<213> ORGANISM: Homo sapiens

<400> SEQUENCE: 262
ggtgcgcggc ccaagagaag gccagcggga ccacagcgcg gctacgcggc cggccgcagt    60
cttcaccgcg cgcctgccct tgtctacgtc cc                                 92

<210> SEQ ID NO 263
<211> LENGTH: 98
<212> TYPE: DNA
<213> ORGANISM: Homo sapiens

<400> SEQUENCE: 263
gcggatgcac gacctgaacg acgcgctgga cgagctgcgc gcggtgatcc cctacgcgca    60
cagcccctcg gtgcgaaagc tctccaagat cgccacgc                           98

<210> SEQ ID NO 264
<211> LENGTH: 95
<212> TYPE: DNA
<213> ORGANISM: Homo sapiens

<400> SEQUENCE: 264
ggcagccggc tacccgttca gcgccggact gccccggct gcctcctgcc cggagaagtg    60
cgccctgttt aacagcgtct cctccagcct ctgca                              95

<210> SEQ ID NO 265
<211> LENGTH: 115
<212> TYPE: DNA
<213> ORGANISM: Homo sapiens

<400> SEQUENCE: 265
cacgtcggag ctcgcctgga tccgggcgtt ggcagccgaa gggccctggc cccgggactc    60
tccgccgcta gccccgtca tatcttctcc gctttcgctt ctccactcta gccgg         115

<210> SEQ ID NO 266
<211> LENGTH: 91
<212> TYPE: DNA
<213> ORGANISM: Homo sapiens

<400> SEQUENCE: 266
ttgtttttct ggaaaagtcg ctgcaatgga cacagcgttg cgcggtttcc ctgcgcgcct    60
ggggcgcttt tgtcttcgc cctccgtgga t                                   91

```
<210> SEQ ID NO 267
<211> LENGTH: 100
<212> TYPE: DNA
<213> ORGANISM: Homo sapiens

<400> SEQUENCE: 267
ggcatctatg cgggcatggt tactgcctct ggtgcccccc gcagccgcgc gcaggtaccg      60
tgcgacatcg cgatggccca gctcctcagc caggtccacg                          100

<210> SEQ ID NO 268
<211> LENGTH: 61
<212> TYPE: DNA
<213> ORGANISM: Homo sapiens

<400> SEQUENCE: 268
agccttctct ttgcgccacg ttcggccgca gctgaattca tttctccttc cacgtcgcgc      60
a                                                                    61

<210> SEQ ID NO 269
<211> LENGTH: 130
<212> TYPE: DNA
<213> ORGANISM: Homo sapiens

<400> SEQUENCE: 269
gtggggtcgt agtggtttcc gaggttggtg accacgtcgt cgaacttgag cacctcgtag      60
ccttcatgct gccgcttgag gccggcgtag aaggcgatct tgggcaccgt gctgtaggtg     120
gcggcgctga                                                           130

<210> SEQ ID NO 270
<211> LENGTH: 68
<212> TYPE: DNA
<213> ORGANISM: Homo sapiens

<400> SEQUENCE: 270
gcgaggatgt ggatggcgcg gatggcgcgg cctccacctg cgggcagtgg agagagcggc      60
gagaggaa                                                             68

<210> SEQ ID NO 271
<211> LENGTH: 79
<212> TYPE: DNA
<213> ORGANISM: Homo sapiens

<400> SEQUENCE: 271
gccagcagcc aaccccctacg acttcaggag gctcctgcgc aaaacctccc agcgccggcg     60
cctcgtccag cagtcctaa                                                 79

<210> SEQ ID NO 272
<211> LENGTH: 105
<212> TYPE: DNA
<213> ORGANISM: Homo sapiens

<400> SEQUENCE: 272
cactgaagct gcggccctga tctccgcaga ggctgcctgc tgcgctcggc cctcaagtgc      60
ccgggccggc cttcgtgctc cgaaacaaga gacctgggag ccctc                    105

<210> SEQ ID NO 273
<211> LENGTH: 108
<212> TYPE: DNA
<213> ORGANISM: Homo sapiens
```

<400> SEQUENCE: 273
ggaaaagcga tgactgccct gaactgctgg ggcgttcgaa atttccaggg tcccgaccct    60
ccgtggggta cgcgcgactt cggcgcagat gtcagtccgc tgccttcc                108

<210> SEQ ID NO 274
<211> LENGTH: 108
<212> TYPE: DNA
<213> ORGANISM: Homo sapiens

<400> SEQUENCE: 274
cagcggcgac tggttctgac ttgccaagta cctggcacga aaggacgtc gtgtgggtcg     60 tccttaccct gaatttaatg aagtcagggg ctgaaaacgg cggtgtaa                108

<210> SEQ ID NO 275
<211> LENGTH: 140
<212> TYPE: DNA
<213> ORGANISM: Homo sapiens

<400> SEQUENCE: 275
ggtgtgaccg ttgttgcacc ccagtcgaca tgacgttagt ttttcatttg ccaaattgct    60
ggttagttgc aaagcctacc ctcggccgcg agcactgaag gatgggaggg tcgagcgccg   120
cgttttgaca ggaggaagtg                                               140

<210> SEQ ID NO 276
<211> LENGTH: 114
<212> TYPE: DNA
<213> ORGANISM: Homo sapiens

<400> SEQUENCE: 276
tgtgcgcgcg tgtgtcttta cacgcgccgc gtgcccagtg ttgcacgggg cgggagaaga    60
atggcaggta gccgcccgaa acacctcgcc ctgtctcctt tctttgggcg aggt         114

<210> SEQ ID NO 277
<211> LENGTH: 114
<212> TYPE: DNA
<213> ORGANISM: Homo sapiens

<400> SEQUENCE: 277
agctgggagg aagacagtag tgatgctgcc gcgggtggcg ggggttgcgc cgccgcccag    60
agaacctcgg cagtgtgcag ggaggtgcat ttcattttgg ctatttccat cccg          114

<210> SEQ ID NO 278
<211> LENGTH: 116
<212> TYPE: DNA
<213> ORGANISM: Homo sapiens

<400> SEQUENCE: 278
ctcatcgtct tggggttaag agttgccgcc cggccagggc aacagccagg gcaaagggag    60
agagaagccg ccccggggcg agaaggagaa aagttagagg gctgaacagg tgacgc        116

<210> SEQ ID NO 279
<211> LENGTH: 84
<212> TYPE: DNA
<213> ORGANISM: Homo sapiens

<400> SEQUENCE: 279
cagagtgaga gtgtccctgc tgccagagga ctacggcggg ctgggcgcgg ggtccccgcc    60
tctcgctcac cacacagacc ccgc                                          84

<210> SEQ ID NO 280
<211> LENGTH: 73
<212> TYPE: DNA
<213> ORGANISM: Homo sapiens

<400> SEQUENCE: 280
gcccactcca atccccaccc tctccatcct tagtcattaa agaacagcag cgcctggcac    60
gttcttggag gac                                                      73

<210> SEQ ID NO 281
<211> LENGTH: 115
<212> TYPE: DNA
<213> ORGANISM: Homo sapiens

<400> SEQUENCE: 281
cctagggccg acttttccat ctcctcctct acctccggct cccgggcgag ggaggccccg    60
cgccgcccct tagactggct gcggccggaa gattgcagcc gctttgagct tactc         115

<210> SEQ ID NO 282
<211> LENGTH: 71
<212> TYPE: DNA
<213> ORGANISM: Homo sapiens

<400> SEQUENCE: 282
cctcggatcc caagcatatc tggcgatgga gcggcggcag cccgaggcac gtgttgtgtg    60
tgctccgatt g                                                        71

<210> SEQ ID NO 283
<211> LENGTH: 98
<212> TYPE: DNA
<213> ORGANISM: Homo sapiens

<400> SEQUENCE: 283
cgcgtgcgaa gtctcctcta gcggagcggg accggccgcg gcggtggatc gtggcggtcc    60
ctgcacttct gctccagccg cgcctggaaa cctgagcc                            98

<210> SEQ ID NO 284
<211> LENGTH: 96
<212> TYPE: DNA
<213> ORGANISM: Homo sapiens

<400> SEQUENCE: 284
cgcgtgcgaa gtctcctcta gcggagcggg accggccgcg gcggtggatc gtggcggtcc    60
ctgcacttct gctccagccg cgcctggaaa cctgag                              96

<210> SEQ ID NO 285
<211> LENGTH: 88
<212> TYPE: DNA
<213> ORGANISM: Homo sapiens

<400> SEQUENCE: 285
ggctctgatt ggcctgcatc ttgcggcgcg ggcggccgca gcccggcgcg agggagggag    60
cgcggaacaa ggcgctgact gtctccca                                      88

<210> SEQ ID NO 286
<211> LENGTH: 124
<212> TYPE: DNA
<213> ORGANISM: Homo sapiens -continued

<400> SEQUENCE: 286
tgcagggacg tacagggcgg tgatccagta tctaaattct ttgggagaaa atgaatagtt    60 ccccccgcccc cgccctccag gaaaaaaaaa aatctgagaa tctgagaatg ttcagcgcac   120
ccgc                                                                124

<210> SEQ ID NO 287
<211> LENGTH: 92
<212> TYPE: DNA
<213> ORGANISM: Homo sapiens

<400> SEQUENCE: 287
aaaaagccaa tctccaagcc tccaaacgga acgtcaccct atcagctggg agacagcgcc    60
gcactgactg acaagccgcg catatttatc ct                                 92

<210> SEQ ID NO 288
<211> LENGTH: 70
<212> TYPE: DNA
<213> ORGANISM: Homo sapiens

<400> SEQUENCE: 288
cgcggccacc caccctagtc gttggagcct ggcgcccgcg cctccggcc ggcagcacgt     60 caaaacggcg                                                           70

<210> SEQ ID NO 289
<211> LENGTH: 102
<212> TYPE: DNA
<213> ORGANISM: Homo sapiens

<400> SEQUENCE: 289
ttctaacgag ggctcagctc cgactacccc aggcctccgg ggaccctctc cggatgcgct    60
ccccgctttg cgctttgcgc tttttgcctg ttccctgggg tc                     102

<210> SEQ ID NO 290
<211> LENGTH: 84
<212> TYPE: DNA
<213> ORGANISM: Homo sapiens

<400> SEQUENCE: 290
ccgcccgcag gatcgagtga gtcacgcggc cgccagacga ggccggtggc gcacgcaccc    60
gagatccgat gtagtgcacc gcct                                          84

<210> SEQ ID NO 291
<211> LENGTH: 129
<212> TYPE: DNA
<213> ORGANISM: Homo sapiens

<400> SEQUENCE: 291
cgctcgttgc gacccaggct cagctccgcg gtgcgcaggg cctggcgcct tcgcggctgc    60
ccgcccgggc tcagctcctc cacagccacg cggcaccgca gctccgagtc ctcatattcc   120
cctgccgcc                                                           129

<210> SEQ ID NO 292
<211> LENGTH: 103
<212> TYPE: DNA
<213> ORGANISM: Homo sapiens

<400> SEQUENCE: 292
caactccgag gagctagcgc agaccgctct ccgccctcag ctgcggcgag gcaagggctg    60

```
gcagcgctcg gacgcctccg tcttgccctt cccatgccta agc         103
```

<210> SEQ ID NO 293
<211> LENGTH: 76
<212> TYPE: DNA
<213> ORGANISM: Homo sapiens

<400> SEQUENCE: 293

```
tgcctaagcg cggggaatta cacgttcccg gtgtagaaca gacgatcggg gctattaggg   60
ctgggcggtg ggagtg                                                   76
```

<210> SEQ ID NO 294
<211> LENGTH: 72
<212> TYPE: DNA
<213> ORGANISM: Homo sapiens

<400> SEQUENCE: 294

```
ctggcttcag tacataacgc gagttacagt tcaacagaac cagatgtgaa aacgtcagcc   60
acccagttca gg                                                       72
```

<210> SEQ ID NO 295
<211> LENGTH: 113
<212> TYPE: DNA
<213> ORGANISM: Homo sapiens

<400> SEQUENCE: 295

```
tattaagaac cgcaagccca ctgtgtgcca gccgccgttg gtagttttac acgtgcgatc   60
ttatttaata cttcctggga cctaatgagt caggtgccat catgatccgt tta          113
```

<210> SEQ ID NO 296
<211> LENGTH: 103
<212> TYPE: DNA
<213> ORGANISM: Homo sapiens

<400> SEQUENCE: 296

```
aggctccgaa tcgcacctct tctcctgtcc taatctcagg ctccaggcct ggcttgcagt   60
ttctggctca ccgcgctgcg gtcaccggcc cacactccca gga                     103
```

<210> SEQ ID NO 297
<211> LENGTH: 102
<212> TYPE: DNA
<213> ORGANISM: Homo sapiens

<400> SEQUENCE: 297

```
ggctctgcct gtttgttccg ccccgcgga aaccgctgct cgctgggcag gggctttctg    60
ttttgcagcc ggaacaggaa cacagatagc ccgccaagcc gc                      102
```

<210> SEQ ID NO 298
<211> LENGTH: 113
<212> TYPE: DNA
<213> ORGANISM: Homo sapiens

<400> SEQUENCE: 298

```
gaaaaacaga gaggcgaggc cagactgccc ccacacctcc tgtagccact gagcgcgaag   60
tgcgttggtt ccgagcgcgc tggtgggatc cacaaagctc gcattctctc agg          113
```

<210> SEQ ID NO 299
<211> LENGTH: 110
<212> TYPE: DNA

<213> ORGANISM: Homo sapiens

<400> SEQUENCE: 299
cgagttctgg gcctctggag gtttccctgt cagcctcccc ggccgccgag ggggcgcgcg    60
cccaacaagg gggtctctag cggccacctg gggacagaaa cagtgaccct              110

<210> SEQ ID NO 300
<211> LENGTH: 95
<212> TYPE: DNA
<213> ORGANISM: Homo sapiens

<400> SEQUENCE: 300
ggtggaggat gtggaggtgg aagtggagcg gatggcgctc cccaagagct ccgccacgcg    60
aggtttcggg ctcgtggttt tgcttcctcc gggtc                              95

<210> SEQ ID NO 301
<211> LENGTH: 76
<212> TYPE: DNA
<213> ORGANISM: Homo sapiens

<400> SEQUENCE: 301
tggcctccaa ctttaacgac atagtcaagc agggctacgt gaaaatccgc agcaggaagc    60
ttggggtgag tggctc                                                   76

<210> SEQ ID NO 302
<211> LENGTH: 121
<212> TYPE: DNA
<213> ORGANISM: Homo sapiens

<400> SEQUENCE: 302
ggcgacgcgt ttccctggtt acctgcgggg ccgcgtcccg gaggagcctg agggccaaga    60
gggccggcgc gcggtgggcg cggcctgcgg ggatgccggg ctctacggag cagcgcgggg   120
t                                                                  121

<210> SEQ ID NO 303
<211> LENGTH: 118
<212> TYPE: DNA
<213> ORGANISM: Homo sapiens

<400> SEQUENCE: 303
tttcggattc tggacttcgg gttccgctga ggacggattt cggaataggc acagtggctg    60
ccccgaaccc ctcaaggcgg cctccgcggg ctgtggctga agataatttt cggcgggc    118

<210> SEQ ID NO 304
<211> LENGTH: 96
<212> TYPE: DNA
<213> ORGANISM: Homo sapiens

<400> SEQUENCE: 304
ttgtgatatt tggttgcgcg ggattatgat gaaatgtgtg atatgtgtgt gattatgatt    60
aaggctgtag cgagtgtgaa cgtggcgaag tgtgcg                             96

<210> SEQ ID NO 305
<211> LENGTH: 71
<212> TYPE: DNA
<213> ORGANISM: Homo sapiens

<400> SEQUENCE: 305
gggagtgggt gtggtgtgag gctggcgctg gagcggtctg ggaatgttag gaggtctagg    60

-continued gtatcgcggc c                                                      71

<210> SEQ ID NO 306
<211> LENGTH: 85
<212> TYPE: DNA
<213> ORGANISM: Homo sapiens

<400> SEQUENCE: 306
aggtaggtac cgcctgcctg tgtgtaccgg ggctgctgtc tccggggagg ggcttctggc    60
ggacaggaga accaagcagc ctcag                                        85

<210> SEQ ID NO 307
<211> LENGTH: 79
<212> TYPE: DNA
<213> ORGANISM: Homo sapiens

<400> SEQUENCE: 307
accctggggt gtagctctgt gtcccactgt gtgatgacgt gtgcgtgctt ctgtgcgtgt    60
gtgtgtgttt gtgcgcgtg                                              79

<210> SEQ ID NO 308
<211> LENGTH: 73
<212> TYPE: DNA
<213> ORGANISM: Homo sapiens

<400> SEQUENCE: 308
tctcgcgatg tttcagggtg agccggacgc aggcgtgcct gcgcagtgcg cggaggagtg    60
ctgttcgtgt gtt                                                    73

<210> SEQ ID NO 309
<211> LENGTH: 86
<212> TYPE: DNA
<213> ORGANISM: Homo sapiens

<400> SEQUENCE: 309
gggcacaggt ggggtccgtc aggccgcccg gggctcctct gtcccagctc tgcggcccag    60
ggggtgacgt gatggcggca gcggtg                                      86

<210> SEQ ID NO 310
<211> LENGTH: 104
<212> TYPE: DNA
<213> ORGANISM: Homo sapiens

<400> SEQUENCE: 310
accggtctcc tcgtatccat cctcgcagtc cccaccccaa actaatgttc tcccctgagc    60
aaatttcgag acacttaaaa tcccagctaa gatcacgtcc ttct                  104

<210> SEQ ID NO 311
<211> LENGTH: 109
<212> TYPE: DNA
<213> ORGANISM: Homo sapiens

<400> SEQUENCE: 311
aggcaggaga ggggaggaag agaacctgtg cccctggaag ctagaggaga gcctcgctct    60
ctctgctgct ctgggttccg caacgaattg agttcgggtt caggcggct             109

<210> SEQ ID NO 312
<211> LENGTH: 65
<212> TYPE: DNA

```
<213> ORGANISM: Homo sapiens

<400> SEQUENCE: 312
ggctcttttg catgcaggcc cgcctgaatg gggcgcctgg aggctgcatt gaggccgggc      60
tgtgt                                                                  65

<210> SEQ ID NO 313
<211> LENGTH: 78
<212> TYPE: DNA
<213> ORGANISM: Homo sapiens

<400> SEQUENCE: 313
gctgcattga ggccgggctg tgtaaactgt agggtgcctc gccgactcgg agccgcagag      60
actggcggcg ggtcaact                                                    78

<210> SEQ ID NO 314
<211> LENGTH: 101
<212> TYPE: DNA
<213> ORGANISM: Homo sapiens

<400> SEQUENCE: 314
cttcccaggt caccattgct cctctgccct ctccacatcc gccctcccgt gagcgcagga      60
tgcacgcaca ggcagcggtt acaaaactca gcgcaacgtt g                         101

<210> SEQ ID NO 315
<211> LENGTH: 111
<212> TYPE: DNA
<213> ORGANISM: Homo sapiens

<400> SEQUENCE: 315
ggcaccacta gctcctcgtc ctcctcggag gggcgcccga gtgcgtccga cacggccagt      60
agcgccgcgg cgagcagcag cagcgtgggt actggcccaa agctccgaga c              111

<210> SEQ ID NO 316
<211> LENGTH: 108
<212> TYPE: DNA
<213> ORGANISM: Homo sapiens

<400> SEQUENCE: 316
atctctttac cctggagcca gaaccagcgt cgccgccgtc ccctgcagct cagccggcaa      60
cgcgcgccga gcctcggggc gcagcttgga gacgcgcttg ctcgttct                  108

<210> SEQ ID NO 317
<211> LENGTH: 81
<212> TYPE: DNA
<213> ORGANISM: Homo sapiens

<400> SEQUENCE: 317
cgcgaggtca tcctgcccta ctcagcggcg cactgccagg gcgcgcccgg ccgcaagctc      60
tccaagatag ccacgctgct g                                                81
```

DETECTION OF COLORECTAL CANCER AND/OR ADVANCED ADENOMAS

SEQUENCE LISTING

The instant application contains a Sequence Listing which has been submitted electronically in ASCII format and is hereby incorporated by reference in its entirety. Said ASCII copy, created on Nov. 6, 2019, is named 2011722-0044_SQL.txt and is 115,038 bytes in size.

FIELD

This invention generally relates to methods and kits for the detection of and/or pre-emptive screening for colorectal cancer and/or advanced adenomas. In certain embodiments, the methods and kits described herein utilize identified differentially-methylated regions of the human genome as markers to determine the presence and/or risk of colorectal cancer and/or advanced adenomas in subjects.

BACKGROUND

Cancer screening is a critical component of cancer prevention, diagnosis, and treatment. Colorectal cancer (CRC) has been identified, according to some reports, as the third most common type of cancer and the second most frequent cause of cancer mortality in the world. According to some reports, there are over 1.8 million new cases of colorectal cancer per year and about 881,000 deaths from colorectal cancer, accounting for about 1 in 10 cancer deaths. Regular colorectal cancer screening is recommended, particular for individuals over age 50. Moreover, incidence of colorectal cancer in individuals below 50 has increased over time. Statistics suggest that current colorectal cancer screening techniques are insufficient. Despite improvements over time, only about 40-44% of colorectal cancers are currently detected by screening in an early, localized stage. This is at least in part due to insufficient sensitivity and/or specificity of current screening techniques. Currently recommended techniques include colonoscopy and/or fecal blood testing for those over age 50.

Most colorectal cancers originate from colon polyps that initially appeared, according to histology, to be benign. Accordingly, the advanced detection and removal of colon polyps are important parts of colon cancer screening. However, determining which polyps will develop into invasive cancers is difficult based on histopathological classifications alone. Histopathological classification of a polyp as an advanced adenoma, which has a tendency to progress to a malignant tumor, is routinely performed on samples resected from colon tissue during, for example, colonoscopies. Advanced adenomas are classified as having one or more of the following features: having a large size (i.e., the adenoma being greater than 1 cm); having high grade dysplasia; having a prominent villous component; and/or having serrated features. However, even when an adenoma is classified as an advanced adenomas according to the aforementioned classification, the adenoma may not progress to an invasive carcinoma.

Without wishing to be bound to any particular theory, adenomas or polyps that progress to an invasive carcinoma will acquire and accumulate genetic alterations that are distinct from normal tissue. Through the identification of these distinct alterations, a molecular fingerprint may be developed to help determine if an adenoma will progress to an invasive carcinoma. Developing tools and techniques to determine the molecular fingerprint of advanced carcinomas and colorectal cancers would aid in the identification of colorectal cancer at its earliest stages. Accordingly, there is a need for tools and screening techniques to accurately screen for colorectal cancer at its earliest stages.

SUMMARY OF THE INVENTION

The present disclosure provides, among other things, methods for colorectal cancer and/or advanced adenoma screening and compositions related thereto. In various embodiments as specifically disclosed herein, the present disclosure provides methods for colorectal cancer and/or advanced adenoma screening that include identification of the methylation status of at least one of one or more methylation sites found within a differentially methylated region (DMR) of DNA of a human subject. In various embodiments as specifically disclosed herein, the present disclosure provides methods for colorectal cancer and/or advanced adenoma screening that include screening methylation status of one or more methylation biomarkers in cfDNA (cell free DNA), e.g., in ctDNA (circulating tumor DNA). In various embodiments, the present disclosure provides methods for colorectal cancer and/or advanced adenoma screening that include screening methylation status of one or more methylation biomarkers in cfDNA, e.g., in ctDNA, using MSRE-qPCR. Various compositions and methods provided herein provide sensitivity and specificity sufficient for clinical application in colorectal cancer and/or advanced adenoma screening. Various compositions and methods provided herein are useful in colorectal cancer and/or advanced adenoma screening by analysis of an accessible tissue sample of a subject, e.g., a tissue sample that is blood or a blood component (e.g., cfDNA, e.g., ctDNA), colorectal tissue, or stool.

In certain embodiments, any of the methods as disclosed herein may be used in vitro.

In one aspect, the present disclosure provides a method of (i) screening for colorectal cancer or (ii) screening for advanced adenoma, or (iii) screening for the presence of either colorectal cancer or advanced adenoma (or both), the method comprising determining a methylation status of at least one methylation site found within a differentially methylated region (DMR) of DNA of a human subject as listed in Table 1 or Table 7.

In various embodiments as specifically referred to in the preceding paragraph, the method comprises, for each of one or more DMRs listed in Table 1 or Table 7, determining a methylation status of at least three methylation sites found within the DMR.

In various embodiments as specifically referred to in the preceding paragraphs, the method comprises, for each of one or more DMRs listed in Table 1 or Table 7, determining a methylation status of at least four methylation sites found within the DMR.

In various embodiments as specifically referred to in the preceding paragraphs, the method comprises, for each of one or more DMRs listed in Table 1 or Table 7, determining a methylation status of at least five methylation sites found within the DMR.

In various embodiments as specifically referred to in the preceding paragraphs, the method comprises, for each of three or more DMRs listed in Table 1 or Table 7, determining a methylation status of at least one methylation site found within the DMR In various embodiments as specifically referred to in the preceding paragraphs, the method comprises, for each of three or more DMRs listed in Table 1 or Table 7, determining a methylation status of at least three methylation sites found within the DMR.

In various embodiments as specifically referred to in the preceding paragraphs, the method comprises, for each of three or more DMRs listed in Table 1 or Table 7, determining a methylation status of at least four methylation sites found within the DMR.

In various embodiments as specifically referred to in the preceding paragraphs, the method comprises, for each of three or more DMRs listed in Table 1 or Table 7, determining a methylation status of at least five methylation sites found within the DMR.

In various embodiments as specifically referred to in the preceding paragraphs, the method comprises, for each of ten or more DMRs listed in Table 1 or Table 7, determining a methylation status of at least one methylation site found within the DMR.

In various embodiments as specifically referred to in the preceding paragraphs, the method comprises, for each of ten or more DMRs listed in Table 1 or Table 7, determining a methylation status of at least three methylation sites found within the DMR.

In various embodiments as specifically referred to in the preceding paragraphs, the method comprises, for each of ten or more DMRs listed in Table 1 or Table 7, determining a methylation status of at least four methylation sites found within the DMR.

In various embodiments as specifically referred to in the preceding paragraphs, the method comprises, for each of ten or more DMRs listed in Table 1 or Table 7, determining a methylation status of at least five methylation sites found within the DMR In various embodiments as specifically referred to in the preceding paragraphs, the method comprises, for each of thirty-five or more DMRs listed in Table 1, determining a methylation status of at least one methylation sites found within the DMR.

In various embodiments as specifically referred to in the preceding paragraphs, the method comprises, for each of thirty-five or more DMRs listed in Table 1, determining a methylation status of at least three methylation sites found within the DMR.

In various embodiments as specifically referred to in the preceding paragraphs, the method comprises, for each of thirty-five or more DMRs listed in Table 1, determining a methylation status of at least four methylation sites found within the DMR.

In various embodiments as specifically referred to in the preceding paragraphs, the method comprises, for each of thirty-five or more DMRs listed in Table 1, determining a methylation status of at least five methylation sites found within the DMR.

In various embodiments as specifically referred to in the preceding paragraphs, the method comprises, for each of forty or more DMRs listed in Table 7, determining a methylation status of at least three methylation sites found within the DMR.

In various embodiments as specifically referred to in the preceding paragraphs, the method comprises, for each of forty or more DMRs listed in Table 7, determining a methylation status of at least four methylation sites found within the DMR.

In various embodiments as specifically referred to in the preceding paragraphs, the method comprises, for each of forty or more DMRs listed in Table 7, determining a methylation status of at least five methylation sites found within the DMR.

In various embodiments as specifically referred to in the preceding paragraphs, the DMR comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, the method comprises determining whether the at least one methylation site is methylated as compared to a reference (e.g., wherein the reference is DNA from a population of one or more human subjects having been confirmed as not suffering from either advanced adenoma or colorectal cancer), wherein methylation is indicative of (i) colorectal cancer, (ii) advanced adenoma, or (iii) either colorectal cancer or advanced adenoma (or both).

In various embodiments as specifically referred to in the preceding paragraph, wherein the method comprises determining the methylation status of at least one methylation site found within each of the DMRs as listed in Table 2.

In various embodiments as specifically referred to in the preceding paragraphs, the method comprises determining the methylation status of at least one methylation site found within each of the DMRs as listed in Table 3.

In various embodiments as specifically referred to in the preceding paragraphs, the method comprises determining the methylation status of at least one methylation site found within each of the DMRs as listed in Table 4.

In various embodiments as specifically referred to in the preceding paragraphs, the one or more of the DMRs are amplified by oligonucleotide primer pairs as listed in Table 5.

In various embodiments as specifically referred to in the preceding paragraphs, the DNA of the human subject is isolated from a member selected from the group consisting of tissue (e.g., colorectal tissue, e.g., a polyp, an adenoma), blood, plasma, urine, saliva, and stool of the human subject.

In various embodiments as specifically referred to in the preceding paragraphs, the DNA is cell-free DNA of the human subject.

In various embodiments as specifically referred to in the preceding paragraphs, the subject was asymptomatic for either colorectal cancer or advanced adenomas (or both) at the time of screening.

In various embodiments as specifically referred to in the preceding paragraphs, the subject had been previously screened for either colorectal cancer or advanced adenomas (or both).

In various embodiments as specifically referred to in the preceding paragraphs, the subject had been screened for either colorectal cancer or advanced adenomas (or both) within the last 10 years, within the last 5 years, within the last 4 years, within the last 3 years, within the last 2 years, or within the last year.

In various embodiments as specifically referred to in the preceding paragraphs, a previous screen for either advanced adenomas or colorectal cancer (or both) in the subject had diagnosed the subject as not having (i) colorectal cancer, (ii) advanced adenoma, or (iii) advanced adenoma or colorectal cancer (or both). In various embodiments of this and specifically referred to in the preceding paragraphs, the previous screen for either advanced adenomas or colorectal cancer (or both) that had diagnosed the subject as not having (i) colorectal cancer, (ii) advanced adenoma, or (iii) advanced adenoma or colorectal cancer (or both) was within one year.

In various embodiments as specifically referred to in the preceding paragraphs, the previous screen for either advanced adenoma or colorectal cancer (or both) that had diagnosed the subject as not having either advanced adenomas or colorectal cancer (or both) was a colonoscopy.

In various embodiments as specifically referred to in the preceding paragraphs, the method includes diagnosis of early stage colorectal cancer (e.g., wherein the colorectal cancer is a stage 0, stage I, stage IIA, stage IIB, or stage IIC colorectal cancer).

In various embodiments as specifically referred to in the preceding paragraphs, the method includes diagnosis of early stage colorectal cancer, wherein the cancer has not metastasized.

In various embodiments as specifically referred to in the preceding paragraphs, methylation status is determined using one or more members selected from the group consisting of methylation sensitive restriction enzyme quantitative polymerase chain reaction (MSRE-qPCR), Methylation-Specific PCR, Methylation Specific Nuclease-assisted Minor-allele Enrichment PCR, hybrid-capture targeted next-generation sequencing, and amplicon based targeted next-generation sequencing.

In various embodiments as specifically referred to in the preceding paragraphs, methylation status is determined using whole genome bisulfite sequencing.

In various embodiments as specifically referred to in the preceding paragraphs, the method is an in vitro method.

In another aspect, the present disclosure provides a method of methylation specific restriction enzyme quantitative polymerase chain reaction (MSRE-qPCR) for (i) screening for colorectal cancer or (ii) screening for advanced adenoma, or (iii) screening for the presence of either colorectal cancer or advanced adenoma (or both), the method comprising: (a) contacting DNA of a human subject with one or more methylation specific restriction enzymes; and (b) performing qPCR of enzyme-digested DNA, or amplicons thereof, to determine the methylation status of one or more regions of DNA, wherein each of the one or more regions of DNA comprises at least a portion of the one or more DMRs of Table 1, each portion being at least 10, at least 15, at least 20, at least 24, at least 30, at least 40, at least 50, at least 100, at least 150, at least 200, at least 250, at least 300, at least 350, at least 400, at least 500, at least 1000 or more base pairs in length.

In various embodiments as specifically referred to in the preceding paragraph, wherein at least one of the one or more of the regions of DNA is amplified by a corresponding oligonucleotide primer pair (e.g., wherein the primer pair comprises a forward and a reverse primer).

In various embodiments as specifically referred to in the preceding paragraphs, each of the one or more regions of DNA comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, a corresponding oligonucleotide primer pair is an oligonucleotide primer pair listed in Table 5. In various embodiments as specifically referred to herein and in the preceding paragraphs, a forward primer of the corresponding oligonucleotide primer pair is at least 80%, at least 85%, at least 90%, at least 95%, at least 99%, or at least 99.5% identical to a forward primer listed in Table 5.

In various embodiments as specifically referred to in the preceding paragraphs, a reverse primer of the corresponding oligonucleotide primer pair is at least 80%, at least 85%, at least 90%, at least 95%, at least 99%, or at least 99.5% identical to a reverse primer listed in Table 5.

In various embodiments as specifically referred to in the preceding paragraphs, the DNA is isolated from a member selected from the group consisting of tissue (e.g., colorectal tissue, e.g., a polyp, an adenoma), blood, plasma, urine, saliva, and stool of the human subject.

In various embodiments as specifically referred to in the preceding paragraphs, the DNA is cell-free DNA of the human subject.

In various embodiments as specifically referred to in the preceding paragraphs, the method provides a sensitivity for detecting colorectal cancer of at least 0.67. In various embodiments as specifically referred to in this and the preceding paragraphs, the method provides the sensitivity for detecting colorectal cancer of at least 0.78.

In various embodiments as specifically referred to in the preceding paragraphs, the method provides an overall sensitivity for detecting a combination of advanced adenoma and colorectal cancer of at least 0.48. In various embodiments as specifically referred to in this and the preceding paragraphs, the method provides an overall sensitivity for detecting the combination of advanced adenoma and colorectal cancer of at least 0.53.

In various embodiments as specifically referred to in the preceding paragraphs, the method provides a specificity of at least 0.9. In various embodiments as specifically referred to in this and the preceding paragraphs, the method provides a specificity of at least 0.93.

In various embodiments as specifically referred to in the preceding paragraphs, the one or more regions of DNA comprise each of the DMRs of Table 2.

In various embodiments as specifically referred to in the preceding paragraphs, each of the one or more regions of DNA is at least 80%, at least 85%, at least 90%, at least 95%, at least 99%, or at least 99.5% identical to, or comprises, a corresponding DMR of Table 2.

In various embodiments as specifically referred to in the preceding paragraphs, the one or more regions of DNA comprise each of the DMRs of Table 3.

In various embodiments as specifically referred to in the preceding paragraphs, each of the one or more regions of DNA is at least 80%, at least 85%, at least 90%, at least 95%, at least 99%, or at least 99.5% identical to, or comprises, a corresponding DMR of Table 3.

In various embodiments as specifically referred to in the preceding paragraphs, the one or more regions of DNA comprise each of the DMRs of Table 4.

In various embodiments as specifically referred to in the preceding paragraphs, each of the one or more regions of DNA is at least 80%, at least 85%, at least 90%, at least 95%, at least 99%, or at least 99.5% identical to, or comprises, a corresponding DMR of Table 4.

In various embodiments as specifically referred to in the preceding paragraphs, the method is an in vitro method.

In another aspect, the present disclosure provides a kit for use in (i) screening for colorectal cancer or (ii) screening for advanced adenoma, or (iii) screening for the presence of either colorectal cancer or advanced adenoma (or both), the kit comprising: (a) at least one oligonucleotide primer pair designed to amplify at least a portion of one or more DMRs of Table 1, each portion being at least 10, at least 15, at least 20, at least 24, at least 30, at least 40, at least 50, at least 100, at least 150, at least 200, at least 250, at least 300, at least 350, at least 400, at least 500, at least 1000 or more base pairs in length; and (b) at least one methylation specific restriction enzyme and/or a bisulfite reagent.

In various embodiments as specifically referred to in the preceding paragraph, the portion of the one or more DMRs comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, the oligonucleotide primer pairs include oligonucleotide primer pairs for amplification of each DMR of Table 2.

In various embodiments as specifically referred to in the preceding paragraphs, the oligonucleotide primer pairs include oligonucleotide primer pairs for amplification of each DMR of Table 3.

In various embodiments as specifically referred to in the preceding paragraphs, the oligonucleotide primer pairs include oligonucleotide primer pairs for amplification of each DMR of Table 4.

In various embodiments as specifically referred to in the preceding paragraphs, the oligonucleotide primer pairs include at least one oligonucleotide primer pair of Table 5.

In various embodiments as specifically referred to in the preceding paragraphs, at least one of the oligonucleotides of the oligonucleotide primer pair is at least 80%, at least 85%, at least 90%, at least 95%, at least 99%, or at least 99.5% identical to or comprises at least one forward primer of Table 5.

In various embodiments as specifically referred to in the preceding paragraphs, at least one of the oligonucleotides of the oligonucleotide primer pair is at least 80%, at least 85%, at least 90%, at least 95%, at least 99%, or at least 99.5% identical to or comprises at least one reverse primer of Table 5.

In various embodiments as specifically referred to in the preceding paragraphs, the kit further comprises using the determined methylation status (e.g., the percent hypermethylation, the ratio of hypermethylation) of the one or more methylation sites to identify at least one of (i) to (iv) as follows: (i) a presence of colorectal cancer in the human subject; (ii) a predisposition for colorectal cancer in the human subject; (iii) an increased risk of colorectal cancer in the human subject, and (iv) a stage of colorectal cancer in the human subject.

In various embodiments as specifically referred to in the preceding paragraphs, the kit further comprises using the determined methylation status (e.g., the percent hypermethylation, the ratio of hypermethylation) of the one or more methylation sites to identify at least one of (i) to (iv) as follows: (i) a presence of one or more advanced adenomas in the human subject; (ii) a predisposition for advanced adenomas in the human subject; (iii) an increased risk of advanced adenomas in the human subject, and (iv) a type of adenoma in the human subject.

In various embodiments as specifically referred to in the preceding paragraphs, the kit further comprises using the determined methylation status (e.g., the percent hypermethylation, the ratio of hypermethylation) of the one or more methylation sites to identify at least one of (i) to (iv) as follows: (i) a presence of either colorectal cancer or advanced adenomas or both in the human subject; (ii) a predisposition for either colorectal cancer or advanced adenomas or both in the human subject; (iii) an increased risk of either colorectal cancer or advanced adenomas or both in the human subject, and (iv) a stage of either colorectal cancer or advanced adenomas or both in the human subject.

In various embodiments as specifically referred to in the preceding paragraphs, the kit is used in vitro.

In another aspect, the present disclosure provides a diagnostic qPCR reaction for (i) screening for colorectal cancer or (ii) screening for advanced adenoma, or (iii) screening for the presence of either colorectal cancer or advanced adenoma (or both), the diagnostic qPCR reaction including: (a) human DNA; (b) a polymerase; and (c) at least one oligonucleotide primer pair designed to amplify at least a portion of one or more DMRs of Table 1, each portion of the one or more DMRs being at least 10, at least 15, at least 20, at least 24, at least 30, at least 40, at least 50, at least 100, 150, 200, 250, 300, 350, 400, 500, 1000 or more base pairs in length, wherein the human DNA is bisulfite-treated human DNA or methylation specific restriction enzyme-digested human DNA.

In various embodiments as specifically referred to in the preceding paragraph, the portion of the one or more DMRs comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, the oligonucleotide primer pairs include oligonucleotide primer pairs for amplification of each DMR of Table 2.

In various embodiments as specifically referred to in the preceding paragraphs, the oligonucleotide primer pairs include oligonucleotide primer pairs for amplification of each DMR of Table 3.

In various embodiments as specifically referred to in the preceding paragraphs, the oligonucleotide primer pairs include oligonucleotide primer pairs for amplification of each DMR of Table 4.

In various embodiments as specifically referred to in the preceding paragraphs, the oligonucleotide primer pairs include at least one oligonucleotide primer pair of Table 5.

In various embodiments as specifically referred to in the preceding paragraphs, at least one of the oligonucleotides of the oligonucleotide primer pair is at least 80%, at least 85%, at least 90%, at least 95%, at least 99%, or at least 99.5% identical to or comprises at least one forward primer of Table 5.

In various embodiments as specifically referred to in the preceding paragraphs, at least one of the oligonucleotides of the oligonucleotide primer pair is at least 80%, at least 85%, at least 90%, at least 95%, at least 99%, or at least 99.5% identical to or comprises at least one reverse primer of Table 5.

In various embodiments as specifically referred to in the preceding paragraphs, the reaction further comprises using the determined methylation status (e.g., the percent hypermethylation, the ratio of hypermethylation) of the one or more methylation sites to identify at least one of (i) to (iv) as follows: (i) a presence of colorectal cancer in the human subject; (ii) a predisposition for colorectal cancer in the human subject; (iii) an increased risk of colorectal cancer in the human subject, and (iv) a stage of colorectal cancer in the human subject.

In various embodiments as specifically referred to in the preceding paragraphs, the reaction further comprises using the determined methylation status (e.g., the percent hypermethylation, the ratio of hypermethylation) of the one or more methylation sites to identify at least one of (i) to (iv) as follows: (i) a presence of one or more advanced adenomas in the human subject; (ii) a predisposition for advanced adenomas in the human subject; (iii) an increased risk of advanced adenomas in the human subject, and (iv) a type of adenoma in the human subject.

In various embodiments as specifically referred to in the preceding paragraphs, the reaction further comprises using the determined methylation status (e.g., the percent hypermethylation, the ratio of hypermethylation) of the one or more methylation sites to identify at least one of (i) to (iv) as follows: (i) a presence of either colorectal cancer or advanced adenomas or both in the human subject; (ii) a predisposition for either colorectal cancer or advanced adenomas or both in the human subject; (iii) an increased risk of either colorectal cancer or advanced adenomas or both in the human subject, and (iv) a stage of either colorectal cancer or advanced adenomas or both in the human subject.

In various embodiments as specifically referred to in the preceding paragraphs, the reaction is performed in vitro.

In another aspect, the present disclosure provides a method of (i) screening for colorectal cancer or (ii) screening for advanced adenoma, or (iii) screening for the presence of either colorectal cancer or advanced adenoma (or both), the method comprising: determining a methylation status of one or more differentially methylated regions (DMRs), each of said one or more DMRs comprising or overlapping with one or more genes selected from the group consisting of PAX7, NTNG1, SYT6, LINC01248, KCNK3, GALNT14, CHST10, THSD7B, UNC80, EPHA6, MED12L, ADGRL3, RNF150, SPOCK3, GPM6A, HELT, GFPT2, HSPA1L, HSPA1A, NKAIN2, TMEM178B, DPP6, MICU3, ALKAL1, LOC401463, BHLHE22, RIMS2, LOC105375690, SLC25A32, DMRT1, CDKN2A, CDKN2B-AS1, PAX5, C1QL3, MYO3A, LOC101929073, GAD2, MYO3A, FOXI2, LOC105369438, AMOTL1, LOC101928847, NCAM1, DSCAML1, PTPRO, RERG, DPY19L2, CUX2, PCDH9, MIR4500HG, SLITRK5, SLC8A3, LOC646548, GATM, PIF1, RASGRF1, VAC14, VAT1L, JPH3, SLFN13, ZACN, SRP68, GALR2, ADCYAP1, CDH2, DOK6, ZNF461, ZNF829, ZNF568, ZNF540, ZNF571-AS1, CIC, ZNF582-AS1, ZNF582, ZNF471, ZNF264, ZNF671, ZNF551, ZNF776, NKX2-2, ADAMTS1, TIAM1, and OLIG1; applying a classification model using as input the determined methylation status of each of said one or more DMRs; and outputting, from the model, a predicted status of colorectal cancer or a predicted status of advanced adenoma or a predicted status of either colorectal cancer or advanced adenoma (e.g., the latter meaning a status of having either or both colorectal cancer and advanced adenoma) of the human subject.

In various embodiments as specifically referred to in the preceding paragraph, the method comprises determining the methylation status of the one or more DMRs comprising or overlapping with at least each of the genes GAD2, MYO3A, and ALKAL1.

In various embodiments as specifically referred to in the preceding paragraphs, the method comprises determining the methylation status of the one or more DMRs comprising or overlapping with at least each of the genes GAD2, MYO3A, ALKAL1, RASGRF1, MICU3, RASGRF1, FOXI2, C1QL3, CDKN2A, and CDKN2B-AS1.

In various embodiments as specifically referred to in the preceding paragraphs, the method comprises determining the methylation status of the one or more DMRs comprising or overlapping with at least each of the genes GAD2, MYO3A, ALKAL1, RASGRF1, MICU3, RASGRF1, FOXI2, C1QL3, CDKN2A, CDKN2B-AS1, SYT6, SLFN13, GPM6A, THSD7B, ZBF582-AS1, ZNF582, GATM, ZNF540, ZNF571-AS1, OLIG1, EPHA6, DPY19L2, SLC8A3, LOC646548, LOC101929073, UNC80, DPP6, ZNF568, JPH3, ZNF461, NTNG1, ADGRL3, ADAMST1, CDH2, LINC01248, PTPRO, RERG, SLC8A3, LOC646548, PAX5, GFPT2.

In various embodiments as specifically referred to in the preceding paragraphs, the classification model is a support-vector machine (SVM) algorithm-based classification model.

In various embodiments as specifically referred to in the preceding paragraphs, the method is an in vitro method.

In another aspect, the present disclosure provides a method of (i) screening for colorectal cancer or (ii) screening for advanced adenoma, or (iii) screening for the presence of either colorectal cancer or advanced adenoma (or both), the method comprising: determining a methylation status of one or more differentially methylated regions (DMRs), each of said one or more DMRs having at least 80%, at least 85%, at least 90%, at least 95%, at least 99%, or at least 99.5% sequence identity to or comprising at least one sequence selected from the group consisting of SEQ ID NO. 190, SEQ ID NO. 191, SEQ ID NO. 192, SEQ ID NO. 193, SEQ ID NO. 194, SEQ ID NO. 195, SEQ ID NO. 196, SEQ ID NO. 197, SEQ ID NO. 198, SEQ ID NO. 199, SEQ ID NO. 200, SEQ ID NO. 201, SEQ ID NO. 202, SEQ ID NO. 203, SEQ ID NO. 204, SEQ ID NO. 205, SEQ ID NO. 206, SEQ ID NO. 207, SEQ ID NO. 208, SEQ ID NO. 209, SEQ ID NO. 210, SEQ ID NO. 211, SEQ ID NO. 212, SEQ ID NO. 213, SEQ ID NO. 214, SEQ ID NO. 215, SEQ ID NO. 216, SEQ ID NO. 217, SEQ ID NO. 218, SEQ ID NO. 219, SEQ ID NO. 220, SEQ ID NO. 221, SEQ ID NO. 222, SEQ ID NO. 223, SEQ ID NO. 224, SEQ ID NO. 225, SEQ ID NO. 226, SEQ ID NO. 227, SEQ ID NO. 228, and SEQ ID NO. 229; applying a classification model using as input the determined methylation status of said one or more DMRs; and outputting, from the model, (i) a predicted status of colorectal cancer or (ii) a predicted status of advanced adenoma or (iii) a predicted status of either colorectal cancer or advanced adenoma (e.g., the latter meaning a status of having either or both colorectal cancer and advanced adenoma) of the human subject.

In various embodiments as specifically referred to in the preceding paragraph, the method comprises determining a methylation status of three or more differentially methylated regions (DMRs).

In various embodiments as specifically referred to in the preceding paragraphs, the method comprises determining a methylation status of ten or more differentially methylated regions (DMRs).

In various embodiments as specifically referred to in the preceding paragraphs, the method comprises determining a methylation status of forty differentially methylated regions (DMRs).

In various embodiments as specifically referred to in the preceding paragraphs, the classification model is a support-vector machine (SVM) algorithm-based classification model.

In various embodiments as specifically referred to in the preceding paragraphs, the method is an in vitro method.

In another aspect, the present disclosure provides a method of (i) screening for colorectal cancer or (ii) screening for advanced adenoma, or (iii) screening for the presence of either colorectal cancer or advanced adenoma (or both), the method comprising: determining a methylation status of at least one methylation site found within a differentially methylated region (DMR) of DNA of a human subject as listed in Table 1 or Table 7; determining, by a processor of a computing device, a methylation status of the differentially methylated region (DMR) of DNA of the human subject based on the methylation status of the at least one methylation site; and determining, by the processor, (i) a predicted status of colorectal cancer, (ii) a predicted status of advanced adenoma, or (iii) a predicted status of either colorectal cancer or advanced adenoma (e.g., the latter meaning a status of having either or both colorectal cancer and advanced adenoma) of the human subject using a classification model.

In various embodiments as specifically referred to in the preceding paragraph, the method comprises, for each of one or more DMRs listed in Table 1 or Table 7, determining a methylation status of at least three methylation sites found within the DMR.

In various embodiments as specifically referred to in the preceding paragraphs, the method comprises, for each of one or more DMRs listed in Table 1 or Table 7, determining a methylation status of at least four methylation sites found within the DMR.

In various embodiments as specifically referred to in the preceding paragraphs, the method comprises, for each of one or more DMRs listed in Table 1 or Table 7, determining a methylation status of at least five methylation sites found within the DMR.

In various embodiments as specifically referred to in the preceding paragraphs, the method comprises, for each of three or more DMRs listed in Table 1 or Table 7, determining a methylation status of at least one methylation site found within the DMR.

In various embodiments as specifically referred to in the preceding paragraphs, the method comprises, for each of three or more DMRs listed in Table 1 or Table 7, determining a methylation status of at least three methylation sites found within the DMR.

In various embodiments as specifically referred to in the preceding paragraphs, the method comprises, for each of three or more DMRs listed in Table 1 or Table 7, determining a methylation status of at least four methylation sites found within the DMR.

In various embodiments as specifically referred to in the preceding paragraphs, the method comprises, for each of three or more DMRs listed in Table 1 or Table 7, determining a methylation status of at least five methylation sites found within the DMR.

In various embodiments as specifically referred to in the preceding paragraphs, the method comprises, for each of ten or more DMRs listed in Table 1 or Table 7, determining a methylation status of at least one methylation site found within the DMR.

In various embodiments as specifically referred to in the preceding paragraphs, the method comprises, for each of ten or more DMRs listed in Table 1 or Table 7, determining a methylation status of at least three methylation sites found within the DMR.

In various embodiments as specifically referred to in the preceding paragraphs, the method comprises, for each of ten or more DMRs listed in Table 1 or Table 7, determining a methylation status of at least four methylation sites found within the DMR.

In various embodiments as specifically referred to in the preceding paragraphs, the method comprises, for each of ten or more DMRs listed in Table 1 or Table 7, determining a methylation status of at least five methylation sites found within the DMR.

In various embodiments as specifically referred to in the preceding paragraphs, the method comprises, for each of thirty-five or more DMRs listed in Table 1, determining a methylation status of at least one methylation sites found within the DMR.

In various embodiments as specifically referred to in the preceding paragraphs, the method comprises, for each of thirty-five or more DMRs listed in Table 1, determining a methylation status of at least three methylation sites found within the DMR.

In various embodiments as specifically referred to in the preceding paragraphs, the method comprises, for each of thirty-five or more DMRs listed in Table 1, determining a methylation status of at least four methylation sites found within the DMR.

In various embodiments as specifically referred to in the preceding paragraphs, the method comprises, for each of thirty-five or more DMRs listed in Table 1, determining a methylation status of at least five methylation sites found within the DMR.

In various embodiments as specifically referred to in the preceding paragraphs, the method comprises, for each of forty or more DMRs listed in Table 7, determining a methylation status of at least three methylation sites found within the DMR.

In various embodiments as specifically referred to in the preceding paragraphs, the method comprises, for each of forty or more DMRs listed in Table 7, determining a methylation status of at least four methylation sites found within the DMR.

In various embodiments as specifically referred to in the preceding paragraphs, the method comprises, for each of forty or more DMRs listed in Table 7, determining a methylation status of at least five methylation sites found within the DMR.

In various embodiments as specifically referred to in the preceding paragraphs, the DMR comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, the method comprises determining, by the processor, whether the at least one methylation site is methylated as compared to a reference (e.g., wherein the reference is DNA from a population of one or more human subjects having been confirmed as not suffering from either advanced adenoma or colorectal cancer), wherein methylation is indicative of (i) colorectal cancer, (ii) advanced adenoma, or (iii) either colorectal cancer or advanced adenoma (or both).

In various embodiments as specifically referred to in the preceding paragraphs, the method comprises determining the methylation status of at least one methylation site found within each of the DMRs as listed in Table 2.

In various embodiments as specifically referred to in the preceding paragraphs, the method comprises determining the methylation status of at least one methylation site found within each of the DMRs as listed in Table 3.

In various embodiments as specifically referred to in the preceding paragraphs, the method comprises determining, by the processor, the methylation status of at least one methylation site found within each of the DMRs as listed in Table 4.

In various embodiments as specifically referred to in the preceding paragraphs, the DMRs are amplified by oligonucleotide primer pairs as listed in Table 5.

In various embodiments as specifically referred to in the preceding paragraphs, the DNA of the human subject is isolated from a member selected from the group consisting of tissue (e.g., colorectal tissue, e.g., a polyp, an adenoma), blood, plasma, urine, saliva, and stool of the human subject.

In various embodiments as specifically referred to in the preceding paragraphs, the DNA is cell-free DNA of the human subject.

In various embodiments as specifically referred to in the preceding paragraphs, the subject was asymptomatic for either colorectal cancer or advanced adenomas (or both) at the time of screening.

In various embodiments as specifically referred to in the preceding paragraphs, the subject had been previously screened for either colorectal cancer or advanced adenomas (or both). In various embodiments as specifically referred to in the current or preceding paragraphs, the subject had been screened for either colorectal cancer or advanced adenomas (or both) within the last 10 years, within the last 5 years, within the last 4 years, within the last 3 years, within the last 2 years, or within the last year.

In various embodiments as specifically referred to in the preceding paragraphs, a previous screen for either advanced adenomas or colorectal cancer (or both) in the subject had diagnosed the subject as not having (i) colorectal cancer, (ii) advanced adenoma, or (iii) advanced adenoma or colorectal cancer (or both). In various embodiments as specifically referred to in the current or preceding paragraphs, the previous screen for either advanced adenomas or colorectal cancer (or both) that had diagnosed the subject as not having (i) colorectal cancer, (ii) advanced adenoma, or (iii) advanced adenoma or colorectal cancer (or both) was within one year.

In various embodiments as specifically referred to in the preceding paragraphs, the previous screen for either advanced adenoma or colorectal cancer (or both) that had diagnosed the subject as not having either advanced adenomas or colorectal cancer (or both) was a colonoscopy.

In various embodiments as specifically referred to in the preceding paragraphs, the method includes, by the processor, identifying the existence of early stage colorectal cancer (e.g., wherein the colorectal cancer is a stage 0, stage I, stage IIA, stage IIB, or stage IIC colorectal cancer).

In various embodiments as specifically referred to in the preceding paragraphs, the method includes, by the processor, identifying the existence of early stage colorectal cancer, wherein the cancer has not metastasized.

In various embodiments as specifically referred to in the preceding paragraphs, the methylation status is determined using one or more members selected from the group consisting of methylation sensitive restriction enzyme quantitative polymerase chain reaction (MSRE-qPCR), Methylation-Specific PCR, Methylation Specific Nuclease-assisted Minor-allele Enrichment PCR, hybrid-capture targeted next-generation sequencing, and amplicon based targeted next-generation sequencing.

In various embodiments as specifically referred to in the preceding paragraphs, the methylation status is determined using whole genome bisulfite sequencing.

In various embodiments as specifically referred to in the preceding paragraphs, the classification model is a support-vector machine (SVM) algorithm-based classification model.

In various embodiments as specifically referred to in the preceding paragraphs, the method is an in vitro method.

In another aspect, the present disclosure provides a method of methylation specific restriction enzyme quantitative polymerase chain reaction (MSRE-qPCR) for (i) screening for colorectal cancer or (ii) screening for advanced adenoma, or (iii) screening for the presence of either colorectal cancer or advanced adenoma (or both), the method comprising: (a) contacting DNA of a human subject with one or more methylation specific restriction enzymes; (b) performing qPCR of enzyme-digested DNA, or amplicons thereof, to determine the methylation status of one or more regions of DNA, wherein each of the one or more regions of DNA comprises at least a portion of the one or more DMRs of Table 1, each portion being at least 10, at least 15, at least 20, at least 24, at least 30, at least 40, at least 50, at least 100, at least 150, at least 200, at least 250, at least 300, at least 350, at least 400, at least 500, at least 1000 or more base pairs in length; (c) applying, by a processor of a computing device, a classification model to the determined methylation status of the one or more regions of DNA; and (d) determining, by the processor, a predicted status of colorectal cancer, a predicted status of advanced adenoma, or a predicted status of either colorectal cancer or advanced adenoma (e.g., the latter meaning a status of having either or both colorectal cancer and advanced adenoma) of the human subject based on the applied classification model.

In various embodiments as specifically referred to in the preceding paragraph, at least one of the one or more of the regions of DNA is amplified by a corresponding oligonucleotide primer pair (e.g., wherein the primer pair comprises a forward and a reverse primer).

In various embodiments as specifically referred to in the preceding paragraphs, each of the one or more regions of DNA comprises at least 1, at least 2, at least 3, at least 4, at least 5, at least 6, at least 7, at least 8, at least 9, at least 10, at least 11, at least 12, at least 13, at least 14, at least 15, or more methylation sensitive restriction sites.

In various embodiments as specifically referred to in the preceding paragraphs, the corresponding oligonucleotide primer pair is an oligonucleotide primer pair listed in Table 5.

In various embodiments as specifically referred to in the preceding paragraphs, a forward primer of the corresponding oligonucleotide primer pair is at least 80%, at least 85%, at least 90%, at least 95%, at least 99%, or at least 99.5% identical to a forward primer listed in Table 5.

In various embodiments as specifically referred to in the preceding paragraphs, a reverse primer of the corresponding oligonucleotide primer pair is at least 80%, at least 85%, at least 90%, at least 95%, at least 99%, or at least 99.5% identical to a reverse primer listed in Table 5.

In various embodiments as specifically referred to in the preceding paragraphs, the DNA is isolated from a member selected from the group consisting of tissue (e.g., colorectal tissue, e.g., a polyp, an adenoma), blood, plasma, urine, saliva, and stool of the human subject.

In various embodiments as specifically referred to in the preceding paragraphs, the DNA is cell-free DNA of the human subject.

In various embodiments as specifically referred to in the preceding paragraphs, the method provides a sensitivity for detecting colorectal cancer of at least 0.67. In various embodiments as specifically referred to in this or the preceding paragraphs, the method provides the sensitivity for detecting colorectal cancer of at least 0.78.

In various embodiments as specifically referred to in the preceding paragraphs, the method provides an overall sensitivity for detecting a combination of advanced adenoma and colorectal cancer of at least 0.48. In various embodiments as specifically referred to in this or the preceding paragraphs, the method provides an overall sensitivity for detecting the combination of advanced adenoma and colorectal cancer of at least 0.53.

In various embodiments as specifically referred to in the preceding paragraphs, the method provides a specificity of at least 0.9. In various embodiments as specifically referred to in this or the preceding paragraphs, the method provides a specificity of at least 0.93.

In various embodiments as specifically referred to in the preceding paragraphs, the one or more regions of DNA comprise each DMR of Table 2.

In various embodiments as specifically referred to in the preceding paragraphs, each of the one or more regions of DNA are at least 80%, at least 85%, at least 90%, at least 95%, at least 99% or at least 99.5% identical to or comprises a corresponding DMR of Table 2.

In various embodiments as specifically referred to in the preceding paragraphs, the one or more regions of DNA comprise each DMR of Table 3.

In various embodiments as specifically referred to in the preceding paragraphs, each of the one or more regions of DNA are at least 80%, at least 85%, at least 90%, at least 95%, at least 99% or at least 99.5% identical to, or comprises, a corresponding DMR of Table 2.

In various embodiments as specifically referred to in the preceding paragraphs, the one or more regions of DNA comprise each of DMR of Table 4.

In various embodiments as specifically referred to in the preceding paragraphs, each of the one or more regions of DNA are at least 80%, at least 85%, at least 90%, at least 95%, at least 99% or at least 99.5% identical to, or comprises, a corresponding DMR of Table 4.

In various embodiments as specifically referred to in the preceding paragraphs, the classification model is a support-vector machine (SVM) algorithm-based classification model.

In various embodiments as specifically referred to in the preceding paragraphs, the method is an in vitro method.

In another aspect, the present disclosure provides a method of (i) screening for colorectal cancer or (ii) screening for advanced adenoma, or (iii) screening for the presence of either colorectal cancer or advanced adenoma (or both), the method comprising: determining (e.g., by a processor of a computing device) a methylation status of one or more differentially methylated regions (DMRs), each of said one or more DMRs comprising or overlapping with one or more genes selected from the group consisting of PAX7, NTNG1, SYT6, LINC01248, KCNK3, GALNT14, CHST10, THSD7B, UNC80, EPHA6, MED12L, ADGRL3, RNF150, SPOCK3, GPM6A, HELT, GFPT2, HSPA1L, HSPA1A, NKAIN2, TMEM178B, DPP6, MICU3, ALKAL1, LOC401463, BHLHE22, RIMS2, LOC105375690, SLC25A32, DMRT1, CDKN2A, CDKN2B-AS1, PAX5, C1QL3, MYO3A, LOC101929073, GAD2, MYO3A, FOXI2, LOC105369438, AMOTL1, LOC101928847, NCAM1, DSCAML1, PTPRO, RERG, DPY19L2, CUX2, PCDH9, MIR4500HG, SLITRK5, SLC8A3, LOC646548, GATM, PIF1, RASGRF1, VAC14, VAT1L, JPH3, SLFN13, ZACN, SRP68, GALR2, ADCYAP1, CDH2, DOK6, ZNF461, ZNF829, ZNF568, ZNF540, ZNF571-AS1, CIC, ZNF582-AS1, ZNF582, ZNF471, ZNF264, ZNF671, ZNF551, ZNF776, NKX2-2, ADAMTS1, TIAM1, and OLIG1; applying, by the processor, a classification model using as input the determined methylation status of each of said one or more DMRs; and outputting from the model, by the processor, (i) a predicted status of colorectal cancer, (ii) a predicted status of advanced adenoma, or (iii) a predicted status of either colorectal cancer or advanced adenoma (e.g., the latter meaning a status of having either or both colorectal cancer and advanced adenoma) of the human subject.

In various embodiments as specifically referred to in the preceding paragraph, the method comprises determining the methylation status of the one or more DMRs comprising or overlapping with at least each of the genes GAD2, MYO3A, and ALKAL1.

In various embodiments as specifically referred to in the preceding paragraphs, the method comprises determining the methylation status of the one or more DMRs comprising or overlapping with at least each of the genes at least each of the genes GAD2, MYO3A, ALKAL1, RASGRF1, MICU3, RASGRF1, FOXI2, C1QL3, CDKN2A, and CDKN2B-AS1.

In various embodiments as specifically referred to in the preceding paragraphs, the method comprises determining the methylation status of the one or more DMRs comprising or overlapping with at least each of the genes GAD2, MYO3A, ALKAL1, RASGRF1, MICU3, RASGRF1, FOXI2, C1QL3, CDKN2A, CDKN2B-AS1, SYT6, SLFN13, GPM6A, THSD7B, ZBF582-AS1, ZNF582, GATM, ZNF540, ZNF571-AS1, OLIG1, EPHA6, DPY19L2, SLC8A3, LOC646548, LOC101929073, UNC80, DPP6, ZNF568, JPH3, ZNF461, NTNG1, ADGRL3, ADAMST1, CDH2, LINC01248, PTPRO, RERG, SLC8A3, LOC646548, PAX5, GFPT2.

In various embodiments as specifically referred to in the preceding paragraphs, the classification model is a support-vector machine (SVM) algorithm-based classification model.

In various embodiments as specifically referred to in the preceding paragraphs, the method is an in vitro method.

In another aspect, the present disclosure provides a method of (i) screening for colorectal cancer or (ii) screening for advanced adenoma, or (iii) screening for the presence of either colorectal cancer or advanced adenoma (or both), the method comprising: determining (e.g., by a processor of a computing device) a methylation status of one or more differentially methylated regions (DMRs), each of said one or more DMRs having at least 80%, at least 85%, at least 90%, at least 95%, at least 99% or at least 99.5% sequence identity with or comprises at least one sequence selected from the group consisting of SEQ ID NO. 190, SEQ ID NO. 191, SEQ ID NO. 192, SEQ ID NO. 193, SEQ ID NO. 194, SEQ ID NO. 195, SEQ ID NO. 196, SEQ ID NO. 197, SEQ ID NO. 198, SEQ ID NO. 199, SEQ ID NO. 200, SEQ ID NO. 201, SEQ ID NO. 202, SEQ ID NO. 203, SEQ ID NO. 204, SEQ ID NO. 205, SEQ ID NO. 206, SEQ ID NO. 207, SEQ ID NO. 208, SEQ ID NO. 209, SEQ ID NO. 210, SEQ ID NO. 211, SEQ ID NO. 212, SEQ ID NO. 213, SEQ ID NO. 214, SEQ ID NO. 215, SEQ ID NO. 216, SEQ ID NO. 217, SEQ ID NO. 218, SEQ ID NO. 219, SEQ ID NO. 220, SEQ ID NO. 221, SEQ ID NO. 222, SEQ ID NO. 223, SEQ ID NO. 224, SEQ ID NO. 225, SEQ ID NO. 226, SEQ ID NO. 227, SEQ ID NO. 228, and SEQ ID NO. 229; applying, by the processor, a classification model using as input the determined methylation status of said one or more DMRs; and outputting from the model, by the processor, (i) a predicted status of colorectal cancer, (ii) a predicted status of advanced adenoma, or (iii) a predicted status of either colorectal cancer or advanced adenoma (e.g., the latter meaning a status of having either or both colorectal cancer and advanced adenoma) of the human subject.

In various embodiments as specifically referred to in the preceding paragraphs, the method comprises determining the methylation status of each of three or more differentially methylated regions (DMRs).

In various embodiments as specifically referred to in the preceding paragraphs, the method comprises determining the methylation status of each of ten or more differentially methylated regions (DMRs).

In various embodiments as specifically referred to in the preceding paragraphs, the method comprises determining the methylation status of each of forty differentially methylated regions (DMRs).

In various embodiments as specifically referred to in the preceding paragraphs, the classification model is a support-vector machine (SVM) algorithm-based classification model.

In various embodiments as specifically referred to in the preceding paragraphs, the method is an in vitro method.

In various aspects, methods and compositions of the present invention can be used in combination with biomarkers known in the art, e.g., as disclosed in U.S. Pat. No. 10,006,925, which is herein incorporated by reference in its entirety.

In another aspect, the invention is directed to a method of identifying one or more differentially methylated regions for the (i) screening for colorectal cancer or (ii) screening for advanced adenoma, or (iii) screening for the presence of either colorectal cancer or advanced adenoma (or both), wherein the method comprises: sequencing DNA of genomes of a first population (e.g., at least 10, at least 20, at least 50, at least 100, or more) of subjects diagnosed as having (i) colorectal cancer, (ii) advanced adenoma, or (iii) either colorectal cancer or advanced adenoma (or both) using whole genome bisulfate sequencing; aligning each of the genomes of the first population with a reference genome (e.g., wherein the reference genome is GRCh38); identifying (e.g., using bioinformatics tools, e.g., MethylKit) a plurality of methylated colorectal cancer and/or advanced adenoma sites, wherein each of the plurality of methylated colorectal cancer and/or advanced adenoma sites is a differentially methylated site of the DNA of the first population relative to the corresponding site of a reference population (e.g., a population comprising healthy subjects)(e.g., wherein the difference in the percent methylation of the DNA of the first population with respect to the reference population is at least 5%, at least 10%, at least 15% or more); generating a list comprising a plurality of differentially methylated regions (DMRs), each of the plurality of the differentially methylated regions (DMRs) comprising one or more of the plurality of the identified methylated colorectal and/or advanced adenoma cancer sites (e.g., wherein the methylated colorectal and/or advanced adenoma cancer sites are or comprise methylated CpG regions) (e.g., wherein the DMRs comprise at least three methylated CpG regions having a maximum distance between the CpGs of 200 base pairs); determining a methylation status (e.g., a percent methylation, a number of methylated sites) of each of the plurality of DMRs of the first population; ranking the plurality of DMRs based, at least in part on, the methylation status of each of the plurality of DMRs; and filtering a set of candidate DMRs (e.g., filtering for DMRs comprising at least five CPG regions) (e.g., wherein the minimum methylation percent difference between the first subject group and the reference population is at least 5%, at least 6%, at least 7%, at least 8%, at least 9%, least 10%, at least 15% or more) from the plurality of the DMRs for the diagnosis of colorectal cancer and/or advanced adenoma.

In various embodiments as specifically referred to in the preceding paragraph, the method comprises: identifying one or more CpG regions within each of the plurality of DMRs; determining the methylation status (e.g., a percent methylation, a number of methylated sites) of each of the identified CpG regions within each of the plurality of DMRs for the first population; and ranking the plurality of DMRs based, at least in part, on the determined methylation status of each of the one or more CpG regions of the DMR.

In certain embodiments as specifically referred to in the preceding paragraphs, the method further comprises: determining a methylation status of each of the plurality of DMRs for the reference population; comparing (e.g., comparing the percent methylation of) the determined methylation status of each of the plurality of DMRs of the reference population with a methylation status of a corresponding DMR of the first population; and ranking the plurality of DMRs based, at least in part, on the comparison.

In certain embodiments as specifically referred to in the preceding paragraphs, the DNA of the first population is isolated from a tissue (e.g., colorectal tissue, e.g., a polyp, an adenoma) of each human subject of the first population.

In certain embodiments as specifically referred to in the preceding paragraphs, the DNA of the first population is isolated from blood, plasma, urine, saliva, or stool of each human subject of the first population.

In other aspects, the invention is directed to a system for performing any of the methods referred to in the preceding paragraphs, the system comprising a processor; and a memory having instructions thereon, the instructions, when executed by the processor, causing the processor to perform one or more (up to all) steps of the method.

Definitions

A or An: The articles "a" and "an" are used herein to refer to one or to more than one (i.e., to at least one) of the grammatical object of the article. By way of example, "an element" refers to one element or more than one element.

About: The term "about", when used herein in reference to a value, refers to a value that is similar, in context, to the referenced value. In general, those skilled in the art, familiar with the context, will appreciate the relevant degree of variance encompassed by "about" in that context. For example, in some embodiments, e.g., as set forth herein, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or with a fraction of a percent, of the referred value.

Advanced adenoma: As used herein, the term "advance adenoma" is used to refer to adenomatous polyps (adenomas) of the colon and rectum that are benign (noncancerous) cellular growths. Advanced adenomas are colonic adenomatous adenoma having at least one of the following features: ≥1 cm in size; tubulovillous or villous adenoma; high grade dysplasia; and serrated adenomas with dysplasia. In certain instances, e.g., as set forth herein, an advanced adenoma may also be classified as a "high risk" adenoma.

Administration: As used herein, the term "administration" typically refers to the administration of a composition to a subject or system, for example to achieve delivery of an agent that is, is included in, or is otherwise delivered by, the composition.

Agent: As used herein, the term "agent" refers to an entity (e.g., for example, a small molecule, peptide, polypeptide, nucleic acid, lipid, polysaccharide, complex, combination, mixture, system, or phenomenon such as heat, electric current, electric field, magnetic force, magnetic field, etc.).

Amelioration: As used herein, the term "amelioration" refers to the prevention, reduction, palliation, or improvement of a state of a subject. Amelioration includes, but does not require, complete recovery or complete prevention of a disease, disorder or condition.

Amplicon or amplicon molecule: As used herein, the term "amplicon" or "amplicon molecule" refers to a nucleic acid molecule generated by transcription from a template nucleic acid molecule, or a nucleic acid molecule having a sequence complementary thereto, or a double-stranded nucleic acid including any such nucleic acid molecule. Transcription can be initiated from a primer.

Amplification: As used herein, the term "amplification" refers to the use of a template nucleic acid molecule in combination with various reagents to generate further nucleic acid molecules from the template nucleic acid molecule, which further nucleic acid molecules may be identical to or similar to (e.g., at least 70% identical, e.g., at least 75%, 80%, 85%, 90%, 91%, 92%, 93%, 94%, 95%, 96%, 97%, 98%, 99%, or 100% identical to) a segment of the template nucleic acid molecule and/or a sequence complementary thereto.

Amplification reaction mixture: As used herein, the terms "amplification reaction mixture" or "amplification reaction" refer to a template nucleic acid molecule together with reagents sufficient for amplification of the template nucleic acid molecule.

Biological Sample: As used herein, the term "biological sample" typically refers to a sample obtained or derived from a biological source (e.g., a tissue or organism or cell culture) of interest, as described herein. In some embodiments, e.g., as set forth herein, a biological source is or includes an organism, such as an animal or human. In some embodiments, e.g., as set forth herein, a biological sample is or include biological tissue or fluid. In some embodiments, e.g., as set forth herein, a biological sample can be or include cells, tissue, or bodily fluid. In some embodiments, e.g., as set forth herein, a biological sample can be or include blood, blood cells, cell-free DNA, free floating nucleic acids, ascites, biopsy samples, surgical specimens, cell-containing body fluids, sputum, saliva, feces, urine, cerebrospinal fluid, peritoneal fluid, pleural fluid, lymph, gynecological fluids, secretions, excretions, skin swabs, vaginal swabs, oral swabs, nasal swabs, washings or lavages such as a ductal lavages or broncheoalveolar lavages, aspirates, scrapings, bone marrow. In some embodiments, e.g., as set forth herein, a biological sample is or includes cells obtained from a single subject or from a plurality of subjects. A sample can be a "primary sample" obtained directly from a biological source, or can be a "processed sample." A biological sample can also be referred to as a "sample."

Biomarker: As used herein, the term "biomarker," consistent with its use in the art, refers to a to an entity whose presence, level, or form, correlates with a particular biological event or state of interest, so that it is considered to be a "marker" of that event or state. Those of skill in the art will appreciate, for instance, in the context of a DNA biomarker, that a biomarker can be or include a locus (such as one or more methylation loci) and/or the status of a locus (e.g., the status of one or more methylation loci). To give but a few examples of biomarkers, in some embodiments, e.g., as set forth herein, a biomarker can be or include a marker for a particular disease, disorder or condition, or can be a marker for qualitative of quantitative probability that a particular disease, disorder or condition can develop, occur, or reoccur, e.g., in a subject. In some embodiments, e.g., as set forth herein, a biomarker can be or include a marker for a particular therapeutic outcome, or qualitative of quantitative probability thereof. Thus, in various embodiments, e.g., as set forth herein, a biomarker can be predictive, prognostic, and/or diagnostic, of the relevant biological event or state of interest. A biomarker can be an entity of any chemical class. For example, in some embodiments, e.g., as set forth herein, a biomarker can be or include a nucleic acid, a polypeptide, a lipid, a carbohydrate, a small molecule, an inorganic agent (e.g., a metal or ion), or a combination thereof. In some embodiments, e.g., as set forth herein, a biomarker is a cell surface marker. In some embodiments, e.g., as set forth herein, a biomarker is intracellular. In some embodiments, e.g., as set forth herein, a biomarker is found outside of cells (e.g., is secreted or is otherwise generated or present outside of cells, e.g., in a body fluid such as blood, urine, tears, saliva, cerebrospinal fluid, and the like). In some embodiments, e.g., as set forth herein, a biomarker is methylation status of a methylation locus. In some instances, e.g., as set forth herein, a biomarker may be referred to as a "marker."

To give but one example of a biomarker, in some embodiments e.g., as set forth herein, the term refers to expression of a product encoded by a gene, expression of which is characteristic of a particular tumor, tumor subclass, stage of tumor, etc. Alternatively or additionally, in some embodiments, e.g., as set forth herein, presence or level of a particular marker can correlate with activity (or activity level) of a particular signaling pathway, for example, of a signaling pathway the activity of which is characteristic of a particular class of tumors.

Those of skill in the art will appreciate that a biomarker may be individually determinative of a particular biological event or state of interest, or may represent or contribute to a determination of the statistical probability of a particular biological event or state of interest. Those of skill in the art will appreciate that markers may differ in their specificity and/or sensitivity as related to a particular biological event or state of interest.

Blood component: As used herein, the term "blood component" refers to any component of whole blood, including red blood cells, white blood cells, plasma, platelets, endothelial cells, mesothelial cells, epithelial cells, and cell-free DNA. Blood components also include the components of plasma, including proteins, metabolites, lipids, nucleic acids, and carbohydrates, and any other cells that can be present in blood, e.g., due to pregnancy, organ transplant, infection, injury, or disease.

Cancer: As used herein, the terms "cancer," "malignancy," "neoplasm," "tumor," and "carcinoma," are used interchangeably to refer to a disease, disorder, or condition in which cells exhibit or exhibited relatively abnormal, uncontrolled, and/or autonomous growth, so that they display or displayed an abnormally elevated proliferation rate and/or aberrant growth phenotype. In some embodiments, e.g., as set forth herein, a cancer can include one or more tumors. In some embodiments e.g., as set forth herein, a cancer can be or include cells that are precancerous (e.g., benign), malignant, pre-metastatic, metastatic, and/or non-metastatic. In some embodiments e.g., as set forth herein, a cancer can be or include a solid tumor. In some embodiments e.g., as set forth herein, a cancer can be or include a hematologic tumor. In general, examples of different types of cancers known in the art include, for example, colorectal cancer, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic agent: As used herein, the term "chemotherapeutic agent," consistent with its use in the art, refers to one or more agents known, or having characteristics known to, treat or contribute to the treatment of cancer. In particular, chemotherapeutic agents include pro-apoptotic, cytostatic, and/or cytotoxic agents. In some embodiments e.g., as set forth herein, a chemotherapeutic agent can be or include alkylating agents, anthracyclines, cytoskeletal disruptors (e.g., microtubule targeting moieties such as taxanes, maytansine, and analogs thereof, of), epothilones, histone deacetylase inhibitors HDACs), topoisomerase inhibitors (e.g., inhibitors of topoisomerase I and/or topoisomerase II), kinase inhibitors, nucleotide analogs or nucleotide precursor analogs, peptide antibiotics, platinum-based agents, retinoids, vinca alkaloids, and/or analogs that share a relevant anti-proliferative activity. In some particular embodiments e.g., as set forth herein, a chemotherapeutic agent can be or include of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g., DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, or a combination thereof. In some embodiments e.g., as set forth herein, a chemotherapeutic agent can be utilized in the context of an antibody-drug conjugate. In some embodiments e.g., as set forth herein, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine. In some embodiments e.g., as set forth herein, a chemotherapeutic agent can be or comprise of farnesyl-thiosalicylic acid (FTS), 4-(4-Chloro-2-methylphenoxy)-N-hydroxybutanamide (CMH), estradiol (E2), tetramethoxystilbene (TMS), δ-tocatrienol, salinomycin, or curcumin.

Comparable: As used herein, the term "comparable" refers to members within sets of two or more conditions, circumstances, agents, entities, populations, etc., that may not be identical to one another but that are sufficiently similar to permit comparison there between, such that one of skill in the art will appreciate that conclusions can reasonably be drawn based on differences or similarities observed. In some embodiments e.g., as set forth herein, comparable sets of conditions, circumstances, agents, entities, populations, etc. are typically characterized by a plurality of substantially identical features and zero, one, or a plurality of differing features. Those of ordinary skill in the art will understand, in context, what degree of identity is required to render members of a set comparable. For example, those of ordinary skill in the art will appreciate that members of sets of conditions, circumstances, agents, entities, populations, etc., are comparable to one another when characterized by a sufficient number and type of substantially identical features to warrant a reasonable conclusion that differences observed can be attributed in whole or part to non-identical features thereof.

Detectable moiety: The term "detectable moiety" as used herein refers to any element, molecule, functional group, compound, fragment, or other moiety that is detectable. In some embodiments e.g., as set forth herein, a detectable moiety is provided or utilized alone. In some embodiments e.g., as set forth herein, a detectable moiety is provided and/or utilized in association with (e.g., joined to) another agent. Examples of detectable moieties include, but are not limited to, various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.), fluorescent dyes, chemiluminescent agents, bioluminescent agents, spectrally resolvable inorganic fluorescent semiconductors nanocrystals (i.e., quantum dots), metal nanoparticles, nanoclusters, paramagnetic metal ions, enzymes, colorimetric labels, biotin, dioxigenin, haptens, and proteins for which antisera or monoclonal antibodies are available.

Diagnosis: As used herein, the term "Diagnosis" refers to determining whether, and/or the qualitative of quantitative probability that, a subject has or will develop a disease, disorder, condition, or state. For example, in diagnosis of cancer, diagnosis can include a determination regarding the risk, type, stage, malignancy, or other classification of a cancer. In some instances, e.g., as set forth herein, a diagnosis can be or include a determination relating to prognosis and/or likely response to one or more general or particular therapeutic agents or regimens.

Diagnostic information: As used herein, the term "diagnostic information" refers to information useful in providing a diagnosis. Diagnostic information can include, without limitation, biomarker status information.

Differentially methylated: As used herein, the term "differentially methylated" describes a methylation site for which the methylation status differs between a first condition and a second condition. A methylation site that is differentially methylated can be referred to as a differentially methylated site. In some instances e.g., as set forth herein, a DMR is defined by the amplicon produced by amplification using oligonucleotide primers, e.g., a pair of oligonucleotide primers selected for amplification of the DMR or for amplification of a DNA region of interest present in the amplicon. In some instances e.g., as set forth herein, a DMR is defined as a DNA region amplified by a pair of oligonucleotide primers, including the region having the sequence of, or a sequence complementary to, the oligonucleotide primers. In some instances e.g., as set forth herein, a DMR is defined as a DNA region amplified by a pair of oligonucleotide primers, excluding the region having the sequence of, or a sequence complementary to, the oligonucleotide primers.

Differentially methylated region: As used herein, the term "differentially methylated region" (DMR) refers to a DNA region that includes one or more differentially methylated sites. A DMR that includes a greater number or frequency of methylated sites under a selected condition of interest, such as a cancerous state, can be referred to as a hypermethylated DMR. A DMR that includes a smaller number or frequency of methylated sites under a selected condition of interest, such as a cancerous state, can be referred to as a hypomethylated DMR. A DMR that is a methylation biomarker for colorectal cancer can be referred to as a colorectal cancer DMR. In some instances e.g., as set forth herein, a DMR that is a methylation biomarker for colorectal cancer may also be useful in identification of advanced adenoma. In some instances e.g., as set forth herein, a DMR that is a methylation biomarker for advanced adenoma can be referred to as an advanced adenoma DMR. In some instances e.g., as set forth herein, a DMR that is a methylation biomarker for advanced adenoma may also be useful in identification of colorectal cancer. In some instances e.g., as set forth herein, a DMR can be a single nucleotide, which single nucleotide is a methylation site. Preferably, a DMR has a length of at least about 10, 15, 20, 24, 50, 100, 150, 200, 250, 300, 350, 400, 500, 1000, 1500, 2000, 2225, 2500 or more base pairs.

DNA region: As used herein, "DNA region" refers to any contiguous portion of a larger DNA molecule. Those of skill in the art will be familiar with techniques for determining whether a first DNA region and a second DNA region correspond, based, e.g., on sequence similarity (e.g., sequence identity or homology) of the first and second DNA regions and/or context (e.g., the sequence identity or homology of nucleic acids upstream and/or downstream of the first and second DNA regions).

Except as otherwise specified herein, sequences found in or relating to humans (e.g., that hybridize to human DNA) are found in, based on, and/or derived from the example representative human genome sequence commonly referred to, and known to those of skill in the art, as Homo sapiens (human) genome assembly GRCh38, hg38, and/or Genome Reference Consortium Human Build 38. Those of skill in the art will further appreciate that DNA regions of hg38 can be referred to by a known system including identification of particular nucleotide positions or ranges thereof in accordance with assigned numbering.

Downstream: As used herein, the term "downstream" means that a first DNA region is closer, relative to a second DNA region, to the C-terminus of a nucleic acid that includes the first DNA region and the second DNA region.

Gene: As used herein, the term "gene" refers to a single DNA region, e.g., in a chromosome, that includes a coding sequence that encodes a product (e.g., an RNA product and/or a polypeptide product), together with all, some, or none of the DNA sequences that contribute to regulation of the expression of coding sequence. In some embodiments e.g., as set forth herein, a gene includes one or more non-coding sequences. In some particular embodiments e.g., as set forth herein, a gene includes exonic and intronic sequences. In some embodiments e.g., as set forth herein, a gene includes one or more regulatory elements that, for example, can control or impact one or more aspects of gene expression (e.g., cell-type-specific expression, inducible expression, etc.). In some embodiments e.g., as set forth herein a gene includes a promoter. In some embodiments e.g., as set forth herein, a gene includes one or both of a (i) DNA nucleotides extending a predetermined number of nucleotides upstream of the coding sequence and (ii) DNA nucleotides extending a predetermined number of nucleotides downstream of the coding sequence. In various embodiments e.g., as set forth herein, the predetermined number of nucleotides can be 500 bp, 1 kb, 2 kb, 3 kb, 4 kb, 5 kb, 10 kb, 20 kb, 30 kb, 40 kb, 50 kb, 75 kb, or 100 kb.

Hybridize: As used herein, "hybridize" refers to the association of a first nucleic acid with a second nucleic acid to form a double-stranded structure, which association occurs through complementary pairing of nucleotides. Those of skill in the art will recognize that complementary sequences, among others, can hybridize. In various embodiments e.g., as set forth herein, hybridization can occur, for example, between nucleotide sequences having at least 70% complementarity, e.g., at least 75%, 80%, 85%, 90%, 91%, 92%, 93%, 94%, 95%, 96%, 97%, 98%, 99%, or 100% complementarity. Those of skill in the art will further appreciate that whether hybridization of a first nucleic acid and a second nucleic acid does or does not occur can dependence upon various reaction conditions. Conditions under which hybridization can occur are known in the art.

Hypomethylation: As used herein, the term "hypomethylation" refers to the state of a methylation locus having at least one fewer methylated nucleotides in a state of interest as compared to a reference state (e.g., at least one fewer methylated nucleotides in colorectal cancer than in healthy control).

Hypermethylation: As used herein, the term "hypermethylation" refers to the state of a methylation locus having at least one more methylated nucleotide in a state of interest as compared to a reference state (e.g., at least one more methylated nucleotide in colorectal cancer than in healthy control).

Identity, identical: As used herein, the terms "identity" and "identical" refers to the overall relatedness between polymeric molecules, e.g., between nucleic acid molecules (e.g., DNA molecules and/or RNA molecules) and/or between polypeptide molecules. Methods for the calculation of a percent identity as between two provided sequences are known in the art. Calculation of the percent identity of two nucleic acid or polypeptide sequences, for example, can be performed by aligning the two sequences (or the complement of one or both sequences) for optimal comparison purposes (e.g., gaps can be introduced in one or both of a first and a second sequences for optimal alignment and non-identical sequences can be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences and, optionally, taking into account the number of gaps and the length of each gap, which may need to be introduced for optimal alignment of the two sequences. The comparison of sequences and determination of percent identity between two sequences can be accomplished using a computational algorithm, such as BLAST (basic local alignment search tool).

"Improved," "increased," or "reduced": As used herein, these terms, or grammatically comparable comparative terms, indicate values that are relative to a comparable reference measurement. For example, in some embodiments e.g., as set forth herein, an assessed value achieved with an agent of interest may be "improved" relative to that obtained with a comparable reference agent or with no agent. Alternatively or additionally, in some embodiments e.g., as set forth herein, an assessed value in a subject or system of interest may be "improved" relative to that obtained in the same subject or system under different conditions or at a different point in time (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments e.g., as set forth herein, comparative terms refer to statistically relevant differences (e.g., differences of a prevalence and/or magnitude sufficient to achieve statistical relevance). Those of skill in the art will be aware, or will readily be able to determine, in a given context, a degree and/or prevalence of difference that is required or sufficient to achieve such statistical significance.

Methylation: As used herein, the term "methylation" includes methylation at any of (i) C5 position of cytosine; (ii) N4 position of cytosine; and (iii) the N6 position of adenine. Methylation also includes (iv) other types of nucleotide methylation. A nucleotide that is methylated can be referred to as a "methylated nucleotide" or "methylated nucleotide base." In certain embodiments e.g., as set forth herein, methylation specifically refers to methylation of cytosine residues. In some instances e.g., as set forth herein, methylation specifically refers to methylation of cytosine residues present in CpG sites.

Methylation assay: As used herein, the term "methylation assay" refers to any technique that can be used to determine the methylation status of a methylation locus or a methylation site.

Methylation biomarker: As used herein, the term "methylation biomarker" refers to a biomarker that is or includes at least one methylation site or locus and/or the methylation status of at least one methylation locus, e.g., a hypermethylated locus. In particular, a methylation biomarker is a biomarker characterized by a change between a first state and a second state (e.g., between a cancerous state and a non-cancerous state) in methylation status of one or more nucleic acid loci.

Methylation locus: As used herein, the term "methylation locus" refers to a DNA region that includes at least one differentially methylated region. A methylation locus that includes a greater number or frequency of methylated sites under a selected condition of interest, such as a cancerous state, can be referred to as a hypermethylated locus. A methylation locus that includes a smaller number or frequency of methylated sites under a selected condition of interest, such as a cancerous state, can be referred to as a hypomethylated locus.

Methylation site: As used herein, a methylation site refers to a nucleotide or nucleotide position that is methylated in at least one condition. In its methylated state, a methylation site can be referred to as a methylated site.

Methylation status: As used herein, "methylation status," "methylation state," or "methylation profile" refer to the number, frequency, or pattern of methylation at methylation sites within a methylation locus. Accordingly, a change in methylation status between a first state and a second state can be or include an increase in the number, frequency, or pattern of methylated sites, or can be or include a decrease in the number, frequency, or pattern of methylated sites. In various instances e.g., as set forth herein, a change in methylation status in a change in methylation value. In various instances e.g., as set forth herein, "methylation status" refers to the presence or absence of methylation at an individual methylation site.

Methylation value: As used herein, the term "methylation value" refers to a numerical representation of a methylation status, e.g., in the form of number that represents the frequency or ratio of methylation of a methylation locus. In some instances e.g., as set forth herein, a methylation value can be generated by a method that includes quantifying the amount of intact nucleic acid present in a sample following restriction digestion of the sample with a methylation dependent restriction enzyme. In some instances e.g., as set forth herein, a methylation value can be generated by a method that includes comparing amplification profiles after bisulfite reaction of a sample. In some instances e.g., as set forth herein, a methylation value can be generated by comparing sequences of bisulfite-treated and untreated nucleic acids. In some instances e.g., as set forth herein a methylation value is, includes, or is based on a quantitative PCR result.

Nucleic acid: As used herein, in its broadest sense, the term "nucleic acid" refers to any compound and/or substance that is or can be incorporated into an oligonucleotide chain. In some embodiments e.g., as set forth herein, a nucleic acid is a compound and/or substance that is or can be incorporated into an oligonucleotide chain via a phosphodiester linkage. As will be clear from context, in some embodiments e.g., as set forth herein, the term nucleic acid refers to an individual nucleic acid residue (e.g., a nucleotide and/or nucleoside), and in some embodiments e.g., as set forth herein refers to an polynucleotide chain comprising a plurality of individual nucleic acid residues. A nucleic acid can be or include DNA, RNA, or a combinations thereof. A nucleic acid can include natural nucleic acid residues, nucleic acid analogs, and/or synthetic residues. In some embodiments e.g., as set forth herein, a nucleic acid includes natural nucleotides (e.g., adenosine, thymidine, guanosine, cytidine, uridine, deoxyadenosine, deoxythymidine, deoxy guanosine, and deoxycytidine). In some embodiments e.g., as set forth herein, a nucleic acid is or includes of one or more nucleotide analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof).

In some embodiments e.g., as set forth herein, a nucleic acid has a nucleotide sequence that encodes a functional gene product such as an RNA or protein. In some embodiments e.g., as set forth herein, a nucleic acid includes one or more introns. In some embodiments e.g., as set forth herein, a nucleic acid includes one or more genes. In some embodiments e.g., as set forth herein, nucleic acids are prepared by one or more of isolation from a natural source, enzymatic synthesis by polymerization based on a complementary template (in vivo or in vitro), reproduction in a recombinant cell or system, and chemical synthesis.

In some embodiments e.g., as set forth herein, a nucleic acid analog differs from a nucleic acid in that it does not utilize a phosphodiester backbone. For example, in some embodiments e.g., as set forth herein, a nucleic acid can include one or more peptide nucleic acids, which are known in the art and have peptide bonds instead of phosphodiester bonds in the backbone. Alternatively or additionally, in some embodiments e.g., as set forth herein, a nucleic acid has one or more phosphorothioate and/or 5'-N-phosphoramidite linkages rather than phosphodiester bonds. In some embodiments e.g., as set forth herein, a nucleic acid comprises one or more modified sugars (e.g., 2'-fluororibose, ribose, 2'-deoxyribose, arabinose, and hexose) as compared with those in natural nucleic acids.

In some embodiments e.g., as set forth herein, a nucleic acid is or includes at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues. In some embodiments e.g., as set forth herein, a nucleic acid is partly or wholly single stranded, or partly or wholly double stranded.

Nucleic acid detection assay: As used herein, the term "nucleic acid detection assay" refers to any method of determining the nucleotide composition of a nucleic acid of interest. Nucleic acid detection assays include but are not limited to, DNA sequencing methods, polymerase chain reaction-based methods, probe hybridization methods, ligase chain reaction, etc.

Nucleotide: As used herein, the term "nucleotide" refers to a structural component, or building block, of polynucleotides, e.g., of DNA and/or RNA polymers. A nucleotide includes of a base (e.g., adenine, thymine, uracil, guanine, or cytosine) and a molecule of sugar and at least one phosphate group. As used herein, a nucleotide can be a methylated nucleotide or an un-methylated nucleotide. Those of skill in the art will appreciate that nucleic acid terminology, such as, as examples, "locus" or "nucleotide" can refer to both a locus or nucleotide of a single nucleic acid molecule and/or to the cumulative population of loci or nucleotides within a plurality of nucleic acids (e.g., a plurality of nucleic acids in a sample and/or representative of a subject) that are representative of the locus or nucleotide (e.g., having the same identical nucleic acid sequence and/or nucleic acid sequence context, or having a substantially identical nucleic acid sequence and/or nucleic acid context).

Oligonucleotide primer: As used herein, the term oligonucleotide primer, or primer, refers to a nucleic acid molecule used, capable of being used, or for use in, generating amplicons from a template nucleic acid molecule. Under transcription-permissive conditions (e.g., in the presence of nucleotides and a DNA polymerase, and at a suitable temperature and pH), an oligonucleotide primer can provide a point of initiation of transcription from a template to which the oligonucleotide primer hybridizes. Typically, an oligonucleotide primer is a single-stranded nucleic acid between 5 and 200 nucleotides in length. Those of skill in the art will appreciate that optimal primer length for generating amplicons from a template nucleic acid molecule can vary with conditions including temperature parameters, primer composition, and transcription or amplification method. A pair of oligonucleotide primers, as used herein, refers to a set of two oligonucleotide primers that are respectively complementary to a first strand and a second strand of a template double-stranded nucleic acid molecule. First and second members of a pair of oligonucleotide primers may be referred to as a "forward" oligonucleotide primer and a "reverse" oligonucleotide primer, respectively, with respect to a template nucleic acid strand, in that the forward oligonucleotide primer is capable of hybridizing with a nucleic acid strand complementary to the template nucleic acid strand, the reverse oligonucleotide primer is capable of hybridizing with the template nucleic acid strand, and the position of the forward oligonucleotide primer with respect to the template nucleic acid strand is 5' of the position of the reverse oligonucleotide primer sequence with respect to the template nucleic acid strand. It will be understood by those of skill in the art that the identification of a first and second oligonucleotide primer as forward and reverse oligonucleotide primers, respectively, is arbitrary inasmuch as these identifiers depend upon whether a given nucleic acid strand or its complement is utilized as a template nucleic acid molecule.

Overlapping: The term "overlapping" is used herein in reference to two regions of DNA, each of which contains a sub-sequence that is substantially identical to a sub-sequence of the same length in the other region (e.g., the two regions of DNA have a common sub-sequence). "Substantially identical" means that the two identically-long sub-sequences differ by fewer than a given number of base pairs. In certain instances e.g., as set forth herein, each sub-sequence has a length of at least 20 base pairs that differ by fewer than 4, 3, 2, or 1 base pairs from each other (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 24 base pairs that differ by fewer than 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 50 base pairs that differ by fewer than 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 100 base pairs that differ by fewer than 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 200 base pairs that differ by fewer than 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 250 base pairs that differ by fewer than 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 300 base pairs that differ by fewer than 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 500 base pairs that differ by fewer than 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, each sub-sequence has a length of at least 1000 base pairs that differ by fewer than 200, 100, 60, 50, 40, 30, 20, 15, 10, 9, 8, 7, 6, 5, 4, 3, 2, or 1 base pairs (e.g., the two sub-sequences having at least 80%, at least 85%, at least 90%, at least 95% similarity, at least 97% similarity, at least 98% similarity, at least 99% similarity, or at least 99.5% similarity). In certain instances e.g., as set forth herein, the subsequence of a first region of the two regions of DNA may comprise the entirety of the second region of the two regions of DNA (or vice versa) (e.g., the common sub-sequence may contain the whole of either or both regions).

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered complete when onset of a disease, disorder, or condition has been delayed for a predefined period of time.

Probe: As used herein, the term "probe" refers to a single- or double-stranded nucleic acid molecule that is capable of hybridizing with a complementary target and includes a detectable moiety. In certain embodiments e.g., as set forth herein, a probe is a restriction digest product or is a synthetically produced nucleic acid, e.g., a nucleic acid produced by recombination or amplification. In some instances e.g., as set forth herein, a probe is a capture probe useful in detection, identification, and/or isolation of a target sequence, such as a gene sequence. In various instances e.g., as set forth herein, a detectable moiety of probe can be, e.g., an enzyme (e.g., ELISA, as well as enzyme-based histochemical assays), fluorescent moiety, radioactive moiety, or moiety associated with a luminescence signal.

Prognosis: As used herein, the term "prognosis" refers to determining the qualitative of quantitative probability of at least one possible future outcome or event. As used herein, a prognosis can be a determination of the likely course of a disease, disorder, or condition such as cancer in a subject, a determination regarding the life expectancy of a subject, or a determination regarding response to therapy, e.g., to a particular therapy.

Prognostic information: As used herein, the term "prognostic information" refers to information useful in providing a prognosis. Prognostic information can include, without limitation, biomarker status information.

Promoter: As used herein, a "promoter" can refer to a DNA regulatory region that directly or indirectly (e.g., through promoter-bound proteins or substances) associates with an RNA polymerase and participates in initiation of transcription of a coding sequence.

Reference: As used herein describes a standard or control relative to which a comparison is performed. For example, in some embodiments e.g., as set forth herein, an agent, subject, animal, individual, population, sample, sequence, or value of interest is compared with a reference or control agent, subject, animal, individual, population, sample, sequence, or value. In some embodiments e.g., as set forth herein, a reference or characteristic thereof is tested and/or determined substantially simultaneously with the testing or determination of the characteristic in a sample of interest. In some embodiments e.g., as set forth herein, a reference is a historical reference, optionally embodied in a tangible medium. Typically, as would be understood by those of skill in the art, a reference is determined or characterized under comparable conditions or circumstances to those under assessment, e.g., with regard to a sample. Those skilled in the art will appreciate when sufficient similarities are present to justify reliance on and/or comparison to a particular possible reference or control.

Risk: As used herein with respect to a disease, disorder, or condition, the term "risk" refers to the qualitative of quantitative probability (whether expressed as a percentage or otherwise) that a particular individual will develop the disease, disorder, or condition. In some embodiments e.g., as set forth herein, risk is expressed as a percentage. In some embodiments e.g., as set forth herein, a risk is a qualitative of quantitative probability that is equal to or greater than 0, 1, 2, 3, 4, 5, 6, 7, 8, 9, 10, 20, 30, 40, 50, 60, 70, 80, 90, or 100%. In some embodiments e.g., as set forth herein risk is expressed as a qualitative of quantitative level of risk relative to a reference risk or level or the risk of the same outcome attributed to a reference. In some embodiments e.g., as set forth herein, relative risk is increased or decreased in comparison to the reference sample by a factor of 1.1, 1.2, 1.3, 1.4, 1.5, 1.6, 1.7, 1.8, 1.9, 2, 3, 4, 5, 6, 7, 8, 9, 10, or more.

Sample: As used herein, the term "sample" typically refers to an aliquot of material obtained or derived from a source of interest. In some embodiments e.g., as set forth herein, a source of interest is a biological or environmental source. In some embodiments e.g., as set forth herein, a sample is a "primary sample" obtained directly from a source of interest. In some embodiments e.g., as set forth herein, as will be clear from context, the term "sample" refers to a preparation that is obtained by processing of a primary sample (e.g., by removing one or more components of and/or by adding one or more agents to a primary sample). Such a "processed sample" can include, for example cells, nucleic acids, or proteins extracted from a sample or obtained by subjecting a primary sample to techniques such as amplification or reverse transcription of nucleic acids, isolation and/or purification of certain components, etc.

In certain instances e.g., as set forth herein, a processed sample can be a DNA sample that has been amplified (e.g., pre-amplified). Thus, in various instances, e.g., as set forth herein, an identified sample can refer to a primary form of the sample or to a processed form of the sample. In some instances, a sample that is enzyme-digested DNA can refer to primary enzyme-digested DNA (the immediate product of enzyme digestion) or a further processed sample such as enzyme-digested DNA that has been subject to an amplification step (e.g., an intermediate amplification step, e.g., pre-amplification) and/or to a filtering step, purification step, or step that modifies the sample to facilitate a further step, e.g., in a process of determining methylation status (e.g., methylation status of a primary sample of DNA and/or of DNA as it existed in its original source context).

Screening: As used herein, the term "screening" refers to any method, technique, process, or undertaking intended to generate diagnostic information and/or prognostic information. Accordingly, those of skill in the art will appreciate that the term screening encompasses method, technique, process, or undertaking that determines whether an individual has, is likely to have or develop, or is at risk of having or developing a disease, disorder, or condition, e.g., colorectal cancer.

Specificity: As used herein, the "specificity" of a biomarker refers to the percentage of samples that are characterized by absence of the event or state of interest for which measurement of the biomarker accurately indicates absence of the event or state of interest (true negative rate). In various embodiments e.g., as set forth herein, characterization of the negative samples is independent of the biomarker, and can be achieved by any relevant measure, e.g., any relevant measure known to those of skill in the art. Thus, specificity reflects the probability that the biomarker would detect the absence of the event or state of interest when measured in a sample not characterized that event or state of interest. In particular embodiments e.g., as set forth herein in which the event or state of interest is colorectal cancer, specificity refers to the probability that a biomarker would detect the absence of colorectal cancer in a subject lacking colorectal cancer. Lack of colorectal cancer can be determined, e.g., by histology.

Sensitivity: As used herein, the "sensitivity" of a biomarker refers to the percentage of samples that are characterized by the presence of the event or state of interest for which measurement of the biomarker accurately indicates presence of the event or state of interest (true positive rate). In various embodiments e.g., as set forth herein, characterization of the positive samples is independent of the biomarker, and can be achieved by any relevant measure, e.g., any relevant measure known to those of skill in the art. Thus, sensitivity reflects the probability that a biomarker would detect the presence of the event or state of interest when measured in a sample characterized by presence of that event or state of interest. In particular embodiments e.g., as set forth herein in which the event or state of interest is colorectal cancer, sensitivity refers to the probability that a biomarker would detect the presence of colorectal cancer in a subject that has colorectal cancer. Presence of colorectal cancer can be determined, e.g., by histology.

Solid Tumor: As used herein, the term "solid tumor" refers to an abnormal mass of tissue including cancer cells. In various embodiments e.g., as set forth herein, a solid tumor is or includes an abnormal mass of tissue that does not contain cysts or liquid areas. In some embodiments e.g., as set forth herein, a solid tumor can be benign; in some embodiments e.g., as set forth herein, a solid tumor can be malignant. Examples of solid tumors include carcinomas, lymphomas, and sarcomas. In some embodiments e.g., as set forth herein, solid tumors can be or include adrenal, bile duct, bladder, bone, brain, breast, cervix, colon, endometrium, esophagum, eye, gall bladder, gastrointestinal tract, kidney, larynx, liver, lung, nasal cavity, nasopharynx, oral cavity, ovary, penis, pituitary, prostate, retina, salivary gland, skin, small intestine, stomach, testis, thymus, thyroid, uterine, vaginal, and/or vulval tumors.

Stage of cancer: As used herein, the term "stage of cancer" refers to a qualitative or quantitative assessment of the level of advancement of a cancer. In some embodiments e.g., as set forth herein, criteria used to determine the stage of a cancer can include, but are not limited to, one or more of where the cancer is located in a body, tumor size, whether the cancer has spread to lymph nodes, whether the cancer has spread to one or more different parts of the body, etc. In some embodiments e.g., as set forth herein, cancer can be staged using the so-called TNM System, according to which T refers to the size and extent of the main tumor, usually called the primary tumor; N refers to the number of nearby lymph nodes that have cancer; and M refers to whether the cancer has metastasized. In some embodiments e.g., as set forth herein, a cancer can be referred to as Stage 0 (abnormal cells are present but have not spread to nearby tissue, also called carcinoma in situ, or CIS; CIS is not cancer, but it can become cancer), Stage I-III (cancer is present; the higher the number, the larger the tumor and the more it has spread into nearby tissues), or Stage IV (the cancer has spread to distant parts of the body). In some embodiments e.g., as set forth herein, a cancer can be assigned to a stage selected from the group consisting of: in situ (abnormal cells are present but have not spread to nearby tissue); localized (cancer is limited to the place where it started, with no sign that it has spread); regional (cancer has spread to nearby lymph nodes, tissues, or organs): distant (cancer has spread to distant parts of the body); and unknown (there is not enough information to identify cancer stage).

Susceptible to: An individual who is "susceptible to" a disease, disorder, or condition is at risk for developing the disease, disorder, or condition. In some embodiments e.g., as set forth herein, an individual who is susceptible to a disease, disorder, or condition does not display any symptoms of the disease, disorder, or condition. In some embodiments e.g., as set forth herein, an individual who is susceptible to a disease, disorder, or condition has not been diagnosed with the disease, disorder, and/or condition. In some embodiments e.g., as set forth herein, an individual who is susceptible to a disease, disorder, or condition is an individual who has been exposed to conditions associated with, or presents a biomarker status (e.g., a methylation status) associated with, development of the disease, disorder, or condition. In some embodiments e.g., as set forth herein, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments e.g., as set forth herein, a subject is suffering from a disease, disorder or condition. In some embodiments e.g., as set forth herein, a subject is susceptible to a disease, disorder, or condition. In some embodiments e.g., as set forth herein, a subject displays one or more symptoms or characteristics of a disease, disorder or condition. In some embodiments e.g., as set forth herein, a subject is not suffering from a disease, disorder or condition. In some embodiments e.g., as set forth herein, a subject does not display any symptom or characteristic of a disease, disorder, or condition. In some embodiments e.g., as set forth herein, a subject is someone with one or more features characteristic of susceptibility to or risk of a disease, disorder, or condition. In some embodiments e.g., as set forth herein, a subject is a patient. In some embodiments e.g., as set forth herein, a subject is an individual to whom diagnosis has been performed and/or to whom therapy has been administered. In some instances e.g., as set forth herein, a human subject can be interchangeably referred to as an "individual."

Therapeutic agent: As used herein, the term "therapeutic agent" refers to any agent that elicits a desired pharmacological effect when administered to a subject. In some embodiments e.g., as set forth herein, an agent is considered to be a therapeutic agent if it demonstrates a statistically significant effect across an appropriate population. In some embodiments e.g., as set forth herein, the appropriate population can be a population of model organisms or a human population. In some embodiments e.g., as set forth herein, an appropriate population can be defined by various criteria, such as a certain age group, gender, genetic background, preexisting clinical conditions, etc. In some embodiments e.g., as set forth herein, a therapeutic agent is a substance that can be used for treatment of a disease, disorder, or condition. In some embodiments e.g., as set forth herein, a therapeutic agent is an agent that has been or is required to be approved by a government agency before it can be marketed for administration to humans. In some embodiments e.g., as set forth herein, a therapeutic agent is an agent for which a medical prescription is required for administration to humans.

Treatment: As used herein, the term "treatment" (also "treat" or "treating") refers to administration of a therapy that partially or completely alleviates, ameliorates, relieves, inhibits, delays onset of, reduces severity of, and/or reduces incidence of one or more symptoms, features, and/or causes of a particular disease, disorder, or condition, or is administered for the purpose of achieving any such result. In some embodiments e.g., as set forth herein, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments e.g., as set forth herein, treatment can be of a subject who has been diagnosed as suffering from the relevant disease, disorder, and/or condition. In some embodiments e.g., as set forth herein, treatment can be of a subject known to have one or more susceptibility factors that are statistically correlated with increased risk of development of the relevant disease, disorder, or condition. In various examples, treatment is of a cancer.

Upstream: As used herein, the term "upstream" means a first DNA region is closer, relative to a second DNA region, to the N-terminus of a nucleic acid that includes the first DNA region and the second DNA region.

Unmethylated: As used herein, the terms "unmethylated" and "non-methylated" are used interchangeably and mean that an identified DNA region includes no methylated nucleotides.

Variant: As used herein, the term "variant" refers to an entity that shows significant structural identity with a reference entity but differs structurally from the reference entity in the presence, absence, or level of one or more chemical moieties as compared with the reference entity. In some embodiments e.g., as set forth herein, a variant also differs functionally from its reference entity. In general, whether a particular entity is properly considered to be a "variant" of a reference entity is based on its degree of structural identity with the reference entity. A variant can be a molecule comparable, but not identical to, a reference. For example, a variant nucleic acid can differ from a reference nucleic acid at one or more differences in nucleotide sequence. In some embodiments e.g., as set forth herein, a variant nucleic acid shows an overall sequence identity with a reference nucleic acid that is at least 80%, 85%, 86%, 87%, 88%, 89%, 90%, 91%, 92%, 93%, 94%, 95%, 96%, 97%, or 99%. In many embodiments e.g., as set forth herein, a nucleic acid of interest is considered to be a "variant" of a reference nucleic acid if the nucleic acid of interest has a sequence that is identical to that of the reference but for a small number of sequence alterations at particular positions. In some embodiments e.g., as set forth herein, a variant has 10, 9, 8, 7, 6, 5, 4, 3, 2, or 1 substituted residues as compared with a reference. In some embodiments e.g., as set forth herein, a variant has not more than 5, 4, 3, 2, or 1 residue additions, substitutions, or deletions as compared with the reference. In various embodiments e.g., as set forth herein, the number of additions, substitutions, or deletions is fewer than about 25, about 20, about 19, about 18, about 17, about 16, about 15, about 14, about 13, about 10, about 9, about 8, about 7, about 6, and commonly are fewer than about 5, about 4, about 3, or about 2 residues.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 2 is a table showing the characteristics of a training set of 166 subjects used to train the computational model for the development of the biomarker signature. The number of female subjects, the number of male subjects, and the average and range of ages of the subjects. The subjects were diagnosed as suffering with colorectal cancer (CRC), healthy control subjects (Control; having been diagnosed with hyperplastic polyps, patients diagnosed as having non-advanced adenomas (NAAs), and patients having no colonoscopy findings). FIG. 2 further distinguishes the location of the cancer of those suffering with CRC as proximal or distal based on a colonoscopy evaluation;

FIG. 3 is a table showing the characteristics of a validation group of 535 human subjects which were used to validate the selected markers. FIG. 3 provides the number of female subjects, the number of male subjects, and the average and range of ages of the subjects. The subjects were diagnosed as suffering with colorectal cancer (CRC), healthy control subjects (Control; having been diagnosed with hyperplastic polyps, patients diagnosed as having non-advanced adenomas (NAAs), and patients having a no colonoscopy findings) and patients suffering with advanced adenomas (AA).

The features and advantages of the present disclosure will become more apparent from the detailed description set forth below when taken in conjunction with the drawings.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Screening for Colorectal Cancer

There is a need for improved methods of screening for colorectal cancer and/or advanced adenomas, including screening for early-stage colorectal cancer. Despite recommendations for screening of individuals, e.g., over age 50, colorectal cancer screening programs are often ineffective or unsatisfactory. Improved colorectal cancer and/or advanced adenoma screening improves diagnosis and reduces colorectal cancer mortality.

Figure 16:
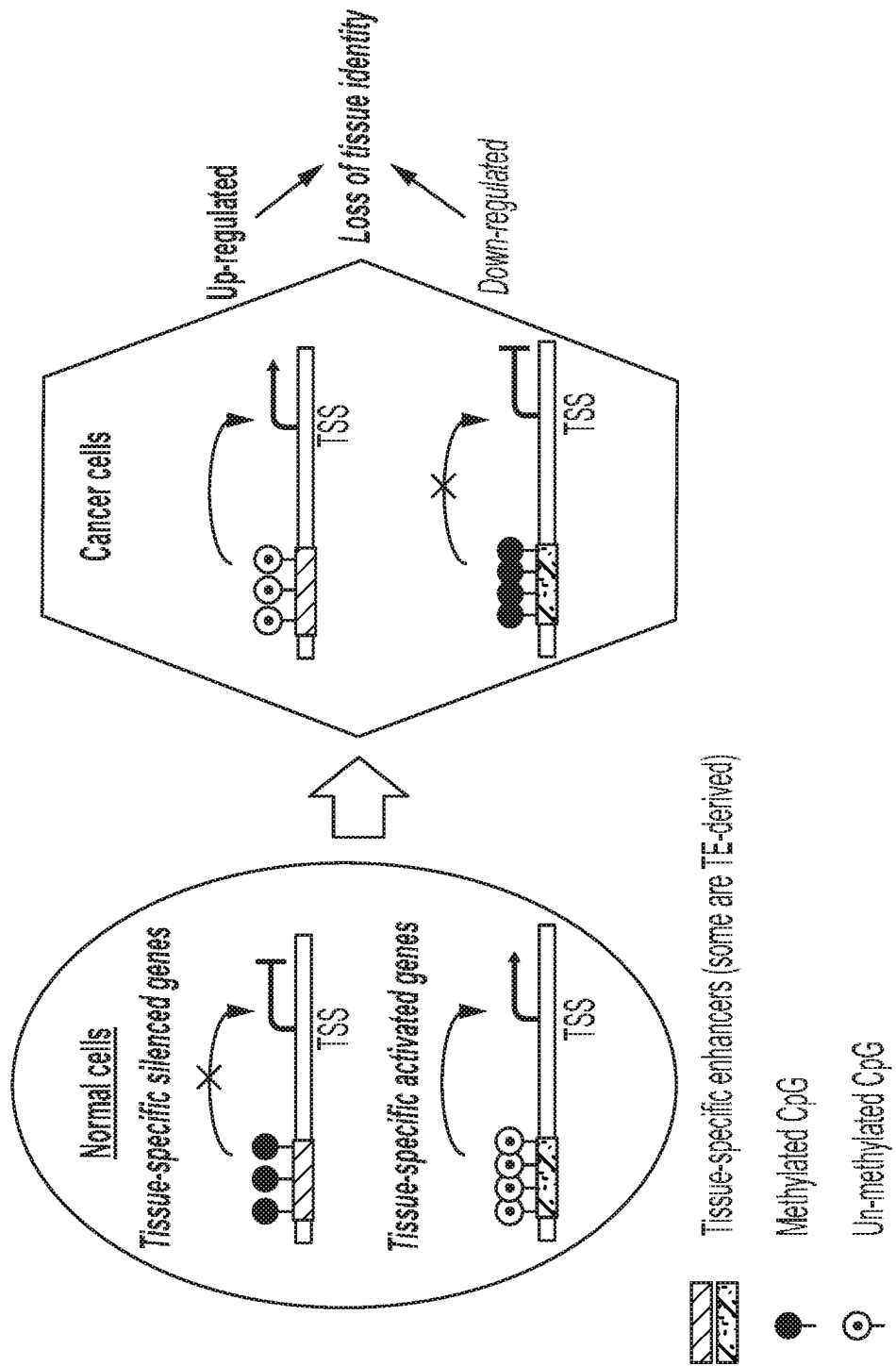
FIG. 16 is a schematic showing example methylation changes in methylation status between normal and cancer cells, and further indicates how changes in methylation status can impact gene expression differences between normal and cancer cells.

DNA methylation (e.g., hypermethylation or hypomethylation) can activate or inactivate genes, including genes that impact cancer development (see, e.g., FIG. 16). Thus, for example, hypermethylation can inactivate one or more genes that typically act to suppress cancer, causing or contributing to development of cancer in a sample or subject.

The present disclosure includes the discovery that determination of the methylation status of one or more methylation loci provided herein, and/or the methylation status of one or more DMRs provided herein, and/or the methylation status of one or more methylation sites provided herein, provides screening for colorectal cancer and/or advanced adenomas, e.g., with a high degree of sensitivity and/or specificity. The present disclosure provides compositions and methods including or relating to colorectal cancer and/or advanced adenoma methylation biomarkers that, individually or in various panels comprising two or more biomarkers, provide for screening of colorectal cancer and/or advanced adenomas, e.g., with a high degree of specificity and/or sensitivity.

In various embodiments e.g., as set forth herein, a colorectal cancer and/or advanced adenoma methylation biomarker of the present disclosure is selected from a methylation locus that is or includes a portion (e.g., at least 1 common base pair) of the sequence of the differentially methylated regions (DMRs) as identified in Table 1 below. The DMRs are identified by a chromosome number (Chr. No.) on which the DMR is located, the start position (start base pair) of the DMR on the chromosome, the end position of the DMR on the chromosome, the width of the DMR, the annotated names of the one or more genes (if available) overlapping with or contained within the DMR, and the Sequence ID Number of the DMR as presented in the Sequences section of the specification and in the sequence listing presented. The chromosome number and the start (start base pair) and end (end base pair) positions of the regions as identified are in reference to the human genome build identified as GRCh38.

TABLE 1

List of 69 DMRs of interest in screening for advanced adenomas and colorectal cancer.

| SEQ ID NO | Chr. | Start base pair | End base pair | Region Width | Annotated Gene Name |
|---|---|---|---|---|---|
| SEQ ID NO: 1 | 1 | 18636183 | 18636479 | 297 | PAX7 |
| SEQ ID NO: 2 | 1 | 107140100 | 107140341 | 242 | NTNG1 |
| SEQ ID NO: 3 | 1 | 114153175 | 114153431 | 257 | SYT6 |
| SEQ ID NO: 4 | 2 | 5673847 | 5674110 | 264 | LINC01248 |
| SEQ ID NO: 5 | 2 | 26692974 | 26693164 | 191 | KCNK3 |
| SEQ ID NO: 6 | 2 | 31136994 | 31138312 | 1319 | GALNT14 |
| SEQ ID NO: 7 | 2 | 100416598 | 100417320 | 723 | CHST10 |
| SEQ ID NO: 8 | 2 | 127025668 | 127025992 | 325 | no annotation |
| SEQ ID NO: 9 | 2 | 136765863 | 136767257 | 1395 | THSD7B |
| SEQ ID NO: 10 | 2 | 209771521 | 209771717 | 197 | UNC80 |
| SEQ ID NO: 11 | 3 | 96812527 | 96814374 | 1848 | EPHA6 |
| SEQ ID NO: 12 | 3 | 151086702 | 151087381 | 680 | MED12L |
| SEQ ID NO: 13 | 4 | 61201658 | 61202419 | 762 | ADGRL3 |
| SEQ ID NO: 14 | 4 | 141133100 | 141133759 | 660 | RNF150 |
| SEQ ID NO: 15 | 4 | 167233855 | 167235112 | 1258 | SPOCK3 |
| SEQ ID NO: 16 | 4 | 176001298 | 176001937 | 640 | GPM6A |
| SEQ ID NO: 17 | 4 | 185020150 | 185020721 | 572 | HELT |
| SEQ ID NO: 18 | 5 | 180353742 | 180353989 | 248 | GFPT2 |
| SEQ ID NO: 19 | 6 | 31815502 | 31815783 | 282 | HSPA1L, HSPA1A |
| SEQ ID NO: 20 | 6 | 123803543 | 123804573 | 1031 | NKAIN2 |
| SEQ ID NO: 21 | 7 | 141072216 | 141073010 | 795 | TMEM178B |
| SEQ ID NO: 22 | 7 | 154304773 | 154304932 | 160 | DPP6 |
| SEQ ID NO: 23 | 8 | 17026468 | 17027021 | 554 | MICU3 |
| SEQ ID NO: 24 | 8 | 52564399 | 52566130 | 1732 | ALKAL1 |
| SEQ ID NO: 25 | 8 | 64581458 | 64581984 | 527 | LOC401463, BHLHE22 |
| SEQ ID NO: 26 | 8 | 103500115 | 103500325 | 211 | RIMS2, LOC105375690, SLC25A32 |
| SEQ ID NO: 27 | 9 | 843218 | 843532 | 315 | DMRT1 |
| SEQ ID NO: 28 | 9 | 21970988 | 21971129 | 142 | CDKN2A, CDKN2B-AS1 |
| SEQ ID NO: 29 | 9 | 36986363 | 36986579 | 217 | PAX5 |
| SEQ ID NO: 30 | 10 | 16520584 | 16520645 | 62 | C1QL3 |
| SEQ ID NO: 31 | 10 | 25933862 | 25934167 | 306 | MYO3A, LOC101929073 |
| SEQ ID NO: 32 | 10 | 26211596 | 26212313 | 718 | GAD2, MYO3A |
| SEQ ID NO: 33 | 10 | 127736443 | 127736756 | 314 | FOXI2 |

TABLE 1-continued

List of 69 DMRs of interest in screening for advanced adenomas and colorectal cancer.

| SEQ ID NO | Chr. | Start base pair | End base pair | Region Width | Annotated Gene Name |
|---|---|---|---|---|---|
| SEQ ID NO: 34 | 11 | 94740674 | 94742025 | 1352 | LOC105369438, AMOTL1 |
| SEQ ID NO: 35 | 11 | 112962067 | 112962734 | 668 | LOC101928847, NCAM1 |
| SEQ ID NO: 36 | 11 | 117795608 | 117796104 | 497 | DSCAML1 |
| SEQ ID NO: 37 | 12 | 15322181 | 15323178 | 998 | PTPRO, RERG |
| SEQ ID NO: 38 | 12 | 63667846 | 63668580 | 735 | DPY19L2 |
| SEQ ID NO: 39 | 12 | 111033274 | 111033632 | 359 | CUX2 |
| SEQ ID NO: 40 | 13 | 67229618 | 67231644 | 2027 | PCDH9 |
| SEQ ID NO: 41 | 13 | 87673128 | 87673271 | 144 | MIR4500HG, SLITRK5 |
| SEQ ID NO: 42 | 14 | 70188797 | 70189400 | 604 | SLC8A3, LOC646548 |
| SEQ ID NO: 43 | 14 | 77966179 | 77966411 | 233 | no annotation |
| SEQ ID NO: 44 | 15 | 45378160 | 45378420 | 261 | GATM |
| SEQ ID NO: 45 | 15 | 64824187 | 64824233 | 47 | PIF1 |
| SEQ ID NO: 46 | 15 | 79089616 | 79089950 | 335 | RASGRF1 |
| SEQ ID NO: 47 | 16 | 70737594 | 70737910 | 317 | VAC14 |
| SEQ ID NO: 48 | 16 | 77789176 | 77789410 | 235 | VAT1L |
| SEQ ID NO: 49 | 16 | 87601415 | 87601495 | 81 | JPH3 |
| SEQ ID NO: 50 | 17 | 35448324 | 35448347 | 24 | SLFN13 |
| SEQ ID NO: 51 | 17 | 76076064 | 76076299 | 236 | ZACN, SRP68, GALR2 |
| SEQ ID NO: 52 | 18 | 907740 | 908272 | 533 | ADCYAP1 |
| SEQ ID NO: 53 | 18 | 28177400 | 28177679 | 280 | CDH2 |
| SEQ ID NO: 54 | 18 | 69401262 | 69401796 | 535 | DOK6 |
| SEQ ID NO: 55 | 18 | 75916571 | 75916639 | 69 | no annotation |
| SEQ ID NO: 56 | 19 | 36666416 | 36667626 | 1211 | ZNF461 |
| SEQ ID NO: 57 | 19 | 36916473 | 36916789 | 317 | ZNF829, ZNF568 |
| SEQ ID NO: 58 | 19 | 36973366 | 36973693 | 328 | ZNF568 |
| SEQ ID NO: 59 | 19 | 37551650 | 37551952 | 303 | ZNF540, ZNF571-AS1 |
| SEQ ID NO: 60 | 19 | 42270825 | 42271072 | 248 | CIC |
| SEQ ID NO: 61 | 19 | 56393726 | 56393946 | 221 | ZNF582-AS1, ZNF582 |
| SEQ ID NO: 62 | 19 | 56507701 | 56507850 | 150 | ZNF471 |
| SEQ ID NO: 63 | 19 | 57191866 | 57192102 | 237 | ZNF264 |
| SEQ ID NO: 64 | 19 | 57726974 | 57727102 | 129 | ZNF671, ZNF551, ZNF776 |
| SEQ ID NO: 65 | 20 | 21518031 | 21518878 | 848 | NKX2-2 |
| SEQ ID NO: 66 | 20 | 56925418 | 56925496 | 79 | no annotation |
| SEQ ID NO: 67 | 21 | 26843133 | 26845357 | 2225 | ADAMTS1 |
| SEQ ID NO: 68 | 21 | 31343542 | 31344538 | 997 | TIAM1 |
| SEQ ID NO: 69 | 21 | 33070564 | 33070847 | 284 | OLIG1 |

For the avoidance of any doubt, any methylation biomarker provided herein can be, or be included in, among other things, a colorectal cancer methylation biomarker and/or an advanced adenoma methylation biomarker.

In some embodiments e.g., as set forth herein, a colorectal cancer and/or advanced adenoma methylation biomarker can be or include a single methylation locus. In some embodiments e.g., as set forth herein, the methylation biomarker can be or include two or more methylation loci. In some embodiments e.g., as set forth herein, the methylation biomarker can be or include a single differentially methylated region (DMR). In some embodiments e.g., as set forth herein, a methylation biomarker can be or include a single methylation site. In other embodiments e.g., as set forth herein, a methylation biomarker can be or include two or more methylation sites. In some embodiments e.g., as set forth herein, a methylation locus can include two or more DMRs and further include DNA regions adjacent to one or more of the included DMRs.

In some instances e.g., as set forth herein, a methylation locus is or includes a gene, such as a gene provided in Table 1. In some instances e.g., as set forth herein a methylation locus is or includes a portion of a gene, e.g., a portion of a gene provided in Table 1. In some instances e.g., as set forth herein, a methylation locus includes but is not limited to identified nucleic acid boundaries of a gene. In some instances e.g., as set forth herein, a methylation locus is found outside of previously annotated genes, e.g., an unannotated region of a genetic sequence as provided in Table 1. In some instances e.g., as set forth herein, a methylation locus is or includes a portion of multiple genes, e.g., as provided in Table 1.

In some instances e.g., as set forth herein, a methylation locus is or includes a coding region of a gene, such as a coding region of a gene provided in Table 1. In some instances e.g., as set forth herein, a methylation locus is or includes a portion of the coding region of gene, e.g., a portion of the coding region a gene provided in Table 1. In some instances e.g., as set forth herein, a methylation locus includes but is not limited to identified nucleic acid boundaries of a coding region of gene.

In some instances e.g., as set forth herein, a methylation locus is or includes a promoter and/or other regulatory region of a gene, such as a promoter and/or other regulatory region of a gene provided in Table 1. In some instances e.g., as set forth herein, a methylation locus is or includes a portion of the promoter and/or regulatory region of gene, e.g., a portion of promoter and/or regulatory region a gene provided in Table 1. In some instances e.g., as set forth herein, a methylation locus includes but is not limited to identified nucleic acid boundaries of a promoter and/or other regulatory region of gene. In some embodiments e.g., as set forth herein a methylation locus is or includes a high CpG density promoter, or a portion thereof.

In some embodiments e.g., as set forth herein, a methylation locus is or includes non-coding sequence. In some embodiments e.g., as set forth herein, a methylation locus is or includes one or more exons, and/or one or more introns.

In some embodiments e.g., as set forth herein, a methylation locus includes a DNA region extending a predetermined number of nucleotides upstream of a coding sequence, and/or a DNA region extending a predetermined number of nucleotides downstream of a coding sequence. In various instances e.g., as set forth herein, a predetermined number of nucleotides upstream and/or downstream and be or include, e.g., 500 bp, 1 kb, 2 kb, 3 kb, 4 kb, 5 kb, 10 kb, 20 kb, 30 kb, 40 kb, 50 kb, 75 kb, or 100 kb. Those of skill in the art will appreciate that methylation biomarkers capable of impacting expression of a coding sequence may typically be within any of these distances of the coding sequence, upstream and/or downstream.

Those of skill in the art will appreciate that a methylation locus identified as a methylation biomarker need not necessarily be assayed in a single experiment, reaction, or amplicon. A single methylation locus identified as a colorectal cancer and/or advanced adenoma methylation biomarker can be assayed, e.g., in a method including separate amplification (or providing oligonucleotide primers and conditions sufficient for amplification of) of one or more distinct or overlapping DNA regions within a methylation locus, e.g., one or more distinct or overlapping DMRs. Those of skill in the art will further appreciate that a methylation locus identified as a methylation biomarker need not be analyzed for methylation status of each nucleotide, nor each CpG, present within the methylation locus. Rather, a methylation locus that is a methylation biomarker may be analyzed, e.g., by analysis of a single DNA region within the methylation locus, e.g., by analysis of a single DMR within the methylation locus.

DMRs of the present disclosure can be a methylation locus or include a portion of a methylation locus. In some instances e.g., as set forth herein, a DMR is a DNA region with a methylation locus that is, e.g., 1 to 5,000 bp in length. In various embodiments e.g., as set forth herein, a DMR is a DNA region with a methylation locus that is equal to or less than 5000 bp, 4,000 bp, 3,000 bp, 2,000 bp, 1,000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, 50 bp, 40 bp, 30 bp, 20 bp, or 10 bp in length. In some embodiments e.g., as set forth herein, a DMR is 1, 2, 3, 4, 5, 6, 7, 8 or 9 bp in length.

Methylation biomarkers, including without limitation methylation loci, methylation sites, and DMRs provided herein.

For clarity, those of skill in the art will appreciate that term methylation biomarker is used broadly, such that a methylation locus can be a methylation biomarker that includes one or more DMRs, each of which DMRs is also itself a methylation biomarker, and each of which DMRs can include one or more methylation sites, each of which methylation sites is also itself a methylation biomarker. Moreover, a methylation biomarker can include two or more methylation loci. Accordingly, status as a methylation biomarker does not turn on the contiguousness of nucleic acids included in a biomarker, but rather on the existence of a change in methylation status for included DNA region(s) between a first state and a second state, such as between colorectal cancer and controls and/or between advanced adenomas and controls.

As provided herein, a methylation locus can be any of one or more methylation loci each of which methylation loci is or includes a genetic region (e.g., a DMR) as identified in Table 1. In some particular embodiments e.g., as set forth herein, a colorectal cancer and/or advanced adenoma methylation biomarker includes a single methylation locus that is or includes (all or a portion of) a gene identified in Table 1.

In some particular embodiments e.g., as set forth herein, a colorectal cancer and/or advanced adenoma methylation biomarker includes two or more methylation loci, each of which is or includes a genetic region identified in Table 1. In some embodiments e.g., as set forth herein, the methylation biomarker includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 methylation loci, each of which includes (all or a portion of) a genetic region identified in Table 1.

The DMR sequences provided in Tables 2-4 are selected regions that consist of, overlap with, or contain portions of the DMRs of Table 1. That is, each identified region of DNA in Tables 2-4 encompasses a portion of, up to and including all of a DMRs identified in Table 1. To clarify, the evaluation of a DMR of Table 1 overlapping with a DMR of Tables 2-4 is made based on the sequence start and end positions and the chromosome number. If both DMRs are found on the same chromosome and a one of the two DMR sequence has a start and/or end point between the start and end points or at one of the start and end points of the second of the two DMR sequence, they are deemed to overlap. For instance, UDX_224.14 (SEQ ID No. 190) of Table 4 encompasses a selection of 111 contiguous base pairs on chromosome 21. All 111 contiguous base pairs are found within SEQ ID No. 67 of Table 1, which is also found on chromosome 21. The start point of UDX_224.14 is 26844767 and the end point is at 26844877, while the start point of SEQ ID No. 67 is 26843133 and the end point is 26845357. As both the start and end points of UDX_224.14 are found between the start and end points of SEQ ID No. 67 and both are on the same chromosome, they overlap with one another and accordingly share an identical overlapping sequence.

In another instance, UDX_244_2 (SEQ ID No. 213) of Table 4 overlaps a portion of (i.e., does not encompass the entirety of) SEQ ID No. 2 of Table 1. UDX_244_2 is 213 base pairs long and shares a contiguous sequence of 73 base pairs in common with SEQ ID No. 2, which is 242 base pairs long. The start position of UDX_224_2 on chromosome 1 is 107140056 and the end position is 107140173. The start position of SEQ ID No. 2 is 107140100 and the end position is 107140341. Accordingly, as the start position of SEQ ID No. 2 is between the start and end positions of UDX_224.2 and both are located on chromosome 1, these sequences are also said to be "overlapping" with one another. In some particular embodiments e.g., as set forth herein, a colorectal cancer and/or advanced adenoma methylation biomarker includes three or more methylation loci, each of three or more methylation loci is or includes a genetic region identified in any one of tables Table 1 to 4, including without limitation and combinations of three or more methylation loci that respectively are or include genetic regions identified in one of Tables 2 to 4.

In some particular embodiments e.g., as set forth herein, a colorectal cancer and/or advanced adenoma methylation biomarker includes three methylation loci, which three methylation loci include methylation loci that are or include the genetic regions identified in Table 2. In some particular embodiments e.g., as set forth herein, a colorectal cancer methylation biomarker includes ten methylation loci, which ten methylation loci include methylation loci that are or include the genetic regions identified in Table 3. In some particular embodiments e.g., as set forth herein, a colorectal cancer methylation biomarker includes forty methylation loci, which forty methylation loci include methylation loci that are or include the genetic regions identified in Table 4.

TABLE 2

Combination of 3 methylation loci ranked in order of importance to the diagnosis of colorectal cancer and/or advanced adenoma.

| Order | UID | Chr. | Start Position | End Position | Sequence Width | Gene Name | SEQ ID NO: |
|---|---|---|---|---|---|---|---|
| 1 | UDX_29_1 | 20 | 56925428 | 56925505 | 78 | no annotation | 210 |
| 2 | UDX_272.3_2 | 10 | 26211885 | 26211963 | 79 | GAD2, MYO3A | 201 |
| 3 | UDX_277.7_2 | 8 | 52565317 | 52565408 | 92 | ALKALI | 192 |

TABLE 3

Combination of 10 methylation loci ranked in order of importance to the diagnosis of colorectal cancer and/or advanced adenoma.

| Order | UID | Chr. | Start Position | End Position | Sequence Width | Gene Name | SEQ ID NO: |
|---|---|---|---|---|---|---|---|
| 1 | UDX_29_1 | 20 | 56925428 | 56925505 | 78 | no annotation | 210 |
| 2 | UDX_272.3_2 | 10 | 26211885 | 26211963 | 79 | GAD2, MYO3A | 201 |
| 3 | UDX_277.7_2 | 8 | 52565317 | 52565408 | 92 | ALKALI | 192 |
| 4 | UDX_272.4 | 10 | 26212056 | 26212160 | 105 | GAD2, MYO3A | 202 |
| 5 | UDX_260.1 | 15 | 79089689 | 79089791 | 103 | RASGRF1 | 218 |
| 6 | UDX_174.3 | 8 | 17026934 | 17027030 | 97 | MICU3 | 208 |
| 7 | UDX_260.2_1 | 15 | 79089783 | 79089858 | 76 | RASGRF1 | 219 |
| 8 | UDX_137.1 | 10 | 127736482 | 127736589 | 108 | FOXI2 | 200 |
| 9 | UDX_17_2 | 10 | 16520590 | 16520719 | 130 | C1QL3 | 193 |
| 10 | UDX_230 | 9 | 21970918 | 21971017 | 100 | CDKN2A, CDKN2B-AS1 | 195 |

TABLE 4

Combination of 40 methylation loci ranked in order of importance to the diagnosis of colorectal cancer and/or advanced adenoma.

| Order | UID | Chr | Start Position | End Position | Sequence Width | Gene Name | SEQ ID NO: |
|---|---|---|---|---|---|---|---|
| 1 | UDX_29_1 | 20 | 56925428 | 56925505 | 78 | no annotation | 210 |
| 2 | UDX_272.3_2 | 10 | 26211885 | 26211963 | 79 | GAD2, MYO3A | 201 |
| 3 | UDX_277.7_2 | 8 | 52565317 | 52565408 | 92 | ALKAL1 | 192 |
| 4 | UDX_272.4 | 10 | 26212056 | 26212160 | 105 | GAD2, MYO3A | 202 |
| 5 | UDX_260.1 | 15 | 79089689 | 79089791 | 103 | RASGRF1 | 218 |
| 6 | UDX_174.3 | 8 | 17026934 | 17027030 | 97 | MICU3 | 208 |
| 7 | UDX_260.2_1 | 15 | 79089783 | 79089858 | 76 | RASGRF1 | 219 |
| 8 | UDX_137.1 | 10 | 127736482 | 127736589 | 108 | FOXI2 | 200 |
| 9 | UDX_17_2 | 10 | 16520590 | 16520719 | 130 | C1QL3 | 193 |
| 10 | UDX_230 | 9 | 21970918 | 21971017 | 100 | CDKN2A, CDKN2B-AS1 | 195 |
| 11 | UDX_117.2 | 1 | 114153293 | 114153403 | 111 | SYT6 | 223 |
| 12 | UDX_1_1 | 17 | 35448306 | 35448407 | 102 | SLFN13 | 222 |
| 13 | UDX_185.1 | 4 | 176001298 | 176001402 | 105 | GPM6A | 205 |
| 13 | UDX_24_1 | 18 | 75916501 | 75916621 | 121 | no annotation | 211 |
| 14 | UDX_221.2_2 | 2 | 136766099 | 136766189 | 91 | THSD7B | 224 |
| 16 | UDX_242_2 | 19 | 56393660 | 56393732 | 73 | ZNF582-AS1, ZNF582 | 229 |
| 17 | UDX_120.2 | 15 | 45378327 | 45378410 | 84 | GATM | 203 |
| 18 | UDX_250.1 | 19 | 37551664 | 37551748 | 85 | ZNF540, ZNF571-AS1 | 227 |
| 19 | UDX_128.1 | 21 | 33070631 | 33070711 | 81 | OLIG1 | 214 |
| 20 | UDX_222.1 | 3 | 96813875 | 96813987 | 113 | EPHA6 | 198 |
| 21 | UDX_197.3 | 12 | 63668266 | 63668380 | 115 | DPY19L2 | 197 |
| 22 | UDX181.2_1 | 14 | 70189010 | 70189101 | 92 | SLC8A3, LOC646548 | 220 |
| 23 | UDX_251.2_1 | 10 | 25934063 | 25934130 | 68 | MYO3A, LOC101929073 | 209 |

TABLE 4-continued

Combination of 40 methylation loci ranked in order of importance to the diagnosis of colorectal cancer and/or advanced adenoma.

| Order | UID | Chr | Start Position | End Position | Sequence Width | Gene Name | SEQ ID NO: |
|---|---|---|---|---|---|---|---|
| 24 | UDX_85.2_1 | 2 | 209771685 | 209771755 | 71 | UNC80 | 225 |
| 25 | UDX_66.2 | 7 | 154304857 | 154304969 | 113 | DPP6 | 196 |
| 26 | UDX_107.2 | 14 | 77966333 | 77966434 | 102 | no annotation | 212 |
| 27 | UDX_258.2_1 | 19 | 36973532 | 36973602 | 71 | ZNF568 | 228 |
| 28 | UDX_30_1 | 16 | 87601409 | 87601511 | 103 | JPH3 | 206 |
| 29 | UDX_217.4_1 | 19 | 36666980 | 36667097 | 118 | ZNF461 | 226 |
| 30 | UDX_244_2 | 1 | 107140056 | 107140173 | 118 | NTNG1 | 213 |
| 31 | UDX_198.5_1 | 4 | 61202277 | 61202367 | 91 | ADGRL3 | 191 |
| 32 | UDX_224.14 | 21 | 26844767 | 26844877 | 111 | ADAMTS1 | 190 |
| 33 | UDX_124.1 | 18 | 28177439 | 28177533 | 95 | CDH2 | 194 |
| 34 | UDX_121.1 | 2 | 5673894 | 5673976 | 83 | LINC01248 | 207 |
| 35 | UDX_274.2_1 | 12 | 15322352 | 15322435 | 84 | PTPRO, RERG | 216 |
| 36 | UDX181.4_1 | 14 | 70189227 | 70189296 | 70 | SLC8A3, LOC646548 | 221 |
| 37 | UDX_222.11_2 | 3 | 96814054 | 96814137 | 84 | EPHA6 | 199 |
| 38 | UDX_94.2_2 | 9 | 36986521 | 36986581 | 61 | PAX5 | 215 |
| 39 | UDX114.1_1 | 5 | 180353709 | 180353815 | 107 | GFPT2 | 204 |
| 40 | UDX_274.3_1 | 12 | 15322477 | 15322549 | 73 | PTPRO, RERG | 217 |

As provided herein, a DMR can be any of one or more DMRs, each of which is present in a methylation locus that is or includes (all or a portion of) a genetic region identified in Table 1. In some particular embodiments e.g., as set forth herein, a colorectal cancer and/or advanced adenoma methylation biomarker is or includes a single DMR that is, includes all or a portion of, or is present in a genetic region identified in Table 1.

In some particular embodiments e.g., as set forth herein, a colorectal cancer methylation biomarker includes three or more DMRs, each of which is, includes all or a portion of, or is present in a genetic region identified in Table 1. In some embodiments e.g., as set forth herein, a colorectal cancer methylation biomarker includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 DMRs, each of which includes (all or a portion of) a genetic region identified in Table 1.

In some particular embodiments e.g., as set forth herein, a colorectal cancer and/or advanced adenoma methylation biomarker includes two or more DMRs, each of which two or more DMRs is, includes all or a portion of, or is present in a gene identified in any one of Tables 1-4. In some particular embodiments e.g., as set forth herein, a colorectal cancer methylation biomarker includes three DMRs, which three DMRs include DMRs that are, include all or a portion of, or are present in the genetic regions identified in Table 2. In some particular embodiments e.g., as set forth herein, a colorectal cancer and/or advanced adenoma methylation biomarker includes ten DMRs, which ten DMRs include DMRs that are, include all or a portion of, or are present in the genetic regions identified in Table 3. In some particular embodiments e.g., as set forth herein, a colorectal cancer methylation biomarker includes forty DMRs, which forty DMRs include DMRs that are, include all or a portion of, or are present in the genetic regions identified in Table 4.

In various embodiments e.g., as set forth herein, a methylation biomarker can be or include one or more individual nucleotides (e.g., a single individual cysteine residue in the context of CpG) or a plurality of individual cysteine residues (e.g., of a plurality of CpGs) present within one or more methylation loci (e.g, one or more DMRs) provided herein. Thus, in certain embodiments a methylation biomarker is or includes methylation status of a plurality of individual methylation sites.

In various embodiments e.g., as set forth herein, a methylation biomarker is, includes, or is characterized by change in methylation status that is a change in the methylation of one or more methylation sites within one or more methylation loci (e.g., one or more DMRs). In various embodiments e.g., as set forth herein, a methylation biomarker is or includes a change in methylation status that is a change in the number of methylated sites within a one or more methylation loci (e.g., one or more DMRs). In various embodiments e.g., as set forth herein, a methylation biomarker is or includes a change in methylation status that is a change in the frequency of methylation sites within one or more methylation loci (e.g., one or more DMRs). In various embodiments e.g., as set forth herein, a methylation biomarker is or includes a change in methylation status that is a change in the pattern of methylation sites within one or more methylation loci (e.g., one or more DMRs).

In various embodiments e.g., as set forth herein, methylation status of one or more methylation loci (e.g., one or more DMRs) is expressed as a fraction or percentage of the one or more methylation loci (e.g., the one or more DMRs) present in a sample that are methylated, e.g., as a fraction of the number of individual DNA strands of DNA in a sample that are methylated at a one or more particular methylation loci (e.g., one or more particular DMRs). Those of skill in the art will appreciate that, in some instances e.g., as set forth herein, the fraction or percentage of methylation can be calculated from the ratio of methylated DMRs to unmethylated DMRs for one or more analyzed DMRs, e.g., within a sample. In certain embodiments e.g., as set forth herein, the methylation status of one or more methylation loci (e.g., one or more DMRs) is expressed as a fraction or percentage of the one or more regions of CpG islands that are methylated.

In various embodiments e.g., as set forth herein, methylation status of one or more methylation loci (e.g., one or more DMRs) is compared to a reference methylation status value and/or to methylation status of the one or more methylation loci (e.g., one or more DMRs) in a reference sample. In certain instances e.g., as set forth herein e.g., as set forth herein, a reference is a non-contemporaneous sample from the same source, e.g., a prior sample from the same source, e.g., from the same subject. In certain instances e.g., as set forth herein e.g., as set forth herein, a reference for the methylation status of one or more methylation loci (e.g., one or more DMRs) is the methylation status of the one or more methylation loci (e.g., one or more DMRs) in a sample (e.g., a sample from a subject), or a plurality of samples, known to represent a particular state (e.g., a cancer state or a non-cancer state). Thus, a reference can be or include one or more predetermined thresholds, which thresholds can be quantitative (e.g., a methylation value) or qualitative. In certain instances e.g., as set forth herein e.g., as set forth herein, a reference for methylation status of a DMR is the methylation status of a nucleotide or plurality of nucleotides (e.g., a plurality of contiguous oligonucleotides) present in the same sample that does not include nucleotides of the DMR. Those of skill in the art will appreciate that a reference measurement is typically produced by measurement using a methodology identical to, similar to, or comparable to that by which the non-reference measurement was taken.

Without wishing to be bound by any particular scientific theory, FIG. 16 provides a schematic of one possible mechanism by which hypermethylation or hypomethylation of a regulatory sequence of gene can impact expression. As shown in FIG. 16, hypomethylation can result in increased expression and/or hypermethylation can result in suppression of expression. In various instances e.g., as set forth herein, increased methylation of express-regulatory regions, such as promoter regions and enhancer regions, as compared to a reference can reduce or silence expression of an operably linked gene, e.g., of an operably linked gene that typically acts to suppress cancer. In various embodiments e.g., as set forth herein, decreased methylation of expression-regulatory regions, such as promoter regions and enhancer regions, as compared to a reference can increase expression of an operably linked gene, e.g., of an operably linked gene having an activity that contributes to oncogenesis. Without wishing to be bound by any particular scientific theory, DNA methylation may provide a more chemically and biologically stable indicator of cancer status than RNA expression or protein expression per se.

Methylation is typically thought to be highly tissue-specific, providing a dimension of information not necessarily present in DNA sequence analysis.

Methylation events that substantially contribute to oncogenesis can occur, e.g., in expression-regulatory regions of DNA (e.g., at a promoter region, enhancer region, transcription factor binding site, CTCF-binding site, CpG island, or other sequence) operably linked with cancer-associated genes such as genes that typically act to suppress cancer. Accordingly, inactivation of genes that typically act to suppress cancer results in or contribute to oncogenesis.

Cancers

Methods and compositions of the present disclosure are useful for screening for cancer, particularly colorectal cancer and precursor tumors to colorectal cancers (e.g., advanced adenomas). Colorectal cancers include, without limitation, colon cancer, rectal cancer, and combinations thereof. Colorectal cancers include metastatic colorectal cancers and non-metastatic colorectal cancers. Colorectal cancers include cancer located in the proximal part of the colon cancer and cancer located the distal part of the colon.

Colorectal cancers include colorectal cancers at any of the various possible stages known in the art, including, e.g., Stage I, Stage II, Stage III, and Stage IV colorectal cancers (e.g., stages 0, I, IIA, IIB, IIC, IIIA, IIIB, IIIC, IVA, IVB, and IVC). Colorectal cancers include all stages of the Tumor/Node/Metastasis (TNM) staging system. With respect to colorectal cancer, T can refer to whether the tumor grown into the wall of the colon or rectum, and if so by how many layers; N can refer to whether the tumor has spread to lymph nodes, and if so how many lymph nodes and where they are located; and M can refer to whether the cancer has spread to other parts of the body, and if so which parts and to what extent. Particular stages of T, N, and M are known in the art. T stages can include TX, T0, Tis, T1, T2, T3, T4a, and T4b; N stages can include NX, N0, N1a, N1b, N1c, N2a, and N2b; M stages can include M0, M1a, and M1b. Moreover, grades of colorectal cancer can include GX, G1, G2, G3, and G4. Various means of staging cancer, and colorectal cancer in particular, are well known in the art summarized, e.g., on the world wide web at cancer.net/cancer-types/colorectal-cancer/stages.

In certain instances e.g., as set forth herein, the present disclosure includes screening of early stage colorectal cancer. Early stage colorectal cancers can include, e.g., colorectal cancers localized within a subject, e.g., in that they have not yet spread to lymph nodes of the subject, e.g., lymph nodes near to the cancer (stage N0), and have not spread to distant sites (stage M0). Early stage cancers include colorectal cancers corresponding to, e.g., Stages 0 to II C.

Thus, colorectal cancers of the present disclosure include, among other things, pre-malignant colorectal cancer (e.g., advanced adenomas) and malignant colorectal cancer. Methods and compositions of the present disclosure are useful for screening of colorectal cancer in all of its forms and stages, including without limitation those named herein or otherwise known in the art, as well as all subsets thereof. Accordingly, the person of skill in art will appreciate that all references to colorectal cancer provided here include, without limitation, colorectal cancer in all of its forms and stages, including without limitation those named herein or otherwise known in the art, as well as all subsets thereof.

Subjects and Samples

A sample analyzed using methods and compositions provided herein can be any biological sample and/or any sample including nucleic acid. In various particular embodiments, a sample analyzed using methods and compositions provided herein can be a sample from a mammal. In various particular embodiments, a sample analyzed using methods and compositions provided herein can be a sample from a human subject. In various particular embodiments, a sample analyzed using methods and compositions provided herein can be a sample form a mouse, rat, pig, horse, chicken, or cow.

In various instances e.g., as set forth herein, a human subject is a subject diagnosed or seeking diagnosis as having, diagnosed as or seeking diagnosis as at risk of having, and/or diagnosed as or seeking diagnosis as at immediate risk of having, a cancer such as a colorectal cancer or a pre-cancerous tumor such as an advanced adenoma. In various instances e.g., as set forth herein, a human subject is a subjected identified as a subject in need of colorectal cancer and/or advanced adenoma screening. In certain instances e.g., as set forth herein, a human subject is a subjected identified as in need of colorectal cancer and/or advanced adenoma screening by a medical practitioner. In various instances e.g., as set forth herein, a human subject is identified as in need of screening due to age, e.g., due to an age equal to or greater than 50 years, e.g., an age equal to or greater than 50, 55, 60, 65, 70, 75, 80, 85, or 90 years. In various instances e.g., as set forth herein, a human subject is a subject not diagnosed as having, not at risk of having, not at immediate risk of having, not diagnosed as having, and/or not seeking diagnosis for a cancer such as a colorectal cancer or pre-cancerous tumor such as an advanced adenoma, or any combination thereof.

A sample from a subject, e.g., a human or other mammalian subject, can be a sample of, e.g., blood, blood component, cfDNA, ctDNA, stool, or colorectal tissue. In some particular embodiments, a sample is an excretion or bodily fluid of a subject (e.g., saliva, stool, blood, lymph, or urine of a subject), a colorectal cancer tissue sample, or an adenoma or polyp tissue sample. A sample from a subject can be a cell or tissue sample, e.g., a cell or tissue sample that is of a cancer or includes cancer cells, e.g., of a tumor or of a metastatic tissue. In various embodiments e.g., as set forth herein, a sample from a subject, e.g., a human or other mammalian subject, can be obtained by biopsy (e.g., fine needle aspiration or tissue biopsy) or surgery.

In various embodiments e.g., as set forth herein, a sample is a sample of cell-free DNA (cfDNA). cfDNA is typically found in human biofluids (e.g., plasma, serum, or urine) in short, double-stranded fragments. The concentration of cfDNA is typically low, but can significantly increase under particular conditions, including without limitation pregnancy, autoimmune disorder, myocardial infraction, and cancer. Circulating tumor DNA (ctDNA) is the component of circulating DNA specifically derived from cancer cells. ctDNA can be present in human biofluids bound to leukocytes and erythrocytes or not bound to leukocytes and erythrocytes. Various tests for detection of tumor-derived cfDNA are based on detection of genetic or epigenetic modifications that are characteristic of cancer (e.g., of a relevant cancer) or pre-cancerous tumor (e.g., an advanced adenoma). Genetic or epigenetic modifications characteristic of cancer can include, without limitation, oncogenic or cancer-associated mutations in tumor-suppressor genes, activated oncogenes, hypermethylation, and/or chromosomal disorders. Detection of genetic or epigenetic modifications characteristic of cancer can confirm that detected cfDNA is ctDNA.

cfDNA and ctDNA provide a real-time or nearly real time metric of the methylation status of a source tissue. cfDNA and ctDNA demonstrate a half-life in blood of about 2 hours, such that a sample taken at a given time provides a relatively timely reflection of the status of a source tissue.

Various methods of isolating nucleic acids from a sample (e.g., of isolating cfDNA from blood or plasma) are known in the art. Nucleic acids can be isolated, e.g., without limitation, standard DNA purification techniques, by direct gene capture (e.g., by clarification of a sample to remove assay-inhibiting agents and capturing a target nucleic acid, if present, from the clarified sample with a capture agent to produce a capture complex, and isolating the capture complex to recover the target nucleic acid).

Methods of Measuring Methylation Status

Methylation status can be measured by a variety of methods known in the art and/or by methods provided herein. Those of skill in the art will appreciate that a method for measuring methylation status can generally be applied to samples from any source and of any kind, and will further be aware of processing steps available to modify a sample into a form suitable for measurement by a given methodology. Methods of measuring methylation status include, without limitation, methods including methylation-status-specific polymerase chain reaction (PCR), methods including nucleic acid sequencing, methods including mass spectrometry, methods including methylation-sensitive nucleases, methods including mass-based separation, methods including target-specific capture, methods including methylation-specific oligonucleotide primers, methods including hybrid-capture targeted next-generation sequencing, methods including amplicon-based targeted next generation sequencing, and methods including whole genome bisulfite sequencing. Certain particular assays for methylation utilize a bisulfite reagent (e.g., hydrogen sulfite ions).

Bisulfite reagents can include, among other things, bisulfite, disulfite, hydrogen sulfite, or combinations thereof, which reagents can be useful in distinguishing methylated and unmethylated nucleic acids. Bisulfite interacts differently with cytosine and 5-methylcytosine. In typical bisulfite-based methods, contacting of DNA with bisulfite deaminates unmethylated cytosine to uracil, while methylated cytosine remains unaffected; methylated cytosines, but not unmethylated cytosines, are selectively retained. Thus, in a bisulfite processed sample, uracil residues stand in place of, and thus provide an identifying signal for, unmethylated cytosine residues, while remaining (methylated) cytosine residues thus provide an identifying signal for methylated cytosine residues. Bisulfite processed samples can be analyzed, e.g., by PCR or by whole genome bisulfite sequencing.

Various methylation assay procedures can be used in conjunction with bisulfite treatment to determine methylation status of a target sequence such as a DMR. Such assays can include, among others, Methylation-Specific Restriction Enzyme qPCR, Methylation-Sensitive Restriction Enzyme qPCR, sequencing of bisulfite-treated nucleic acids, PCR (e.g., with sequence-specific amplification), Methylation Specific Nuclease-assisted Minor-allele Enrichment PCR, Methylation-Sensitive High Resolution Melting, hybrid-capture targeted next-generation sequencing, and amplicon-based targeted next-generation sequencing. In some embodiments, DMRs are amplified from a bisulfite-treated DNA sample and a DNA sequencing library is prepared for sequencing according to, e.g., an Illumina protocol or transpose-based Nextera XT protocol. In certain embodiments, high-throughput and/or next-generation sequencing techniques are used to achieve base-pair level resolution of DNA sequence, permitting analysis of methylation status. When combined with bisulfite treatment and covering a significant portion (e.g., >50%) of the human genome, these whole genome sequencing technologies may be collectively referred to as Whole Genome Bisulfite Sequencing (WGBS).

In various embodiments e.g., as set forth herein, methylation status is detected by a method including PCR amplification with methylation-specific oligonucleotide primers (MSP methods), e.g., as applied to bisulfite-treated sample (see, e.g., Herman 1992 Proc. Natl. Acad. Sci. USA 93: 9821-9826, which is herein incorporated by reference with respect to methods of determining methylation status). Use of methylation-status-specific oligonucleotide primers for amplification of bisulfite-treated DNA allows differentiation between methylated and unmethylated nucleic acids. Oligonucleotide primer pairs for use in MSP methods include at least one oligonucleotide primer capable of hybridizing with sequence that includes a methylation site, e.g., a CpG. An oligonucleotide primer that includes a T residue at a position complementary to a cytosine residue will selectively hybridize to templates in which the cytosine was unmethylated prior to bisulfite treatment, while an oligonucleotide primer that includes a G residue at a position complementary to a cytosine residue will selectively hybridize to templates in which the cytosine was methylated cytosine prior to bisulfite treatment. MSP results can be obtained with or without sequencing amplicons, e.g., using gel electrophoresis. MSP (methylation-specific PCR) allows for highly sensitive detection (detection level of 0.1% of the alleles, with full specificity) of locus-specific DNA methylation, using PCR amplification of bisulfite-converted DNA.

Another method that can be used to determine methylation status after bisulfite treatment of a sample is Methylation-Sensitive High Resolution Melting (MS-HRM) PCR (see, e.g., Hussmann 2018 Methods Mol Biol. 1708:551-571, which is herein incorporated by reference with respect to methods of determining methylation status). MS-HRM is an in-tube, PCR-based method to detect methylation levels at specific loci of interest based on hybridization melting. Bisulfite treatment of the DNA prior to performing MS-HRM ensures a different base composition between methylated and unmethylated DNA, which is used to separate the resulting amplicons by high resolution melting. A unique primer design facilitates a high sensitivity of the assays enabling detection of down to 0.1-1% methylated alleles in an unmethylated background. Oligonucleotide primers for MS-HRM assays are designed to be complementary to the methylated allele, and a specific annealing temperature enables these primers to anneal both to the methylated and the unmethylated alleles thereby increasing the sensitivity of the assays.

Another method that can be used to determine methylation status after bisulfite treatment of a sample is Quantitative Multiplex Methylation-Specific PCR (QM-MSP). QM-MSP uses methylation specific primers for sensitive quantification of DNA methylation (see, e.g., Fackler 2018 Methods Mol Biol. 1708:473-496, which is herein incorporated by reference with respect to methods of determining methylation status). QM-MSP is a two-step PCR approach, where in the first step, one pair of gene-specific primers (forward and reverse) amplifies the methylated and unmethylated copies of the same gene simultaneously and in multiplex, in one PCR reaction. This methylation-independent amplification step produces amplicons of up to $10^9$ copies per μL after 36 cycles of PCR. In the second step, the amplicons of the first reaction are quantified with a standard curve using real-time PCR and two independent fluorophores to detect methylated/unmethylated DNA of each gene in the same well (e.g., 6FAM and VIC). One methylated copy is detectable in 100,000 reference gene copies.

Another method that can be used to determine methylation status after bisulfite treatment of a sample is Methylation Specific Nuclease-assisted Minor-allele Enrichment (MS-NaME) (see, e.g., Liu 2017 Nucleic Acids Res. 45(6): e39, which is herein incorporated by reference with respect to methods of determining methylation status). Ms-NaME is based on selective hybridization of probes to target sequences in the presence of DNA nuclease specific to double-stranded (ds) DNA (DSN), such that hybridization results in regions of double-stranded DNA that are subsequently digested by the DSN. Thus, oligonucleotide probes targeting unmethylated sequences generate local double stranded regions resulting to digestion of unmethylated targets; oligonucleotide probes capable of hybridizing to methylated sequences generate local double-stranded regions that result in digestion of methylated targets, leaving methylated targets intact. Moreover, oligonucleotide probes can direct DSN activity to multiple targets in bisulfite-treated DNA, simultaneously. Subsequent amplification can enrich non-digested sequences. Ms-NaME can be used, either independently or in combination with other techniques provided herein.

Another method that can be used to determine methylation status after bisulfite treatment of a sample is Methylation-sensitive Single Nucleotide Primer Extension (Ms-SNuPE™) (see, e.g., Gonzalgo 2007 Nat Protoc. 2(8):1931-6, which is herein incorporated by reference with respect to methods of determining methylation status). In Ms-SNuPE, strand-specific PCR is performed to generate a DNA template for quantitative methylation analysis using Ms-SNuPE. SNuPE is then performed with oligonucleotide(s) designed to hybridize immediately upstream of the CpG site(s) being interrogated. Reaction products can be electrophoresed on polyacrylamide gels for visualization and quantitation by phosphor-image analysis. Amplicons can also carry a directly or indirectly detectable labels such as a fluorescent label, radionuclide, or a detachable molecule fragment or other entity having a mass that can be distinguished by mass spectrometry. Detection may be carried out and/or visualized by means of, e.g., matrix assisted laser desorption/ionization mass spectrometry (MALDI) or using electron spray mass spectrometry (ESI).

Certain methods that can be used to determine methylation status after bisulfite treatment of a sample utilize a first oligonucleotide primer, a second oligonucleotide primer, and an oligonucleotide probe in an amplification-based method. For instance, the oligonucleotide primers and probe can be used in a method of real-time polymerase chain reaction (PCR) or droplet digital PCR (ddPCR). In various instances e.g., as set forth herein, the first oligonucleotide primer, the second oligonucleotide primer, and/or the oligonucleotide probe selectively hybridize methylated DNA and/or unmethylated DNA, such that amplification or probe signal indicate methylation status of a sample.

Other bisulfite-based methods for detecting methylation status (e.g., the presence of level of 5-methylcytosine) are disclosed, e.g., in Frommer (1992 Proc Natl Acad Sci USA. 1; 89(5):1827-31, which is herein incorporated by reference).

Bisulfite-based method for detecting methylation status may include amplicon-based targeted next generation sequencing, e.g., see Masser (2015 J Vis Exp, (96):52488, doi: 10.3791/52488, which is herein incorporated by reference). Generally, amplicon-based targeted next generation sequencing utilizes a bisulfite conversion and region-specific PCR amplification in combination with next-generation library construction to examine the methylation status of a targeted region of interest in a high-throughput manner.

Another bisulfite-based method for detecting methylation status may include hybrid-capture based targeted next generation sequencing, e.g., see Ivanov (2013, Nucleic Acids Res, doi: 10.1093/nar.gks1467, which is herein incorporated by reference). Generally, the method comprises treatment of the genomic DNA with bisulfite. Then, target regions are hybridized with DNA or RNA probes either in solution or bound to a solid support. Bound target regions are then enriched and sequenced according to known protocols, see Gasc (2016, Front. Microbiol., doi: 10.1093/nar/gkw309, which is incorporated herein by reference).

Certain methods that can be used to determine methylation status do not include bisulfite treatment of a sample. For instance, changes in methylation status can be detected by a PCR-based process in which DNA is digested with one or more methylation-sensitive restriction enzymes (MSREs) prior to PCR amplification (e.g., by MSRE-qPCR). Typically, MSREs have recognition sites that include at least one CpG motif, such that activity of the MSRE is blocked from cleaving a possible recognition site if the site includes 5-methylcytosine. (see, e.g., Beikircher 2018 Methods Mol Biol. 1708:407-424, which is herein incorporated by reference). Thus, MSREs selectively digest nucleic acids based upon methylation status of the recognition site of the MSRE; they can digest DNA at MSRE recognition sites that are unmethylated, but not digest DNA in MSRE recognition sites that are methylated. In certain embodiments, an aliquot of sample can be digested with MSREs, generating a processed sample in which unmethylated DNA has been cleaved by the MSREs, such that, the proportion of uncleaved and/or amplifiable DNA with at least one methylated site within MSRE recognition sites (e.g., at least one methylated site within each MSRE recognition site of the DNA molecule) is increased relative to uncleaved and/or amplifiable DNA that did not include at least one methylated site within MSRE recognition sites (e.g., did not include at least one methylated site within each MSRE recognition site of the DNA molecule). Uncleaved sequences of a restriction-enzyme-digested sample can then be preamplified, e.g, in PCR, and quantified e.g. by qPCR, real-time PCR, or digital PCR. Oligonucleotide primers for MSRE-qPCR amplify regions that include one or more MSRE cleavage sites, and/or a plurality of MSRE cleavage sites. Amplicons including a plurality of MSRE cleavage sites are typically more likely to yield robust results. The number of cleavage sites within a DMR amplicon, and in some instances e.g., as set forth herein the resulting robustness of methylation status determination for the DMR, can be increased by design of DMRs that include a plurality of MSRE recognition sites (as opposed to a single recognition site) in a DMR amplicon. In various instances e.g., as set forth herein, a plurality of MSREs can be applied to the same sample, including, e.g., two or more of AciI, Hin6I, HpyCH4IV, and HpaII (e.g., including AciI, Hin6I, and HpyCH4IV). A plurality of MSREs (e.g., the combination of AciI, Hin6I, HpyCH4IV, and HpaII, or the combination of AciI, Hin6I, and HpyCH4IV) can provide improved frequency of MSRE recognition sites within DMR amplicons.

MSRE-qPCR can also include a pre-amplification step following sample digestion by MSREs but before qPCR in order to improve the amount of available sample, given the low prevalence of cfDNA in blood.

In certain MSRE-qPCR embodiments, e.g., as set forth herein, the amount of total DNA is measured in an aliquot of sample in native (e.g., undigested) form using, e.g., real-time PCR or digital PCR.

Various amplification technologies can be used alone or in conjunction with other techniques described herein for detection of methylation status. Those of skill in the art, having reviewed the present specification, will understand how to combine various amplification technologies known in the art and/or described herein together with various other technologies for methylation status determination known in the art and/or provided herein. Amplification technologies include, without limitation, PCR, e.g., quantitative PCR (qPCR), real-time PCR, and/or digital PCR. Those of skill in the art will appreciate that polymerase amplification can multiplex amplification of multiple targets in a single reaction. PCR amplicons are typically 100 to 2000 base pairs in length. In various instances e.g., as set forth herein, an amplification technology is sufficient to determine methylations status.

Digital PCR (dPCR) based methods involve dividing and distributing a sample across wells of a plate with 96-, 384-, or more wells, or in individual emulsion droplets (ddPCR) e.g., using a microfluidic device, such that some wells include one or more copies of template and others include no copies of template. Thus, the average number of template molecules per well is less than one prior to amplification. The number of wells in which amplification of template occurs provides a measure of template concentration. If the sample has been contacted with MSRE, the number of wells in which amplification of template occurs provides a measure of the concentration of methylated template.

In various embodiments e.g., as set forth herein, a fluorescence-based real-time PCR assay, such as MethyLight™, can be used to measure methylation status (see, e.g., Campan 2018 Methods Mol Biol. 1708:497-513, which is incorporated by reference). MethyLight is a quantitative, fluorescence-based, real-time PCR method to sensitively detect and quantify DNA methylation of candidate regions of the genome. MethyLight is uniquely suited for detecting low-frequency methylated DNA regions against a high background of unmethylated DNA, as it combines methylation-specific priming with methylation-specific fluorescent probing. Additionally, MethyLight can be combined with Digital PCR, for the highly sensitive detection of individual methylated molecules, with use in disease detection and screening.

Real-time PCR-based methods for use in determining methylation status typically include a step of generating a standard curve for unmethylated DNA based on analysis of external standards. A standard curve can be constructed from at least two points and can permit comparison of a real-time Ct value for digested DNA and/or a real-time Ct value for undigested DNA to known quantitative standards. In particular instances e.g., as set forth herein, sample Ct values can be determined for MSRE-digested and/or undigested samples or sample aliquots, and the genomic equivalents of DNA can be calculated from the standard curve. Ct values of MSRE-digested and undigested DNA can be evaluated to identify amplicons digested (e.g., efficiently digested; e.g., yielding a Ct value of 45). Amplicons not amplified under either digested or undigested conditions can also be identified. Corrected Ct values for amplicons of interest can then be directly compared across conditions to establish relative differences in methylation status between conditions. Alternatively or additionally, delta-difference between the Ct values of digested and undigested DNA can be used to establish relative differences in methylation status between conditions.

Methods of measuring methylation status can include, without limitation, massively parallel sequencing (e.g., next-generation sequencing) to determine methylation state, e.g., sequencing by—synthesis, real-time (e.g., single-molecule) sequencing, bead emulsion sequencing, nanopore sequencing, or other sequencing techniques known in the art. In some embodiments, e.g., as set forth herein, a method of measuring methylation status can include whole-genome sequencing, e.g., with base-pair resolution.

In certain particular embodiments e.g., as set forth herein, MSRE-qPCR, among other techniques, can be used to determine the methylation status of a colorectal cancer methylation biomarker that is or includes a single methylation locus. In certain particular embodiments e.g., as set forth herein, MSRE-qPCR, among other techniques, can be used to determine the methylation status of a colorectal cancer and/or advanced adenoma methylation biomarker that is or includes two or more methylation loci. In certain particular embodiments e.g., as set forth herein, MSRE-qPCR, among other techniques, can be used to determine the methylation status of a colorectal cancer and/or advanced adenoma methylation biomarker that is or includes a single differentially methylated region (DMR). In certain particular embodiments e.g., as set forth herein, MSRE-qPCR, among other techniques, can be used to determine the methylation status of a colorectal cancer and/or advanced adenoma methylation biomarker that is or includes two or more DMRs. In certain particular embodiments e.g., as set forth herein, MSRE-qPCR, among other techniques, can be used to determine the methylation status of a colorectal cancer and/or advanced adenoma methylation biomarker that is or includes a single methylation site. In certain particular embodiments e.g., as set forth herein, MSRE-qPCR, among other techniques, can be used to determine the methylation status of a colorectal cancer and/or advanced adenoma methylation biomarker that is or includes two or more methylation sites. In various embodiments e.g., as set forth herein, a colorectal cancer and/or advanced adenoma methylation biomarker can be any colorectal cancer and/or advanced adenoma methylation biomarker provided herein. The present disclosure includes, among other things, oligonucleotide primer pairs for amplification of DMRs, e.g., for amplification of DMRs identified in Table 5.

In certain particular embodiments e.g., as set forth herein, a cfDNA sample is derived from subject plasma and contacted with MSREs (methylation sensitive restriction enzymes) that are or include one or more of AciI, Hin6I, HpyCH4IV, and HpaII (e.g., AciI, Hin6I, and HpyCH4IV). The digested sample can be amplified with oligonucleotide primer pairs of one or more DMRs, e.g., with one or more oligonucleotide primer pairs provided in Table 5 below. Table 5 identifies the chromosome number (Chr. No.), unique ID (UID), start position of the genetic region on the chromosome (start position), end position of the genetic region on the chromosome (end position), the width of the region (Seq. Width), the sequence ID numbers (SEQ ID NO.) of the forward primer (Fp) and the reverse primer (Rp) used in MSRE-qPCR, and the SEQ ID NO. of the DNA region amplified by the forward and reverse primer. Digested DNA, e.g., preamplified digested DNA, can be quantified with qPCR with oligonucleotide primer pairs of one or more DMRs, e.g., with one or more oligonucleotide primer pairs provided in Table 5 below. qPCR Ct values can then be determined and used to determine methylation status of each DMR amplicon. Lower Ct values (and thus higher 45−Ct values) correspond to higher methylation status, demonstrating hypermethylation in subjects with colorectal cancer and/or advanced adenoma.

TABLE 5

40 Highly Ranked DMRs identified with corresponding primer pairs.

| Chr. No. | UID | Start Position | End Position | Seq. Width | Gene (if annotated) | Forward Primer SEQ ID NO: | Reverse Primer SEQ ID NO: | Amplified Region SEQ ID NO: |
|---|---|---|---|---|---|---|---|---|
| 21 | UDX_224.14 | 26844767 | 26844877 | 111 | ADAMTS1 | 70 | 110 | 150 |
| 4 | UDX_198.5_1 | 61202277 | 61202367 | 91 | ADGRL3 | 71 | 111 | 151 |
| 8 | UDX_277.7_2 | 52565317 | 52565408 | 92 | ALKAL1 | 72 | 112 | 152 |
| 10 | UDX_17_2 | 16520590 | 16520719 | 130 | C1QL3 | 73 | 113 | 153 |
| 18 | UDX_124.1 | 28177439 | 28177533 | 95 | CDH2 | 74 | 114 | 154 |
| 9 | UDX_230 | 21970918 | 21971017 | 100 | CDKN2A, CDKN2B-AS1 | 75 | 115 | 155 |
| 7 | UDX_66.2 | 154304857 | 154304969 | 113 | DPP6 | 76 | 116 | 156 |
| 12 | UDX_197.3 | 63668266 | 63668380 | 115 | DPY19L2 | 77 | 117 | 157 |
| 3 | UDX_222.1 | 96813875 | 96813987 | 113 | EPHA6 | 78 | 118 | 158 |
| 3 | UDX_222.11_2 | 96814054 | 96814137 | 84 | EPHA6 | 79 | 119 | 159 |
| 10 | UDX_137.1 | 127736482 | 127736589 | 108 | FOXI2 | 80 | 120 | 160 |
| 10 | UDX_272.3_2 | 26211885 | 26211963 | 79 | GAD2, MYO3A | 81 | 121 | 161 |
| 10 | UDX_272.4 | 26212056 | 26212160 | 105 | GAD2, MYO3A | 82 | 122 | 162 |
| 15 | UDX_120.2 | 45378327 | 45378410 | 84 | GATM | 83 | 123 | 163 |
| 5 | UDX114.1_1 | 180353709 | 180353815 | 107 | GFPT2 | 84 | 124 | 164 |
| 4 | UDX_185.1 | 176001298 | 176001402 | 105 | GPM6A | 85 | 125 | 165 |
| 16 | UDX_30_1 | 87601409 | 87601511 | 103 | JPH3 | 86 | 126 | 166 |
| 2 | UDX_121.1 | 5673894 | 5673976 | 83 | LINC01248 | 87 | 127 | 167 |
| 8 | UDX_174.3 | 17026934 | 17027030 | 97 | MICU3 | 88 | 128 | 168 |
| 10 | UDX_251.2_1 | 25934063 | 25934130 | 68 | MYO3A, LOC101929073 | 89 | 129 | 169 |
| 20 | UDX_29_1 | 56925428 | 56925505 | 78 | no annotation | 90 | 130 | 170 |
| 18 | UDX_24_1 | 75916501 | 75916621 | 121 | no annotation | 91 | 131 | 171 |
| 14 | UDX_107.2 | 77966333 | 77966434 | 102 | no annotation | 92 | 132 | 172 |
| 1 | UDX_244_2 | 107140056 | 107140173 | 118 | NTNG1 | 93 | 133 | 173 |
| 21 | UDX_128.1 | 33070631 | 33070711 | 81 | OLIG1 | 94 | 134 | 174 |
| 9 | UDX_94.2_2 | 36986521 | 36986581 | 61 | PAX5 | 95 | 135 | 175 |
| 12 | UDX_274.2_1 | 15322352 | 15322435 | 84 | PTPRO, RERG | 96 | 136 | 176 |
| 12 | UDX_274.3_1 | 15322477 | 15322549 | 73 | PTPRO, RERG | 97 | 137 | 177 |
| 15 | UDX_260.1 | 79089689 | 79089791 | 103 | RASGRF1 | 98 | 138 | 178 |
| 15 | UDX_260.2_1 | 79089783 | 79089858 | 76 | RASGRF1 | 99 | 139 | 179 |
| 14 | UDX181.2_1 | 70189010 | 70189101 | 92 | SLC8A3, LOC646548 | 100 | 140 | 180 |
| 14 | UDX181.4_1 | 70189227 | 70189296 | 70 | SLC8A3, LOC646548 | 101 | 141 | 181 |
| 17 | UDX_1_1 | 35448306 | 35448407 | 102 | SLFN13 | 102 | 142 | 182 |
| 1 | UDX_117.2 | 114153293 | 114153403 | 111 | SYT6 | 103 | 143 | 183 |
| 2 | UDX_221.2_2 | 136766099 | 136766189 | 91 | THSD7B | 104 | 144 | 184 |
| 2 | UDX_85.2_1 | 209771685 | 209771755 | 71 | UNC80 | 105 | 145 | 185 |

TABLE 5-continued

40 Highly Ranked DMRs identified with corresponding primer pairs.

| Chr. No. | UID | Start Position | End Position | Seq. Width | Gene (if annotated) | Forward Primer SEQ ID NO: | Reverse Primer SEQ ID NO: | Amplified Region SEQ ID NO. |
|---|---|---|---|---|---|---|---|---|
| 19 | UDX_217.4_1 | 36666980 | 36667097 | 118 | ZNF461 | 106 | 146 | 186 |
| 19 | UDX_250.1 | 37551664 | 37551748 | 85 | ZNF540, ZNF571-AS1 | 107 | 147 | 187 |
| 19 | UDX_258.2_1 | 36973532 | 36973602 | 71 | ZNF568 | 108 | 148 | 188 |
| 19 | UDX_242_2 | 56393660 | 56393732 | 73 | ZNF582-AS1, ZNF582 | 109 | 149 | 189 |

It will be appreciated by those of skill in the art that oligonucleotide primer pairs provided in Table 5 can be used in accordance with any combination of colorectal cancer and/or advanced adenoma methylation biomarkers identified herein. The skilled artisan will be aware that the oligonucleotide primer pairs of Table 5 may be individually included or not included in a given analysis in order to analyze particularly desired combination of DRMs.

The person of skill in the art will further appreciate that while other oligonucleotide primer pairs may be used, selection and pairing of oligonucleotide primers to produce useful DMR amplicons is non-trivial and represents a substantial contribution.

Those of skill in the art will further appreciate that methods, reagents, and protocols for qPCR are well-known in the art. Unlike traditional PCR, qPCR is able to detect the production of amplicons over time in amplification (e.g., at the end of each amplification cycle), often by use of an amplification-responsive fluorescence system, e.g., in combination with a thermocycler with fluorescence-detection capability. Two common types of fluorescent reporters used in qPCR include (i) double-stranded DNA binding dyes that fluoresce substantially more brightly when bound than when unbound; and (ii) labeled oligonucleotides (e.g., labeled oligonucleotide primers or labeled oligonucleotide probes).

Those of skill in the art will appreciate that in embodiments in which a plurality of methylation loci (e.g., a plurality of DMRs) are analyzed for methylation status in a method of screening for colorectal cancer provided herein, methylation status of each methylation locus can be measured or represented in any of a variety of forms, and the methylation statuses of a plurality of methylation loci (preferably each measured and/or represented in a same, similar, or comparable manner) be together or cumulatively analyzed or represented in any of a variety of forms. In various embodiments e.g., as set forth herein, methylation status of each methylation locus can be measured as a Ct value. In various embodiments e.g., as set forth herein, methylation status of each methylation locus can be represented as the difference in Ct value between a measured sample and a reference. In various embodiments e.g., as set forth herein, methylation status of each methylation locus can be represented as a qualitative comparison to a reference, e.g., by identification of each methylation locus as hypermethylated or not hypermethylated.

In some embodiments e.g., as set forth herein in which a single methylation locus is analyzed, hypermethylation of the single methylation locus constitutes a diagnosis that a subject is suffering from or possibly suffering from colorectal cancer and/or advanced adenomas, while absence of hypermethylation of the single methylation locus constitutes a diagnosis that the subject is likely not suffering from colorectal cancer or advanced adenomas. In some embodiments e.g., as set forth herein, hypermethylation of a single methylation locus (e.g., a single DMR) of a plurality of analyzed methylation loci constitutes a diagnosis that a subject is suffering from or possibly suffering from colorectal cancer or an advanced adenoma, while the absence of hypermethylation at any methylation locus of a plurality of analyzed methylation loci constitutes a diagnosis that a subject is likely not suffering from either affliction. In some embodiments e.g., as set forth herein, hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is suffering from or possibly suffering from colorectal cancer, while the absence of hypermethylation of a determined percentage (e.g., a predetermined percentage) of methylation loci (e.g., at least 10% (e.g., at least 10%, at least 20%, at least 30%, at least 40%, at least 50%, at least 60%, at least 70%, at least 80%, at least 90%, or 100%)) of a plurality of analyzed methylation loci constitutes a diagnosis that a subject is not likely suffering from colorectal cancer or advanced adenomas. In some embodiments e.g., as set forth herein, hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 methylation loci DMRs) constitutes a diagnosis that a subject is suffering from or possibly suffering from colorectal cancer and/or advanced adenomas, while the absence of hypermethylation of a determined number (e.g., a predetermined number) of methylation loci (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 DMRs) of a plurality of analyzed methylation loci (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 DMRs) constitutes a diagnosis that a subject is not likely suffering from colorectal cancer or advanced adenoma.

In some embodiments e.g., as set forth herein, methylation status of a plurality of methylation loci (e.g., a plurality of DMRs) is measured qualitatively or quantitatively and the measurement for each of the plurality of methylation loci are combined to provide a diagnosis. In some embodiments e.g., as set forth herein, the quantitatively measured methylation status of each of a plurality of methylation loci is individually weighted, and weighted values are combined to provide a single value that can be comparative to a reference in order to provide a diagnosis. To provide but one example of such an approach, a support vector machine (SVM) algorithm can be used to analyze the methylation statuses of a plurality of methylation loci of the present disclosure to produce a diagnosis. At least one objective of the support vector machine algorithm is to identify a hyperplane in an N-dimensional space (N—the number of features) that distinctly classifies the data points with the objective to find a plane that has the maximum margin, i.e., the maximum distance between data points of both classes. As discussed in the present Examples, an SVM model is built on marker values (e.g., Ct values) derived from a training sample set (e.g., the training subject group) that are transformed to support vector values upon which a prediction is made. In application of the SVM model to new samples of a validation sample set, samples will be mapped onto vectoral space the model and categorized as having a probability of belonging to a first condition (e.g., the control group), a second condition (e.g., the group diagnosed with colorectal cancer), or a third group (e.g., the group diagnosed with advanced adenomas), e.g., based on each new sample's location relative to the gap between the conditions. Those of skill in the art will appreciate that, once relevant compositions and methods have been identified, vector values can be used in conjunction with an SVM algorithm defined by predict( ) function of R-package (see Hypertext Transfer Protocol Secure (HTTPS)://cran.r-project.org/web/packages/e1071/index.html, the SVM of which is hereby incorporated by reference) to easily generate a prediction on a new sample. Accordingly, with compositions and methods for colorectal cancer and/or advanced adenoma diagnosis disclosed herein in hand (and only then), generation of a predictive model utilizing algorithm input information in combination to predict( ) function of R-package (see Hypertext Transfer Protocol Secure (HTTPS)://cran.r-project.org/web/packages/e1071/index.html, the SVM of which is hereby incorporated by reference) to provide colorectal cancer and/or advanced adenoma diagnosis would be straightforward. Those of skill in the art will appreciate that, with the present disclosure in hand, generation of SVM vectors can be accomplished according to methods provided herein and otherwise known in the art.

Applications

Methods and compositions of the present disclosure can be used in any of a variety of applications. For example, methods and compositions of the present disclosure can be used to screen, or aid in screening for, colorectal cancer or advanced adenomas. In various instances e.g., as set forth herein, screening using methods and compositions of the present disclosure can detect any stage of colorectal cancer, including without limitation early-stage colorectal cancer, and can detect advanced adenomas. In some embodiments e.g., as set forth herein, colorectal cancer and advanced adenoma screening using methods and compositions of the present disclosure is applied to individuals 50 years of age or older, e.g., 50, 55, 60, 65, 70, 75, 80, 85, or 90 years or older. In some embodiments e.g., as set forth herein, colorectal cancer and advanced adenoma screening using methods and compositions of the present disclosure is applied to individuals 20 years of age or older, e.g., 20, 25, 30, 35, 40, 45, 50, 55, 60, 65, 70, 75, 80, 85, or 90 years or older. In some embodiments e.g., as set forth herein, colorectal cancer and/or advanced adenoma screening using methods and compositions of the present disclosure is applied to individuals 20 to 50 years of age, e.g., 20 to 30 years of age, 20 to 40 years of age, 20 to 50 years of age, 30 to 40 years of age, 30 to 50 years of age, or 40 to 50 years of age. In various embodiments e.g., as set forth herein, colorectal cancer and/or advanced adenoma screening using methods and compositions of the present disclosure is applied to individuals experiencing abdominal pain or discomfort, e.g., experiencing undiagnosed or incompletely diagnosed abdominal pain or discomfort. In various embodiments e.g., as set forth herein, colorectal cancer and/or advanced adenoma screening using methods and compositions of the present disclosure is applied to individuals experiencing no symptoms likely to be associated with colorectal cancer. Thus, in certain embodiments e.g., as set forth herein, colorectal cancer screening using methods and compositions of the present disclosure is fully or partially preventative or prophylactic, at least with respect to later or non-early stages of colorectal cancer.

In various embodiments e.g., as set forth herein, colorectal cancer and/or advanced adenoma screening using methods and compositions of the present disclosure can be applied to an asymptomatic human subject. As used herein, a subject can be referred to as "asymptomatic" if the subject does not report, and/or demonstrate by non-invasively observable indicia (e.g., without one, several, or all of device-based probing, tissue sample analysis, bodily fluid analysis, surgery, or colorectal cancer screening), sufficient characteristics of colorectal cancer and/or advanced adenomas to support a medically reasonable suspicion that the subject is likely suffering from colorectal cancer and/or advanced adenomas. Detection of early stage colorectal cancer or the presence of advanced adenomas is particularly likely in asymptomatic individuals screened in accordance with methods and compositions of the present disclosure.

In various embodiments e.g., as set forth herein, colorectal cancer and/or screening using methods and compositions of the present disclosure can be applied to a symptomatic human subject. As used herein, a subject can be referred to as "symptomatic" if the subject report, and/or demonstrates by non-invasively observable indicia (e.g., without one, several, or all of device-based probing, tissue sample analysis, bodily fluid analysis, surgery, or colorectal cancer screening), sufficient characteristics of colorectal cancer and/or advanced adenomas to support a medically reasonable suspicion that the subject is likely suffering from colorectal cancer, advanced adenomas, and/or from cancer. Symptoms of colorectal cancer and advanced adenomas can include, without limitation, change in bowel habits (diarrhea, constipation, or narrowing of the stool) that are persistent (e.g., lasting more than 3 days), feeling of a need to have a bowel movement which feeling is not relieved upon bowel movement, rectal bleeding (e.g., with bright red blood), blood in stool (which can cause stool to appear dark), abdominal cramping, abdominal pain, weakness, fatigue, unintended weight loss, anemia, and combinations thereof. Those of skill in the art will appreciate that individual symptoms that would not alone indicate or raise a suspicion of colorectal cancer and/or advanced adenomas may do so when presented in combination, e.g., a combination of abdominal cramping and blood in stool, to provide but one non-limiting example.

Those of skill in the art will appreciate that regular, preventative, and/or prophylactic screening for colorectal cancer and advanced adenomas improves diagnosis of colorectal cancer, including and/or particularly early stage cancer. As noted above, early stage cancers include, according to at least one system of cancer staging, Stages 0 to II C of colorectal cancer. Thus, the present disclosure provides, among other things, methods and compositions particularly useful for the diagnosis and treatment of early stage colorectal cancer. Generally, and particularly in embodiments (e.g., as set forth herein) in which colorectal cancer screening in accordance with the present disclosure is carried out annually, and/or in which a subject is asymptomatic at time of screening, methods and compositions of the present invention are especially likely to detect early stage colorectal cancer and/or advanced adenomas.

In various embodiments e.g., as set forth herein, colorectal cancer or advanced adenoma screening in accordance with the present disclosure is performed once for a given subject or multiple times for a given subject. In various embodiments e.g., as set forth herein, screening in accordance with the present disclosure is performed on a regular basis, e.g., every six months, annually, every two years, every three years, every four years, every five years, or every ten years.

In various embodiments e.g., as set forth herein, screening for colorectal cancer and/or advanced adenomas using methods and compositions disclosed herein will provide a diagnosis of colorectal cancer and/or advanced adenomas. In other instances e.g., as set forth herein, screening for colorectal cancer and/or advanced adenomas using methods and compositions disclosed herein will be indicative of colorectal cancer diagnosis (e.g., through finding advanced adenomas) but not definitive for colorectal cancer and/or advanced adenoma diagnosis. In various instances e.g., as set forth herein in which methods and compositions of the present disclosure are used to screen for colorectal cancer and/or advanced adenomas, screening using methods and compositions of the present disclosure can be followed by a further diagnosis-confirmatory assay, which further assay can confirm, support, undermine, or reject a diagnosis resulting from prior screening, e.g., screening in accordance with the present disclosure. As used herein, a diagnosis-confirmatory assay can be a colorectal cancer and/or advanced adenoma assay that provides a diagnosis recognized as definitive by medical practitioners, e.g., a colonoscopy-based diagnosed, or a colorectal cancer and/or advanced adenoma assay that substantially increases or decreases the likelihood that a prior diagnosis was correct, e.g., a diagnosis resulting from screening in accordance with the present disclosure. Diagnosis-confirmatory assays could include existing screening technologies, which are generally in need of improvement with respect to one or more of sensitivity, specificity, and non-invasiveness, particularly in the detection of early stage colorectal cancers.

In some instances e.g., as set forth herein, a diagnosis-confirmatory assay is a test that is or includes a visual or structural inspection of subject tissues, e.g., by colonoscopy. In some embodiments e.g., as set forth herein, colonoscopy includes or is followed by histological analysis. Visual and/or structural assays for colorectal cancer can include inspection of the structure of the colon and/or rectum for any abnormal tissues and/or structures. Visual and/or structural inspection can be conducted, for example, by use of a scope via the rectum or by CT-scan. In some instances e.g., as set forth herein, a diagnosis-confirmatory assay is a colonoscopy, e.g., including or followed by histological analysis. According to some reports, colonoscopy is currently the predominant and/or most relied upon diagnosis-confirmatory assay.

Another visual and/or structural diagnosis confirmatory assay based on computer tomography (CT) is CT colonography, sometimes referred to as virtual colonoscopy. A CT scan utilizes numerous x-ray images of the colon and/or rectum to produce dimensional representations of the colon. Although useful as a diagnosis-confirmatory assay, some reports suggest that CT colonography is not sufficient for replacement of colonoscopy, at least in part because a medical practitioner has not physically accessed the subject's colon to obtain tissue for histological analysis.

Another diagnosis-confirmatory assay can be a sigmoidoscopy. In sigmoidoscopy, a sigmoidoscope is used via the rectum to image portions of the colon and/or rectum. According to some reports, sigmoidoscopy is not widely used.

One particular screening technology is a stool-based screening test (Cologuard® (Exact Sciences Corporation, Madison, WI, United States), which combines an FIT assay with analysis of DNA for abnormal modifications, such as mutation and methylation. The Cologuard® test demonstrates improved sensitivity as compared to FIT assay alone, but can be clinically impracticable or ineffective due to low compliance rates, which low compliance rates are at least in part due to subject dislike of using stool-based assays (see, e.g., doi: 10.1056/NEJMc1405215 (e.g., 2014 N Engl J Med. 371(2):184-188)). The Cologuard® test appears to leave almost half of the eligible population out of the screening programs (see, e.g., van der Vlugt 2017 Br J Cancer. 116(1):44-49). Use of screening as provided herein, e.g., by a blood-based analysis, would increase the number of individuals electing to screen for colorectal cancer (see, e.g., Adler 2014 BMC Gastroenterol. 14:183; Liles 2017 Cancer Treatment and Research Communications 10: 27-31). To present knowledge, only one existing screening technology for colorectal cancer, Epiprocolon, is FDA-approved and CE-IVD marked and is blood-based. Epiprocolon is based on hypermethylation of SEPT9 gene. The Epiprocolon test suffers from low accuracy for colorectal cancer detection with sensitivity of 68% and advanced adenoma sensitivity of only 22% (see, e.g., Potter 2014 Clin Chem. 60(9):1183-91). There is need in the art for, among other things, a non-invasive colorectal cancer and advanced adenoma screen that will likely achieve high subject adherence with high and/or improved specificity and/or sensitivity.

In various embodiments e.g., as set forth herein, screening in accordance with methods and compositions of the present disclosure reduces colorectal cancer mortality, e.g., by early colorectal cancer diagnosis, e.g., through the detection of advanced adenomas. Data supports that colorectal cancer screening reduces colorectal cancer mortality (see, e.g., Shaukat 2013 N Engl J Med. 369(12):1106-14). Moreover, colorectal cancer is particularly difficult to treat at least in part because colorectal cancer, absent timely screening, may not be detected until cancer is past early stages. For at least this reason, treatment of colorectal cancer is often unsuccessful. To maximize population-wide improvement of colorectal cancer outcomes, utilization of screening in accordance with the present disclosure can be paired with, e.g., recruitment of eligible subjects to ensure widespread screening.

In various embodiments e.g., as set forth herein, screening for colorectal cancer and/or advanced adenomas including one or more methods and/or compositions disclosed herein is followed by treatment of colorectal cancer, e.g., treatment of early stage colorectal cancer. In various embodiments e.g., as set forth herein, treatment of colorectal cancer, e.g., early stage colorectal cancer, includes administration of a therapeutic regimen including one or more of surgery, radiation therapy, and chemotherapy. In various embodiments e.g., as set forth herein, treatment of colorectal cancer, e.g., early stage colorectal cancer, includes administration of a therapeutic regimen including one or more of treatments provided herein for treatment of stage 0 colorectal cancer, stage I colorectal cancer, and/or stage II colorectal cancer.

In various embodiments e.g., as set forth herein, screening for advanced adenomas and/or colorectal cancer is a stool-based assay. Typically, stool-based assays, when used in place of visual or structural inspection, are recommended to be utilized at a greater frequency than would be required if using visual or structural inspection. In some instances e.g., as set forth herein, a screening assay is a guiac-based fecal occult blood test or a fecal immunochemical test (gFOBTs/FITs) (see, e.g., Navarro 2017 World J Gastroenterol. 23(20):3632-3642, which is herein incorporated by reference with respect to colorectal cancer assays). FOBTs and FITs are sometimes used for diagnosis of colorectal cancer (see, e.g., Nakamura 2010 J Diabetes Investig. October 19; 1(5):208-11, which is herein incorporated by reference with respect to colorectal cancer assays). FIT is based on detection of occult blood in stool, the presence of which is often indicative of colorectal cancer or advanced adenoma but is often not in sufficient volume to permit identification by the unaided eye. For example, in a typical FIT, the test utilizes hemoglobin-specific reagent to test for occult blood in a stool sample. In various instances e.g., as set forth herein, FIT kits are suitable for use by individuals in their own homes. FIT may be recommended for use on an annual basis. FIT is generally not relied upon to provide sufficient diagnostic information for conclusive diagnosis of colorectal cancer or advanced adenomas.

In various embodiments e.g., as set forth herein, screening for advanced adenomas and/or colorectal cancer also includes gFOBT, which is designed to detect occult blood in stool by chemical reaction Like FIT, gFOBT may be recommended for use on an annual basis. gFOBT is generally not relied upon to provide sufficient diagnostic information for conclusive diagnosis of colorectal cancer or advanced adenomas.

In some instances e.g., as set forth herein, a screening assay can also include stool DNA testing. Stool DNA testing for colorectal cancer or advanced adenomas can be designed to identify DNA sequences characteristic of colorectal cancer and/or advanced adenomas in stool samples. When used in the absence of other diagnosis-confirmatory assays, stool DNA testing may be recommended for use every three years. Stool DNA testing is generally not relied upon to provide sufficient diagnostic information for conclusive diagnosis of colorectal cancer and/or advanced adenomas.

In various embodiments e.g., as set forth herein, treatment of colorectal cancer includes treatment of early stage colorectal cancer, e.g., stage 0 colorectal cancer or stage I colorectal cancer, by one or more of surgical removal of cancerous tissue e.g., by local excision (e.g., by a colonoscope), partial colectomy, or complete colectomy.

In various embodiments e.g., as set forth herein, treatment of colorectal cancer includes treatment of early stage colorectal cancer, e.g., stage II colorectal cancer, by one or more of surgical removal of cancerous tissue (e.g., by local excision (e.g., by colonoscope), partial colectomy, or complete colectomy), surgery to remove lymph nodes near to identified colorectal cancer tissue, and chemotherapy (e.g., administration of one or more of 5-FU and leucovorin, oxaliplatin, or capecitabine).

In various embodiments e.g., as set forth herein, treatment of colorectal cancer includes treatment of stage III colorectal cancer, by one or more of surgical removal of cancerous tissue (e.g., by local excision (e.g., by colonoscopy-based excision), partial colectomy, or complete colectomy), surgical removal of lymph nodes near to identified colorectal cancer tissue, chemotherapy (e.g., administration of one or more of 5-FU, leucovorin, oxaliplatin, capecitabine, e.g., in a combination of (i) 5-FU and leucovorin, (ii) 5-FU, leucovorin, and oxaliplatin (e.g., FOLFOX), or (iii) capecitabine and oxaliplatin (e.g., CAPEOX)), and radiation therapy.

In various embodiments e.g., as set forth herein, treatment of colorectal cancer includes treatment of stage IV colorectal cancer, by one or more of surgical removal of cancerous tissue (e.g., by local excision (e.g., by colonoscope), partial colectomy, or complete colectomy), surgical removal of lymph nodes near to identified colorectal cancer tissue, surgical removal of metastases, chemotherapy (e.g., administration of one or more of 5-FU, leucovorin, oxaliplatin, capecitabine, irinotecan, VEGF-targeted therapeutic agent (e.g., bevacizumab, ziv-aflibercept, or ramucirumab), EGFR-targeted therapeutic agent (e.g., cetuximab or panitumumab), Regorafenib, trifluridine, and tipiracil, e.g., in a combination of or including (i) 5-FU and leucovorin, (ii) 5-FU, leucovorin, and oxaliplatin (e.g., FOLFOX), (iii) capecitabine and oxaliplatin (e.g., CAPEOX), (iv) leucovorin, 5-FU, oxaliplatin, and irinotecan (FOLFOXIRI), and (v) trifluridine and tipiracil (Lonsurf)), radiation therapy, hepatic artery infusion (e.g., if cancer has metastasized to liver), ablation of tumors, embolization of tumors, colon stent, colorectomy, colostomy (e.g., diverting colostomy), and immunotherapy (e.g., pembrolizumab).

Those of skill in the art that treatments of colorectal cancer provided herein can be utilized, e.g., as determined by a medical practitioner, alone or in any combination, in any order, regimen, and/or therapeutic program. Those of skill in the art will further appreciate that advanced treatment options may be appropriate for earlier stage cancers in subjects previously having suffered a cancer or colorectal cancer, e.g., subjects diagnosed as having a recurrent colorectal cancer.

In some embodiments e.g., as set forth herein, methods and compositions for colorectal cancer and advanced adenoma screening provided herein can inform treatment and/or payment (e.g., reimbursement for or reduction of cost of medical care, such as screening or treatment) decisions and/or actions, e.g., by individuals, healthcare facilities, healthcare practitioners, health insurance providers, governmental bodies, or other parties interested in healthcare cost.

In some embodiments e.g., as set forth herein, methods and compositions for colorectal cancer and advanced adenoma screening provided herein can inform decision making relating to whether health insurance providers reimburse a healthcare cost payer or recipient (or not), e.g., for (1) screening itself (e.g., reimbursement for screening otherwise unavailable, available only for periodic/regular screening, or available only for temporally- and/or incidentally-motivated screening); and/or for (2) treatment, including initiating, maintaining, and/or altering therapy, e.g., based on screening results. For example, in some embodiments e.g., as set forth herein, methods and compositions for colorectal cancer and advanced adenoma screening provided herein are used as the basis for, to contribute to, or support a determination as to whether a reimbursement or cost reduction will be provided to a healthcare cost payer or recipient. In some instances e.g., as set forth herein, a party seeking reimbursement or cost reduction can provide results of a screen conducted in accordance with the present specification together with a request for such reimbursement or cost reduction of a healthcare cost. In some instance e.g., as set forth herein s, a party making a determination as to whether or not to provide a reimbursement or cost reduction of a healthcare cost will reach a determination based in whole or in part upon receipt and/or review of results of a screen conducted in accordance with the present specification.

For the avoidance of any doubt, those of skill in the art will appreciate from the present disclosure that methods and compositions for colorectal cancer and/or advanced adenoma diagnosis of the present specification are at least for in vitro use. Accordingly, all aspects and embodiments of the present disclosure can be performed and/or used at least in vitro.

Kits

The present disclosure includes, among other things, kits including one or more compositions for use in colorectal cancer and/or advanced adenoma screening as provided herein, optionally in combination with instructions for use thereof in colorectal cancer screening. In various embodiments, e.g., as set forth herein, a kit for screening of colorectal cancer and/or advanced adenomas can include one or more of: one or more oligonucleotide primers (e.g., one or more oligonucleotide primer pairs, e.g., as found in Table 5), one or more MSREs, one or more reagents for qPCR (e.g., reagents sufficient for a complete qPCR reaction mixture, including without limitation dNTP and polymerase), and instructions for use of one or more components of the kit for colorectal cancer screening. In various embodiments, a kit for screening of colorectal cancer can include one or more of: one or more oligonucleotide primers (e.g., one or more oligonucleotide primer pairs, e.g., as found in Table 5), one or more bisulfite reagents, one or more reagents for qPCR (e.g., reagents sufficient for a complete qPCR reaction mixture, including without limitation dNTP and polymerase), and instructions for use of one or more components of the kit for colorectal cancer screening.

In certain embodiments, a kit of the present disclosure includes at least one oligonucleotide primer pair for amplification of a methylation locus and/or DMR as disclosed herein.

In some instances e.g., as set forth herein, a kit of the present disclosure includes one or more oligonucleotide primer pairs for amplification of one or more methylation regions of the present disclosure. In some instances e.g., as set forth herein, kit of the present disclosure includes one or more oligonucleotide primer pairs for amplification of one or more methylation regions that are or include all or a portion of one or more genetic regions provided in Table 1. In some particular instances e.g., as set forth herein, a kit of the present disclosure includes oligonucleotide primer pairs for a plurality of methylation regions that each include (all or a portion of) a genetic region identified in Table 1, the plurality of methylation regions including (all or a portion of), e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 of the methylation regions provided in any of Tables 1 to 4.

In some instances e.g., as set forth herein, a kit of the present disclosure includes one or more oligonucleotide primer pairs for amplification of one or more DMRs of the present disclosure. In some instances e.g., as set forth herein, kit of the present disclosure includes one or more oligonucleotide primer pairs for amplification of one or more DMRs that include (all or a portion of) a gene identified in Table 1. In some particular embodiments, a kit of the present disclosure includes oligonucleotide primer pairs for a plurality of DMRs, wherein each of the DMRs include (all or a portion of) a genetic region identified in Table 1, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 DMRs, e.g., in accordance with any one of Tables 1 to 4.

In some instances e.g., as set forth herein, kit of the present disclosure includes one or more oligonucleotide primer pairs for amplification of one or more DMRs of Table 5. In some particular instances e.g., as set forth herein, a kit of the present disclosure includes oligonucleotide primer pairs for a plurality of DMRs of Table 5, the plurality of DMRs including (all or a portion of), e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 DMRs of Table 1, e.g., as provided in any of Tables 2 to 4.

In various embodiments e.g., as set forth herein, a kit of the present disclosure includes one or more oligonucleotide primer pairs provided in Table 5. Those of skill in the art will appreciate that oligonucleotide primer pairs provided in Table 5 can be provided in any combination of one or more oligonucleotide primer pairs, e.g., in a combination as provided in any one of Tables 2-4.

A kit of the present disclosure can further include one or more MSREs individually or in a single solution. In various embodiments, one or more MSREs are selected from the set of MSREs including AciI, Hin6I, HpyCH4IV, and HpaII (e.g., such that the kit includes AciI, Hin6I, and HpyCH4IV, either individually or in a single solution). In certain embodiments, a kit of the present disclosure includes one or more reagents for qPCR (e.g., reagents sufficient for a complete qPCR reaction mixture, including without limitation dNTP and polymerase).

EXAMPLES

The present Examples confirm that the present disclosure provides methods and compositions for, among other things, screening for and treatment of colorectal cancer and/or advanced adenomas. The present Examples further demonstrate that compositions and methods provided herein provide a remarkably high degree of sensitivity and specificity in screening and/or treatment of colorectal cancer and/or advanced adenomas. Also provided are clinical studies comparing methylation of biomarkers in samples from subjects diagnosed as having colorectal cancer and methylation of biomarkers in samples from control subjects, further demonstrating screening for colorectal cancer including methods and/or compositions of the present disclosure. Samples of the present Examples are humans or of human origin.

Example 1. Identification of Methylation Biomarkers Associated with Colorectal Cancer The present Example includes identification of hypermethylation of CpG regions of DMRs in colorectal cancer and advanced adenoma as compared to healthy tissue. In particular, experiments of the present example examined colorectal tissue samples from a total of 150 subjects. The groupings of the subjects were as follows: (i) 52 subjects previously diagnosed as suffering with colorectal cancer, (ii) 33 subjects diagnosed as suffering with advanced adenomas, and (iii) 65 healthy colon tissue samples obtained from the subset of the 52 patients diagnosed as suffering with colorectal cancer and the 33 subjects diagnosed as suffering with advanced adenomas. Tissue samples were of fresh frozen tissue.

DNA of the samples were analyzed with whole genome bisulfite sequencing using the NovaSeq™ 6000 Sequencing system from Illumina. Whole genome bisulfite sequencing has been described previously herein. In general, whole genome bisulfite sequencing involves treatment of the DNA samples with a bisulfite (e.g., sodium bisulfite) prior to sequencing the genome using any one of a number of next generation technologies as previously discussed.

The samples had an average sequencing coverage of 37.5×, meaning that, a given region of the sequenced genome had been uniquely sequenced approximately 37-38 times. Having an average coverage greater than 30× indicates that the sequencing has been conducted with clinical grade (i.e., high) reliability.

The raw sequencing files obtained from the samples were then processed to determine the differentially methylated regions (DMRs) as compared to the control tissue samples. First, the raw sequences were aligned with the reference genome of GRCh38 (Genome Research Consortium human build 38) and deduplicated using Bismark Bisulfite Mapper. Bismark output the methylation call files for each of the samples. These methylation call files contain a percent methylation score per base output. The methylation call output files were then further analyzed using MethylKit. MethylKit was used to compare the output files from colorectal cancer tissues to control tissues and the output files from the advanced adenoma tissues to control tissues. These comparisons resulted in the identification of DMRs for both colorectal cancer and advanced adenoma samples. The identified DMRs output from MethylKit were considered to be a region where at least 3 CpGs are present with maximum distance between the CpGs being 200 bp. The minimum methylation percentage difference between control and case was set to 10%.

The DMRs were then filtered for regions of hypermethylation in the advanced adenoma and colorectal cancer samples with respect to the control samples. The DMRs were again filtered to select for a higher number of methylated CpGs per region length. A minimum of 5 CpGs with maximum of 200 bp between two adjacent methylated CpGs was considered. Additionally, a highest average methylation percent difference between the condition (e.g., colorectal cancer or advanced adenoma) and the control was used by excluding regions where the difference between the methylation of the condition and the control was less than 25%.

The processing of the resulted in a list of 69 DMRs (i.e., as seen in Table 6 below), which were selected for further, targeted assay development. As can be seen below in Table 6, each of the DMRs are identified by their sequence ID (SEQ ID NO) corresponding to their sequence as provided herein, the chromosome number the DMR is on, the start and end base pairs of the DMR on the chromosome, the width of the DMR region (region width), and the annotated name of the one (or more) genes falling within the DMR region (if available). The start and end base pairs and chromosome number of the DMRs correspond to locations on the reference genome of GRCh38. The annotations of the gene names are according to Ensemble genome browser 98.

TABLE 6

69 DMRs identified for targeted assay development.

| SEQ ID NO | Chr. Number | Start base pair | End base pair | Region Width | Annotated Gene Name |
|---|---|---|---|---|---|
| SEQ ID NO: 1 | 1 | 18636183 | 18636479 | 297 | PAX7 |
| SEQ ID NO: 2 | 1 | 107140100 | 107140341 | 242 | NTNG1 |
| SEQ ID NO: 3 | 1 | 114153175 | 114153431 | 257 | SYT6 |
| SEQ ID NO: 4 | 2 | 5673847 | 5674110 | 264 | LINC01248 |
| SEQ ID NO: 5 | 2 | 26692974 | 26693164 | 191 | KCNK3 |
| SEQ ID NO: 6 | 2 | 31136994 | 31138312 | 1319 | GALNT14 |
| SEQ ID NO: 7 | 2 | 100416598 | 100417320 | 723 | CHST10 |
| SEQ ID NO: 8 | 2 | 127025668 | 127025992 | 325 | no annotation |
| SEQ ID NO: 9 | 2 | 136765863 | 136767257 | 1395 | THSD7B |
| SEQ ID NO: 10 | 2 | 209771521 | 209771717 | 197 | UNC80 |
| SEQ ID NO: 11 | 3 | 96812527 | 96814374 | 1848 | EPHA6 |
| SEQ ID NO: 12 | 3 | 151086702 | 151087381 | 680 | MED12L |
| SEQ ID NO: 13 | 4 | 61201658 | 61202419 | 762 | ADGRL3 |
| SEQ ID NO: 14 | 4 | 141133100 | 141133759 | 660 | RNF150 |
| SEQ ID NO: 15 | 4 | 167233855 | 167235112 | 1258 | SPOCK3 |
| SEQ ID NO: 16 | 4 | 176001298 | 176001937 | 640 | GPM6A |
| SEQ ID NO: 17 | 4 | 185020150 | 185020721 | 572 | HELT |
| SEQ ID NO: 18 | 5 | 180353742 | 180353989 | 248 | GFPT2 |
| SEQ ID NO: 19 | 6 | 31815502 | 31815783 | 282 | HSPA1L, HSPA1A |
| SEQ ID NO: 20 | 6 | 123803543 | 123804573 | 1031 | NKAIN2 |
| SEQ ID NO: 21 | 7 | 141072216 | 141073010 | 795 | TMEM178B |
| SEQ ID NO: 22 | 7 | 154304773 | 154304932 | 160 | DPP6 |
| SEQ ID NO: 23 | 8 | 17026468 | 17027021 | 554 | MICU3 |
| SEQ ID NO: 24 | 8 | 52564399 | 52566130 | 1732 | ALKAL1 |
| SEQ ID NO: 25 | 8 | 64581458 | 64581984 | 527 | LOC401463, BHLHE22 |
| SEQ ID NO: 26 | 8 | 103500115 | 103500325 | 211 | RIMS2, LOC105375690, SLC25A32 |
| SEQ ID NO: 27 | 9 | 843218 | 843532 | 315 | DMRT1 |
| SEQ ID NO: 28 | 9 | 21970988 | 21971129 | 142 | CDKN2A, CDKN2B-AS1 |
| SEQ ID NO: 29 | 9 | 36986363 | 36986579 | 217 | PAX5 |
| SEQ ID NO: 30 | 10 | 16520584 | 16520645 | 62 | C1QL3 |
| SEQ ID NO: 31 | 10 | 25933862 | 25934167 | 306 | MYO3A, LOC101929073 |
| SEQ ID NO: 32 | 10 | 26211596 | 26212313 | 718 | GAD2, MYO3A |
| SEQ ID NO: 33 | 10 | 127736443 | 127736756 | 314 | FOXI2 |
| SEQ ID NO: 34 | 11 | 94740674 | 94742025 | 1352 | LOC105369438, AMOTL1 |
| SEQ ID NO: 35 | 11 | 112962067 | 112962734 | 668 | LOC101928847, NCAM1 |

TABLE 6-continued

69 DMRs identified for targeted assay development.

| SEQ ID NO | Chr. Number | Start base pair | End base pair | Region Width | Annotated Gene Name |
|---|---|---|---|---|---|
| SEQ ID NO: 36 | 11 | 117795608 | 117796104 | 497 | DSCAML1 |
| SEQ ID NO: 37 | 12 | 15322181 | 15323178 | 998 | PTPRO, RERG |
| SEQ ID NO: 38 | 12 | 63667846 | 63668580 | 735 | DPY19L2 |
| SEQ ID NO: 39 | 12 | 111033274 | 111033632 | 359 | CUX2 |
| SEQ ID NO: 40 | 13 | 67229618 | 67231644 | 2027 | PCDH9 |
| SEQ ID NO: 41 | 13 | 87673128 | 87673271 | 144 | MIR4500HG, SLITRK5 |
| SEQ ID NO: 42 | 14 | 70188797 | 70189400 | 604 | SLC8A3, LOC646548 |
| SEQ ID NO: 43 | 14 | 77966179 | 77966411 | 233 | no annotation |
| SEQ ID NO: 44 | 15 | 45378160 | 45378420 | 261 | GATM |
| SEQ ID NO: 45 | 15 | 64824187 | 64824233 | 47 | PIF1 |
| SEQ ID NO: 46 | 15 | 79089616 | 79089950 | 335 | RASGRF1 |
| SEQ ID NO: 47 | 16 | 70737594 | 70737910 | 317 | VAC14 |
| SEQ ID NO: 48 | 16 | 77789176 | 77789410 | 235 | VAT1L |
| SEQ ID NO: 49 | 16 | 87601415 | 87601495 | 81 | JPH3 |
| SEQ ID NO: 50 | 17 | 35448324 | 35448347 | 24 | SLFN13 |
| SEQ ID NO: 51 | 17 | 76076064 | 76076299 | 236 | ZACN, SRP68, GALR2 |
| SEQ ID NO: 52 | 18 | 907740 | 908272 | 533 | ADCYAP1 |
| SEQ ID NO: 53 | 18 | 28177400 | 28177679 | 280 | CDH2 |
| SEQ ID NO: 54 | 18 | 69401262 | 69401796 | 535 | DOK6 |
| SEQ ID NO: 55 | 18 | 75916571 | 75916639 | 69 | no annotation |
| SEQ ID NO: 56 | 19 | 36666416 | 36667626 | 1211 | ZNF461 |
| SEQ ID NO: 57 | 19 | 36916473 | 36916789 | 317 | ZNF829, ZNF568 |
| SEQ ID NO: 58 | 19 | 36973366 | 36973693 | 328 | ZNF568 |
| SEQ ID NO: 59 | 19 | 37551650 | 37551952 | 303 | ZNF540, ZNF571-AS1 |
| SEQ ID NO: 60 | 19 | 42270825 | 42271072 | 248 | CIC |
| SEQ ID NO: 61 | 19 | 56393726 | 56393946 | 221 | ZNF582-AS1, ZNF582 |
| SEQ ID NO: 62 | 19 | 56507701 | 56507850 | 150 | ZNF471 |
| SEQ ID NO: 63 | 19 | 57191866 | 57192102 | 237 | ZNF264 |
| SEQ ID NO: 64 | 19 | 57726974 | 57727102 | 129 | ZNF671, ZNF551, ZNF776 |
| SEQ ID NO: 65 | 20 | 21518031 | 21518878 | 848 | NKX2-2 |
| SEQ ID NO: 66 | 20 | 56925418 | 56925496 | 79 | no annotation |
| SEQ ID NO: 67 | 21 | 26843133 | 26845357 | 2225 | ADAMTS1 |
| SEQ ID NO: 68 | 21 | 31343542 | 31344538 | 997 | TIAM1 |
| SEQ ID NO: 69 | 21 | 33070564 | 33070847 | 284 | OLIG1 |

Example 2: Development of Cell-Free DNA Assay for Methylation Biomarkers by MSRE-qPCR The present Example develops an assay for determining the methylation status of colorectal cancer and advanced adenoma methylation biomarkers based on circulating cell free DNA (cfDNA). cfDNA is incomplete and fragmented, and the mechanism by which the cfDNA is transmitted from cancer cells to blood (as a portion called circulating tumor DNA) is unknown. At least because the 69 methylation biomarkers of Example 1 were identified from tissue samples, it was not known prior to the experiments of the present Example whether identified colorectal cancer methylation biomarkers could be sufficiently analyzed from cfDNA to successfully capture the ctDNA portion that allows for identifying subjects or samples of subjects corresponding to a diagnosis of colorectal cancer and/or advanced adenoma.

As a critical step toward determining whether the colorectal cancer and advanced adenoma methylation biomarkers identified in Example 1 could be sufficiently analyzed from cfDNA to successfully capture the ctDNA portion that allows for identification of subjects or samples for colorectal cancer, a sensitive assay was developed for screening of these biomarkers. In particular, a Methylation-Sensitive Restriction Enzyme (MSRE)-qPCR methodology was developed. The MSRE-qPCR methodology was developed to measure methylation of DMRs covering identified CpG sites in blood samples, in particular in cell-free DNA (cfDNA) of tumors present in blood.

Development of the MSRE-qPCR methodology was significant at least in part because analyzing CpG methylation biomarkers derived from tumor tissue by analysis of cfDNA is challenging due to the low concentration of tumor-derived DNA circulating in blood (0.1-1%) as compared to the non-tumor DNA background of the sample. Thus, while it is generally preferred to develop biomarker analyses that rely on readily obtainable samples such as blood, urine, or stool, use of blood for analysis of tumor derived methylation biomarkers is challenging. Thus, even after identification of methylation biomarkers characteristic of colorectal cancer and advanced adenoma in tissue, as discussed above, it cannot be predicted whether the fragmented and poorly understood nature of ctDNA will permit successful screening using methylation biomarkers identified in tissue.

MSRE-qPCR requires design of oligonucleotide primers (MSRE-qPCR oligonucleotide primer pairs) that amplify regions of DNA that each include at least one MSRE cleavage site (i.e., an MSRE cleavage site that covers at least one methylation biomarker site, such that cleavage of the MSRE cleavage site is permitted in nucleic acid molecules where all of the least one of the methylation biomarker sites are unmethylated and blocked in nucleic acid molecules where at least one of the methylation biomarker sites is methylated). MSRE-qPCR assays can utilize multiple restriction enzymes to enhance the range of methylation biomarker sites that can be assayed by a single MSRE-qPCR reaction, as a single MSRE is unlikely to cleave sites that together include all methylation biomarker sites of interest. MSRE-qPCR assays of the present Examples utilize the MSREs AciI, Hin6I, and HpyCH4IV, which together were found to provide sufficient coverage.

Figure 1:
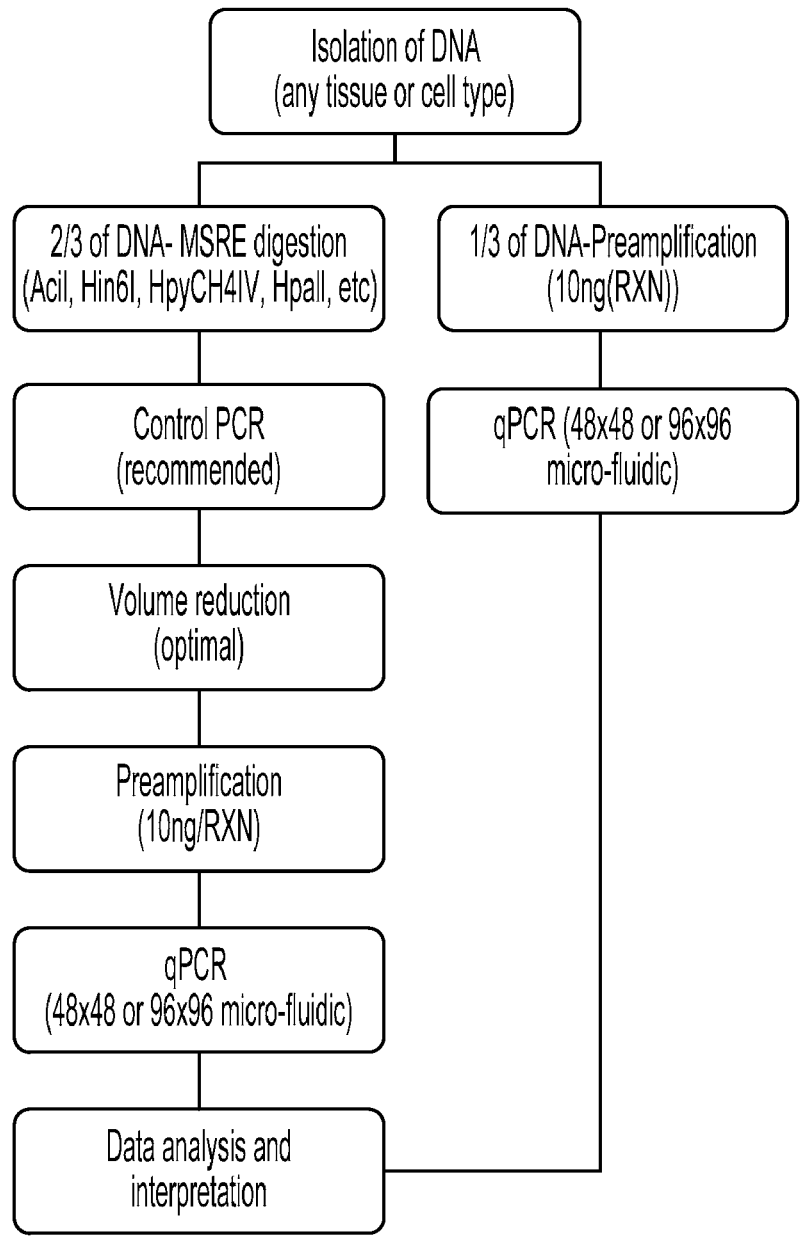
FIG. 1 is a schematic showing an example MSRE-qPCR approach.

An exemplary schematic work flow for MSRE-qPCR is provided in FIG. 1. As performed in the present Examples, circulating cell-free tumor DNA was extracted from subject blood (typically a plasma sample of approximately 10 mL) by QIAamp MinElute ccfDNA Kit in accordance with manufacturer protocol (QIAamp MinElute ccfDNA Handbook August 2018, Qiagene). As shown in FIG. 1, isolated cfDNA was divided into two aliquots, a first of which aliquots is utilized in a qPCR quality control analysis, and a second of which aliquots is used in MSRE-qPCR.

For MSRE-qPCR, ⅔ of eluted cfDNA by volume was digested with MSREs. Because non-methylated DNA is selectively cleaved, contacting the cfDNA with the MSREs enriches the sample for methylation-derived signal; methylated DNA remains intact and quantifiable. The remaining ⅓ of eluted cfDNA by volume was used for qPCR using the MSRE-qPCR oligonucleotide primers to confirm that amplicons were successfully amplified from cfDNA, which amplification confirms that template is present, hence providing technical quality control.

As applied herein, MSRE-qPCR oligonucleotide primer pairs were successfully developed for amplification of DMRs, thus yielding 88 different target DMRs from the methylation biomarker regions identified in the DMRs of Example 1. The 88 different target DMRs are listed in Table 7 below. The identified regions have significantly higher hypermethylation in colorectal cancer and advanced adenoma as compared to matching control tissue. Gene annotation has been added for genes that have annotation according to Ensembl genome browser 98. As some of the DMRs overlap different genes, all overlapping genes in the regions are listed. Table 7 below contains the unique identifier (UID) of the DMR, the chromosome number (Chr) the DMR is found on, the start and end positions of the DMR, the length/number of base pairs of the DMR, the name of an annotated gene (or multiple genes) found within the DMR, and the SEQ ID NO of the identified DMR. The genomic region parameters listed, including chromosome number and DMR start and end location, correspond to the reference genome of GRCh38.

DMRs typically included 1 to 15 MSRE cleavage sites, which MSRE cleavage sites together covered each of the 88 methylation biomarker regions. As applied herein, methylation status of four genes (JUB, H19, SNRPN, IRF4) provided a methylation control, which permitted monitoring of assay robustness and reproducibility.

TABLE 7

88 Candidate DMRs Identified For MSRE-qPCR.

| UID | Chr | Start Position | End Position | Sequence Width | Annotated Gene Name(s) | SEQ ID NO. |
|---|---|---|---|---|---|---|
| UDX131.2_1 | 1 | 18636323 | 18636442 | 120 | PAX7 | 230 |
| UDX_244_2 | 1 | 107140056 | 107140173 | 118 | NTNG1 | 231 |
| UDX_244_1 | 1 | 107140136 | 107140204 | 69 | NTNG1 | 232 |
| UDX_117.2 | 1 | 114153293 | 114153403 | 111 | SYT6 | 233 |
| UDX_121.1 | 2 | 5673894 | 5673976 | 83 | LINC01248 | 234 |
| UDX_79.1 | 2 | 26692903 | 26692983 | 81 | KCNK3 | 235 |
| UDX_219.7_2 | 2 | 31138019 | 31138112 | 94 | GALNT14 | 236 |
| UDX_196.4_1 | 2 | 100417126 | 100417223 | 98 | CHST10 | 237 |
| UDX_257.2_1 | 2 | 127025856 | 127025946 | 91 | no annotation | 238 |
| UDX_221.1_2 | 2 | 136765920 | 136766016 | 97 | THSD7B | 239 |
| UDX_221.2_2 | 2 | 136766099 | 136766189 | 91 | THSD7B | 240 |
| UDX_221.2_1 | 2 | 136766115 | 136766191 | 77 | THSD7B | 241 |
| UDX_221.4_1 | 2 | 136766444 | 136766530 | 87 | THSD7B | 242 |
| UDX_85.2_1 | 2 | 209771685 | 209771755 | 71 | UNC80 | 243 |
| UDX_222.1 | 3 | 96813875 | 96813987 | 113 | EPHA6 | 244 |
| UDX_222.11_2 | 3 | 96814054 | 96814137 | 84 | EPHA6 | 245 |
| UDX_192.2 | 3 | 151086946 | 151087030 | 85 | MED12L | 246 |
| UDX_198.5_1 | 4 | 61202277 | 61202367 | 91 | ADGRL3 | 247 |
| UDX_190.1 | 4 | 141133118 | 141133232 | 115 | RNF150 | 248 |
| UDX_218.4_2 | 4 | 167234344 | 167234453 | 110 | SPOCK3 | 249 |
| UDX_218.4_1 | 4 | 167234345 | 167234442 | 98 | SPOCK3 | 250 |
| UDX_185.1 | 4 | 176001298 | 176001402 | 105 | GPM6A | 251 |
| UDX_176.2 | 4 | 185020392 | 185020498 | 107 | HELT | 252 |
| UDX114.1_1 | 5 | 180353709 | 180353815 | 107 | GFPT2 | 253 |
| UDX114.1_2 | 5 | 180353728 | 180353815 | 88 | GFPT2 | 254 |
| UDX_125.2 | 6 | 31815718 | 31815803 | 86 | HSPA1L, HSPA1A | 255 |
| UDX_213.3 | 6 | 123803960 | 123804070 | 111 | NKAIN2 | 256 |
| UDX_201.3 | 7 | 141072555 | 141072639 | 85 | TMEM178B | 257 |
| UDX_201.5_1 | 7 | 141072898 | 141072970 | 73 | TMEM178B | 258 |
| UDX_177.1 | 7 | 141073214 | 141073310 | 97 | TMEM178B | 259 |
| UDX_66.2 | 7 | 154304857 | 154304969 | 113 | DPP6 | 260 |
| UDX_174.3 | 8 | 17026934 | 17027030 | 97 | MICU3 | 261 |
| UDX_277.7_2 | 8 | 52565317 | 52565408 | 92 | ALKAL1 | 262 |
| UDX_168.1 | 8 | 64581549 | 64581646 | 98 | LOC401463, BHLHE22 | 263 |
| UDX_168.3 | 8 | 64581819 | 64581913 | 95 | LOC401463, BHLHE22 | 264 |
| UDX_90.1 | 8 | 103500053 | 103500167 | 115 | RIMS 2, LOC105375690, SLC25A32 | 265 |
| UDX_253.1 | 9 | 843262 | 843352 | 91 | DMRT1 | 266 |
| UDX_230 | 9 | 21970918 | 21971017 | 100 | CDKN2A, CDKN2B-AS1 | 267 |

TABLE 7-continued

88 Candidate DMRs Identified For MSRE-qPCR.

| UID | Chr | Start Position | End Position | Sequence Width | Annotated Gene Name(s) | SEQ ID NO. |
|---|---|---|---|---|---|---|
| UDX_94.2_2 | 9 | 36986521 | 36986581 | 61 | PAX5 | 268 |
| UDX_17_2 | 10 | 16520590 | 16520719 | 130 | C1QL3 | 269 |
| UDX_251.2_1 | 10 | 25934063 | 25934130 | 68 | MYO3A, LOC101929073 | 270 |
| UDX_272.3_2 | 10 | 26211885 | 26211963 | 79 | GAD2, MYO3A | 271 |
| UDX_272.4 | 10 | 26212056 | 26212160 | 105 | GAD2, MYO3A | 272 |
| UDX_137.1 | 10 | 127736482 | 127736589 | 108 | FOXI2 | 273 |
| UDX_220.5_1 | 11 | 94741361 | 94741468 | 108 | LOC105369438, AMOTL1 | 274 |
| UDX_191.2_1 | 11 | 112962254 | 112962393 | 140 | LOC101928847, NCAM1 | 275 |
| UDX_191.3 | 11 | 112962451 | 112962564 | 114 | LOC101928847, NCAM1 | 276 |
| UDX_191.4 | 11 | 112962596 | 112962709 | 114 | LOC101928847, NCAM1 | 277 |
| UDX_158.2 | 11 | 117795852 | 117795967 | 116 | DSCAML1 | 278 |
| UDX_274.2_1 | 12 | 15322352 | 15322435 | 84 | PTPRO, RERG | 279 |
| UDX_274.3_1 | 12 | 15322477 | 15322549 | 73 | PTPRO, RERG | 280 |
| UDX_197.3 | 12 | 63668266 | 63668380 | 115 | DPY19L2 | 281 |
| UDX_143.2_1 | 12 | 111033456 | 111033526 | 71 | CUX2 | 282 |
| UDX_223.11_2 | 13 | 67231170 | 67231267 | 98 | PCDH9 | 283 |
| UDX_223.13_1 | 13 | 67231170 | 67231265 | 96 | PCDH9 | 284 |
| UDX_223.6_1 | 13 | 67230402 | 67230489 | 88 | PCDH9 | 285 |
| UDX_56_1 | 13 | 87673121 | 87673244 | 124 | MIR4500HG, SLITRK5 | 286 |
| UDX181.2_1 | 14 | 70189010 | 70189101 | 92 | SLC8A3, LOC646548 | 287 |
| UDX181.4_1 | 14 | 70189227 | 70189296 | 70 | SLC8A3, LOC646548 | 288 |
| UDX_107.2 | 14 | 77966333 | 77966434 | 102 | no annotation | 289 |
| UDX_120.2 | 15 | 45378327 | 45378410 | 84 | GATM | 290 |
| UDX_6_2 | 15 | 64824187 | 64824315 | 129 | PIF1 | 291 |
| UDX_260.1 | 15 | 79089689 | 79089791 | 103 | RASGRF1 | 292 |
| UDX_260.2_1 | 15 | 79089783 | 79089858 | 76 | RASGRF1 | 293 |
| UDX_255.2_1 | 16 | 70737814 | 70737885 | 72 | VAC14 | 294 |
| UDX_109.2 | 16 | 77789273 | 77789385 | 113 | VAT1L | 295 |
| UDX_30_1 | 16 | 87601409 | 87601511 | 103 | JPH3 | 296 |
| UDX_1_1 | 17 | 35448306 | 35448407 | 102 | SLFN13 | 297 |
| UDX_110.1 | 17 | 76076051 | 76076163 | 113 | ZACN, SRP68, GALR2 | 298 |
| UDX_171.3 | 18 | 908129 | 908238 | 110 | ADCYAP1 | 299 |
| UDX_124.1 | 18 | 28177439 | 28177533 | 95 | CDH2 | 300 |
| UDX_172.1 | 18 | 69401246 | 69401321 | 76 | DOK6 | 301 |
| UDX_24_1 | 18 | 75916501 | 75916621 | 121 | no annotation | 302 |
| UDX_217.4_1 | 19 | 36666980 | 36667097 | 118 | ZNF461 | 303 |
| UDX_254.2_2 | 19 | 36916694 | 36916789 | 96 | ZNF829, ZNF568 | 304 |
| UDX_258.2_1 | 19 | 36973532 | 36973602 | 71 | ZNF568 | 305 |
| UDX_250.1 | 19 | 37551664 | 37551748 | 85 | ZNF540, ZNF571-AS1 | 306 |
| UDX_245_1 | 19 | 42270787 | 42270865 | 79 | CIC | 307 |
| UDX_242_2 | 19 | 56393660 | 56393732 | 73 | ZNF582-AS1, ZNF582 | 308 |
| UDX111.1_1 | 19 | 57191843 | 57191928 | 86 | ZNF264 | 309 |
| UDX_48_1 | 19 | 57726972 | 57727075 | 104 | ZNF671, ZNF551, ZNF776 | 310 |
| UDX_204.3_2 | 20 | 21518391 | 21518499 | 109 | NKX2-2 | 311 |
| UDX_29_2 | 20 | 56925386 | 56925450 | 65 | no annotation | 312 |
| UDX_29_1 | 20 | 56925428 | 56925505 | 78 | no annotation | 313 |
| UDX_224.5_2 | 21 | 26843742 | 26843842 | 101 | ADAMTS1 | 314 |
| UDX_224.14 | 21 | 26844767 | 26844877 | 111 | ADAMTS1 | 315 |
| UDX_210.3 | 21 | 31343869 | 31343976 | 108 | TIAM1 | 316 |
| UDX_128.1 | 21 | 33070631 | 33070711 | 81 | OLIG1 | 317 |

Example 3: MSRE-qPCR of cfDNA Successfully Distinguishes Subjects by Colorectal Cancer Status To probe clinical diagnostic and prognostic power of identified methylation biomarkers, the DMRs amplified by the MSRE-qPCR oligonucleotide primer pairs covering the 88 methylation biomarker regions, and appropriate controls, were assayed in cfDNA extracted from plasma of human subjects. In particular, cfDNA was sampled from individuals seeking, or in the process of obtaining, a diagnosis regarding possible colorectal cancer at screening centers and oncology clinics in Spain, the United Kingdom, and the United States between 2017 and 2018. A first subject group (the "training set") included 166 such individuals (see description of the first subject group in FIG. 2), and a second subject group (the "validation set") included 535 such individuals (see description of second subject group in FIG. 3).

To verify the predictive power of methylation biomarker DMRs for colorectal cancer, data derived from MSRE-qPCR analysis of samples from the training set of subjects were further analyzed to perform an initial feature selection based on the 88 methylation biomarker sites of Table 7. Monte-Carlo cross-validation was used over 50 runs and random forest algorithm was used for feature ranking and markers with VIP >2 were used for building a support-vector machine (SVM) algorithm-based classification model. This analysis identified several subsets of markers (3, 10, and 40 as described in Tables 2-4) that in the SVM-model gave a good prediction.

Oligonucleotide primer pairs (Table 5) for amplification of the 40 DRMs in MSRE-qPCR cover at least one MSRE cleavage site. However, typically 3 to 15 MSRE cleavage sites are covered. MSRE-qPCR was carried out according to the methodology described in Example 2.

Figure 4:
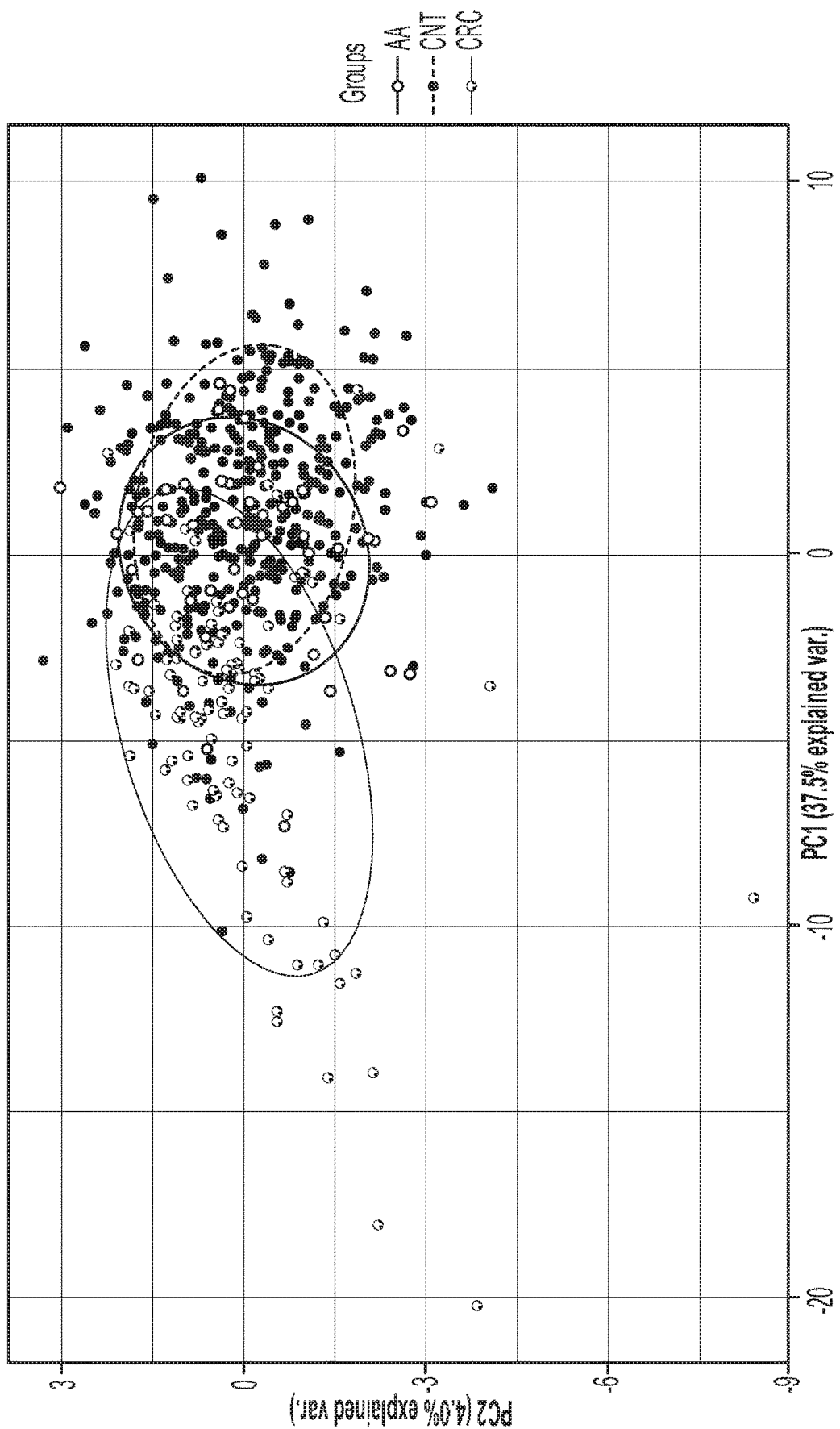
FIG. 4 shows a graph of an initial principle component analysis conducted on the validation set of subjects. The subjects were divided into three groups: patients suffering with advanced adenomas (AA), control patients (CNT), and patients suffering with colorectal cancer (CRC). Control (CNT) patients are defined as patients with no colonoscopy findings, patients with hyperplastic polyps, and patients with non-advanced adenomas (NAAs). Correlation circles have been drawn around each of the three groupings.

Initial principal component analysis based on the 40 marker panel revealed a good separation between colorectal cancer patients (i.e., those who are suffering colorectal cancer) and control patients (i.e., patients having no colonoscopy findings, hyperplastic polyps, and/or non-advanced adenomas) in 535 subjects tested as can be seen in FIG. 4. In the tested subject group, only some of the patients diagnosed with having advanced adenomas showed good separation from the control group. Without wishing to be bound to any particular theory, the similarity of the characteristics of the results to colorectal cancer in certain subjects may indicate that the advanced adenomas are further along in their path in progressing to a malignant, colorectal carcinoma.

Figure 5B:
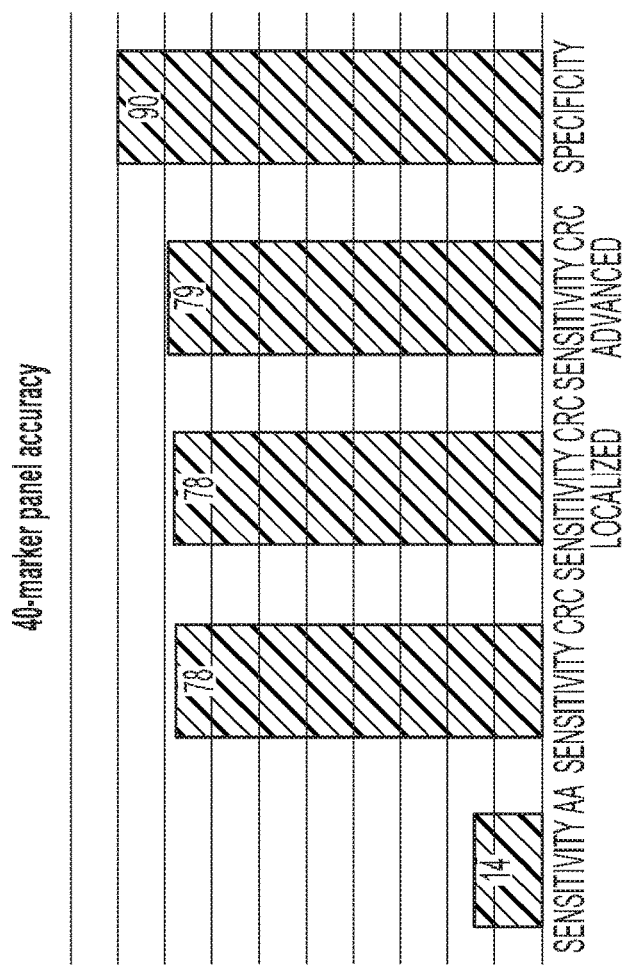
FIG. 5B is a chart showing accuracy values, including, from left to right, overall sensitivity of screening for advanced adenomas, overall sensitivity of screening for colorectal cancer, sensitivity of colorectal screening for localized colorectal cancer, sensitivity of colorectal screening for advanced colorectal cancer, and specificity of colorectal screening for control subjects (those with no colonoscopy findings, having hyperplastic polyps, and/or patients diagnosed as having non-advanced adenomas (NAAs)).
Figure 5A:
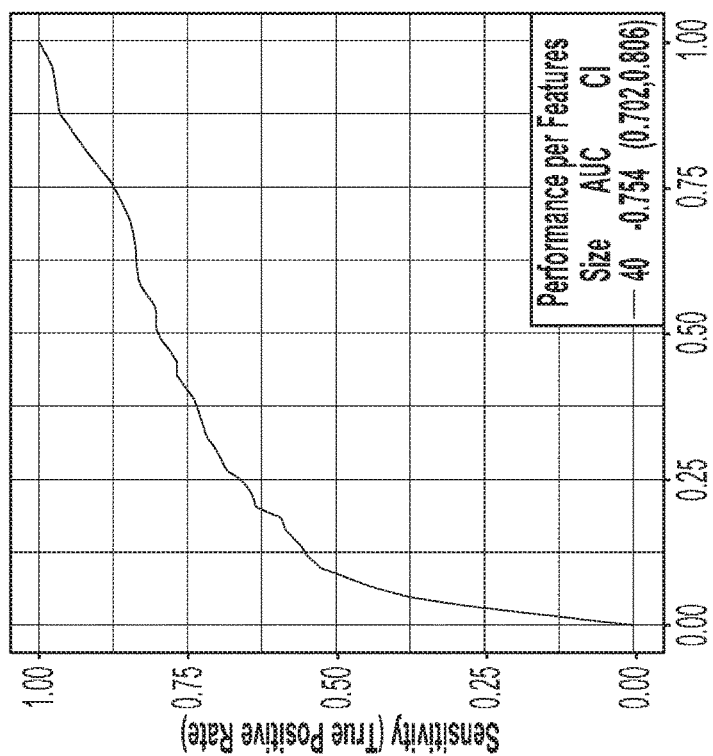
FIG. 5A is a graph showing performance of colorectal cancer screening using a 40 marker panel of DMRs on a 535 subject group. ROC and AUC for all subjects of the validation group are shown.
Figure 6:
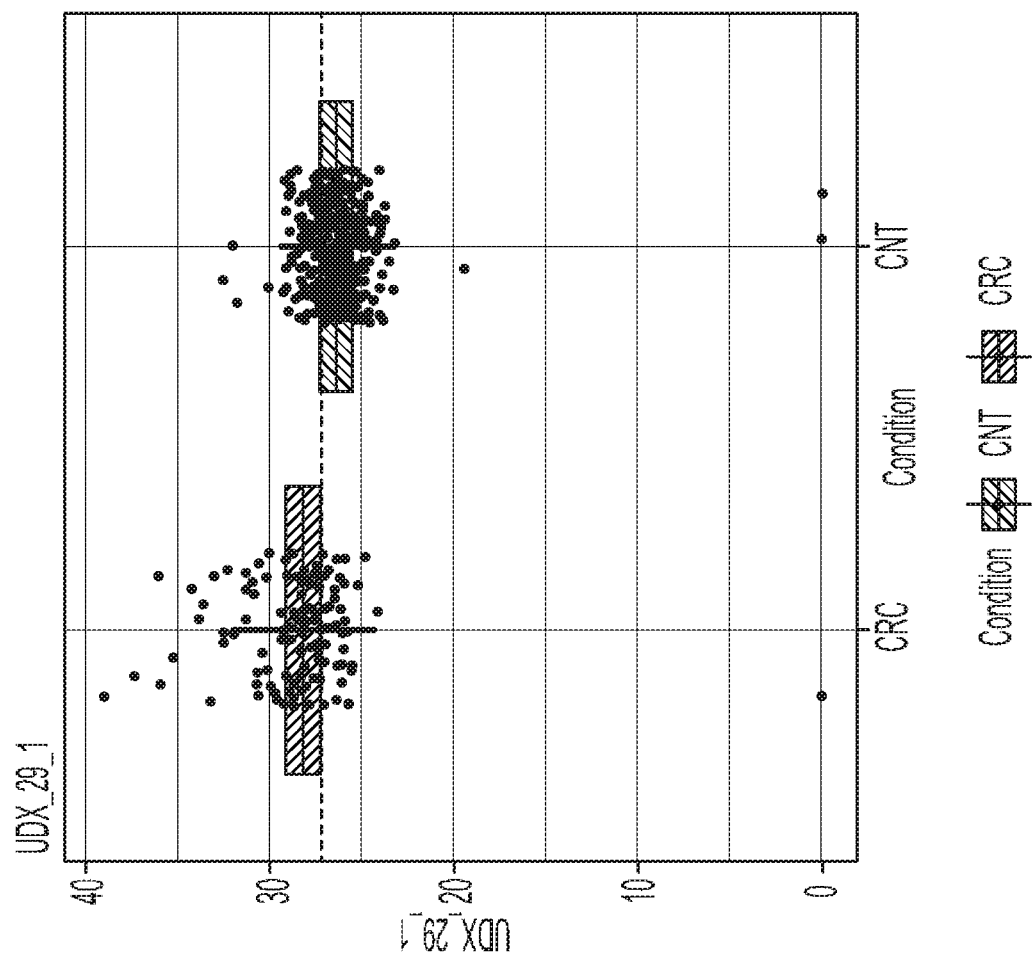
FIG. 6 shows a graph representing Ct (Cycle Threshold) values from MSRE-qPCR of the region identified as UDX_29_1 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45−Ct). Higher 45−Ct values correspond to higher methylation status, demonstrating hypermethylation in subjects with colorectal cancer.
Figure 7:
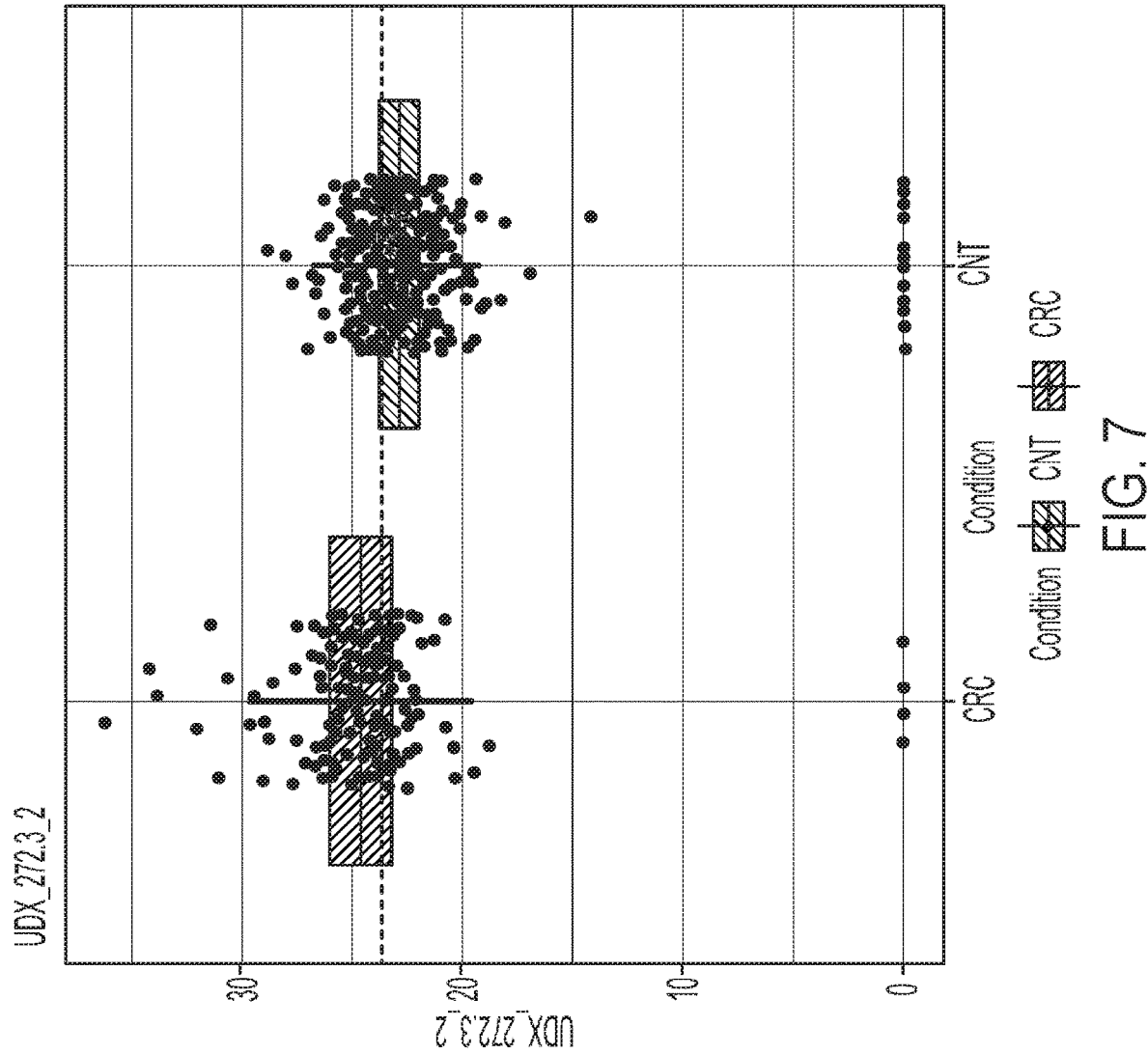
FIG. 7 shows a graph representing Ct (Cycle Threshold) values from MSRE-qPCR of the region identified as UDX_272.3_2 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 8:
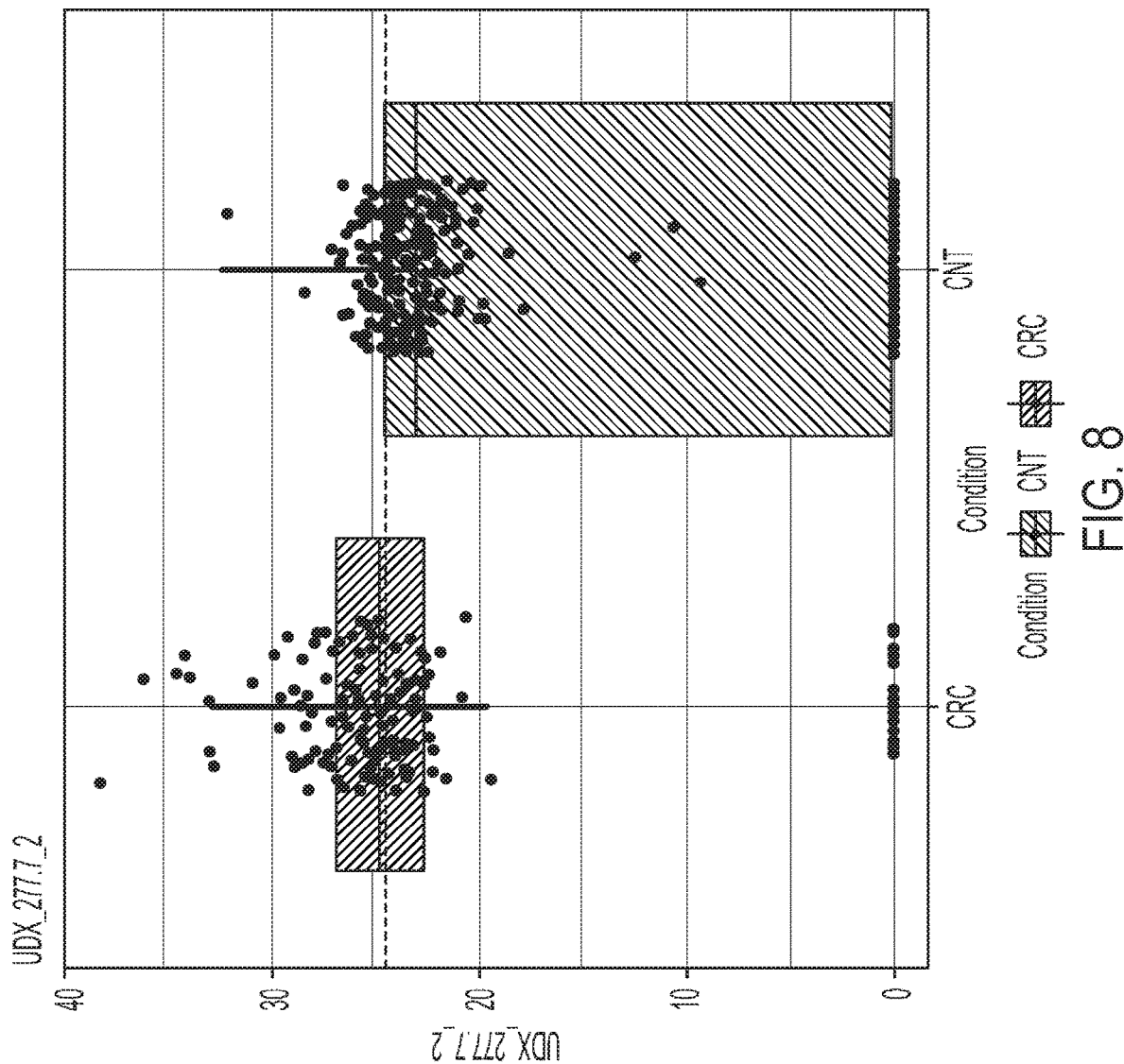
FIG. 8 shows a graph representing Ct (Cycle Threshold) values from MSRE-qPCR of the region identified as UDX_277.7_2 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.

Statistical analysis of the SVM algorithm based results are shown in FIGS. 5A and 5B. The 40 marker panel allowed identification of control patients from those suffering with colorectal cancer with a sensitivity of 78%. The sensitivity of determining patients suffering with advanced adenomas from control patients was 14%. The sensitivity of early localized cancer detection was 78%. A ROC curve analysis of the data based on the 40-marker panel of Table 4 as identified by the SVM model is provided in FIG. 5A.

Table 8, shown below, shows additional studies of panels having less than 40 DMRs. The list of DMRs utilized for the 3 DMR combination study is shown in Table 2. The list of DMRs utilized for the 10 DMR combination study is shown in Table 3. The list of DMRs utilized for the 40 DMR combination study is shown in Table 4. "SensitivityALL" refers to the sensitivity when detecting if a subject is suffering from either colorectal cancer or advanced adenomas. "SensitivityCRC" refers to the sensitivity of detecting a subject suffering from colorectal cancer. "SensitivityAA" refers to the sensitivity of detecting a subject suffering from advanced adenomas. To highlight one particular example, the 3 marker panel indicates an especially good separation of colorectal cancer and advanced adenomas from the control subjects with overall sensitivity of 48% and specificity of 93%. At 93% specificity, advanced adenomas were detected with a sensitivity of 14% and colorectal cancer was detected with a sensitivity of 67%.

TABLE 8

Accuracy metrics for application of 40 colorectal cancer DMR panel and subsets thereof to the verification group.

| | Number of Markers in Panel | | |
|---|---|---|---|
| Metric | 3 | 10 | 40 |
| AUC | 0.78 | 0.77 | 0.75 |
| AUC_CI_Low | 0.73 | 0.72 | 0.70 |
| AUC_CI_High | 0.83 | 0.82 | 0.81 |
| SensitivityALL | 0.48 | 0.53 | 0.53 |
| SensitivityCRC | 0.67 | 0.75 | 0.78 |
| SensitivityAA | 0.14 | 0.14 | 0.14 |
| Specificity | 0.93 | 0.90 | 0.90 |

Figure 9:
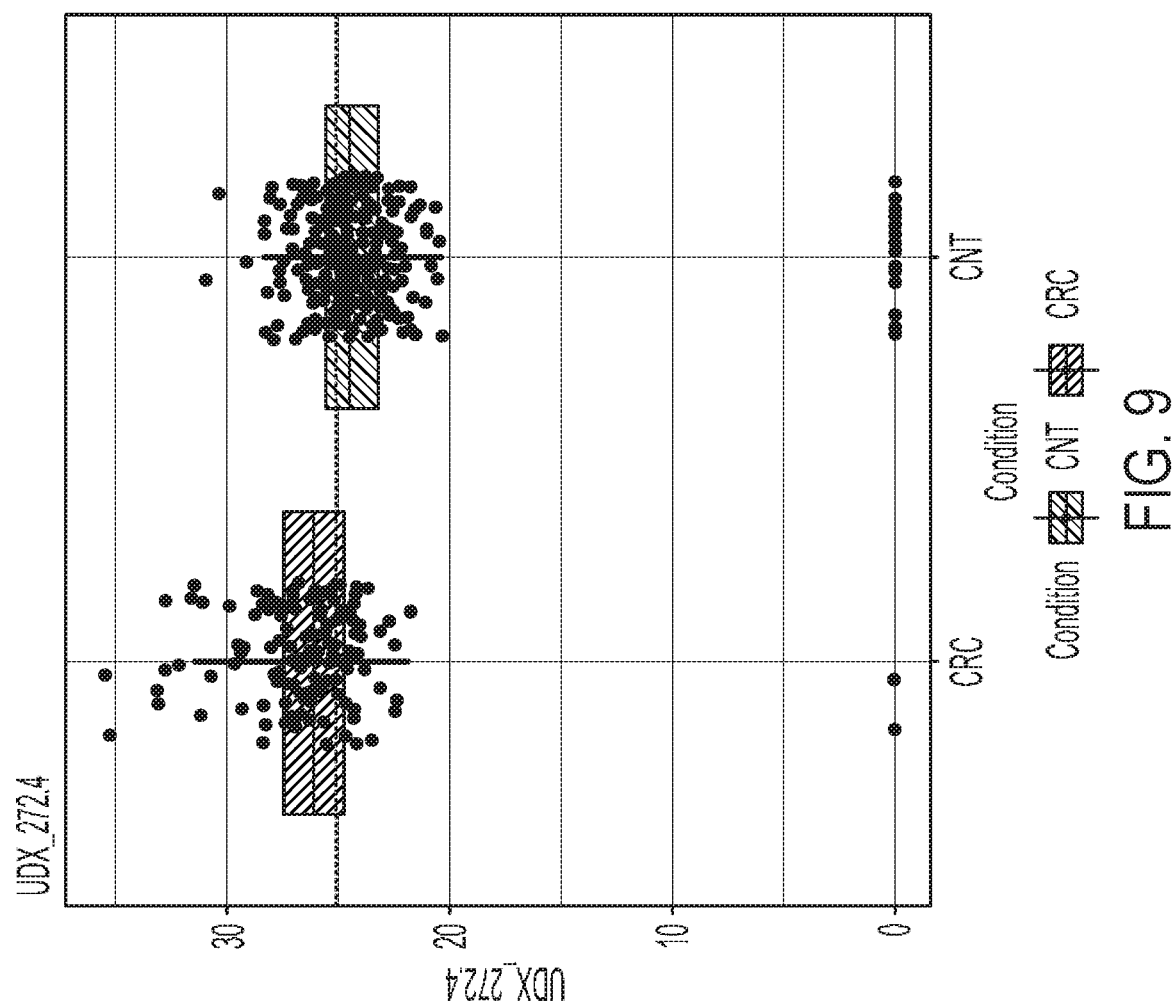
FIG. 9 shows a graph representing Ct (Cycle Threshold) values from MSRE-qPCR of the region identified as UDX_272.4 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 10:
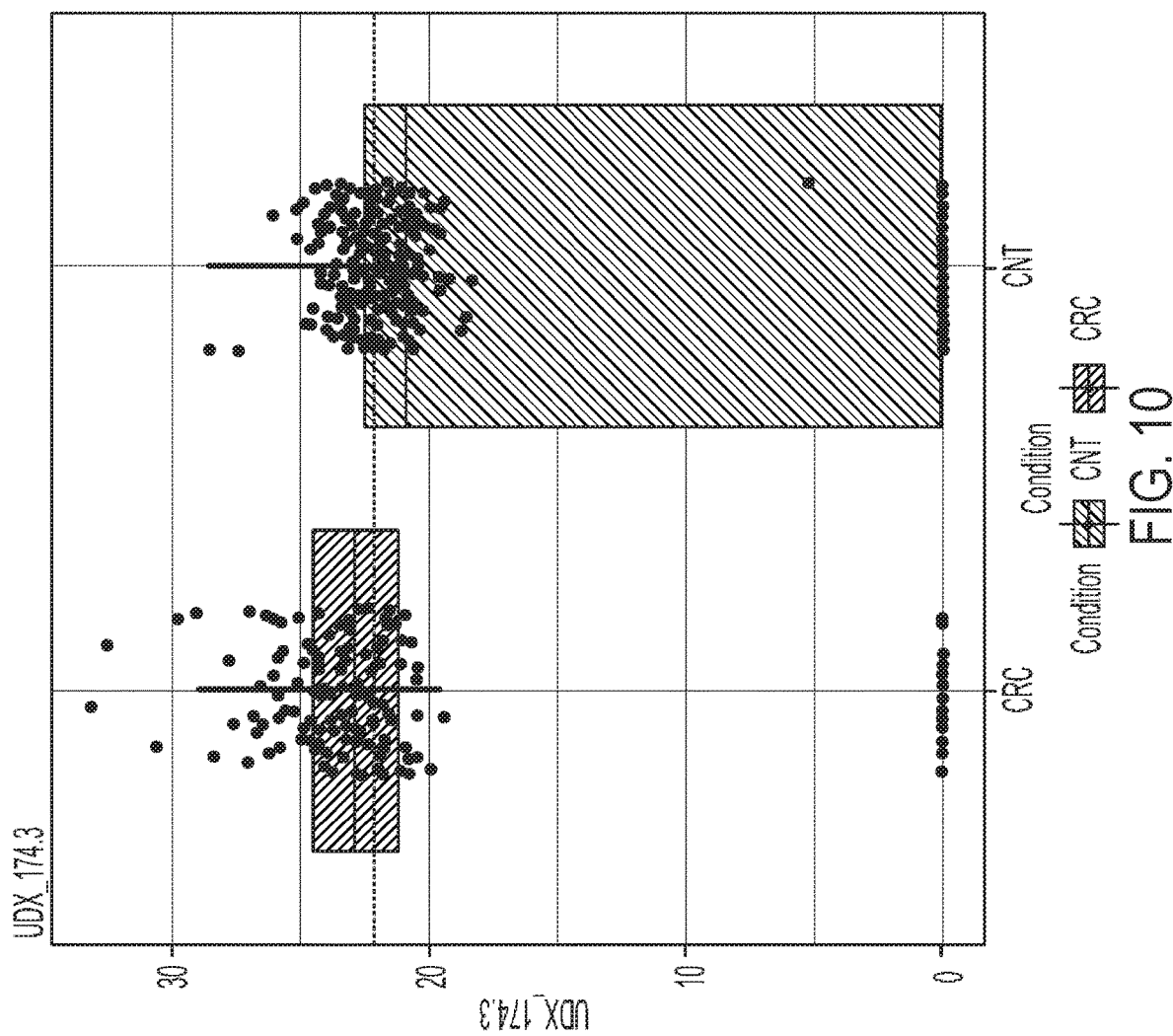
FIG. 10 shows a graph representing Ct (Cycle Threshold) values from MSRE-qPCR of the region identified as UDX_174.3 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 11:
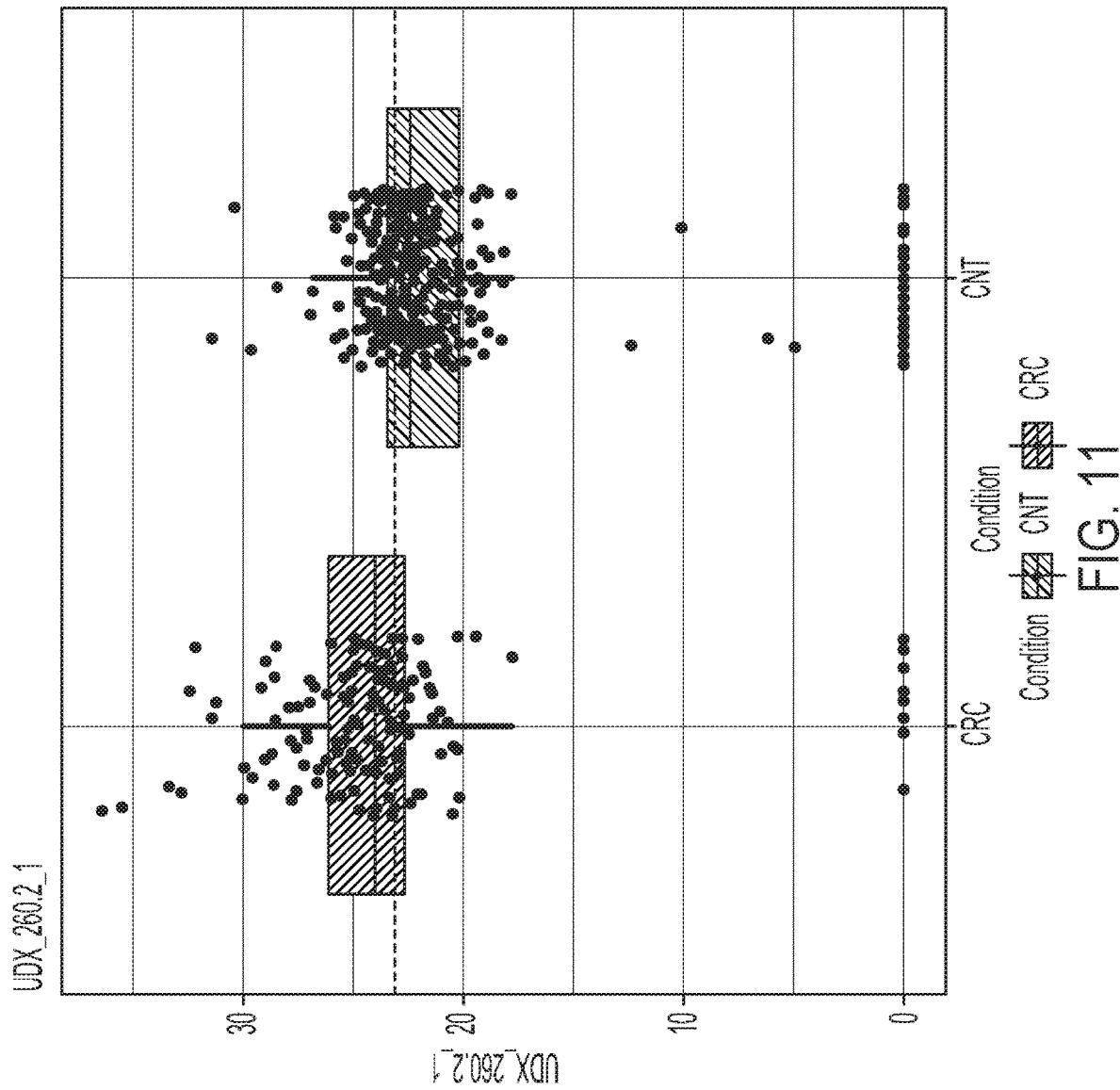
FIG. 11 shows a graph representing Ct (Cycle Threshold) values from MSRE-qPCR of the region identified as UDX_260.2_1 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 12:
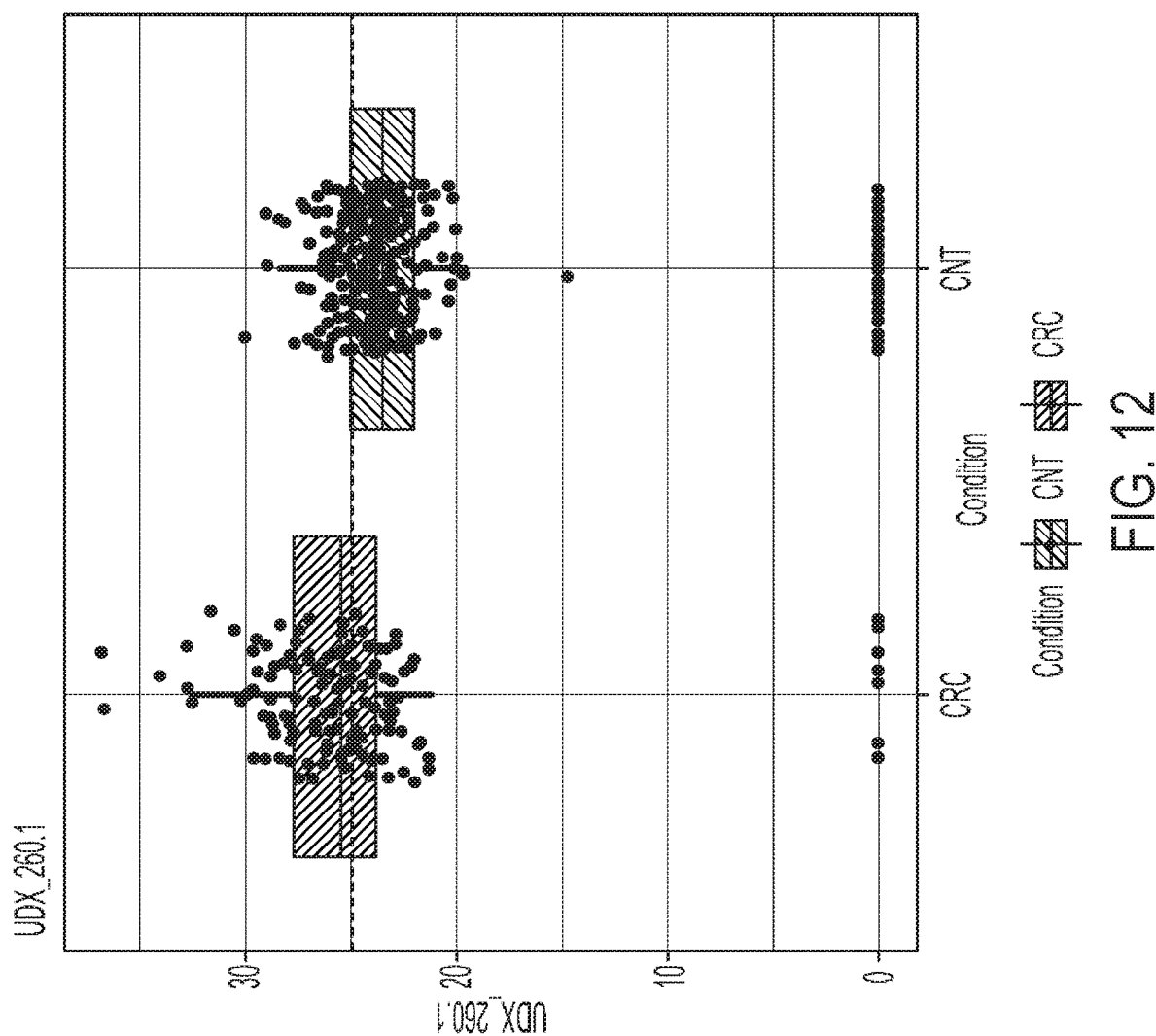
FIG. 12 shows a graph representing Ct (Cycle Threshold) values from MSRE-qPCR of the region identified as UDX_260.1 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 13:
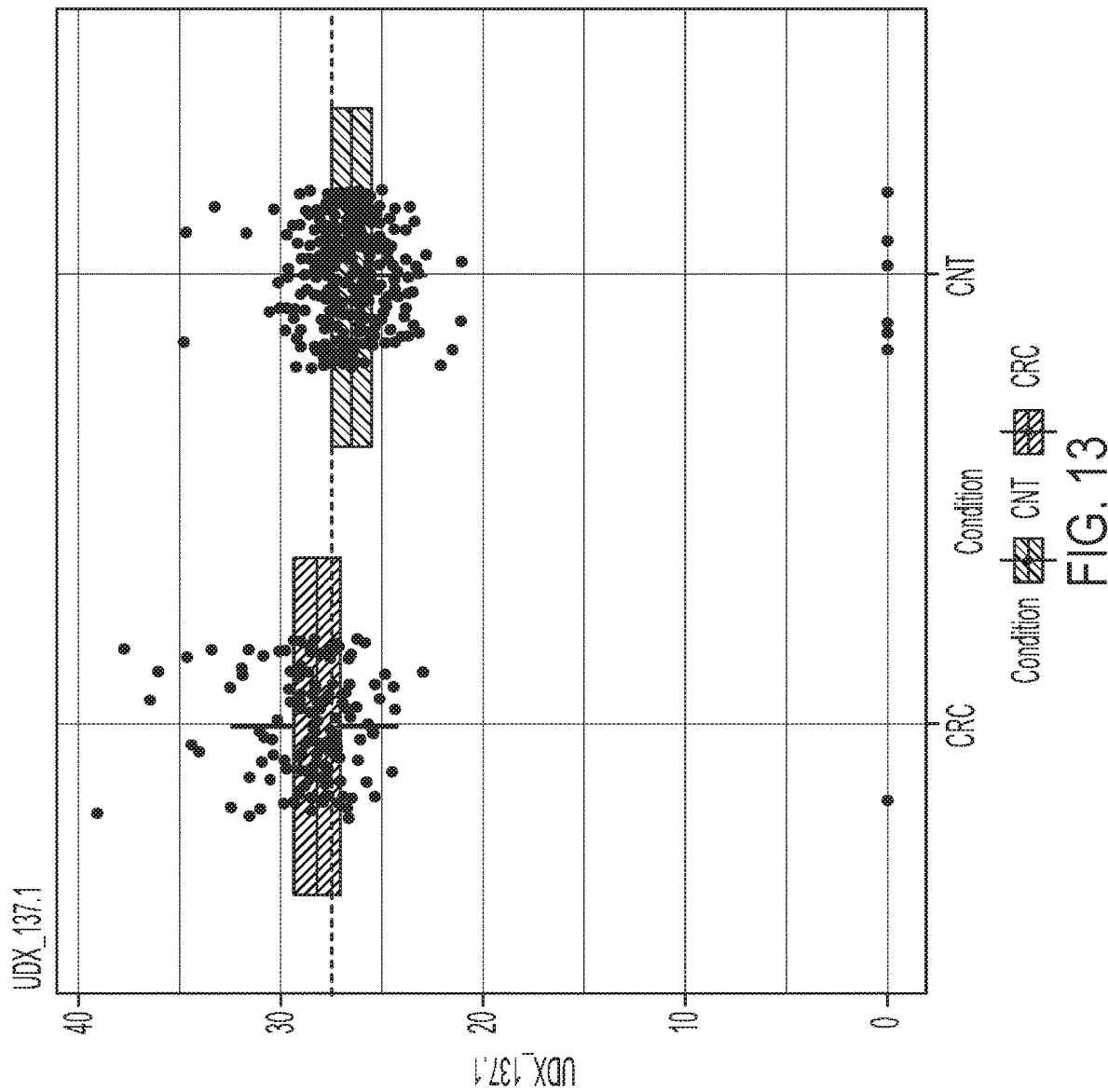
FIG. 13 shows a graph representing Ct (Cycle Threshold) values from MSRE-qPCR of the region identified as UDX_137.1 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 14:
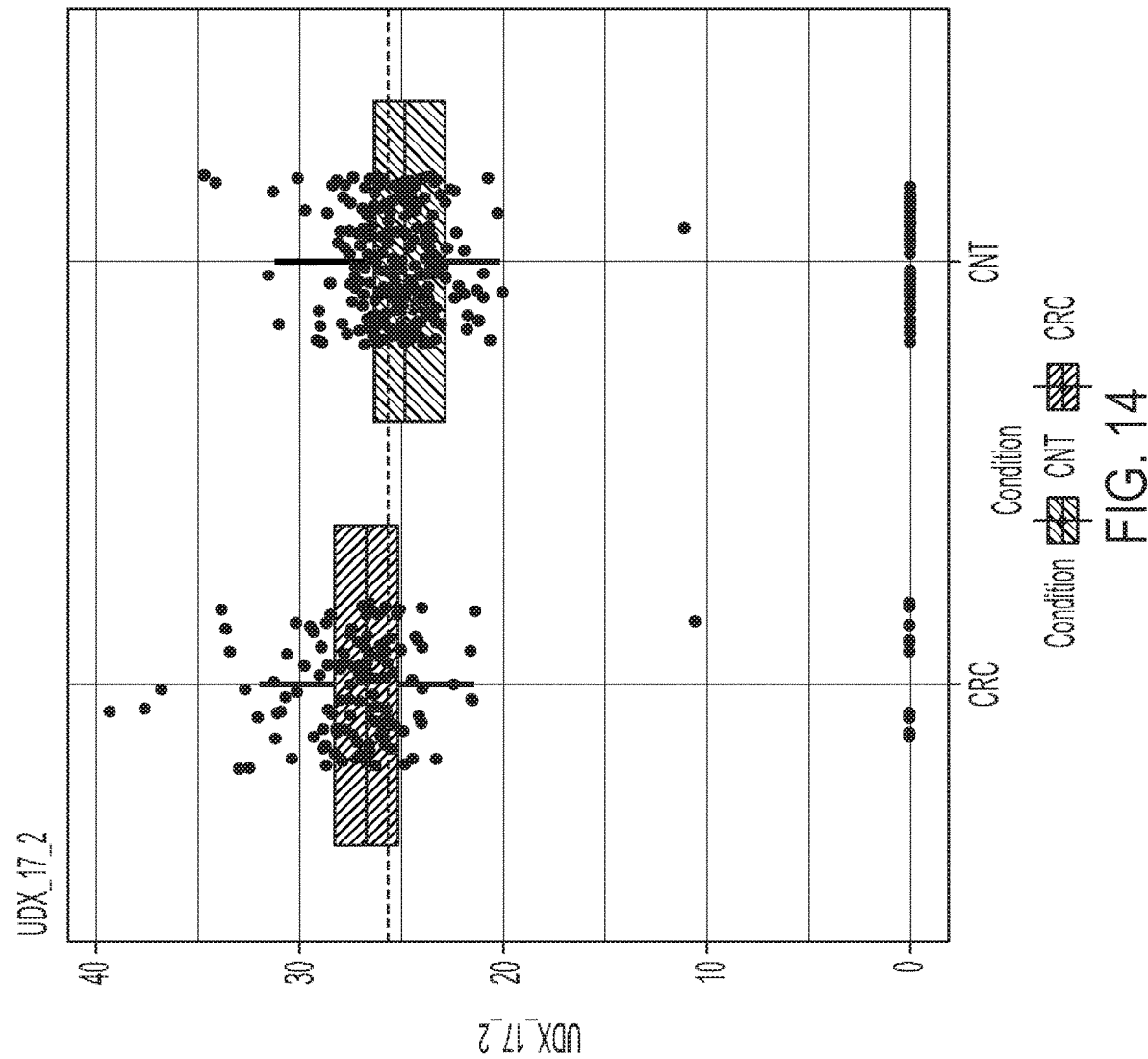
FIG. 14 shows a graph representing Ct (Cycle Threshold) values from MSRE-qPCR of the region identified as UDX_17_2 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.
Figure 15:
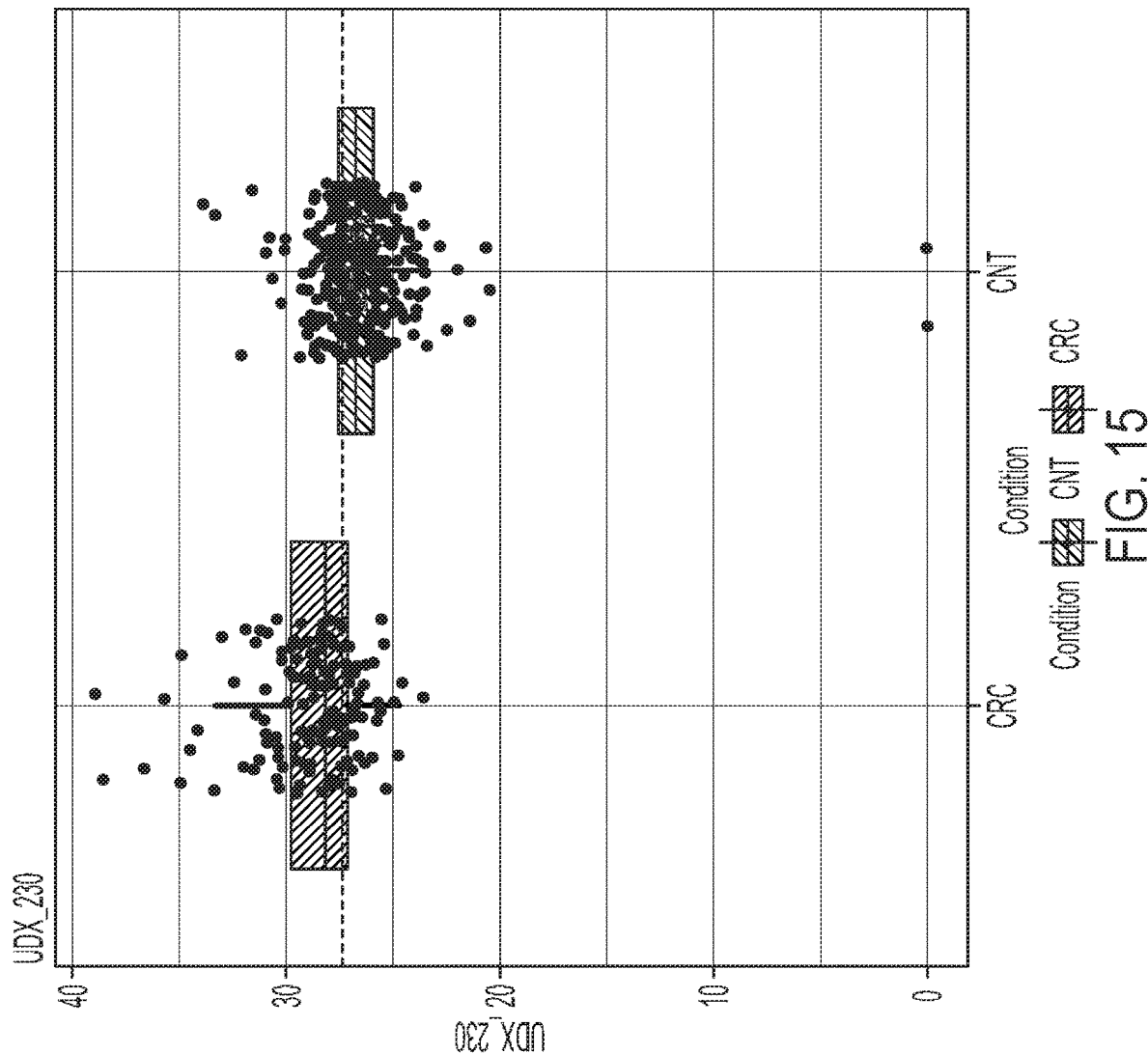
FIG. 15 shows a graph representing Ct (Cycle Threshold) values from MSRE-qPCR of the region identified as UDX_230 for subjects from the validation group with colorectal cancer (colorectal cancer and advanced adenoma) and control subjects (healthy subjects, patients with hyperplastic polyps and subjects with non-advanced adenoma). Data represent the second subject group (530 subjects) used for testing. For display purposes, Ct values are subtracted from 45 (45–Ct). Higher 45–Ct values correspond to higher methylation status, demonstrating hypermethylation in subjects with colorectal cancer.

Example 4. Various Individual Methylation Biomarkers are Each Highly Informative Evaluation of the performance of individual colorectal cancer and advanced adenoma DMRs from among the 40 colorectal cancer DMR panel reveal that various individual colorectal cancer DMRs are sufficient for screening of colorectal cancer and advanced adenomas (See FIGS. 6-15). FIGS. 6-15, respectively, show graphs representing Ct (Cycle Threshold) values from MSRE-qPCR of the DMRs identified as UDX_29_1 (FIG. 6), UDX_272.3_2 (FIG. 7), UDX_277.7_2 (FIG. 8), UDX_272.4 (FIG. 9). UDX_174.3 (FIG. 10), UDX_260.2_1 (FIG. 11), UDX_260.1 (FIG. 12), UDX_137.1 (FIG. 13), UDX_17_2 (FIG. 14), and UDX_230 (FIG. 15).

For selected colorectal cancer and advance adenoma DMRs, FIGS. 6-15 show methylation status of the indicated DMR in colorectal cancer and advanced adenoma samples (collectively denoted as "CRC") and control samples (denoted as "CNT"; healthy subjects, patients with hyperplastic polyps and subjects with non-advanced adenoma). Results are displayed as the MSRE-qPCR Ct ("cycle threshold") value subtracted from 45 (i.e., 45–Ct value) for display purposes.

The higher the 45–Ct value is, the higher the degree of methylation in the sample. Data provided in this Example, as well as data provided by the present Examples, cumulatively (including, e.g., FIGS. 4-9) demonstrate that for each individual DMR identified, the methylation status signal is sufficiently stable across subject groups to permit clinical screening for the combination of colorectal cancer and advanced adenomas. Results presented in FIGS. 4-15 therefore confirm that methylation markers of colorectal cancer and advanced adenoma provided herein can provide an overall, robust signal for screening of colorectal cancer and advanced adenomas. Moreover, those of skill in the art will appreciate that the present disclosure provides methylation biomarkers that are individually independently useful in screening for the combination of colorectal cancer and advanced adenomas, and specifically that methylation biomarkers provided herein are useful both individually or in combination with one another.

Computer System and Network Environment

Figure 17:
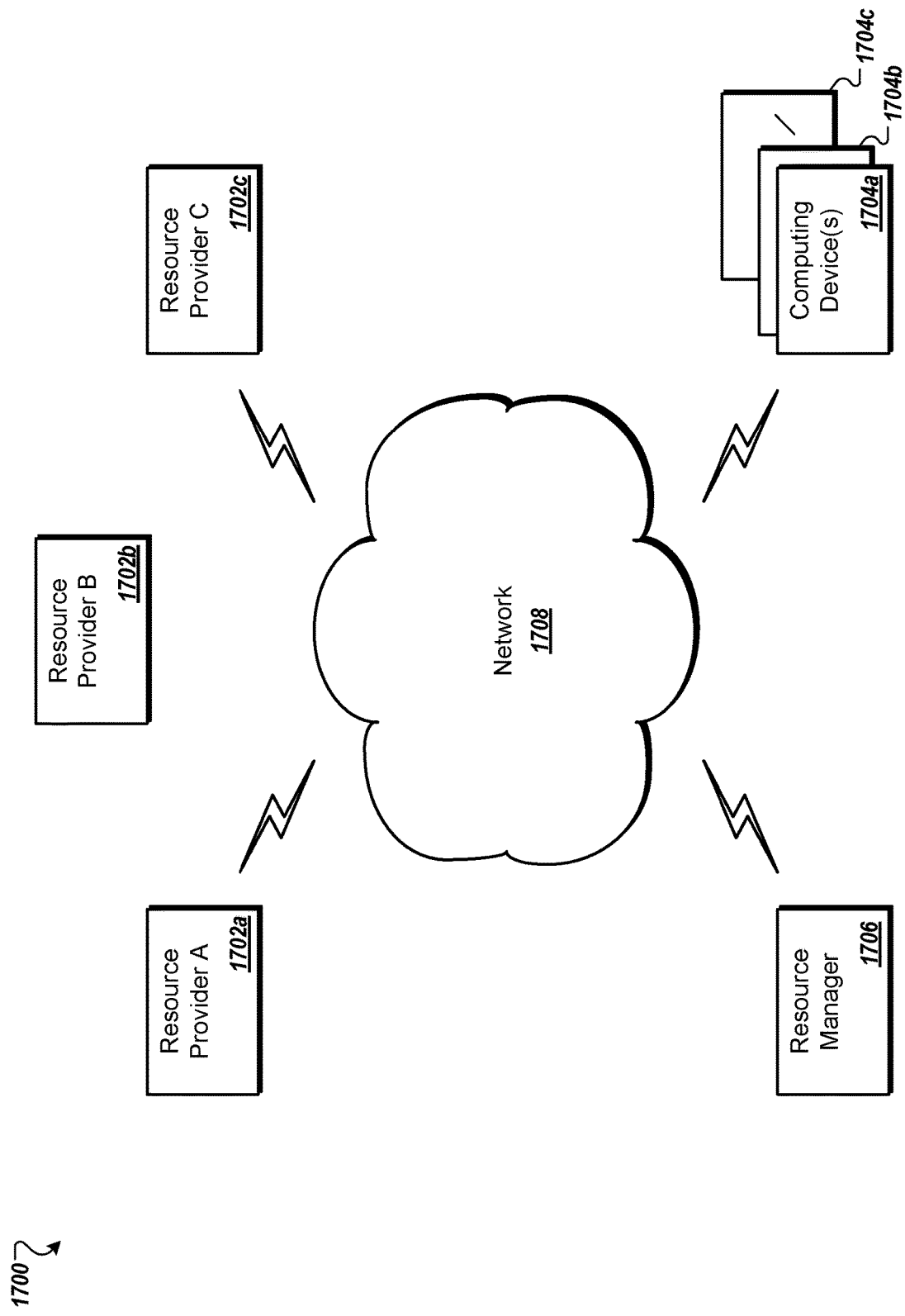
FIG. 17 is a block diagram of an exemplary cloud computing environment, used in certain embodiments e.g., as set forth herein.

As shown in FIG. 17, an implementation of a network environment 1700 for use in providing systems, methods, and architectures for retrieving, managing, and analyzing data from a plurality of sources as described herein is shown and described. In brief overview, referring now to FIG. 17, a block diagram of an exemplary cloud computing environment 1700 is shown and described. The cloud computing environment 1700 may include one or more resource providers 1702*a*, 1702*b*, 1702*c* (collectively, 1702). Each resource provider 1702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1702 may be connected to any other resource provider 1702 in the cloud computing environment 1700. In some implementations, the resource providers 1702 may be connected over a computer network 1708. Each resource provider 1702 may be connected to one or more computing device 1704*a*, 1704*b*, 1704*c* (collectively, 1704), over the computer network 1708.

The cloud computing environment 1700 may include a resource manager 1706. The resource manager 1706 may be connected to the resource providers 1702 and the computing devices 1704 over the computer network 1708. In some implementations, the resource manager 1706 may facilitate the provision of computing resources by one or more resource providers 1702 to one or more computing devices 1704. The resource manager 1706 may receive a request for a computing resource from a particular computing device 1704. The resource manager 1706 may identify one or more resource providers 1702 capable of providing the computing resource requested by the computing device 1704. The resource manager 1706 may select a resource provider 1702 to provide the computing resource. The resource manager 1706 may facilitate a connection between the resource provider 1702 and a particular computing device 1704. In some implementations, the resource manager 1706 may establish a connection between a particular resource provider 1702 and a particular computing device 1704. In some implementations, the resource manager 1706 may redirect a particular computing device 1704 to a particular resource provider 1702 with the requested computing resource.

Figure 18:
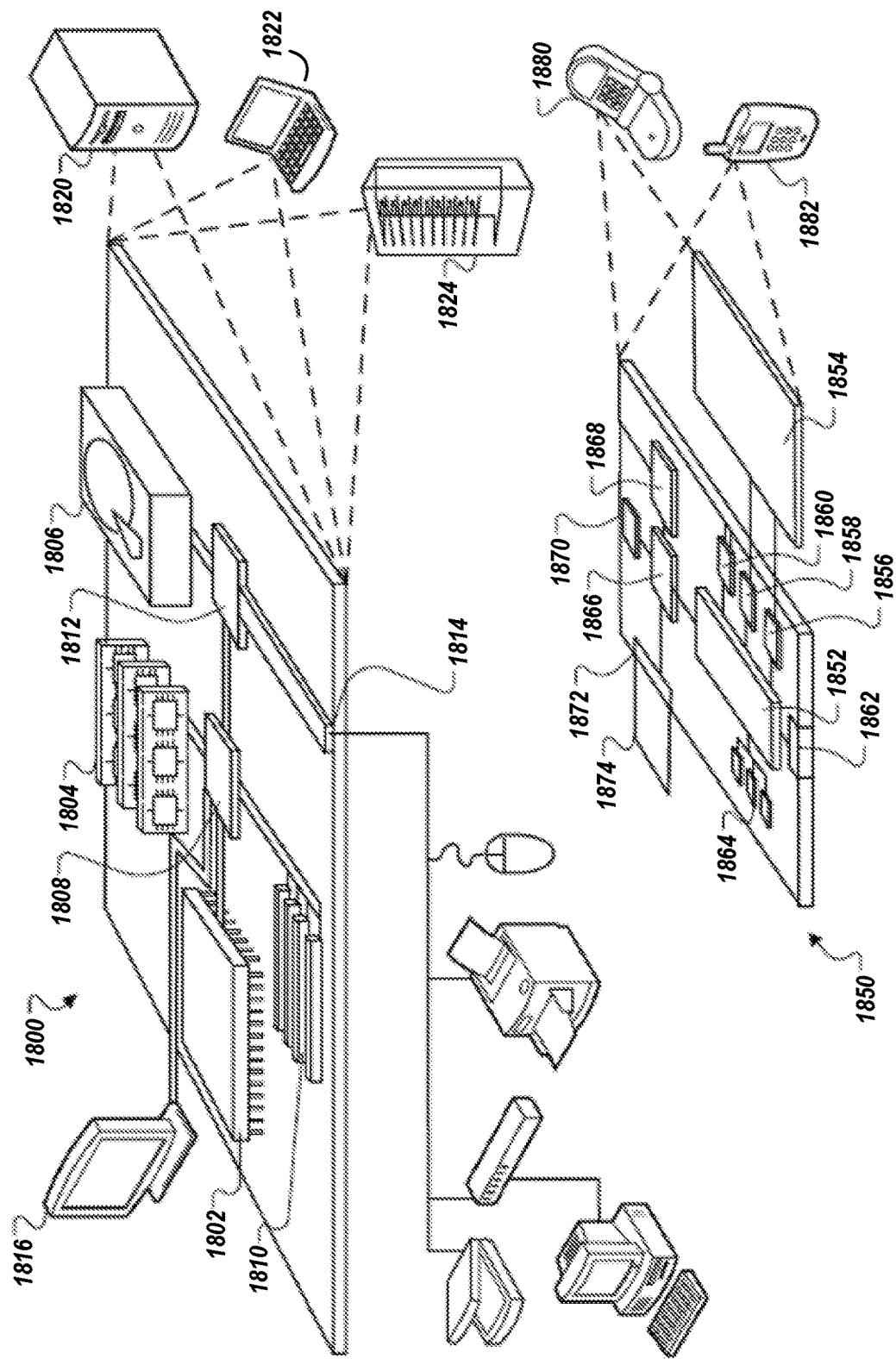
FIG. 18 is a block diagram of an example computing device and an example mobile computing device used in certain embodiments e.g., as set forth herein.

FIG. 18 shows an example of a computing device 1800 and a mobile computing device 1850 that can be used to implement the techniques described in this disclosure. The computing device 1800 is intended to represent various forms of digital computers, such as laptops, desktops, workstations, personal digital assistants, servers, blade servers, mainframes, and other appropriate computers. The mobile computing device 1850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1800 includes a processor 1802, a memory 1804, a storage device 1806, a high-speed interface 1808 connecting to the memory 1804 and multiple high-speed expansion ports 1810, and a low-speed interface 1812 connecting to a low-speed expansion port 1814 and the storage device 1806. Each of the processor 1802, the memory 1804, the storage device 1806, the high-speed interface 1808, the high-speed expansion ports 1810, and the low-speed interface 1812, are interconnected using various busses, and may be mounted on a common motherboard or in other manners as appropriate. The processor 1802 can process instructions for execution within the computing device 1800, including instructions stored in the memory 1804 or on the storage device 1806 to display graphical information for a GUI on an external input/output device, such as a display 1816 coupled to the high-speed interface 1808. In other implementations, multiple processors and/or multiple buses may be used, as appropriate, along with multiple memories and types of memory.

The memory 1804 stores information within the computing device 1800. In some implementations, the memory 1804 is a volatile memory unit or units. In some implementations, the memory 1804 is a non-volatile memory unit or units. The memory 1804 may also be another form of computer-readable medium, such as a magnetic or optical disk.

The storage device 1806 is capable of providing mass storage for the computing device 1800. In some implementations, the storage device 1806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1802), perform one or more methods, such as those described above. The instructions can also be stored by one or more storage devices such as computer- or machine-readable mediums (for example, the memory 1804, the storage device 1806, or memory on the processor 1802).

The high-speed interface 1808 manages bandwidth-intensive operations for the computing device 1800, while the low-speed interface 1812 manages lower bandwidth-intensive operations. Such allocation of functions is an example only. In some implementations, the high-speed interface 1808 is coupled to the memory 1804, the display 1816 (e.g., through a graphics processor or accelerator), and to the high-speed expansion ports 1810, which may accept various expansion cards (not shown). In the implementation, the low-speed interface 1812 is coupled to the storage device 1806 and the low-speed expansion port 1814. The low-speed expansion port 1814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1800 may be implemented in a number of different forms, as shown in the figure. For example, it may be implemented as a standard server 1820, or multiple times in a group of such servers. In addition, it may be implemented in a personal computer such as a laptop computer 1822. It may also be implemented as part of a rack server system 1824. Alternatively, components from the computing device 1800 may be combined with other components in a mobile device (not shown), such as a mobile computing device 1850. Each of such devices may contain one or more of the computing device 1800 and the mobile computing device 1850, and an entire system may be made up of multiple computing devices communicating with each other.

The mobile computing device 1850 includes a processor 1852, a memory 1864, an input/output device such as a display 1854, a communication interface 1866, and a transceiver 1868, among other components. The mobile computing device 1850 may also be provided with a storage device, such as a micro-drive or other device, to provide additional storage. Each of the processor 1852, the memory 1864, the display 1854, the communication interface 1866, and the transceiver 1868, are interconnected using various buses, and several of the components may be mounted on a common motherboard or in other manners as appropriate.

The processor 1852 can execute instructions within the mobile computing device 1850, including instructions stored in the memory 1864. The processor 1852 may be implemented as a chipset of chips that include separate and multiple analog and digital processors. The processor 1852 may provide, for example, for coordination of the other components of the mobile computing device 1850, such as control of user interfaces, applications run by the mobile computing device 1850, and wireless communication by the mobile computing device 1850.

The processor 1852 may communicate with a user through a control interface 1858 and a display interface 1856 coupled to the display 1854. The display 1854 may be, for example, a TFT (Thin-Film-Transistor Liquid Crystal Display) display or an OLED (Organic Light Emitting Diode) display, or other appropriate display technology. The display interface 1856 may comprise appropriate circuitry for driving the display 1854 to present graphical and other information to a user. The control interface 1858 may receive commands from a user and convert them for submission to the processor 1852. In addition, an external interface 1862 may provide communication with the processor 1852, so as to enable near area communication of the mobile computing device 1850 with other devices. The external interface 1862 may provide, for example, for wired communication in some implementations, or for wireless communication in other implementations, and multiple interfaces may also be used.

The memory 1864 stores information within the mobile computing device 1850. The memory 1864 can be implemented as one or more of a computer-readable medium or media, a volatile memory unit or units, or a non-volatile memory unit or units. An expansion memory 1874 may also be provided and connected to the mobile computing device 1850 through an expansion interface 1872, which may include, for example, a SIMM (Single In Line Memory Module) card interface. The expansion memory 1874 may provide extra storage space for the mobile computing device 1850, or may also store applications or other information for the mobile computing device 1850. Specifically, the expansion memory 1874 may include instructions to carry out or supplement the processes described above, and may include secure information also. Thus, for example, the expansion memory 1874 may be provide as a security module for the mobile computing device 1850, and may be programmed with instructions that permit secure use of the mobile computing device 1850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1852), perform one or more methods, such as those described above. The instructions can also be stored by one or more storage devices, such as one or more computer- or machine-readable mediums (for example, the memory 1864, the expansion memory 1874, or memory on the processor 1852). In some implementations, the instructions can be received in a propagated signal, for example, over the transceiver 1868 or the external interface 1862.

The mobile computing device 1850 may communicate wirelessly through the communication interface 1866, which may include digital signal processing circuitry where necessary. The communication interface 1866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1868 using a radio-frequency. In addition, short-range communication may occur, such as using a Bluetooth®, Wi-Fi™, or other such transceiver (not shown). In addition, a GPS (Global Positioning System) receiver module 1870 may provide additional navigation- and location-related wireless data to the mobile computing device 1850, which may be used as appropriate by applications running on the mobile computing device 1850.

The mobile computing device 1850 may also communicate audibly using an audio codec 1860, which may receive spoken information from a user and convert it to usable digital information. The audio codec 1860 may likewise generate audible sound for a user, such as through a speaker, e.g., in a handset of the mobile computing device 1850. Such sound may include sound from voice telephone calls, may include recorded sound (e.g., voice messages, music files, etc.) and may also include sound generated by applications operating on the mobile computing device 1850.

The mobile computing device 1850 may be implemented in a number of different forms, as shown in the figure. For example, it may be implemented as a cellular telephone 1880. It may also be implemented as part of a smart-phone 1882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules (e.g. data aggregation module 1830, mapping module 1850, specifications module 1870) described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

SEQUENCES

```
SEQ ID NO: 1
tcgctcctct gctccaacaa cttatacttg ctcttttgcc tttgaatttc tgaggtttag tgagttcgat tagccgcgtg ctcagaatca
agttcgggaa gaaagaggag gaggatgaag cggacaagaa ggaggacgac ggcgaaaaga aggccaaaca cagcatcgac
ggcatcctgg gcgacaaagg tagggaactt ccctgggctg cgaggcccca gcccgggttt tcccacgctc cggtgtgcgg
gccagtggtt cgctcccgcc gccggagcag gcgaccagaa ctccagc SEQ ID NO: 2
cgaggtcgtg gagcggcagc agctgcagcc ggagcagcac cagcaacagc aacagcgagc gggacggagt taggaccgct
cggagcgcac aggtctcgag gtagtataag gtttgctatc cttccacttg ctggcagttg cagaagaaga tctgcttttt
aagtgaaacg tacatgccac ccctccgagg gctgcggctt ccccgggctt gcttctttgc cgctcctctt tccggctctc gc SEQ ID NO: 3
cgacgcacgg acccggggac ctcgacactc gctaggaggc aagccctatt cctcagccgg gcgcccctcg tctcccgctc
tctccatgga ccctctcct ggcaaatcgc ccgcagagcg agcttggaga tgcgagggaa actgaagccc caagggtgcc
ccgtcctggg agcctggctg tctgcggggt cccccgcatt ccgcagtagt aatacaggag ggccggggggc ttctacccca
acctccgctc cccttcg SEQ ID NO: 4
cgtcctgcgc aggaccggca gcccgaggcg gagacgaagg gggcccgcag ggactcctgg ccttgcgtct tgggagagcg
cacgctggcc tgcgctacac acacacactt cacagttgcg ctgaaacaga gtcgggtttt ctgtacagga gataaaatga
cggtagtgtg tgtgttttt gaaagagctg ttaaaaagct aagttcttct catttcagtg agagttcccc cttggattgt ttgtgcgtgt
attcaattca gccg SEQ ID NO: 5
cgagctgatc gagcggcagc ggctggagct gcggcagcag gagctgcggg cgcgctacaa cctcagccag ggcggctacg
aggagctgga gcgcgtcgtg ctgcgcctca agccgcacaa ggccggcgtg cagtggcgct tcgccggctc cttctacttc
gccatcaccg tcatcaccac catcggtaac g SEQ ID NO: 6
acgactgttc tggacccagt ttataaagac tgcctggctg gccaggaaat cccccagagg cctccttccg tgtcccggg
ccaaatctgt gaagagaaaa cggaaggcta ccatgtcacg aaaaactatg atcaaataaa ttattatgcc ttttctccta ttgatctgcc
ttttgtcaac tgattttcag tgaaccttcg gagagccatg gggaagtttt cccttcccc ctacagggct ctgaatctga aggtaagagt
gagcctatag ggggaacctt ctggctccct cacaggaact gactgagcag gagttggaaa agccacttgg attcccattt
cctcaactcc ccgccaatac caaggcgtct gttttacag gctctttcgt ggtgttctgg gcacattcaa cttccaatgc agctgagagg
gtcgggaaca gttagagaac aggggtggca gccgcccggg aggctgcaag gcgctcgccc gcaacgcaca ggcgcgcgcg
gcgcaccgg cctccggcct ccccaggtcg ggcctggcag ctgcgggaag gaggtcagcg cagccgccac acttcgcccg
ggcgctggcc cgacccgacc gccggcgact ctctggcagc gcccggagac cgccagcccc tgggccgccc gtccgcagag
cccctccgc cccgggaccc tcgcgcgcag ctcaagttgg gagccccgct ccgcaggcga gcgcgcgccc accacccaca
```

| SEQUENCES |
|---|
| cccactgcca ctcatgcaca ccgcgggtcc ggagatgccc ccgagcgttt taaaatccag aaacatcaca tggtagccac<br>atccggcggc tgttacctgc tcgcagcacc cagaccctcg ccctggtttc ccgggagccc gcaaacccgg cacgcgggct<br>gcgcgccctc ccgcaagcca ccgctcagcg ccagcgcgcc ggcaagccgc ctaccttagg ggtctgcact tcaggtcccg<br>tcggcacctc caacttcctc ttggttaccc agaagaacag cagcaccgtg atccagagca ccccgaagac tggcagaacc<br>agccgacgag tcaggcgccg catggtcccc tttgccgctt cctctccgcg gcgctacgtc ccgggggcac ccccggcgg<br>tcagggttgg cggggcagga gtcctggcga gcgcctcgct ctggggagct ctagaccag gatccggttg gaggggcggc<br>aggatcctgc aaggcgccct tcccgcttcg aagagaagcg agcctgggtg gggggtgcag ggcgacccga aacgtggcag<br>ggaaggacc |
| SEQ ID NO: 7<br>gcgtctgaga catttctcac tctggcactc taagcaatgc aataaccaa ctcctcatgg cccaaagccc cagactctgg<br>ttttcagaca aaacaacaac aacaacaaca acaacaaaaa cccaccgtta tgacagtcct gccgctgagc taaccagaac<br>ctggctgcac tactttccat tcactgccca acccttcct gccttgcaga cttgaaagc aaaaatgaca ttttggaaaa cctggttcac<br>cttcccagcc agaagtgcag aactgcatgc ctcaacctcc aacttcggac aggcctcctg acagcgaaga tcagaggctc<br>agggcacccc ggggcccctc aggcagggaa cgtgcattcc caccctgac tcccctcgca ccgaagctgc acatgctcct<br>tcttccctgc cttcctctgc atgctccttg gacccaagct gaaccctttc ttcctctc catctacaat tacaaacgca aattctcagc<br>caaggatgaa agaagtaaat tgtaggctcg cacaatatca ataattccgc gggtcacagc atcccgcaca aggacgcctt<br>cttattgcat aattaacgcg aggaaggctc ttcccgctac tcccgcgaaac tagggaggtc ttcaagtcgc caaaacacac<br>cgggatgtgg ctcgccagga caaaaccgc gggttcccg gttttttccgt gcgcccgcg gcg |
| SEQ ID NO: 8<br>gtttgcttgt tctcactctg cagccgcagc cagtggcgcc gctaccaagg tccccgcctc gccatccggg tcctgcctga<br>gcatcctat tggtgctcag ggctaggcgt gcattgctgc taggggcgcg gaaaggttta tcgtgggtgg atgctgcccg<br>gggcttgagt ggttttttaga ggtcttgagt ggctcactct ccaatcagcg cttttctagag acagcgtggt cagcgtactt gcttactttc<br>aggattgcga gacgtctttta acccttgctg atcggctgac gctgcagctt cctgtggctt cctgctcatt tcccg |
| SEQ ID NO: 9<br>cggatcttct cggacgcctc tggcttgggg ctgcggaag cgtgggctgc ccggggcgca gtgtgcggag accctctagg<br>cgggcgggga cgcccacgc ggcgacctga gcaccgacct catgcaacgg gaccgaacct tgggacccgg gcagcaggag<br>ctctgttccc ttcacctcca gcttggtttg agggatactg atgaaggaaa ccgggggttt cccgtcctgc gcggagagcc<br>tcggcgccca aaatcgaaag gccgggagtt gttctgcagg ctttgcaaac aggttgactg agggtttcct ttcccgtagc<br>gctgactgcg aaatctgtgc ataggcgttc agtgccagtg gaggatagct gagcaagcca agaagttttg cagcttcctc<br>tgatttatcg gtggagtgtc aggaggctgt agcaacagtt tacatttccc ctgctccctgc gagtggctag agggcaagctg<br>ggctcggacg tgatatcctg ctgtttgtgg agaggaaact gggaacggg cttgagagtg aggggcaggg aggggggac<br>aggcatattt tctactgcat cgcccatctg cacctgtccc ctttgctgtc ttacatgtcc catagtatta aagttatttg aataagcaaa<br>tgaacccgc tctttggtga ccgcgtattt tgaagttgga aaactttgca ggggacgagg gaatgttgag gagggggcgt<br>taagctctct cactctatcc cttttttaaag acaagaaaa aactttcgtt ggcgaaggtg gtactttttt cttttggaat gtctgagctc<br>agagcttccc ataagaggta ttgcgattca atactgtaca gtcaaggtga agttccacta agattatgg accgtgcat<br>attctacgga agataccagg gttccttggc gctctgttca ttgccagggt ggtctgctga aagccggcag tttccacc<br>tcagactcct tggagctctt taaatgacg tctgcctggt gtttctcagc ggtacacctg tgagtgctct gttatcatgg aaatggtaac<br>ccatgcaggt agggctcatg ccaaccagac tgtggtgggg tgtgtgtgtg tttgtgtgtg tgtgtataca tgcgcgtgcg<br>tgtgaacgtg tgtgtttgga gtttcctttt gacaggtaat ctttggatgt caaagggata cagttatttg tctggcagtg tcagggcaat<br>ctgagtttct cgagtaacta ggaggagta atctccaggg aagccttttt gtgctcttga ctgtctactc agcagttggt gaaggcttcc<br>tgaaagccac ttagggtgtt actaaccaaa tcaagaagtc ttactcagtg gtgagtgaaa gctcg |
| SEQ ID NO: 10<br>gcgactgctc tgcggttccc caaagctcct cctacccaga cggcgacagt ttggatgctg aggttggaaa gcaggacagg<br>ggacactcct gagtgcagct cggagcgggg aaagccgaat tccggggct gaagaggccg cgcaggggac gagcgcctgc<br>gatgcggagc gtggacttct tgggccgtac ccctgcg |
| SEQ ID NO: 11<br>ccgatatata aactccacac atggtatctt tttagaaatg atttgcatac atttaagttg gtgtggacac accttcaaag agaggcagag<br>gtgtatgaat tcctaatgag aatgagagta tagtcaccaa tcagaaccct tcctcacatt ctccaaatcg cttgtatttc accatttctc<br>tccacgcagc agaatttttg acatgggaca tttcttgctc tcattcttc tttccttcca atttactgta aggcattaag tgaaacttct<br>tcagctatgt tgtgtggcac aaaaacatcg cagcgcagga atgcatgaa tagaagggtc ctttcccttc cagaactctg<br>taagcgtcaa acgccgaccc ttggctccat ctcccgctcc cctgacctct tgtcactgtg ccatttccct cctgtgcttt ctgcccactt<br>ggaaaatatc gtatatcctt tacaagaccg ctactttctc tcctcgtc acatttctcc attaccatcc acattttctc aaaacattcc<br>gacgggtttt gaagtgggt ttcaacctc cctcgactgt gatagccgaa gtccttcaa gaaagaaaaa tgatgttgga<br>aatactagta acaaataaag tatcacgaa atcccaccc aagcgatacg gtttccttga cgcgccctta accaaggcgt<br>taagtttagc ctgacagcat ccctccctcc tttcggttcc tggcctgatg agccgcctcc acctgcgagc ggtgcaggca ttttttgttgt<br>cgactaaccc cctctagcgc cgaactggcg gcatccgagc cgcggctgcc aggccgggag aaggctgggc ttggccgggc<br>tctgcagcgc tccgggctcc gccctgccc ctccgcgcc ctccgcgg ggcgaggt ggtggagacc cgggagccg<br>agggtcctcc cagtcagcac gccgcgttgc cccggccctg gggcggggc cgcggagtgc caccaagtgg cccgcgcctc<br>ggcttccggg agacccgagc gcggggaggg agtgggtgcc gcgaggggc ggctcgcgcg gggagagccg tcagcccacg<br>gcgcccctgc gctgctgtgg atgtggccac gccactcg gcccttggac tgctaggaga gcgcggcccg acgccaccac<br>gccgtggacg ctcggggacc cctgaatccc agcgtcaagg ctgcgacgat gtcgtgacc tccaccgcca agtcacctcc<br>gcaaggcgac gcaaggacct gggcgatccc ggcgccgta caccgccac tttccagcct catgtaaccc ccctctgct<br>gcttcctccc ggcgctttgc ttttctacaa ctgaagccg cgaaggcggc tactgcgctg agccgctcgc tctgctggtc<br>aagtttgggc gacccgcgcg gagagggtc ggctgactgg ccgccgctga gctgtccccg gacgggagcg cctgtccacg<br>gcactcaccc cctccagcgg tggaaatgtg gagaagtaag tgggaggcgg tgtcgggaac tgactcctct taaaacggtc<br>ggcgcgctg ctctgaaatg gcggctaag tgcttgtggg actaagggcg gcctcagaga tgcccggaaa atcgctgcca<br>cggccagagt gcggcgcaga ttggaggtgt ccgcggtgca ggctgctgcc cacgccgctc aggcaggtg<br>ctgagggctc agcccgcgcc tcggccgaac cactctcagc cccgttgagc cacctcgtcc gcccggcttt catcgcaccg<br>gccagaggaa agttcccgcg gcccccac |
| SEQ ID NO: 12<br>gcgcagccga gtacccgccg aaggctgtcc ccatcagtgc gtgtctgctg ccgggcagcg gcagcatcca acctgcttta |

|   |
|---|
| SEQUENCES |
| ttcctcctgc ctgcagcgcc acagcgagcg agcgagcgag gagggggaga gagggagtct gtctgcaaag tgctgctccc<br>tggtgctcag aggcggctgc tccagctcca actctcattc atttcgccgg ttaacatgag agatcatggc cgccttcggg<br>cttctcagct atgagcagag accgctgaag cgccccgggc tcgggccgcc cgacgtcac ccacaggacc ccaagcagaa<br>ggaggtaagg gcgccggcgg cctcccggc aaccggggcc gcgctctgca gcactgaccc ggggccaagt tggcccagcg<br>ggcatcgccg gcgctgcggt ggaagaggtc ggggagggg attagaggcg ggggccaggc tgggggtgct gggcgacccc<br>ccggcggcgg agaccgagcg gctgtcagtc cccgcgctcc actggggcgc tcgctttcca tgtgccggtc gctttcccgt<br>tgccgggcct tgcacggcgc cgccgggcgc ttctcgggct tcttccctgc cgaaaccttg ctcgctctca cccgtttctg<br>cctgctttat ttttcttctt gccgcttcgg taaatcgtcg |
| SEQ ID NO: 13<br>cggccggtct tttgccccgg gctcaatggc tggattgtgg aaactgcacc cgccttcagg ttgttgagca actgatggga<br>cgatctcagg gaccggcgtt tacgaaaggt aatttattct tcgcactctt cataataggg gtcgccctgg ccgggcgcag<br>gcggcggcat ccaccgggcg ggcaacaaga ggggtgcgg ggtgcatgca cactcgcct tccactcaca cactcgccct<br>cacacacaca cacactcatc cggtcgtggt gcggggcggg aagggaacct cctggctggt gggcgctcgg gtctggcgcg<br>ggttggagtt ttttccagcc attgggcgat ttgaccggcc gaggggagtg aggggataa gagactgggc gcattcgcag<br>ctgcacacgc tggggaatag gaacagttcc caccccgtta attttccctc tcctcctcacc ccagtggcat ccctggctgg<br>gggcagaaag cggacaggag ggcgacttt ctccgtcagg ctggaactgg tgccgctgga ggcgggagcg ggctggagga<br>cggacaggggt ctgggtgaga agctgggctc tgggaagatg gaaaatgcag ggtgccgagc ccggcgcgat tctccctcaa<br>cgcttgcctg gagcatccct ggcccctttt gccaggtcg cgccctgag tcttggagtc gcgctgcctc cccgcgccct<br>gcctgttgtg tctccttcac ggcagtttgg tttagacctg cg |
| SEQ ID NO: 14<br>cgagcgtcct gctccttcgc ccggcttcgc cttctctcat aagggtggcc gggggcccac gaacttgcag ggtggcggcc<br>ctgcgccctc cagccccggc gggacgggc acgattgctc gtagtctggg gtgctgcggt gcggggtgct gccaggggtg<br>tcccggccgc cgccactgag cgctgggcg cgcgaatcca gctgcagccg ctgctgccct gcgccggttc cctcaggctg<br>cgggcgctgc gctcctgatc tcgccggtgg ctgcgcctgg gcacgcactt gccgcgggcg gggcgggctt ggggacagtg<br>ggagcgagca ggcagagcgg agtaagcggt ccgtgtgtgt gtgtctgtat gtttgtgtgt gtgtgtgtgt gtgtgtataa<br>tgtgtgcgtg caaggaggag cttagtgtga tgtcaaagcc cctgggattc tcttgccatg ttccctttggt ctctctttat gggcagcagc<br>gaccctgtc gggtctcaaa ttcaacctca atcggcgact taatctaggt ggaggtaaag aggaagcgac ccctcgacct<br>ttgagtacgg gaataacttc ctgagcgtta catttagcaa atgtatgtgc ctctcgtaaa cgaccctccc gttgctgga agtactgccg |
| SEQ ID NO: 15<br>cgccgccgcg tttccctaaa cccctctcct cagaaaacgg agcccactcc ccacccacat ccggcggccg cggccccgc<br>ctcggagcag cgcgcgcgtg tgcccgggga tgtgggtgcg cggaacttac gtctcggaat ttgttccact gtccgacttc<br>cttgtcatac tgagagattg tggtgagcca ttgtttatca tccagaaaat taccgccgtc cgaccgcccc ccggctgcag<br>ccaccgccgc ggcagctgcg agagactgac tgcaccaagc ggctgcacac acacacagta cggctgacac cttgagcatc<br>tgggagagga gacacaacgg ggggtggggg ggcatgtcag tgtcaaataa gggggtacgaa gccaggagcg accctggaaa<br>acatgcatta gcaacgacga gggtagaggg aggaggagac aagcagaggc aagcgtgtcc cctccccgca ggctttaccc<br>ccaaaagccg ggcactcaca cacacgcaga cccagaggag gagaggtggg tataaggaag caagcccag ccgcagcagc<br>ccgagcgggc acaaaaccgc ttcctggcac atcaccttgt tgtgagccag cactgtgctc gcagctcctg ctgaaatgc<br>agccctgctc tgccaactcg tgctttctg gagctgctgc acgcgccgcc gtctcgagcc gtccactcag ctccctgcgc<br>ccggcgcgct cccccatct ccaccctccc ttcgcgcgcg gatctccagc ttactcccct ccgttccccc tcctccccg<br>acctccgttt ttttcctctt ccacctcctc ctatcccacc ttcctctcgc tggatccag ctacagttgg ctccggatag gacgcttggc<br>tggagccaga ggacgaggta gctcctagcc taggaatcct tatctgcttt gtaacctctc ccctccagaa gaggttctca<br>tgttccggag acagcctgct cattctctgc tcctggattt aacacaaagt tgtactactc tcgcagttgc ctctgctcca caatttccag<br>ggttgtcagg cagacgtgag aaacaagatc tgaggaaaac tttatgcatt aataaataag aatacctgga cttcctaccc<br>tgtaaagctc ctgaactcag ctcctcccta aagaaaggcc atctatccac aaggtcttgg gagatctgtt taatttcaga aaatttaaag<br>tttgctgtga gcttctggat tactaccg |
| SEQ ID NO: 16<br>gcgggctggg gttggaagag taactcgggc tgcgggctga acgcagtcgg caaccgcgga agagcagcat ctcccctgcg<br>cctgtggata cgccagtcca gggatggcga gtgctttctc ctccccagct tctccctcgc tcttcgaggt gactcgtggg<br>accctgcgtc ctagtgctgg gtgtgaatca gctatttcac acccagttct tcctccccctc cgccacacgc agtcacattc ctggagctat<br>tccaagctgc ctccgctaag caccgaataa gcggacccctg cctggaaact tgagcgaagc tgaactgcgc cgaactccac<br>cgtccagtga cccgagccag tgtggacgcc ctttaatca cgctgtttac ccaggtggaa tttaggaaga atcagccttc<br>agcctcaacc tcaaaccttt tgtgcaaatg ggcacttcgt ttggaaaggg actagaaatt gtcccagtc tggccctgca<br>ccagcacctt cctctgctca aacctgtaca aagtggaagt tttaggaagt ttccattct cgtgccccgt ttcaacttgc tccccaaaga<br>gaacatgaaa acgtgggaac tcgggaggac agagatctcc ctgtaatcgc ctcgctattc |
| SEQ ID NO: 17<br>cgggcctcaa atgggaactt tggccagaaa atgtggtggg aggtgccctg cacccgcttt gggctcgcgt ggggaagggg<br>cactcagggt gtgtccgtcc tacgggcttt ctcgttcctc cagcagaact tctagcggag tttgccaact acttccacta tggctaccac<br>gagtgcatga agaacctggt gcattacctc accacgctgg agcggatgga gaccaaggac acgaagtacg cgcgcatcct<br>cgccttcttg cagtccaagg cggcctgggg cgcggagccc gcctttccgc cgctgggttc gctcccggag ccggatttct<br>cctatcagct gcaccctgcg ggcccgaat tcgctggtca cagcccgggc gaggccgctg tgttcccgca gggctctggt<br>gccggggcctt tcccctggcc gcctggcgcg cccgcagcc ccgcgctgcc ctacctgccc agcgcgccag tgccgctcgc<br>tagcccagcc cagcagcaca gcccttcct gacaccggtg cagggcctgg accggcatta cctcaacctg atcggccacg cg |
| SEQ ID NO: 18<br>gcgagggtc cggcatcact cgcgcgctcc ggaaacccgc gtgagccgct gttcctgccg cgctcccatc tgagtgacag<br>gcttgtttca gagctccgca gacctctaag cctggccctc accctgcgtg gagagaacgc ccgggcttgg cggagagacg<br>agaaaaccga ggctcccgga ggcagacaag gactctgcca aaaccggacg ccggcggcgg gcagaattc gacctggga<br>tttgccgc |
| SEQ ID NO: 19<br>ccgtgacgac ttataaaagc ccaggggcaa gcggtccgga taacggctag cctgaggagc tgctgcgaca gtccactacc<br>tttttcgaga gtgactcccg ttgtcccaag gcttcccaga gcgaacctgt gcggctgcag gcaccggcgc gtcgagtttc |

```
cggcgtccgg aaggaccgag ctcttctcgc ggatccagtg ttccgtttcc agccccaat  ctcagagcgg agccgacaga
gagcagggaa ccggcatggc caaagccgcg gcgatcggca tc SEQ ID NO: 20
gcgccgctgc tgggacgcgg cgcggacccg catcattgcg cgcagcagcc gctgcagcag ccgccgggga ccgcggagcc
gggacgcccc cgctcggccc gcgccccgct ccccgcccca ccccgcccg ccgggcccag caacgcaggg tgcctaggag
ccgcgggctg cgcagggagg cgggcagcgg ccctcgcgcg cttctgccgc cccggagcc ggcgcgcggc gagcgcaggg
cgagcgcgcg tcgggcgcgg gccgcgctgg gggcgtgag gcgagcggcg cggagacgg caggggcgaa acttcgcggg
ccagatgccc gagggcgcgg cggcgctgcc aggcgccgc tgctgccct gcgggccccg agcgcgcctc cgcaggcggc
actcccgcg gcgcggcgtg tgcaccgagc gagtgaaggt atgtgtggcg ggcgcggctg gagctgccgc cgccgccgcc
gccgcgccag caggtcctaa tgcctgtcac ttcccaggac gctggcagca gcagcagccc ggagcccccg agccctcggc
aggtttgcgt gtccttcccc gcgatctgat tggataaagt ggggggctcga cggtgggcca cgtgggacag tctggctgtg
gcaggggtct cggaaaccat gggttattgc agtggcaggt gcacgcttat ctttatctgt ggcatgcaac tggtaagtga
cacttgggtc cccttattct gtaatgtgtc tttgagatag tgggcagggg agtgcagcaa agggtctgcc attgactaga
atggacgaaa aagataaaag agaaggtgac agatatattg cctatattga agatgatttc agggagacgc actctggggt
acaggagagg tgagccttc cgttcccacc tatttctgtc ccttttaaga cagtttggca ggtgcgggtt aaacttgtct ttaatttctt
taggaaaagc aagatgtagc tcttgttctt tatgctttgc attcctattc atgtaacaac g SEQ ID NO: 21
gcgacccaaa ccggggatgc agggagctcg cttggcccct ttgaaggccg actccgcaat aagcagtttt tcctttaaat
aaccgtagtg gatttgagag aattttccat ggctgaaaag agaaacagga gctgtaggca acatccctaa atttataata
atgcatgtaa acatgctaca taccacatat atgtatatgt gcataaatat ggatgtggtt gggcacatac ctatctagac accattgact
tgcctggtca aagaataaga cttagacatt tcgtgcctgg gaaatggtgc agtttatctt taaggagact agaaaaataa
gagatgaggc tcacgttgca cggatgacat cactagcttt tggctgcgcg ctcggttgtc tcgtctgtgg gttttagcca
aggctgcagc tacccgcgcc ggacgagaga gcgcggcagc agcttcctcc ggcgcccgca cccgggcaat gcgatttccc
cagtcccctg ggcgcagcct gggctctcgc gcctcccggg caccagccga gcctgcgagg cctcggagcc gccgcggcta
gaggaggagg cgacgagggg aagccgagtg acccagcctc cctcccccac cctctcccca ttcatctcgg cgaccaccgc
gcgccggag ccggatcgtg ggacgccgag gccaggacgg gattctctgc acgctgtcga gtgagccggc atctcggcgc
ccgggtgggc tgcgaagaaa atggtgcaat ctgagagcga ctgagcccag ctgggcagag cagac SEQ ID NO: 22
ccggtgctcc cagacccct tccttctcaa acacgcatca gacactttgc accaagaaaa aacaaagggc atccctcctg
gggccaccctc tgccccctgt ccaggtacgc gctgtctggc gcgccctgcg tgggggccgc aggttcagac acccgggcgc SEQ ID NO: 23
acgcttctca tttatttat atttatacaa acagcgcttc cctgaaaaat cagggtatcg ttcaagattt tatctttatt cacagaagtt
ttaaaattt taacttttat atgcacaaga cagttctgat tgttgaatt aagtgaccgc gggtgtgcta atgcttctaa aaaacagcat
tagccttctc ccatcaaaag tccggaagct gcccttcagt cgtcaaagtg tttgccttaa tttgcaatcg ttatgacttg agccaaatgc
ttatacctca tttgtgtcgt atatgtgaaa atacaattgc aaatcgttca cgaccttgag tcaagacctt gagtttcctg aggtcaggag
accgttaggg aatgtgagtg tcccagacgg gcgctgagcc cagctcggag acccaccccg cccgtagcag ggcgcggg
cccagagagc cccgcactcg gccgcgcctc agttacgctg actcggctgt gcccgcagtg tcgcgctgtc gcgtagccag
gtgtcgccgg gctggcgcgg ttatttatga ctgc SEQ ID NO: 24
acacgacttc tctgcctgtg gatgtctcat gaccctctag agcagcgact ttttcctccc tcattccttc cactcccctc gggcatctaa
gtagcaggaa cctgactgtc caaagttgat ttgggagcag ccggctgccc ttctaaaatg atctaggaaa ggtgccagta
acataagccg ccgcctgctg aaactggcgc ttcctcagcc actcgctgcg gccagcgtga aaggggaggg gaaagggggca
ttcctggcac ggtcaggtgt ctacggacag caatcttagt taattctcaa aaccccggaa gatccagaaa tggggtgctg
acagggacct aacctgtcca ccaccctcg gtcggtggga ctgaaaccca tgtctttgag ctgctttacc agttttatttc
caaaagtcc tcctacacct gggaagggac ataaaaagct gatcccattg ccagccggat ttctttactt aactctcaac
cgtggtaaat ctaattcgct tacgacctct ttccgagagc tgggaatctg cagagatgct ctgttttctg ctgtactaat ctcaggcttc
ccaaagcgag tgcctcgccc agctcctagg ggaatccacg gagccccagg cgcagggcaa aggatgggc gggatgggga
catcgtacct gcgctccggg agccgctggg agtccggccg gccccggccg cggggaggaa aagcaacggc ttgggctcct
tatccgtgac gcgcgctccc ctgcgccccc gggcctccc gtgggctccg tgccaggaca aagccagcgc cagcaggaag
agtgcgggca aaggggcgcc gggcttaagg gccgcatgt tcgcaagccg ggaggagaga gcgggagact ccgggaggat
cccgacgcag gtccggaggg tgcgcggccc aagagaaggc cagcgggacc acagcgcggg tacgcggccg gccgcagtct
tcaccgcgcg cctgcccttg tctacgtccc ggggtcggc tggagctgca ctggactcg gtcctcagtg tgccgaagcc
taagcgctgc ggggcgcggg gcgggaacgg gaggcggtgc ctggggccac ggggtcgtcc cccaggatga gggcgtgtcc
cagccgcgcg gaccctcgga agtccgccct gggccgggcg ggcaccagcc tcggactcag cgggtctcag ggctccctgc
gcaacgcctg cctcggatcc gaccccggg ctcgctctct ggtcgccgtc cccggagga cccagtaggg taactgccgc
gtcgccccgg cggttctccc tgggctctgt ctcccgccgc ctccacccc cgagcctcgg ggtccgtcac ggcttcccct
ggctggcggg gtcagtagaa cccgcggcgc ctaggtccgg acggaaaaa gcagggccgg ggtgcggcct ggatgagcgg
agatctccgc gccttgggct caaaggtgcg gggtgcgctc tgctgccgag cccctgctcg ctcaggaaca ctggccacgc
cgtcacgcca gccgccctg cccaggtct ggaggcccga cctgctctcc taggcgcagc accgcgttct cttccgcgtg
ggggagcggc gggcggaaga ggtctgggc tgggcaccgg ggacacgcgc ccagctcccc tggcctcccct gggggggagtg
gccggtttca gtgcttcccc aggtgaaatc gc SEQ ID NO: 25
gcggcggcag cagcagcagc agcagcagca gcagcaagaa atccaaagag caaaaggcgc tgcggcttaa catcaatgcc
cgagagcgcc ggcggatgca cagcctgaac gacgcgctgg acgagctgcg cgcggttgatc ccctacgcgc acagccctc
ggtgcgaaag ctctccaaga tcgccacgct gctgctcgcc aagaactaca tcctcatgca ggcgcaggcc ctggaggaga
tgcggcgcct agtcgcctac ctcaaccagg gccaggccat ctcggctgcc tccctgccca gctcggcggc tgcagcggca
gcagctgctg ccctgcaccc ggcgctcggc gcctacgagc aggcagcgg ctacccgttc agcgccggac tgcccccggc
tgcctcctgc ccggagaagt gcgccctgtt taacagcgtc cctcagcc tctgcaaaca gtgcacggag aagccttaaa
cacacccccg aaaaacacaa gaccgaccca aaatctagag gaaagcg
```

```
SEQ ID NO: 26
cgccgctagc ccccgtcata tcttctccgc tttcgcttct ccactctagc cggggtggg gtgggtgggg ttggggtctc
cgcgggggtt tccggccccg cggcccgctc ccgggtgtgc ctggaggagt tctccctctg tggcgcgcgg gagccctgtg
atgcgtcagc cggcgggacg gatgagttgc ttctccggga aaccgtcctc g SEQ ID NO: 27
cggccggctg ctgcttacgc gggtaacctg tcggaaagcc ttgtttgttt ttctggaaaa gtcgctgcaa tggacacagc
gttgcgcggt ttccctgcgc gcctggggcg cttttttgtct tcgccctccg tggatggagg ctgagcgcct cagccatttt
gagagctctg gaaattttat tagcatttta aaatttgcat tctcgaccga agattaaagt gcaaattact ttgaagatgt tttaaagcac
gcttaagaat tttaaagaat atgcgcaggt ggaaaaaagc gcgccaggt ttgagatttg gtccg SEQ ID NO: 28
cgatggccca gctcctcagc caggtccacg ggcagacggc cccaggcatc gcgcacgtcc agccgcgccc cggcccggtg
cagcaccacc agcgtgtcca ggaagccctc ccgggcagcg tcgtgcacgg gtcgggtgag ag SEQ ID NO: 29
cgcgccggcg ggggcagcgc cggccgccga ttagttttat ctcggaacgt caattgactt agactgattg gcttcctgcc
gccaatgtca attaaattgc aaatgcttgg cggaggccgg cgcgagcggg cggcctcctt cccgggggcg ccgcgctcag
ccttctcttt gcgccacgtt cggccgcagc tgaattcatt tctccttcca cgtcgcg SEQ ID NO: 30
ccggtggtgg ggtcgtagtg gtttccgagg ttggtgacca cgtcgtcgaa cttgagcacc tc SEQ ID NO: 31
cgggtccgag accctcgtag tgtggggaat ttcctgggag gaagatacta cgcggggccc ggagcagaat ttgctccagg
cactgggcca gtccatgagg gctccaggat ccaggggccc cactccctc tcgccgggct ccgggccaag gaagcgcggc
cggagtcccg ggaagcccct cggcagccag ccaagggccc tgcgaggatg tggatggcgc ggatggcgcg gcctccacct
gcgggcagtg gagagagcgg cgagaggaag aatattcccc gcgagccggg ataagggggcc ccttcg SEQ ID NO: 32
acgtatctaa acaccattac caggctccac cagcccctct gctcctcagc ttagaggagt ttttaaaacc tgttgagaat tatcgcagat
acgtttggcc attatccagt cgtttcgatt gtgcctttcc taaatgtccg cggttggcag aacgtgggag gaagaggacc
cgcctaactc gggtaggtg gggacgcgct gctcactgtg gtgaggttga cacttgggcc ctgggtttca cttgcaggtg
ctgggcggcg gagagccccg agaaggagga ggagagagag ccagcagcca accccctacga cttcaggagg ctcctgcgca
aaacctccca gcgccggcgc ctcgtccagc agtcctaacc gttcaacgag gcagtcaccg ccgtcggaag gcgctggagc
ctgcgggggca gcaggggcca agcaggcact ctggggctgg caccagcagg cactgaagct gcggccctga tctccgcaga
ggctgcctgc tgcgctcggc cctcaagtgc ccggggccgg cttcgtgctc cgaaacaaga gacctgggag ccctcgggaa
acctccccg acgctctctc tcggaactcc cgcaccctcc tttctcacca gcccgccagt tgtggcaacc ctgtccttgt
tccccctaatc tatcactttg ttcttttttt ttgtgactcc tgtggactcc actgcgcctg ggatctcg SEQ ID NO: 33
cgcggagaaa cctggcgggg ccccggactc cccggcttgg gaaaagcgat gactgccctg aactgctggg gcgttcgaaa
tttccagggt cccgaccctc cgtggggtac gcgcgacttc ggcgcagatg tcagtccgct gccttccggg ttgagggagc
gaggactcca gacgaccccca gggccgctgt ccaggcccag cccgcgttc tccacctcgc cacctcgctc tgcggctcca
gcctggagat ctacggactt cattgcgatc tcttgcgcag tgtagtcgcc ctctatccct agccccgagt cccg SEQ ID NO: 34
cgcggggaaa gttggcgcgc gcctgaccgc gcctggaagc cgcgcggtgc cagggccgag ttgtccccca agtttctgcg
gcgatttgtc actccctggg gatctggcgg tctgaatccc gcggggcctc cggctcaggg attctgagcg ctgggagaga
gaagcccgcg cttttcccgg ggacctgcgc ttgagctggt gcttgtgcgg gttcgtcctg aatggtagcg attcgagttg ttttctgctt
ttcttctccc ccagacagtg agtttgtgga agcctcgccc gcatcctaca gcccagacga gttaggtaag tctgctcatt ttgtctttta
tttcttggtc gcaattctgc ccgagaactg cgagtttggg gggcgtccat aggaactcag ctagggatgg ggctggggtt
ggagggcgga gggaaagggt caggggacac ctgctgcctt gcgggccgaa accggcctt cctcggcgct gtgctttcgg
gggtggcagg gcaagtgtcc aatgagccgt gcgtgtgtgt gtgtgtcgt gcgtgtgcgt gtgtgtgtgt gtgagtgcgt
gtgtgtgcgt gttcgtctgg ggcagtggtg ctgctccgag gagcctggca cagcaaactt ccagagctgg ggcttctgaa
acctgcgctc atcttgccgg gaggacacag cggcagctgg ttctgacttg ccaagtacct ggcacgagaa ggacgtcgtg
tgggtcgtcc ttaccctgaa tttaatgaag tcagggggctg aaaacgcgcg tgtaatcatt aaactgtaag acctaggagc
tgcttccctc cctgatttct attcctcagt tagcctgtag gtgtctcgag ataggacatt ccatcctcat gcctgtcatg gtaagtggag
atttgcgatg ggtgaaccgg gacactcttg tcaagacaa ggctgaagag agagtgaaga gaaggaaatg cgaatgggca
ggatctctct aactcttcct gccacccatt ctcactcggt ggcttagtgg ctctcttttt tttttcttct gctttcaagg ttagttagc
tgctactggt ctggggctaa aagtctctcc ttactgttct ttcatcacta gcctgaatat cttgccttcc taagatgaaa tgaaaggatt
tattttatga tatatgttga cagtaaagga ggagggggaac tgtccacaaa cagcggttta aatatgttta tcctcagtaa cacactcagc
tgtggcaccc tgtccctggt cagcttcttg tgctgggaag aatgtcctca tcaagtccca caggacctga agcaaaattc
cacctcaaca ac SEQ ID NO: 35
cgaggggggaa gtggcttgtc agccccggct ccgggaagag tgaacaataa ggctagggca gccgccccag atcgttatat
tcctgggtct aataaagtca ggatcgctgc tttgcttccc ccgccccaga agaataacg tttgcaaaat ggggcaaaat
gggcagaatc gcacggccgt tgttgttggt gtgaccgttg ttgcacccca gtcgacatga cgttagtttt tcatttgcca aattgctggt
tagttgcaaa gcctaccctc ggccgcgagc actgaaggat gggagggtcg agccgccgcgt tttgacagga ggaagtgcgg
aggggcggag ggcgaggagg ggctgattgg ggctgcgtgc tgtgtgcgcg cgcgtgtgcg cgcgtgtgtc tttacacgcg
ccgcgtgccc agtgtggcac ggggcgggag aagaatggca ggtagccgcc gcaaacacct cgcctgtct cctttcttg
ggcgaggttc ccgatcctgg caaagtgtga acaataggga gctgggagga agacagtagt gatgctgccg cggtgggcgg
gggttgcgcc gccgcccaga gaacctcggc agtgtgcagg gaggtgcatt tcattttggc tatttccatc ccggcctccc
tggaaaattc ttctgtgc
```

SEQUENCES

SEQ ID NO: 36
```
cgacgatttt tgaggccacc cttccttgtc ccgcaatccg atcgcctagt aaatgccagc agtatctggg ccttgagtct ggctttgacc
cggcagtatc tacaaataag ggttatcctc tttcccccaa cccacgatgt atcgcagtgg gctccggcag gctgcagact
ccagacccct ggagcaccgg cagggcaggg ttggacccct ccccgggtgg caaccctcca ctggagtgcc cttcctcatc
gtcttggggt taagagttgc cgcccggcca gggcaacagc cagggcaaag ggagagagaa gccgcccgg ggcgagaagg
agaaagtta gagggctgaa caggtgacgc tgagcttgtt ggagcgtgtg tgctccacca cgcaagggcg cggagttcgg
ccgcctcatc tcccgccatc tgcgcgcccg ggggcacgtc ctctgcgata gcctggaacc cagactacct gcgcctgcct
ggtcccg
```

SEQ ID NO: 37
```
gcgcctggat tgctcaagag aggtcaggga aacccctcag aactcctgag acccagagat tgaggagggg gttgaggcgg
agtctgcaat gggggctgtc cagcagtagc aagcagcggg ccgatcctgc tggagggttg ggaggctgct gtcattttat
gggtcggcag ccagagtgag agtgtccctg ctgccagagg actacggcgg gctgggcgcg gggtccccgc ctctcgctca
ccacacagac cccgcgcctc ctctggcagc cgcggtggtg gcggcggcag agcctcgccc actccaatcc caccctctc
catccttagt cattaaagaa cagcagccgc tggcacgttc ttggaggacc ccgggcgcag aggaggaaag ggagcaggcg
cagggggact ggaaaggcag catgcgctcg ccaggagcaa cctcgcgcg cagggtctga ggctgcagcc ccagttcgcc
attgtgagcc gccgccgggg gagtccgcta gcgcagccgt gcccccgagt ccccgtccgc gcagcgatgg ggcacctgcc
cacgggggata cacggcgccc gccgcctcct gcctctgctc tggctctttg tgctgttcaa ggtaggggag ctcctccacc
ccttttttccc agcggtccgg gcggcagccg cgctccggcg ccctcgctct gccgttggga gcggcgcgcc ccagggcacg
atggcccagc cgcgggaagc gcctgccgtg cagcctgggc gcacgctttg ttgtcctcgc gtgtgcgtgt tcctggtggt
cttgagaggt agggggcggg gggaagaata agggaagttt gctccctccg gctttcgccc tttgtgctct tttatcgctg
ctgaaatcca catcaaaggt gggcttgttg gatcgtgctt tctcaggcaa aatgaggtca cttttctttcc tggtttccac tgcaccccaa
cgctgcttaa cctttccgcc ctccctcg
```

SEQ ID NO: 38
```
cgatctgaca gcccttcaaa ccaatatact ccctatctct ctctctcccc tggttcaatg acaagatctt tggccaactt cttctactc
ggaccttgct attatttcct actaggcacc cacaaaccct tgcttgttaa actgatctcc ttcaagactc aagaaaagcg ccatgcgct
ccctcctagg gctctcctgc cctctcctca ccgatgccga gagtggttct gctggagaac cgccgccgct gcagttcctg
cacctttttcc cggagctgcg ccagggaatt acggacgaac tggaaggggc cgagaagaaa ggtcttggcc accacctcta
gctcaagcc ttttttcgctct ttcagactttt ggatcctccc cgggagggac ctccaggagc cccttggcag tttccccgccg
cctagggccg acttttccat ctcctcctct acctccggct cccgggcgag ggaggccccg cgccgcccct tagactggct
gcggccggaa gattgcagcc gctttgagct tactccttgt ttttctcataa tcaaggagta tggtggagct gggtcaattt
caggcacagc ccagccgagt caggcgaggt ccagagagac ctgactcgcc tggcagcctc aacggacttg tcccccgcagc
cgttgcggac ctcccggtcg tcatggcgac tgtgaaatgt ggggtggggc gcatgcgttg gaagccattc gcgcg
```

SEQ ID NO: 39
```
ccgtaaagaa ccctgagcta ctactcagac gaagcccccc tccccgccaa taataataat ataatggcgc ggaaactgtg
ggcggtggtg gtgacatttc ccacgactca gtgcgcccc cgggcggctc ccaccctccc tccggccggc gcgtctacgc
agccccaagt gctggctgcg accctcggat cccaagcata tctggcgatg gagcggcggc agcccgaggc acgtgttgtg
tgtgctccga ttgcaaaaga aaaaaaaatg catttcaaac tattaacttt tttttaagcg tgcaatgccg ggagctgggg
gtagacaggt gcaagcgggg gtaggcgccc cgcgcgccc
```

SEQ ID NO: 40
```
ccgcgattag ttccggcaga gtgatgcagg tagggatgca gatacagccg agtaggtgag ctctgcccca accgtctacc
caattacaag catctttcgc ctacactgag gacacatcta acacagaat ttacaattgt gcatgcgaaa cttttacactt acgttagttg
cctcaacctt tccccttttcc cagtatgctg cagttaggaca tgatttgttc caacacatag aaagccatgc atctggtagc accagtttgg
ggagaaatca gaagcagcaa aatgtttcct ccttgtaaaa tgtgttgctt cgggctggca aattagcaac tccagagaac
aaattcacgg atttgtcgtt agtcattctc tccacatttc gtctctctta cccactgggt ctggggttctt ctgggcatt agcacacaca
acacatagtt gcacttcttc agctcaggga tattttccac agcagcatgc atacccattc catccgatgc caatactgct taagtctcta
acttcttgta ggaaacgtca gagttgcggt gatgatgatt ctctgacagc tatccgggtg acagttgccc gaaaaattcc taatcggtta
tctcttgcgt gcttcagaga ctctgaggcg ctccttttccg tctcgcgtgc tctccctctc tcccttcccc tctgcccctc tctccttctc
cctctcctct ctctgaactg aatttcttga tataactctc aataagccca gagggagggc gtgactgccc aggccccgcc
cccgggctct gattggcctg catcttgcgg cgcaggccgc cgcagcccga cgcgagggag ggagcgcgga acaaggcgct
gactgtctcc cagcctcccc tcctccgcgc cccctcggca gcagcgaaaa cccggaaatc tgatcctggc cccaggagag
ccgggttcca tgaggtgcac tgagcatgct ctgcagggtc cggcgtggga gggacgcgct ggcgctcccc aggcccgggc
ggaagcggcg ctcgcaggcg ctgaaagcga gcgaccctct gagcccgggt ggtccggcgg gcaagggcgg cgcgggagac
ccgcagggcg cgggcgcaga tccggggaac cagggcacc gctgcgggcg gatggggtc accgaggcgg ctcgtctcca
ggcgcacact tcgcacatct ctttgctaag tgaaggggca aaatgcaca gatggggac tctacccagg aacagaggcg
cgagacgtat agccacccct gggttggag cacgagccag cagatccccg gagcgcgtta aacggacaac atgcccggtg
ctgcaaatag aggcttttgc tggcagggac attggaaaga agggcggaga gggagtacag cgaaaggtgg ggaccgcaga
atttggaatc tctgcggaga ccggaaagaa aattaatcgg agcacttcct acatgcgagg ccacggaaac tgccttgaa
agagaaagtg gcagcgtctg ggtccccctcg gtcagccgcg tgcgcgtcge aagtctcctc tagccgagcg
ggaccggccg cggcggtgga tcgtggcggt ccctgcactt ctgctccagc cgcgcctgga aacctgagcc cggactcgcg
gctgctgcaa aacccgcttc cagcccacct cactgcgaac tttgcttccg aggggctgga aggagtccca ggcagctgtt
tcccaagctg tggaacactt cctttcccct aggcactttc tgctgattcc aactttcttt cctgtgattt tcgtctttc ccgtgcattt
catttctccg actccagctc tgtactaaat cctcacaagt ttctcgtttt catacggaaa ctggatggaa tgactcccca aaaaatacag
ctttatttct caaatactga cccccaaagc actatctagt aatatatttg attgatcttt caaagtcagt aaaccacaaa ggtttgtgta
atggcttgta cttaacg
```

SEQ ID NO: 41
```
acgtacaggg cggtgatcca gtatctaaat tctttgggag aaaatgaata gttccccgc cccgccctc caggaaaaaa
aaaaatctga gaatctgaga atgttcagcg cacccgcgaa tttgcatcgg aggtgcgttt cccc
```

SEQ ID NO: 42
```
gcgcgccctg gcggctccga gggacctggg ctcgggcttg cggtcgcgtc gcctgggctt tccctgggct gggagcgcgc
cgggtctccg ccttgcacgc tgtcaccgcg ggagacgtct cggcctcgcc gcgcgcagag gggacgcgcg gagaggctgg
tttctggggcg agcggagagc tttgcccatt aagctgccgg aagaagccaa atcaaaaagc caatctccaa gcctccaaac
```

```
ggaacgtcac cctatcagct gggagacagc gccgcactga ctgacaagcc gcgcatattt atcctcgcgc gcggagggga
gactctcaga acgctcctcg accagcagcg aggaagtcga gccgcatcc cgcatcccg atcccgcatc cagagccccc
gagggacgaa ttcagatcca accctgccc cgcggccacc cacccagtc gttggagcct ggcgccgcg cctcccggcc
ggcagcacgt caaaacggcg gcgcgtcctg acctggattc cgccgagttg ggagctccag gcagcaggcg ggcgcgcggc
accggctttc cccttgtcct caggagacgc tgcctgcaat tccg SEQ ID NO: 43
cgcgagcggc tgggtgtcgg tgccctgctc tcctctgggc gccaggatgt tcctgcccag tgcgtgtcca gaatagccgc
tcagacaccg gctccaggtt cagccaggcg gggcgcgtcc ctgcctcct ccccttgcc tgccactgcc ctccttctaa
cgagggctca gctccgacta ccccaggcct ccggggaccc tctccggatg cgctccccgc tttgcgcttt gcg SEQ ID NO: 44
acgcaagttc cccctgactg ggggacgccg cccagctcct ggagcctgcg aaggctcttg aagctgagct tcccagggat
accagaaggg acactctcgt gcaattccgg ctagggaaag cgagggaagg tggcggctcc gggcagggag cgagcgagtg
ctccacgccg cccgcaggat cgagtgagtc acgcggccgc cagacgaggc cggtggcgca cgcacccgag atccgatgta
gtgcaccgcc tcggcgccgc g SEQ ID NO: 45
cgctcgttgc gacccaggct cagctccgcg gtgcgcaggg cctggcg SEQ ID NO: 46
ggcggccgcc agctgggagc ccaccaccgc tcgatggtac cgaaccgacc cgtgtagccc cataaccccca gcccaactcc
gaggagctag cgcagaccgc tctccgccct cagctgcggc gaggcaaggg ctggcagcgc tcggacgcct ccgtcttgcc
cttcccatgc ctaagcgcgg ggaattacac gttcccggtg tagaacagac gatcgggggct attagggctg ggcggtggga
gtggggggttg ggagcaccat ttttggctgg acgtgtgtcc agactcatcg tctctggtcc ttaggacccc atcttcctct gcatctccag
gtgtc SEQ ID NO: 47
cggcggctgg ccaggggcac agagacgcac tccacacaga aacccaggct ggcggggtgg gcggccgggg agccagccct
gcagatgtta ctaagtgaaa cctgatgtgg tgacatgaga atccacagaa cgtctcacaa acaacctgcc ccgggatgtt
ttggattgag ttttgtggtt atgacgtgaa gaaacctcac atgtcaggat aaaaataacc ctggcttcag tacataacgc gagttacagt
tcaacagaac cagatgtgaa aacgtcagcc acccagttca ggcccagcag ggtccctgct ccactcc SEQ ID NO: 48
cgggtctgga agattgcgct acgggagttc tccgtctgag aggacaactc agctttcgca cgggagggtt gatgcttaac
agaattaaaa atatatgtat taagaaccgc aagcccactg tgtgccagcc gccgttggta gttttacacg tgcgatctta tttaatactt
cctgggacct aatgagtcag gtgccatcat gatccgttta caggtaagaa agccgccgct SEQ ID NO: 49
cgaatcgcac ctcttctcct gtcctaatct caggctccag gcctggcttg cagtttctgg ctcaccgcgc tgcggtcacc g SEQ ID NO: 50
cgcccccgcg gaaaccgctg ctcg SEQ ID NO: 51
gcgaggccag actgccccca cacctcctgt agccactgag cgcgaagtgc gttggttccg agcgcgctgg tgggatccac
aaagctcgca ttctctcagg aatccctga gaaattaact gtcccttgcc caacatgtct tctccaggct gtctgctaga
gcctcaggcg cctccgccct ccctcccgcg gcaccgtcac cagtgggtag tcacagcctc ccggagccca tagccg SEQ ID NO: 52
cgcctccgcg ccgcgcgccg ccgccgcctg gtaccgcccg gccgggagaa ggtgagattc gcgcggcctc gcgcacaccc
gcggctggga gctcgggact gcggtgacgg gaggggcagt gtggtgaccc accaggatt tttttttttt tcccgtgaaa
gtcctcaagc ctgtcctctc cctggcccga tcctattgca gcgacagaaa atcagcagcg ggcgggtctg tgtggacctg
agggccgcgt ggggaccgag gggggctgtg gcccaaagag tggcagtgag tggcgtcaag gaacccacac tccgcatctg
ccactcctag agccgggact agctcccgat cctagcagtt gctctcgaga tcatcccgag agttattggc gagttctggg
cctctggagg tttccctgtc agcctccccg gccgccgagg ggcgcgcgc caacaagggg ggtctctagc ggccacctgg
ggacagaaac agtgaccctg ggcgcgcact ttgcctcccc gttagagatg tcg SEQ ID NO: 53
gcggaagccg cgagggatgc agcgcggggg accttggccg gtggaggatg tggaggtgga agtggagcgg atggcgctcc
ccaagagctc cgccacgcga ggtttcgggc tcgtggtttt gcttcctccg ggtccccgct ccaggccgc tcggcgcgac
gaagacgccg gggacagcgc gcggggagg gcgctccggg tcgtgcgtgc tgcacccaca aagagcagca gtcccgccac
tccgcgcctc cgctgcgtgg gggccgaggg gcgcttctcg SEQ ID NO: 54
cgacatagtc aagcagggct acgtgaaaat ccgcagcagg aagcttgggg tgagtggctc gctcggcttg ctccttcccc
ggcgctcgtt cggcccggct ggctgcctgg ggggggggca gggagaggtg accgtgcgg gtacagggca gagagggacc
cggcccttag gcgatggcc cgcttgttgc cttggccaggt ggggggccac acctgccggg gggctccgca gacggacctg
gggactccag gagcgcctga gtcccatcc tcgagtgcac cgggctgtct tcgaccgtgc ggggaagtca gtagacgaaa
ggggtttgtca gttccaacga ggaacgtgcc ttggaggagg tttcttttcg gtgctatcca cgatggtctg ttctcaaaag
tgtgcgcctt tcgggtggaa ctgctgtgtg tggcgacgct cgcgtgtgtt tagaatcacc atttttctggt ctccgcttcc caagctcaat
tcgaaattcc cgtctgatgc cctcccagcg ccgcgcgtcc ctgcc SEQ ID NO: 55
gcggtggggcg cggcctgcgg ggatgccggg ctctacggag cagcgcgggg tcccgaagcc ccctaccgc
```

```
SEQ ID NO: 56
cgtaaataaa tgagatttac acaaatagcc attcacaatc atggtcacag tcacctacaa accccattta cacaaatgat
caggcacaca atcacactgt cactaaagca cacccacgca ccaggtcgct gtcccaacag taacacacag cccaaagaga
aaccctactt cctcacgcat tcaaaacaca cccacctaag ggctgatccc gcactcagag gcctaaaact atagacattc
ccttccgcgg cactggtgag ccaggatttc ttaccttcag cattctcagg gaaggctctg gtccaagctc tgattcggat
tccaagcgaa gccacacgcc cagctcttcc ttctccaccg gcccgggaca tccttacctg cctctacccg gagaccattc
ctgcgaggct cctaccggaa gtagctgtgg acagcagtgt cctctgggaa atgcagtccg aggggagagc gcctggggtg
gagcgggtgt gttccgccgg gctccgggat gcacttgcgc agtttcaccc gaggctgagg tgacgccaac ctgttaatgt
tcgtttcgg attctggact tcgggttccg ctgaggacgg atttcggaat aggcacagtg gctgccccga acccctcaag
gcggcctccg cgggctgtgg ctgaagataa ttttcggcgg gcgcggacta acccggcttc cctttgtgga gttgtggtga
gaaaggtgtt ttgttgtgcg cgtgtccgaa ggtgactccg gaggagaagg tggatatgaa ctgacggtga gggtgtagcg
cgtgagattt gtatgtgaaa cgatttaaaa aaaaattttt tttttggccg ggcgcggtgg ctcacgccaa ggcgggcgga
tcaccgagac cagcctgacc aacatggaga aaccccgtct ctactaaaaa tacaaaatta gccgggcgtg atggcgcatg
cctgtaatcc cagctactcg ggaggctgag gcaggagaat cgcttgaacc cgggaggcag aggttgcggt gagccaggt
cgcgccattg cactccagcc tgggcgacag agcaactcct tctcaaacaa acaaacaaaa ctgtatgtca tatatttgac tccatttatt
tatttattta gagacagagt cttcttgccc tgttgcccgg gcaagaaaaa acaaacaaca acaacaacaa aaaactgtac g SEQ ID NO: 57
gctgccgagt ccccgcagca gggggcgagc aagggactcg cggttgacgg gacacggatc ctctaaggcc cagagtgtcc
cgagtagcgg cagtggggag tgctcagggt acgctaatgg tgagtggttg cagttgatgg gacaaaaaac tgtgatggga
gttagtgtgg gtgtgtggtt gtgtgtgtga gtgtgacggc acgaataatc tgatggggtg attgtgatat ttggttgcgc gggattatga
tgaaatgtgt gatatgtgtg tgattatgat taaggctgta gcgagtgtga acgtggcgaa gtgtgcg SEQ ID NO: 58
tcggagatgt gcgggctgca tgcccacgct tcaccgctag ggaggtcag ggctgtgcga tggggaagga agagagtgtc
ggggcggtgc agtcgggatg ggagaaggg gtcagggcca ctggccccca gctcggcaga gggcagtgtc gggccgcgcg
caggcaggga gtgggtgtgg tgtgaggctg gcgctgagc ggtctgggaa tgttaggagg tctagggtat cgcggccctg
cgtcctcttg tctggactaa aagtccgggc agttctcccc ggacctggat tgtgggccca gcgacaggtg cttggcgatc
tgtgcccg SEQ ID NO: 59
cgcctgggat tgcgaggtag gtaccgcctg cctgtgtgta ccggggctgc tgtctccggg gaggggcttc tggcggacag
gagaaccaag cagcctcagg agctgcctgg gtgtgtgtgt ttctgtgcga gtgttgcata tctctgtgtg tgtttctgtg caagtgttgc
atgtctgtgt gtgtggggg ggtggtgtct ggtgaaaaga atgtgtctcg tgcggtggag cgccgtttct ctgtagtccg
cgggctctct tatgcgccct cttgtggtcc caagtgtgct tttcttgttt ttc SEQ ID NO: 60
gtgtgcgtgc ttctgtgcgt gtgtgtgtgt ttgtgcgcgt gcgtgtgctc atgcacggcc ccgtggcagt gctgggtatg
agctcttgcc ccagacatgc ccctgcctgc tccctgccag gatctgggga gatggctgta cctggcagcc ctagggtgca
gagcagagtg ggcagccgtc cctcgggact ctcagctgcc cacttcttcc cacagtgcct ggccatgcca ggctgcccag
aggggcag SEQ ID NO: 61
gtgtgttcga gtccctgggt tgcttcctgg ggtctgtggt gctgggtgtg ctatctgcgt gtgattctct agcgagagat tgtgggcgag
tgaccgagtg ggcaagggc cgtcactgtg tgtgcgtgat tttgacagtg tgtggtggta gcttctgact ccgcgtgggt
cgttgaatgt atgactggga ccgtttagcg gtggatacac aactgtgtgc g SEQ ID NO: 62
gcgtaatcac gcactgcgca ggcaccgccc gctctgctct aaggtccctc tcactccttc agcagcccga ggacaatccc
ctcaacacta ggccacgcct tgtctccgcc cctctcgtcc gaccctgga gagaggctgg cgcctgcgcg SEQ ID NO: 63
ccgcccgggg ctcctctgtc ccagctctgc ggcccagggg gtgacgtgat ggcggcagcg gtgctgacgg accgggccca
ggtgagtgga cggtggcttc gcggttgccg cttccttgcc agcgctgagg cggttccga agtgggtggg agcccaggta
tccccctggat ttgtcttcgc agtcgtcgtt cgctttggtg tgtggagctg gtttgccact taatttatac ctggccg SEQ ID NO: 64
cggtctcctc gtatccatcc tcgcagtccc caccccaaac taatgttctc ccctgagcaa atttcgagac acttaaaatc
ccagctaaga tcacgtcctt ctattcaaaa ccctcagtta atctcaacg SEQ ID NO: 65
gcgagttcaa tgtcctccgt tccgtcaagt ttgggtttga gctttgggct cagctgccgt ggtctggaga cctcgtaggc
actctgcaag atgcctcgtt ctgctgcatg cttggggagg aagttgagct gggtgctgga agttctgaac ccagcatgcc
ccgggccgga ggagatttgc ttggtgtctc cttagcgtcc cgaacaccgc gcgccctgc tggggtaacc tgaacagctg
gacccctcaa ctcgatcttt attatcagca ttggggctcc agattccgta cacatctcta gctctattca ttcttcctag gttgagaacg
gacgcattgg gagtcctacg cccggggaa aggcaggaga gggaggaag agaacctgtg ccctcgaaag ctagaggaga
gcctcgctct ctctgctgct ctgggttccg caacgaattg agttcgggtt caggcggctg gagcgggcgc gggaggctg
aacaatcgcc ggaggcccag gaggggaggc gaatgtacac aggctaagtg gccccactcc aggacaagtg gccctctaag
tcggctcagt gtttacctgt ttactttccc aggtagctca aacacgagcg cctttctgc gctccaggc acggggccg
cccagaggca ccctgctttc ccggcttctg ccctccacg cctcagcttt acgcccctg ttgtgggggt gcgctctaaa
caacagcaaa ccaggcaaga aaggaagata caggagagca ggcgaggcct cggcacaccc tacggagggg agcctttctt
gtgcctgtgg aagaagtggg ctccgtggac ggcatccg SEQ ID NO: 66
gcgcctggag gctgcattga ggccgggctg tgtaaactgt agggtgcctc gccgactcgg agccgcagag actggcggc
```

| SEQUENCES |
|---|
| SEQ ID NO: 67
cgggccttaa ggaatctcag actgcacagc tctgctgtct cattccaggg gtccctgggg tgctccgctc ttgccaattc
cgggcacaag gaccacccac tctgcccagc agcctctggc cccactccca ctgccccagc gaaataagtt ccagcttcca
ggcatgattg attatttgga acagagcctt ccactccgga ctgagaccca acccctgcag aaagtcctaa actgggctgc
gaccactttg ctcccaggag cagaggagca ggggaaaagg ggagaattct ttaaaaaatg acacgcgaga gagttaaaga
aggaaaaagg caccaaagtg atgaaacaaa agaactggaa gaataagcac tgcacagaga gaaggccgta gcaggaagga
ccggcagtga ctttcaacag tgcttgagag cagaattatg gccgcgagag ggagtgcaaa ctgggaggcg gggcaaacc
gggaaagacc tcccaagcag gttctgcgaa ggggccccac cgccttcagc ccgccttcag ccgcctgggt cagccttata aggggggaaag
gggacagaag tctgcagaac agagatccta gcgtagccgc tcagggtacc ttccaggtc accattgctc ctctgccctc
tccacatccg ccctccgtg agcgcaggat gcacgcacag gcagcggtta caaaactcag cgcaacgttg caacccgcac
aaaaggcgca cacaaaatca ttaaaagaa atacacagag tggaaagaac tcgcacaagc tccaactcgc taaaggtgga
aggagtcagg ttacaaactc tccctccccg gcctaaatgc tttgctttag tttgcagaaa atcgtttgtc agttttttc ttggttattc
attattcggg caaatgcaag tatgttttct agctgagttc accaatccaa acctcaaacc acattcctcc actccaggcc tccgttctgt
ccgcggactt atgatcctgc ctgccagcag gagtctaccc tgaagtcgcg tgggatagat aaagtgagga gaggaggatg
aatggacaga caaacgagag caattcttct acctgtgggc tgtcctacgc cttgcagtgc cgggtcctgc ggcgaccact
gagcccttc gtcctcgccc tcagtcccct cgtcctcgtc ttcggtctcc gcttccag tcggccgggg ctcgtcgtcc
acgaccccgc acgtgccgcc gacgtcgccc tgccgattcc gccgcaggag gtgaactgt agtggtgccg gcggcttctc
ccctggggcg gcggtggcga ggcgctcgct ggcggcgggc agcggctgga tgaaatacgc ctccccagc aggtagaagg
cgccgcgcac gccctcgcag aggctgaggg cggcagccga gctgggatcg ccattcacgg tgccggagta gaagcagtgc
gccaggtcgg tttccggaag cggcgtctcg gacccggatt tgcgcccac gttctggagc gtgaagccgg cgccaaaaa
gctgctgtcg ggccgcagct ccagatccag ctgctggtca aaggcgtgca ggcggaggcg cgtggtcccg tgtcccgggg
cgcgctccag ctccggcacc actagctcct cgtcctcctc ggaggggcgc ccgagtgcgt ccgacacggc cagtagcgcc
gcggcgagca gcagcagcgt gggtactggc ccaaagctcc gagacccgg agcccgctcc gcgttcccca tgtcgctgcc
cagcttgcgc cttccgaacc cctcgggcac agctcgtcgc attgagcccc caggagacac cgctcgtagc agcgcacgga
gcgagggacc tttagttcgg gtcgggagag caaagcctcg ttggcctgct ctggattgtt aaaattaaca atttctatta ttcgttggaa
gggcgcgcag agccggctac agccgaagct cccggagtca ctaaaaggag gcgctgcagt tctgccggcg cgcgggaagt
ttttcttcca gcgcaaagtt ggagacactg agaggcaggc gcaggcagag tggctctgct gggacaagaa gcgctctggg
gcgcctccgg ggctgaggca acgcggagat tggtgcctgg cgcccctctt cggcctccgc cttggctgcg atgttgctca
ctctgctcag ggctctcccc tctccgtccg gtagc SEQ ID NO: 68
tcgaactaat ttaatcagat gtaaaattaa tgagaacccc gagacttccg acgtccccact ccagaactcc catccaggtg
cggtcgggag ccacagcttc tgaatattcc ttcggaactt ttttctcact tgattcccaa gcctgtcatg gggttctttt tcaatggcac
tgacctgcaa ttacccaacg agcagcggga cagccccggg caggacgcat cctgggtggg tgacgtgatc ccgcagtctc
ctccccgacc ccatatccca tacaatgatc ctcgcttaca gaagtcaagg gggaaagatg acgctttcaa agcccgaatc
tctttaccct ggagccagaa ccagcgtcgc cgccgtcccc tgcagctcag ccggcaacgc gcgccgagcc tcggggcgca
gcttggagac gcgcttgctc gttctggaa ggggcacggg acgcacggtt ccccgcccc agctgcacag ctcagctcgg
ggctctcacc tatcctcgtt cagagccaca ttcggctgcc tcccctgacc acccgacaca aagagattcg ccggtggaaa
gaatcgattt caaaattcaa gctcaccgct gctcaacaag gcgcgcacgt ttctccccgt ctggcttcac atgtcccaaa
cttcagtaa cagaaatgag gaagcagcag ccttccccgg ctgctggcgg aggcagtggg tgtaacttgt gaagtttcgt
gctatgatga atctggtcac ttgggtgtgt tggagagggt tggtcgctcc tcccttcctc ctcccaccat cacctccctc ctctccgcct
ccctctccaa tttaattctt ccctctggca ttcgccggct gtcactcaga atccagcac cctcccacc acatccttgg gggcaatgta
tttcgaaaag gtcttaacca ttttacggat gaacctggtc accctgcaca aagcgtgagt gcttgtcaaa taattttcta cagcacg SEQ ID NO: 69
gcggcgcaag atcaacagcc gcgagcgaa gcgcatgcag gacctgaacc tggccatgga cgccctgcgc gaggtcatcc
tgccctactc agcggcgcac tgccaggcg cgccccggcg caagctctcc aagatagcca cgctgctgct cgcccgcaac
tacatcctac tgctgggcag ctcgctgcag gagctgcgcc gcgcgctggg cgagggcgcc gggcccgccg cgccgcgcct
gctgctggcc gggctgcccc tgctcgccgc cgcgcccggc tccg SEQ ID NO: 70
gcaccactag ctcctcgtcc tcct SEQ ID NO: 71
ccggcgcgat tctccctcaa cg SEQ ID NO: 72
gtgcgcggcc caagagaagg SEQ ID NO: 73
tggggtcgta gtggtttccg aggt SEQ ID NO: 74
gtggaggatg tggaggtgga agtg SEQ ID NO: 75
gcatctatgc gggcatggtt actg SEQ ID NO: 76
acctctgccc cctgtccagg ta SEQ ID NO: 77
ctagggccga cttttccatc tcctc SEQ ID NO: 78
cggcgctttg cttttctaca |

| SEQUENCES |
| --- |
| SEQ ID NO: 79<br>tggagaagta agtgggaggc ggtgt |
| SEQ ID NO: 80<br>gaaaagcgat gactgccctg aactg |
| SEQ ID NO: 81<br>ccagcagcca acccctacga cttc |
| SEQ ID NO: 82<br>actgaagctg cggccctgat ct |
| SEQ ID NO: 83<br>cgcccgcagg atcgagtgag tc |
| SEQ ID NO: 84<br>tgagaagtca gacgggccgc gtaa |
| SEQ ID NO: 85<br>cgggctgggg ttggaagagt aac |
| SEQ ID NO: 86<br>ggctccgaat cgcacctctt ctcc |
| SEQ ID NO: 87<br>agggactcct ggccttgcgt ctt |
| SEQ ID NO: 88<br>ctcagttacg ctgactcggc tgtg |
| SEQ ID NO: 89<br>cgaggatgtg gatggcgcgg atg |
| SEQ ID NO: 90<br>ctgcattgag gccgggctgt gt |
| SEQ ID NO: 91<br>gcgacgcgtt tccctggtta cct |
| SEQ ID NO: 92<br>tctaacgagg gctcagctcc gacta |
| SEQ ID NO: 93<br>gggatgggga gtagagggag ggg |
| SEQ ID NO: 94<br>gcgaggtcat cctgccctac tcag |
| SEQ ID NO: 95<br>gccttctctt tgcgccacgt tcg |
| SEQ ID NO: 96<br>agagtgagag tgtccctgct gcca |
| SEQ ID NO: 97<br>cccactccaa tccccaccct ctcc |
| SEQ ID NO: 98<br>aactccgagg agctagcgca gac |
| SEQ ID NO: 99<br>gcctaagcgc ggggaattac acgt |
| SEQ ID NO: 100<br>aaaagccaat ctccaagcct ccaaacgg |
| SEQ ID NO: 101<br>gcggccaccc accctagtcg ttg |
| SEQ ID NO: 102<br>gctctgcctg tttgttccgc cc |
| SEQ ID NO: 103<br>gagcttggag atgcgaggga aact |
| SEQ ID NO: 104<br>gcctcggcgc ccaaaatcga aagg |

| SEQUENCES |
|---|

SEQ ID NO: 105
ggagcgtgga cttcttgggc cg

SEQ ID NO: 106
ttcggattct ggacttcggg ttcc

SEQ ID NO: 107
ggtaggtacc gcctgcctgt gtgta

SEQ ID NO: 108
ggagtgggtg tggtgtgagg ctgg

SEQ ID NO: 109
ctcgcgatgt ttcagggtga gcc

SEQ ID NO: 110
gtctcggagc tttgggccag tacc

SEQ ID NO: 111
gaggcagcgc gactccaaga ctcag

SEQ ID NO: 112
gggacgtaga caagggcagg cg

SEQ ID NO: 113
tcagcgccgc cacctacagc ac

SEQ ID NO: 114
gacccggagg aagcaaaacc ac

SEQ ID NO: 115
cgtggacctg gctgaggagc tg

SEQ ID NO: 116
acagcctcgg tcaccgcatc

SEQ ID NO: 117
gagtaagctc aaagcggctg caatc

SEQ ID NO: 118
gcagtcagcc cgaccctcct

SEQ ID NO: 119
acttagccgc ccatttcaga gcagc

SEQ ID NO: 120
ggaaggcagc ggactgacat ctg

SEQ ID NO: 121
ttaggactgc tggacgaggc gccg

SEQ ID NO: 122
gagggctccc aggtctcttg tttc

SEQ ID NO: 123
aggcggtgca ctacatcgga tctc

SEQ ID NO: 124
ctcagatggg agcgcggcag gaacag

SEQ ID NO: 125
atccctggac tggcgtatcc acag

SEQ ID NO: 126
tcctgggagt gtgggccggt ga

SEQ ID NO: 127
tctgtttcag cgcaactgtg aagtg

SEQ ID NO: 128
cccaaccacg cagtcataaa taacc

SEQ ID NO: 129
ttcctctcgc cgctctctcc actg

| SEQUENCES |
| --- |

SEQ ID NO: 130
agttgacccg ccgccagtct ct

SEQ ID NO: 131
accccgcgct gctccgtaga

SEQ ID NO: 132
gaccccaggg aacaggcaaa aag

SEQ ID NO: 133
cctaactccg tcccgctcgc tgtt

SEQ ID NO: 134
cagcagcgtg gctatcttgg agag

SEQ ID NO: 135
tgcgcgacgt ggaaggagaa atga

SEQ ID NO: 136
gcggggtctg tgtggtgagc gag

SEQ ID NO: 137
gtcctccaag aacgtgccag gcg

SEQ ID NO: 138
gcttaggcat gggaagggca agac

SEQ ID NO: 139
cactcccacc gcccagccct aata

SEQ ID NO: 140
aggataaata tgcgcggctt gtcagtca

SEQ ID NO: 141
cgccgttttg acgtgctgcc g

SEQ ID NO: 142
gcggcttggc gggctatctg tg

SEQ ID NO: 143
cccccggccc tcctgtatta ct

SEQ ID NO: 144
agtcagcgct acgggaaagg aaacc

SEQ ID NO: 145
ctgcacggcc ggagaagcga at

SEQ ID NO: 146
gcccgccgaa aattatcttc agcca

SEQ ID NO: 147
ctgaggctgc ttggttctcc tgtc

SEQ ID NO: 148
ggccgcgata ccctagacct ccta

SEQ ID NO: 149
aacacacgaa cagcactcct ccgc

SEQ ID NO: 150
gcaccactag ctcctcgtcc tcctgtctcg gagctttggg ccagtaccgc accactagct cctcgtcctc ctcggagggg
cgcccgagtg cgtccgacac ggccagtagc gccgcggcga gcagcagcag cgtgggtact ggcccaaagc tccgagac SEQ ID NO: 151
ccggcgcgat tctccctcaa cggaggcagc gcgactccaa gactcagccg gcgcgattct ccctcaacgc ttgcctggag
catccctggc ccttttgcc caggtcgcgc ccctgagtct tggagtcgcg ctgcctc SEQ ID NO: 152
gtgcgcggcc caagagaagg gggacgtaga caagggcagg cggtgcgcgg cccaagagaa ggccagcggg accacagcgc
ggctacgcgg ccggccgcag tcttcaccgc gcgcctgccc ttgtctacgt ccc SEQ ID NO: 153
ggggtcgtag tggtttccga ggttcagcgc cgccacctac agcactgggg tcgtagtggt ttccgaggtt ggtgaccacg
tcgtcgaact tgagcacctc gtagccttca tgctgccgct tgaggccggc gtagaaggcg atcttgggca ccgtgctgta
ggtggcggcg ctga

SEQUENCES

SEQ ID NO: 154
gtggaggatg tggaggtgga agtggacccg gaggaagcaa aaccacgtgg aggatgtgga ggtggaagtg gagcggatgg
cgctccccaa gagctccgcc acgcgaggtt tcgggctcgt ggttttgctt cctccgggtc SEQ ID NO: 155
gcatctatgc gggcatggtt actgcgtgga cctggctgag gagctggcat ctatgcgggc atggttactg cctctggtgc
cccccgcagc cgcgcgcagg taccgtgcga catcgcgatg gcccagctcc tcagccaggt ccacg SEQ ID NO: 156
cctctgcccc ctgtccaggt aacagcctcg gtcaccgcat cacctctgcc cctgtccag gtacgcgctg tctggcgcgc
cctgcgtggg ggccgcaggt tcagacaccc gggcgcggcc cggggccctg atggatgcgg tgaccgaggc tgt SEQ ID NO: 157
ctagggccga cttttccatc tcctcgagta agctcaaagc ggctgcaatc ctagggccga cttttccatc tcctcctcta cctccggctc
ccgggcgagg gaggccccgc gccgccccttt agactggctg cggccggaag attgcagccg ctttgagctt actc SEQ ID NO: 158
cggcgctttg cttttctaca actggcagtc agcccgaccc tcctcggcgc tttgcttttc tacaactgga agccgcgaag
gcggctactg cgctgagccg ctcgctctgc tggtcaagtt tgggcgaccc gcgcggagga gggtcgggct gactgc SEQ ID NO: 159
tggagaagta agtgggaggc ggtgtactta gccgcccatt tcagagcagc tggagaagta agtgggaggc ggtgtcggga
actgactcct cttaaaacgg tcggcgccgc tgctctgaaa tgggcggcta agt SEQ ID NO: 160
gaaaagcgat gactgccctg aactgggaag gcagcggact gacatctgga aaagcgatga ctgccctgaa ctgctgggc
gttcgaaatt tccagggtcc cgaccctccg tggggtacgc gcgacttcgg cgcagatgtc agtccgctgc cttcc SEQ ID NO: 161
ccagcagcca acccctacga cttcttagga ctgctggacg aggcgccgcc agcagccaac ccctacgact tcaggaggct
cctgcgcaaa acctcccagc gccggcgcct cgtccagcag tcctaa SEQ ID NO: 162
actgaagctg cggccctgat ctgagggctc ccaggtctct tgtttcactg aagctgcggc cctgatctcc gcagaggctg
cctgctgcgc tcggccctca agtgcccggg ccggccttcg tgctccgaaa caagagacct gggagccctc SEQ ID NO: 163
cgcccgcagg atcgagtgag tcaggcggtg cactacatcg gatctccgcc cgcaggatcg agtgagtcac gcggccgcca
gacgaggccg gtggcgcacg cacccgagat ccgatgtagt gcaccgcct SEQ ID NO: 164
tgagaagtca gacgggccgc gtaactcaga tgggagcgcg gcaggaacag tgagaagtca gacgggccgc gtaaggggca
gagcgagggg tccggcatca ctcgcgcgct ccggaaaccc gcgtgagccg ctgttcctgc cgcgctccca tctgag SEQ ID NO: 165
cgggctgggg ttggaagagt aacatccctg gactggcgta tccacagcgg gctgggggttg gaagagtaac tcgggctgcg
ggctgaacgc agtcggcaac cgcggaagag cagcatctcc cctgcgcctg tggatacgcc agtccaggga t SEQ ID NO: 166
ggctccgaat cgcacctctt ctcctcctgg gagtgtgggc cggtgaggct ccgaatcgcc cctcttctcc tgtcctaatc
tcaggctcca ggcctggctt gcagtttctg gctcaccgcg ctgcggtcac cggcccacac tcccagga SEQ ID NO: 167
agggactcct ggccttgcgt cttttctgttt cagcgcaact gtgaagtgag ggactcctgg ccttgcgtct tgggagagcg
cacgctggcc tgcgctacac acacacactt cacagttgcg ctgaaacaga SEQ ID NO: 168
ctcagttacg ctgactcggc tgtgcccaac cacgcagtca taaataaccc tcagttacgt tgactcggct gtgcccgcag
tgtcgcgctg tcgcgtagcc aggtgtcgcc gggctggcgc ggttatttat gactgcgtgg ttggg SEQ ID NO: 169
cgaggatgtg gatggcgcgg atgttcctct cgccgctctc tccactgcga ggatgtggat ggcgcggatg gcgcggcctc
cacctgcggg cagtggagag agcggcgaga ggaa SEQ ID NO: 170
ctgcattgag gccgggctgt gtagttgacc cgccgccagt ctctctgcat tgaggccggg ctgtgtaaac tgtagggtgc
ctcgccgact cggagccgca gagactggcg gcgggtcaac t SEQ ID NO: 171
gcgacgcgtt tccctggtta cctaccccgc gctgctccgt agagcgacgc gtttccctgg ttacctgcgg ggccgcgtcc
cggaggagcc tgagggccaa gagggccggc gcgcggtggg cgcggcctgc ggggatgccg ggctctacgg agcagcgcgg
ggt SEQ ID NO: 172
tctaacgagg gctcagctcc gactagaccc cagggaacag gcaaaaagtc taacgagggc tcagctccga ctaccccagg
cctccgggga ccctctccgg atgcgctccc cgctttgcgc tttgcgcttt ttgcctgttc cctggggtc

| SEQUENCES |
| --- |

SEQ ID NO: 173
gggatgggga gtagagggag gggcctaact ccgtcccgct cgctgttggg atggggagta gagggagggg gccctgttgc
ctcagcgccc cgaggtcgtg gagcggcagc agctgcagcc ggagcagcac cagcaacagc aacagcgagc gggacggagt
tagg SEQ ID NO: 174
gcgaggtcat cctgccctac tcagcagcag cgtggctatc ttggagaggc gaggtcatcc tgccctactc agcggcgcac
tgccagggcg cgcccggccg caagctctcc aagatagcca cgctgctg SEQ ID NO: 175
gccttctctt tgcgccacgt tcgtgcgcga cgtggaagga gaaatgagcc ttctctttgc gccacgttcg gccgcagctg
aattcatttc tccttccacg tcgcgca SEQ ID NO: 176
agagtgagag tgtccctgct gccagcgggg tctgtgtggt gagcgagaga gtgagagtgt ccctgctgcc agaggactac
ggcgggctgg gcgcggggtc cccgcctctc gctcaccaca cagacccccgc SEQ ID NO: 177
cccactccaa tccccaccct ctccgtcctc caagaacgtg ccaggcgccc actccaatcc ccaccctctc catccttagt
cattaaagaa cagcagcgcc tggcacgttc ttggaggac SEQ ID NO: 178
aactccgagg agctagcgca gacgcttagg catgggaagg gcaagacaac tccgaggagc tagcgcagac cgctctccgc
cctcagctgc ggcgaggcaa gggctggcag cgctcggacg cctccgtctt gcccttccca tgcctaagc SEQ ID NO: 179
gcctaagcgc ggggaattac acgtcactcc caccgcccag ccctaatagc ctaagcgcgg ggaattacac gttcccggtg
tagaacagac gatcggggct attagggctg ggcggtggga gtg SEQ ID NO: 180
aaaagccaat ctccaagcct ccaaacggag gataaatatg cgcggcttgt cagtcaaaaa gccaatctcc aagcctccaa
acggaacgtc accctatcag ctgggagaca gcgccgcact gactgacaag ccgcgcatat ttatcct SEQ ID NO: 181
gcggccaccc accctagtcg ttgcgccgtt ttgacgtgct gccggcggcc acccacccta gtcgttggag cctggcgccc
gcgcctcccg gccggcagca cgtcaaaacg gcg SEQ ID NO: 182
gctctgcctg tttgttccgc ccgcggcttg gcgggctatc tgtggctctg cctgtttgtt ccgcccccgc ggaaaccgct
gctcgctggg cagggggcttt ctgttttgca gccggaacag gaacacagat agcccgccaa gccgc SEQ ID NO: 183
gagcttggag atgcgaggga aactcccccg gccctcctgt attactgagc ttggagatgc gagggaaact gaagcccaa
gggtgccccg tcctgggagc ctggctgtct gcggggtccc ccgcattccg cagtagtaat acaggagggc cggggg SEQ ID NO: 184
gcctcggcgc ccaaaatcga aaggagtcag cgctacggga aaggaaaccg cctcggcgcc caaaatcgaa aggccgggag
ttgttctgca ggctttgcaa acaggttgac tgagggtttc ctttcccgta gcgctgact SEQ ID NO: 185
ggagcgtgga cttcttgggc cgctgcacgg ccggagaagc gaatggagcg tggacttctt gggccgtacc cctgcggctc
aagctgcccc ggattcgctt ctccggccgt gcag SEQ ID NO: 186
ttcggattct ggacttcggg ttccgcccgc cgaaaattat cttcagccat tcggattctg gacttcgggt tccgctgagg acggatttcg
gaataggcac agtggctgcc ccgaacccct caaggcggcc tccgcgggct gtggctgaag ataattttcg gcgggc SEQ ID NO: 187
ggtaggtacc gcctgcctgt gtgtactgag gctgcttggt tctcctgtcg gtaggtaccg cctgcctgtg tgtaccgggg
ctgctgtctc cggggagggg cttctggcgg acaggagaac caagcagcct cag SEQ ID NO: 188
ggagtgggtg tggtgtgagg ctgggccgcg gataccctag acctcctagg agtgggtgtg gtgtgaggct ggcgctggag
cggtctggga atgttaggag gtctagggta tcgcggcc SEQ ID NO: 189
ctcgcgatgt ttcagggtga gccaacacac gaacagcact cctccgcctc gcgatgtttc agggtgagcc ggacgcaggc
gtgcctgcgc agtgcgcgga ggagtgctgt tcgtgtgtt SEQ ID NO: 190
ggcaccacta gctcctcgtc ctcctcggag gggcgcccga gtgcgtccga cacggccagt agcgccgcgg cgagcagcag
cagcgtgggt actggcccaa agctccgaga c SEQ ID NO: 191
cccgcgcgca ttctccctca acgcttgcct ggagcatccc tggccccttt tgcccaggtc gcgcccctga gtcttggagt
cgcgctgcct c

SEQUENCES

SEQ ID NO: 192
ggtgcgcggc ccaagagaag gccagcggga ccacagcgcg gctacgcggc cggccgcagt cttcaccgcg cgcctgccct
tgtctacgtc cc SEQ ID NO: 193
gtggggtcgt agtggtttcc gaggttggtg accacgtcgt cgaacttgag cacctcgtag ccttcatgct gccgcttgag
gccggcgtag aaggcgatct tgggcaccgt gctgtaggtg gcggcgctga SEQ ID NO: 194
ggtggaggat gtggaggtgg aagtggagcg gatggcgctc cccaagagct ccgccacgcg aggtttcggg ctcgtggttt
tgcttcctcc gggtc SEQ ID NO: 195
ggcatctatg cgggcatggt tactgcctct ggtgccccc gcagccgcgc gcaggtaccg tgcgacatcg cgatggccca
gctcctcagc caggtccacg SEQ ID NO: 196
cacctctgcc ccctgtccag gtacgcgctg tctggcgcgc cctgcgtggg ggccgcaggt tcagacaccc gggcgcggcg
cggggccctg atggatgcgg tgaccgaggc tgt SEQ ID NO: 197
cctagggccg acttttccat ctcctcctct acctccggct cccgggcgag ggaggccccg cgccgcccct tagactggct
gcggccggaa gattgcagcc gctttgagct tactc SEQ ID NO: 198
ccggcgcttt gcttttctac aactggaagc cgcgaaggcg gctactgcgc tgagccgctc gctctgctgg tcaagtttgg
gcgacccgcg cggaggaggg tcgggctgac tga SEQ ID NO: 199
gtggaagaagt aagtgggagg cggtgtcggg aactgactcc tcttaaaacg gtcggcgccg ctgctctgaa atgggcggct aagt SEQ ID NO: 200
ggaaaagcga tgactgccct gaactgctgg ggcgttcgaa atttccaggg tcccgaccct ccgtggggta cgcgcgactt
cggcgcagat gtcagtccgc tgccttcc SEQ ID NO: 201
gccagcagcc aaccctacg acttcaggag gctcctgcgc aaaacctccc agcgccggcg cctcgtccag cagtcctaa SEQ ID NO: 202
cactgaagct gcggccctga tctccgcaga ggctgcctgc tgcgctcggc cctcaagtgc ccgggccggc cttcgtgctc
cgaaacaaga gacctgggag ccctc SEQ ID NO: 203
ccgcccgcag gatcgagtga gtcacgcggc cgccagacga ggccggtggc gcacgcaccc gagatccgat gtagtgcacc
gcct SEQ ID NO: 204
ctgagaagtc agacgggccg cgtaaggggc agagcgaggg gtccggcatc actcgcgcgc tccggaaacc cgcgtgagcc
gctgttcctg ccgcgctccc atctgag SEQ ID NO: 205
gcgggctggg gttggaagag taactcgggc tgcgggctga acgcagtcgg caaccgcgga agagcagcat ctcccctgcg
cctgtggata cgccagtcca gggat SEQ ID NO: 206
aggctccgaa tcgcacctct tctcctgtcc taatctcagg ctccaggcct ggcttgcagt ttctggctca ccgcgctgcg
gtcaccggcc cacactccca gga SEQ ID NO: 207
cagggactcc tggccttgcg tcttgggaga gcgcacgctg gcctgcgcta cacacacaca cttcacagtt gcgctgaaac aga SEQ ID NO: 208
cctcagttac gctgactcgg ctgtgcccgc agtgtcgcgc tgtcgcgtag ccaggtgtcg ccgggctggc gcggttattt
atgactgcgt ggttggg SEQ ID NO: 209
gcgaggatgt ggatggcgcg gatggcgcgg cctccacctg cgggcagtgg agagagcggc gagaggaa SEQ ID NO: 210
gctgcattga ggccgggctg tgtaaactgt agggtgcctc gccgactcgg agccgcagag actggcggcg ggtcaact SEQ ID NO: 211
ggcgacgcgt ttccctggtt acctgcgggg ccgcgtcccg gaggagcctg agggccaaga gggccggcgc gcggtgggcg
cggcctgcgg ggatgccggg ctctacggag cagcgcgggg t

| SEQUENCES |
|---|

SEQ ID NO: 212
ttctaacgag ggctcagctc cgactacccc aggcctccgg ggaccctctc cggatgcgct ccccgctttg cgctttgcgc tttttgcctg ttccctgggg tc SEQ ID NO: 213
ggggatgggg agtagaggga gggggccctg ttgcctcagc gccccgaggt cgtggagcgg cagcagctgc agccggagca gcaccagcaa cagcaacagc gagcgggacg gagttagg SEQ ID NO: 214
cgcgaggtca tcctgcccta ctcagcggcg cactgccagg gcgcgcccgg ccgcaagctc tccaagatag ccacgctgct g SEQ ID NO: 215
agccttctct ttgcgccacg ttcggccgca gctgaattca tttctccttc cacgtcgcgc a SEQ ID NO: 216
cagagtgaga gtgtccctgc tgccagagga ctacggcggg ctgggcgcgg ggtccccgcc tctcgctcac cacacagacc ccgc SEQ ID NO: 217
gcccactcca atccccaccc tctccatcct tagtcattaa agaacagcag cgcctggcac gttcttggag gac SEQ ID NO: 218
caactccgag gagctagcgc agaccgctct ccgccctcag ctgcggcgag gcaagggctg gcagcgctcg gacgcctccg tcttgcccct cccatgccta agc SEQ ID NO: 219
tgcctaagcg cggggaatta cacgttcccg gtgtagaaca gacgatcggg gctattaggg ctgggcggtg ggagtg SEQ ID NO: 220
aaaaagccaa tctccaagcc tccaaacgga acgtcaccct atcagctggg agacagcgcc gcactgactg acaagccgcg catatttatc ct SEQ ID NO: 221
cgcggccacc caccctagtc gttggagcct ggcgcccgcg cctccggcc ggcagcacgt caaaacggcg SEQ ID NO: 222
ggctctgcct gtttgttccg ccccgcgga aaccgctgct cgctgggcag gggctttctg ttttgcagcc ggaacaggaa cacagatagc ccgccaagcc gc SEQ ID NO: 223
cgagcttgga gatgcgaggg aaactgaagc cccaagggtg ccccgtcctg ggagcctggc tgtctgcggg gtccccgca ttccgcagta gtaatacagg agggccgggg g SEQ ID NO: 224
agcctcggcg cccaaaatcg aaaggccggg agttgttctg caggctttgc aaacaggttg actgagggtt tcctttcccg tagcgctgac t SEQ ID NO: 225
cggagcgtgg acttcttggg ccgtaccct gcggctcaag ctgccccgga ttcgcttctc cggccgtgca g SEQ ID NO: 226
tttcggattc tggacttcgg gttccgctga ggacggattt cggaataggc acagtggctg ccccgaaccc ctcaaggcgg cctccgcggg ctgtggctga agataatttt cggcgggc SEQ ID NO: 227
aggtaggtac cgcctgcctg tgtgtaccgg ggctgctgtc tccggggagg ggcttctggc ggacaggaga accaagcagc ctcag SEQ ID NO: 228
gggagtgggt gtggtgtgag gctggcgctg gagcggtctg ggaatgttag gaggtctagg gtatcgcggc c SEQ ID NO: 229
tctcgcgatg tttcagggtg agccggacgc aggcgtgcct gcgcagtgcg cggaggagtg ctgttcgtgt gtt SEQ ID NO: 230
ggcgaaaaga aggccaaaca cagcatcgac ggcatcctgg gcgacaaagg tagggaactt ccctgggctg cgaggcccca gcccgggttt tccacgctc cggtgtgcgg gccagtggtt SEQ ID NO: 231
ggggatgggg agtagaggga gggggccctg ttgcctcagc gccccgaggt cgtggagcgg cagcagctgc agccggagca gcaccagcaa cagcaacagc gagcgggacg SEQ ID NO: 232
gcaccagcaa cagcaacagc gagcgggacg gagttaggac cgctcggagc gcacaggtct cgaggtagt

| SEQUENCES |
| --- |

SEQ ID NO: 233
cgagcttgga gatgcgaggg aaactgaagc cccaagggtg ccccgtcctg ggagcctggc tgtctgcggg gtccccgca
ttccgcagta gtaatacagg agggccgggg g SEQ ID NO: 234
cagggactcc tggccttgcg tcttgggaga gcgcacgctg gcctgcgcta cacacacaca cttcacagtt gcgctgaaac aga SEQ ID NO: 235
gcgctcatcg tgtgcacctt cacctacctg ctggtgggcg ccgcggtctt cgacgcgctg gagtcggagc ccgagctgat c SEQ ID NO: 236
aacagcagca ccgtgatcca gagcaccccg aagactggca gaaccagccg acgagtcagg cgccgcatgg tccccttgc
cgcttcctct ccgc SEQ ID NO: 237
cgcacaatat caataattcc gcgggtcaca gcatcccgca caaggacgcc ttcttattgc ataattaacg cgaggaaggc
tcttcccgct actcccgc SEQ ID NO: 238
gtggctcact ctccaatcag cgctttctag agacagcgtg gtcagcgtac ttgcttactt tcaggattgc gagacgtctt taaccttgc
t SEQ ID NO: 239
gcagtgtgcg gagaccctct aggcgggcgg ggacgcccca cgcggcgacc tgagcaccga cctcatgcaa cgggaccgaa
ccttgggacc cgggcag SEQ ID NO: 240
agcctcggcg cccaaaatcg aaaggccggg agttgttctg caggctttgc aaacaggttg actgagggtt tcctttcccg
tagcgctgac t SEQ ID NO: 241
atcgaaaggc cgggagttgt tctgcaggct ttgcaaacag gttgactgag ggtttccttt cccgtagcgc tgactgc SEQ ID NO: 242
gcccatctgc acctgtcccc tttgctgtct tacatgtccc atagtattaa agttatttga ataagcaaat gaaccccgct cttggt
87

SEQ ID NO: 243
cggagcgtgg acttcttggg ccgtaccccct gcggctcaag ctgccccgga ttcgcttctc cggccgtgca g SEQ ID NO: 244
ccggcgcttt gcttttctac aactggaagc cgcgaaggcg gctactgcgc tgagccgctc gctctgctgg tcaagtttgg
gcgacccgcg cggaggaggg tcgggctgac tgc SEQ ID NO: 245
gtggagaagt aagtgggagg cggtgtcggg aactgactcc tcttaaaacg gtcggcgccg ctgctctgaa atgggcggct aagt SEQ ID NO: 246
tcagctatga gcagagaccg ctgaagcgcc cccggctcgg gccgcccgac gtctacccac aggaccccaa gcagaaggag
gtaag SEQ ID NO: 247
cccggcgcga ttctccctca acgcttgcct ggagcatccc tggcccctt tgcccaggtc gcgcccctga gtcttggagt
cgcgctgcct c SEQ ID NO: 248
gcccggcttc gccttctctc ataagggtgg ccggggcc acgaacttgc agggtggcgg ccctgcgccc tccagcccg
gcgggacgg gcacgattgc tcgtagtctg gggtg SEQ ID NO: 249
gggcactcac acacgcag acccagagga ggagaggtgg gtataaggaa gcaagccccca gccgcagcag cccgagcggg
cacaaaaccg cttcctggca catcaccttg SEQ ID NO: 250
ggcactcaca cacagcaga cccagaggag gagaggtggg tataaggaag caagccccag ccgcagcagc ccgagcgggc
acaaaaccgc ttcctggc SEQ ID NO: 251
gcgggctggg gttgaagag taactcgggc tgcgggctga acgcagtcgg caaccgcgga agagcagcat ctcccctgcg
cctgtggata cgccagtcca gggat SEQ ID NO: 252
cgcatcctcg ccttcttgca gtccaaggcc cgcctgggcg cggagcccgc ctttccgccg ctgggttcgc tcccggagcc
ggatttctcc tatcagctgc accctgc

| SEQUENCES |
|---|

SEQ ID NO: 253
ctgagaagtc agacgggccg cgtaaggggc agagcgaggg gtccggcatc actcgcgcgc tccggaaacc cgcgtgagcc
gctgttcctg ccgcgctccc atctgag SEQ ID NO: 254
gcgtaagggg cagagcgagg ggtccggcat cactcgcgcg ctccggaaac ccgcgtgagc cgctgttcct gccgcgctcc
catctgag SEQ ID NO: 255
caatctcaga gcggagccga cagagagcag ggaaccggca tggccaaagc cgcggcgatc ggcatcgacc tgggcaccac
ctactc SEQ ID NO: 256
gtgtgcaccg agcgagtgaa ggtatgtgtg gcgggcgcgg ctggagctgc cgccgccgcc gccgccgcgc cagcaggtcc
taatgcctgt cacttcccag gacgctggca g SEQ ID NO: 257
ctcacgttgc acgatgacta tcactagctt ttggctgcgc gctcggtgtt ctcgtctgtg ggttttagcc aaggctgcag ctacc SEQ ID NO: 258
caggacggga ttctctgcac gctgtcgagt gagccggcat ctcggcgccc gggtgggctg cgaagaaaat ggt SEQ ID NO: 259
gcagaagacg gcgctgggaa gagctgcgtg acgctcgggg gctggcggct gggccggcag cgcgccgtgg cggcgtgacc
tgtccatggt gttgaag SEQ ID NO: 260
cacctctgcc ccctgtccag gtacgcgctg tctggcgcgc cctgcgtggg ggccgcaggt tcagacaccc gggcgcggcg
cggggccctg atggatgcgg tgaccgaggc tgt SEQ ID NO: 261
cctcagttac gctgactcgg ctgtgcccgc agtgtcgcgc tgtcgcgtag ccaggtgtcg ccgggctggc gcggttattt
atgactgcgt ggttggg SEQ ID NO: 262
ggtgcgcggc ccaagagaag gccagcggga ccacagcgcg gctacgcggc cggccgcagt cttcaccgcg cgcctgccct
tgtctacgtc cc SEQ ID NO: 263
gcggatgcac gacctgaacg acgcgctgga cgagctgcgc gcggtgatcc cctacgcgca cagcccctcg gtgcgaaagc
tctccaagat cgccacgc SEQ ID NO: 264
ggcagccggc tacccgttca gcgccggact gccccggct gcctcctgcc cggagaagtg cgccctgttt aacagcgtct
cctccagcct ctgca SEQ ID NO: 265
cacgtcggag ctcgcctgga tccgggcgtt ggcagccgaa gggccctggc cccgggactc tccgccgcta gcccccgtca
tatcttctcc gctttcgctt ctccactcta gccgg SEQ ID NO: 266
ttgttttct ggaaaagtcg ctgcaatgga cacagcgttg cgcggtttcc ctgcgcgcct ggggcgcttt ttgtcttcgc cctccgtgga
t SEQ ID NO: 267
ggcatctatg cgggcatggt tactgcctct ggtgcccccc gcagccgcgc gcaggtaccg tgcgacatcg cgatggccca
gctcctcagc caggtccacg SEQ ID NO: 268
agccttctct ttgcgccacg ttcggccgca gctgaattca tttctccttc cacgtcgcgc a SEQ ID NO: 269
gtggggtcgt agtggtttcc gaggttggtg accacgtcgt cgaacttgag cacctcgtag ccttcatgct gccgcttgag
gccggcgtag aaggcgatct tgggcaccgt gctgtaggtg gcggcgctga SEQ ID NO: 270
gcgaggatgt ggatggcgcg gatggcgcgg cctccacctg cgggcagtgg agagagcggc gagaggaa SEQ ID NO: 271
gccagcagcc aaccc ctacg acttcaggag gctcctgcgc aaaacctccc agcgccggcg cctcgtccag cagtcctaa SEQ ID NO: 272
cactgaagct gcggccctga tctccgcaga ggctgcctgc tgcgctcggc cctcaagtgc ccgggccggc cttcgtgctc
cgaaacaaga gacctgggag ccctc

| SEQUENCES |
| --- |

SEQ ID NO: 273
ggaaaagcga tgactgccct gaactgctgg ggcgttcgaa atttccaggg tcccgaccct ccgtggggta cgcgcgactt
cggcgcagat gtcagtccgc tgccttcc SEQ ID NO: 274
cagcggcgac tggttctgac ttgccaagta cctggcacga aaggacgtc gtgtgggtcg tccttaccct gaatttaatg
aagtcagggg ctgaaaacgg cggtgtaa SEQ ID NO: 275
ggtgtgaccg ttgttgcacc ccagtcgaca tgacgttagt ttttcatttg ccaaattgct ggttagttgc aaagcctacc ctcggccgcg
agcactgaag gatgggaggg tcgagcgccc cgttttgaca ggaggaagtg SEQ ID NO: 276
tgtgcgcgcg tgtgtcttta cacgcgccgc gtgcccagtg ttgcacgggg cgggagaaga atggcaggta ccgcccgaa
acacctcgcc ctgtctcctt tctttgggcg aggt SEQ ID NO: 277
agctgggagg aagacagtag tgatgctgcc gcgggtggcg ggggttgcgc cgccgcccag agaacctcgg cagtgtgcag
ggaggtgcat ttcattttgg ctatttccat cccg SEQ ID NO: 278
ctcatcgtct tggggttaag agttgccgcc cggccagggc aacagccagg gcaaagggag agagaagccg ccccggggcg
agaaggagaa aagttagagg gctgaacagg tgacgc SEQ ID NO: 279
cagagtgaga gtgtccctgc tgccagagga ctacggcggg ctgggcgcgg ggtccccgcc tctcgctcac cacacagacc
ccgc SEQ ID NO: 280
gcccactcca atccccaccc tctccatcct tagtcattaa agaacagcag cgcctggcac gttcttggag gac SEQ ID NO: 281
cctagggccg acttttccat ctcctcctct acctccggct cccgggcgag ggaggccccg cgccgcccct tagactggct
gcggccggaa gattgcagcc gctttgagct tactc SEQ ID NO: 282
cctcggatcc caagcatatc tggcgatgga gcggcggcag cccgaggcac gtgttgtgtg tgctccgatt g SEQ ID NO: 283
cgcgtgcgaa gtctcctcta gcggagcggg accggccgcg gcggtggatc gtggcggtcc ctgcacttct gctccagccg
cgcctggaaa cctgagcc SEQ ID NO: 284
cgcgtgcgaa gtctcctcta gcggagcggg accggccgcg gcggtggatc gtggcggtcc ctgcacttct gctccagccg
cgcctggaaa cctgag SEQ ID NO: 285
ggctctgatt ggcctgcatc ttgcggcgcg ggcggccgca gcccggcgcg agggagggag cgcggaacaa ggcgctgact
gtctccca SEQ ID NO: 286
tgcagggacg tacagggcgg tgatccagta tctaaattct ttgggagaaa atgaatagtt ccccgcccc cgccctccag
gaaaaaaaaa aatctgagaa tctgagaatg ttcagcgcac ccgc SEQ ID NO: 287
aaaaagccaa tctccaagcc tccaaacgga acgtcaccct atcagctggg agacagcgcc gcactgactg acaagccgcg
catatttatc ct SEQ ID NO: 288
cgcggccacc caccctagtc gttggagcct ggcgcccgcg cctcccgcc ggcagcacgt caaaacggcg SEQ ID NO: 289
ttctaacgag ggctcagctc cgactacccc aggcctccgg ggaccctctc cggatgcgct cccgctttg cgctttgcgc
tttttgcctg ttccctgggg tc SEQ ID NO: 290
ccgcccgcag gatcgagtga gtcacgcggc cgccagacga ggccggtggc gcacgcaccc gagatccgat gtagtgcacc
gcct SEQ ID NO: 291
cgctcgttgc gacccaggct cagctccgcg gtgcgcaggg cctggcgcct tgcggctgc ccgcccgggc tcagctcctc
cacagccacg cggcaccgca gctccgagtc ctcatattcc
cctgccgcc

| SEQUENCES |
| --- |

SEQ ID NO: 292
caactccgag gagctagcgc agaccgctct ccgccctcag ctgcggcgag gcaagggctg gcagcgctcg gacgcctccg
tcttgccctt cccatgccta agc SEQ ID NO: 293
tgcctaagcg cggggaatta cacgttcccg gtgtagaaca gacgatcggg gctattaggg ctgggcggtg ggagtg SEQ ID NO: 294
ctggcttcag tacataacgc gagttacagt tcaacagaac cagatgtgaa aacgtcagcc acccagttca gg SEQ ID NO: 295
tattaagaac cgcaagccca ctgtgtgcca gccgccgttg gtagttttac acgtgcgatc ttatttaata cttcctggga cctaatgagt
caggtgccat catgatccgt tta SEQ ID NO: 296
aggctccgaa tcgcacctct tctcctgtcc taatctcagg ctccaggcct ggcttgcagt ttctggctca ccgcgctgcg
gtcaccggcc cacactccca gga SEQ ID NO: 297
ggctctgcct gtttgttccg cccccgcgga aaccgctgct cgctgggcag gggctttctg ttttgcagcc ggaacaggaa
cacagatagc ccgccaagcc gc SEQ ID NO: 298
gaaaaacaga gaggcgaggc cagactgccc ccacacctcc tgtagccact gagcgcgaag tgcgttggtt ccgagcgcgc
tggtgggatc cacaaagctc gcattctctc agg SEQ ID NO: 299
cgagttctgg gcctctggag gtttccctgt cagcctcccc ggccgccgag ggggcgcgcg cccaacaagg gggtctctag
cggccacctg gggacagaaa cagtgaccct SEQ ID NO: 300
ggtggaggat gtggaggtgg aagtggagcg gatggcgctc cccaagagct ccgccacgcg aggtttcggg ctcgtggttt
tgcttcctcc gggtc SEQ ID NO: 301
tggcctccaa ctttaacgac atagtcaagc agggctacgt gaaaatccgc agcaggaagc ttggggtgag tggctc SEQ ID NO: 302
ggcgacgcgt ttccctggtt acctgcgggg ccgcgtcccg gaggagcctg agggccaaga gggccggcgc gcggtgggcg
cggcctgcgg ggatgccggg ctctacggag cagcgcgggg
t SEQ ID NO: 303
tttcggattc tggacttcgg gttccgctga ggacggattt cggaataggc acagtggctg ccccgaaccc ctcaaggcgg
cctccgcggg ctgtggctga agataatttt cggcgggc SEQ ID NO: 304
ttgtgatatt tggttgcgcg ggattatgat gaaatgtgtg atatgtgtgt gattatgatt aaggctgtag cgagtgtgaa cgtggcgaag
tgtgcg SEQ ID NO: 305
gggagtgggt gtggtgtgag gctggcgctg gagcggtctg ggaatgttag gaggtctagg gtatcgcggc c SEQ ID NO: 306
aggtaggtac cgcctgcctg tgtgtaccgg ggctgctgtc tccggggagg ggcttctggc ggacaggaga accaagcagc
ctcag SEQ ID NO: 307
accctggggt gtagctctgt gtcccactgt gtgatgacgt gtgcgtgctt ctgtgcgtgt gtgtgtgttt gtgcgcgtg SEQ ID NO: 308
tctcgcgatg tttcagggtg agccggacgc aggcgtgcct gcgcagtgcg cggaggagtg ctgttcgtgt gtt SEQ ID NO: 309
gggcacaggt ggggtccgtc aggccgcccg gggctcctct gtcccagctc tgcggcccag ggggtgacgt gatggcggca
gcggtg SEQ ID NO: 310
accggtctcc tcgtatccat cctcgcagtc cccaccccaa actaatgttc tccctgagc aaatttcgag acacttaaaa
tcccagctaa gatcacgtcc ttct SEQ ID NO: 311
aggcaggaga ggggaggaag agaacctgtg cccctggaag ctagaggaga gcctcgctct ctctgctgct ctgggttccg
caacgaattg agttcggggtt caggcggct

| SEQUENCES |
|---|

SEQ ID NO: 312
ggctcttttg catgcaggcc cgcctgaatg gggcgcctgg aggctgcatt gaggccgggc tgtgt SEQ ID NO: 313
gctgcattga ggccgggctg tgtaaactgt agggtgcctc gccgactcgg agccgcagag actggcggcg ggtcaact SEQ ID NO: 314
cttcccaggt caccattgct cctctgccct ctccacatcc gccctcccgt gagcgcagga tgcacgcaca ggcagcggtt
acaaaactca gcgcaacgtt g SEQ ID NO: 315
ggcaccacta gctcctcgtc ctcctcggag gggcgcccga gtgcgtccga cacggccagt agcgccgcgg cgagcagcag
cagcgtgggt actggcccaa agctccgaga c SEQ ID NO: 316
atctctttac cctggagcca gaaccagcgt cgccgccgtc ccctgcagct cagccggcaa cgcgcgccga gcctcggggc
gcagcttgga gacgcgcttg ctcgttct SEQ ID NO: 317
cgcgaggtca tcctgcccta ctcagcggcg cactgccagg gcgcgccgg ccgcaagctc tccaagatag ccacgctgct g

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

What is claimed is:

1. A method of detecting hypermethylation of differentially methylated regions (DMRs), the method comprising:
 detecting a methylation status of at least one methylation site within each of three or more differentially methylated regions (DMRs) of cell-free DNA from blood or plasma of a human subject suspected of having colorectal cancer and/or advanced adenoma, wherein the three or more DMRs comprise SEQ ID NO: 192, SEQ ID NO: 201, and SEQ ID NO: 210,
 wherein detecting the methylation status comprises determining whether at least one methylation site within each of the three or more DMRs is hypermethylated.

2. The method of claim 1, wherein the three or more DMRs further comprise at least one member selected from the group consisting of SEQ ID NO: 193, SEQ ID NO: 195, SEQ ID NO: 200, SEQ ID NO: 202, SEQ ID NO: 208, SEQ ID NO: 218, and SEQ ID NO: 219.

3. The method of claim 1, wherein the three or more DMRs further comprise at least one member selected from the group consisting of SEQ ID NO: 190, SEQ ID NO: 191, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, and SEQ ID NO: 229.

4. The method of claim 1, wherein the subject is suspected of having early stage colorectal cancer.

5. The method of claim 1, wherein the methylation status is detected using one or more members selected from the group consisting of Methylation-Specific PCR, Methylation Specific Nuclease-assisted Minor-allele Enrichment PCR, hybrid-capture targeted next-generation sequencing, and amplicon based targeted next-generation sequencing.

6. The method of claim 1, wherein the method further comprises detecting the methylation status of at least one methylation site found within the gene CDKN2A.

7. The method of claim 1, wherein the method further comprises detecting the methylation status of at least one methylation site found within the gene CDKN2B-AS1.

8. The method of claim 1, wherein the method further comprises detecting the methylation status of at least one methylation site found within SEQ ID NO: 195.

9. A method of using methylation sensitive restriction enzyme quantitative polymerase chain reaction (MSRE-qPCR), the method comprising:
(a) contacting cell-free DNA from blood or plasma of a human subject suspected of having colorectal cancer and/or advanced adenoma with one or more methylation sensitive restriction enzymes;
(b) performing qPCR of enzyme-digested DNA, or amplicons thereof; and
(c) detecting the methylation status of at least one methylation site found within each of three or more differentially methylated regions (DMRs) of DNA, wherein the three or more DMRs comprise SEQ ID NO: 192, SEQ ID NO: 201, and SEQ ID NO: 210.

10. The method of claim 9, wherein the three or more DMRs further comprise at least one member selected from the group consisting of SEQ ID NO: 193, SEQ ID NO: 195, SEQ ID NO: 200, SEQ ID NO: 202, SEQ ID NO: 208, SEQ ID NO: 218, and SEQ ID NO: 219.

11. The method of claim 9, wherein the three or more DMRs further comprise at least one member selected from the group consisting of SEQ ID NO: 190, SEQ ID NO: 191, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, and SEQ ID NO: 229.

* * * * *